United States Patent
Chappie et al.

(10) Patent No.: US 10,590,128 B2
(45) Date of Patent: Mar. 17, 2020

(54) 6,7,8,9-TETRAHYDRO-5H-PYRIDO [2,3-D]AZEPINE DOPAMINE D3 LIGANDS

(71) Applicant: Pfizer Inc., New York, NY (US)

(72) Inventors: Thomas Allen Chappie, Carlisle, MA (US); Jaclyn Louise Henderson, Cambridge, MA (US); Joseph Michael Young, Castro Valley, CA (US); Travis T. Wager, Brookline, MA (US); Bethany Lyn Kormos, Somerville, MA (US); Nandini Chaturbhai Patel, Waban, MA (US); Simone Sciabola, Cambridge, MA (US); Jamison Bryce Tuttle, Marblehead, MA (US); Patrick Robert Verhoest, Newton, MA (US); Joseph Walter Tucker, New London, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 16/069,585

(22) PCT Filed: Jan. 9, 2017

(86) PCT No.: PCT/IB2017/050094
§ 371 (c)(1),
(2) Date: Jul. 12, 2018

(87) PCT Pub. No.: WO2017/122116
PCT Pub. Date: Jul. 20, 2017

(65) Prior Publication Data
US 2019/0047997 A1 Feb. 14, 2019

Related U.S. Application Data

(60) Provisional application No. 62/279,037, filed on Jan. 15, 2016.

(51) Int. Cl.
| | | |
|---|---|---|
| *C07D 471/04* | (2006.01) | |
| *A61K 31/55* | (2006.01) | |
| *A61P 25/16* | (2006.01) | |
| *A61P 25/18* | (2006.01) | |
| *A61P 25/24* | (2006.01) | |
| *A61P 25/22* | (2006.01) | |

(52) U.S. Cl.
CPC .......... *C07D 471/04* (2013.01); *A61K 31/55* (2013.01); *A61P 25/16* (2018.01); *A61P 25/18* (2018.01); *A61P 25/22* (2018.01); *A61P 25/24* (2018.01)

(58) Field of Classification Search
CPC .............................. A61K 31/55; C07D 471/04
See application file for complete search history.

(56) References Cited

U.S. PATENT DOCUMENTS

| 7,732,442 B2 | 6/2010 | Habashita et al. |
|---|---|---|
| 2005/0137186 A1 | 6/2005 | Braje et al. |

FOREIGN PATENT DOCUMENTS

| EA | 200701856 | 2/2008 |
|---|---|---|
| WO | WO2006103559 | 10/2006 |
| WO | WO2007140213 | 12/2007 |
| WO | 2008/009125 | 1/2008 |
| WO | 2008/149163 | 12/2008 |
| WO | 2011/097300 | 8/2011 |

OTHER PUBLICATIONS

Le Foll et al. (Prog. Brain Res., 2014, vol. 211, abstract only, pp. 1-2).*

* cited by examiner

*Primary Examiner* — Susanna Moore
(74) *Attorney, Agent, or Firm* — Haley Guiliano LLP; James F. Haley, Jr.; Brittany J. Barrett

(57) ABSTRACT

The present invention provides compounds of Formula (I): and pharmaceutically acceptable salts thereof wherein the variables $R^1$, $R^2$, $R^3$, $R^4$, $R^5$, a and A are as defined herein; processes for the preparation of; intermediates used in the preparation of; and compositions containing such compounds or salts, and their uses for treating D3-mediated (or D3-associated) disorders including, e.g., substance addiction, substance abuse, schizophrenia (e.g., its cognitive symptoms), cognitive impairment (e.g., cognitive impairment associated with schizophrenia, AD or PD), Parkinson's disease, mania, anxiety, impulse control disorders, sexual disorders and depression.

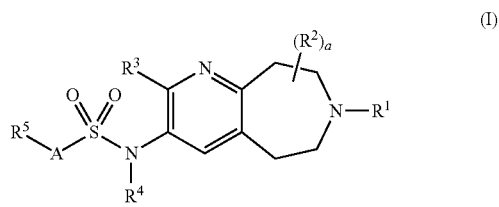

(I)

29 Claims, No Drawings

6,7,8,9-TETRAHYDRO-5H-PYRIDO [2,3-D]AZEPINE DOPAMINE D3 LIGANDS

This application is a national phase filing under 35 U.S.C. § 371 of international patent application number PCT/IB2017/050094 filed Jan. 9, 2017, which in turn claims the benefit of priority to U.S. Provisional Patent Application Ser. No. 62/279,037 filed Jan. 15, 2016, the disclosure of each of these applications is hereby incorporated by reference in its entirety.

FIELD OF THE INVENTION

The present invention generally relates to 6,7,8,9-tetrahydro-5H-pyrido[2,3-d]azepine compounds, which are dopamine D3 ligands, for example dopamine D3 antagonists or partial agonists, and to pharmaceutical compositions comprising the compounds and methods of treatment using the compounds.

BACKGROUND OF THE INVENTION

Dopamine acts upon neurons through two families of dopamine receptors, D1-like receptors (D1Rs) and D2-like receptors (D2Rs). The D2-like receptor family consists of D2, D3 and D4 receptors, with the D2 and D3 receptors being the most homologous pair and sharing extensive sequence identity in the transmembrane domain and in the putative ligand binding site. See Chien, E. Y. T., et al. "Structure of the Human Dopamine D3 Receptor in Complex with a D2/D3 Selective Antagonist", *Science* 330:1091-1095 (2010). Pharmacological studies have reported that D1 and D5 receptors (D1/D5), namely D1-like receptors, couple to stimulatory $G_s$ proteins and stimulate adenylyl cyclase (AC) activity and increase cytosolic cyclic adenosine monophosphate (cAMP) levels, whereas D2, D3, and D4 receptors, namely D2-like receptors, couple to inhibitory $G_{i/o}$ proteins that suppress AC activity and decrease cAMP production.

D3 receptor mRNA has been found in specific regions of the rodent and human brain that have been associated with addiction. See e.g., Micheli, F.; Heidbreder, C. "Selective dopamine $D_3$ receptor antagonists. A decade of progress: 1997-2007", *Expert Opin. Ther. Patents* 18(8):821-840 (2008). In the human brain, D3 receptors are expressed primarily in mesolimbic regions such as the ventral striatum, ventral pallidum, internal globus pallidus, nucleus accumbens, islands of Calleja, olfactory tubercle, lateral septum, amygdala and ventral tegmental area (VTA). See e.g., Cho, D. I. et al. "Current perspectives on the selective regulation of dopamine D(2) and D(3) receptors", *Archives of Pharmacol. Research,* 33:1521-1538 (2010); Gurevich, E. V., Joyce, J. N. "Distribution of dopamine D3 receptor expressing neurons in the human forebrain: Comparison with D2 receptor expressing neurons." *Neuropsychopharmacology,* 20:60-80 (1999); and Searle, G. et al. "Imaging dopamine D3 receptors in the human brain with positron emission tomography, [$^{11}$C]PHNO, and a selective D3 receptor antagonist." *Biological Psychiatry,* 68:392-399 (2010). These brain areas have been found to govern certain motivational behaviors and the reward properties of addictive drugs. See Heidbreder, C. A.; Newman, A. H. "Current perspectives on selective dopamine $D_3$ receptor antagonists as pharmacotherapeutics for addictions and related disorders" *Ann. N.Y. Acad. Sci.* Addiction Reviews 2, 1187:4-34 (2010). In addition, certain D3 receptor gene polymorphisms have been linked to neuropsychiatric disorders. For example, the rs6280 polymorphism which encodes the functional missense mutation Ser9Gly, may enhance reward-related dopamine release and this polymorphism has been associated with nicotine dependence, alcohol dependence and early onset heroin dependence. See Keck, T. M. et al. "Identifying Medication Targets for Psychostimulant Addiction: Unraveling the Dopamine D3 Receptor Hypothesis" *J. Med. Chem.* 58:5361-5380 (2015). Based on efficacy observed in various animal models of reinstatement to drug-seeking behavior, antagonism of the D3 receptor would likely reduce relapse to drug-induced, cue-induced and stress-induced consumption post-abstinence as well as provide for pro-cognitive effects. See e.g., Heidbreder, C. "Rationale in support of the use of selective dopamine $D_3$ receptor antagonists for the pharmacotherapeutic management of substance use disorders" *Naunyn-Schmiedeberg's Arch. Pharmacol.* 386:167-176 (2013); Hachimine, P. et al. "The novel dopamine D3 receptor antagonist, SR 21502, reduces cocaine conditioned place preference in rats" *Neuroscience Letters* 569:137-141 (2014); and Galaj, E. et al. "The selective dopamine D3 receptor antagonist, SR 21502, reduces cue-induced reinstatement of heroin seeking and heroin conditioned place preference in rats" *Drug and Alcohol Dependence* 156:228-233 (2015). For example, D3 antagonist compounds may be useful in the treatment of addiction, such as relapse addiction, to drug substances such as the psychostimulants cocaine, amphetamine, methamphetamine and the like; opioids such as heroin, morphine, oxycodone, hydrocodone, hydromorphone and the like; nicotine; cannabinoids, such as marijuana; and alcohol.

Dopamine D3 receptors have also been implicated in numerous other neuropharmacological and neurobiological functions. For example, D3 receptors have been implicated as having a role in different types of memory function, such as cognition. Antagonism of the D3 receptor has been shown to improve cognitive deficits in certain animal models. See e.g., Watson, D. J. G., et al. "Selective Blockade of Dopamine $D_3$ Receptors Enhances while $D_2$ Antagonism Impairs Social Novelty Discrimination and Novel Object Recognition in Rats: A Key Role for the Prefrontal Cortex", *Neuropsychopharmacology* 37:770-786 (2012). D3 receptors have also been associated with numerous other diseases and disorders. D3 antagonists may be useful for the treatment of the following diseases or disorders: impulse control disorders such as pathological gambling, hypersexuality, compulsive shopping [See Moore, T. et al. "Reports of Pathological Gambling, Hypersexuality, and Compulsive Shopping Associated with Dopamine Receptor Agonist Drugs", JAMA Internal Medicine 2014, 174(12), 1930-1933], obsessive control disorders; eating disorders such as anorexia nervosa, activity-based anorexia [See e.g., Klenotich, S. J. et al. "Dopamine D2/3 receptor antagonism reduces activity-based anorexia" *Transl. Psychiatry* 5:e613 (2015)] or binge eating and obesity [See e.g., Nathan, P. J. et al. "The effects of the dopamine $D_3$ receptor antagonist GSK598809 on attentional bias to palatable food cues in overweight and obese subjects", *International Journal of Neuropsychopharmacology* 15:149-161 (2012)]; aggressiveness; tremors; schizophrenia and other psychoses [See e.g., Gross, G. et al. "Dopamine $D_3$ receptor antagonism—still a therapeutic option for the treatment of schizophrenia", *Naunyn-Schmiedeberg's Arch. Pharmacol.* 386:155-166 (2013)]; unipolar and bipolar depression; disorders caused by stress such as anxiety and toxicomania; autistic spectrum disorder; attention-deficit hyperactivity disorder (ADHD); restless leg syndrome; pain; nausea (such as nausea caused by cytotoxic agents or dopaminergic agents); Parkinson's disease; premature ejaculation; L-Dopa induced dyskinesia (LID) and Tardive dyskinesia [See e.g. Solis, O. et al. "Dopamine D3 receptor modulates L-DOPA-Induced Dyskinesia by Targeting D1 Receptor Mediated Striatal Signaling", Cerebral Cortex Oct. 18, 2015, 1-12; Payer, D. et al. "D3 dopamine receptor preferring [11C]PHNO PET imaging in Parkinson patients with dyskinesia" Neurology published ahead of print Dec. 30, 2015; and Mahmoudi, S. et al. "Upregulation of Dopamine D3, Not D2, Receptors Correlates With Tardive Dyskinesia in a Primate Model", Movement Disorders 2014, 29(9), 1125. Antagonism of the D3 receptor may provide efficacious treatments for these diseases and disorders. In addition, antagonism of peripheral D3 receptors in the kidney may provide a renoprotective effect, for example in patients with diabetes or who have been treated with a metabolism-disrupting antipsychotic agent. See e.g., Micheli, F.; Heidbreder, C. "Dopamine D3 receptor antagonists: A patent review (2007-2012)", *Expert Opin. Ther. Patents* 23(3):363-381 (2013).

New or improved agents that modulate (such as antagonize or partially agonize) D3 receptors are needed to provide improved therapeutic options for the treatment of diseases or conditions associated with dysregulated activation of the D3 receptor, such as those described herein. It may also be desirable to devise new agents which exhibit selectivity for the D3 receptor over the closely related D2 receptor. See Keck, T. M. et al. "Beyond Small-Molecule SAR: Using the Dopamine D3 Receptor Crystal Structure to Guide Drug Design" *Advances in Pharmacology*, 69:267-300 (2014).

SUMMARY OF THE INVENTION

A first embodiment of a first aspect of the present invention is a compound of Formula I

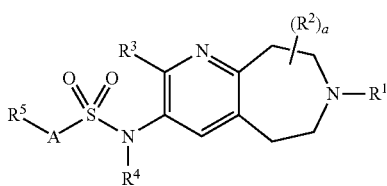

I wherein $R^1$ is selected from the group consisting of hydrogen, $C_1$-$C_6$alkyl, $C_3$-$C_7$cycloalkyl and $C_3$-$C_7$cycloalkyl$C_1$-$C_3$alkyl; wherein the $C_1$-$C_6$alkyl, $C_3$-$C_7$cycloalkyl and $C_3$-$C_7$cycloalkyl$C_1$-$C_3$alkyl are each optionally substituted with one to three independently selected halo, hydroxy or $C_1$-$C_3$alkoxy; $R^2$ is independently selected at each occurrence from the group consisting of halo, hydroxy and $C_1$-$C_3$alkyl; a is 0, 1, 2, 3 or 4; $R^3$ is selected from the group consisting of hydrogen, hydroxy, $C_1$-$C_6$alkyl and $C_1$-$C_6$alkoxy, wherein the $C_1$-$C_6$alkyl and $C_1$-$C_6$alkoxy are each optionally substituted with 1 to 3 fluoro; $R^4$ is hydrogen or $C_1$-$C_6$alkyl optionally substituted with one to three substituents independently selected from the group consisting of fluoro, $C_1$-$C_3$alkoxy and hydroxy; A is selected from the group consisting of $C_6$-$C_{10}$aryl and 5- to 10-membered heteroaryl; wherein the $C_6$-$C_{10}$aryl and 5- to 10-membered heteroaryl are optionally substituted with 1 to 3 $R^6$; $R^5$ is selected from the group consisting of halo, $C_1$-$C_6$alkyl, $C_1$-$C_6$alkoxy, $C_1$-$C_6$alkoxy$C_1$-$C_6$alkyl, $C_3$-$C_7$cycloalkyl, $C_3$-$C_7$cycloalkyl$C_1$-$C_6$alkyl, $C_3$-$C_7$cycloalkoxy, phenoxy, 4- to 10-membered heterocycloalkyl and 4- to 10-membered heterocycloalkoxy; wherein the $C_1$-$C_6$alkyl, $C_1$-$C_6$alkoxy and $C_1$-$C_6$alkoxy$C_1$-$C_6$alkyl are optionally substituted with one to four independently selected halo or hydroxy; and wherein the $C_3$-$C_7$cycloalkyl, $C_3$-$C_7$cycloalkyl$C_1$-$C_6$alkyl, $C_3$-$C_7$cycloalkoxy, phenoxy, 4- to 10-membered heterocycloalkyl and 4- to 10-membered heterocycloalkoxy are optionally substituted with one to four $R^7$; or $R^4$ and $R^5$ taken together are a $C_1$-$C_3$alkylene; $R^6$ is selected from the group consisting of halo, cyano, $C_1$-$C_6$alkyl optionally substituted with one to three fluoro, $C_1$-$C_6$alkoxy optionally substituted with one to three fluoro, and $C_1$-$C_6$alkoxy$C_1$-$C_6$alkyl; or $R^4$ and $R^6$ taken together are a $C_1$-$C_3$alkylene; or $R^5$ and $R^6$ when attached to adjacent carbons and taken together with the adjacent carbons to which they are attached form a fused 5- to 7-membered cycloalkyl ring or a 5- to 7-membered heterocycloalkyl ring, each of which is optionally substituted with one to four $R^8$; $R^7$ at each occurrence is independently selected from the group consisting of halo, hydroxy, $C_1$-$C_3$alkyl optionally substituted with one to three fluoro or $C_1$-$C_3$alkoxy, and $C_1$-$C_3$alkoxy optionally substituted with one to three fluoro; and $R^8$ at each occurrence is independently selected from halo, hydroxy, $C_1$-$C_3$alkyl optionally substituted with one to three fluoro, and $C_1$-$C_3$alkoxy optionally substituted with one to three fluoro; or a pharmaceutically acceptable salt thereof.

Another embodiment of the present invention is a pharmaceutical composition comprising compounds of Formula I, or a pharmaceutically acceptable salt thereof together with a pharmaceutically acceptable vehicle, diluent or carrier. The pharmaceutical compositions described herein can be used for modulating the D3 receptor (such as antagonizing the D3 receptor) in a patient; and for treating diseases or disorders associated with the D3 receptor, such as addiction, impulse control disorders or schizophrenia.

The present invention is also directed to methods of treatment employing the compounds of Formula I, such as:

(1) Methods of modulating the D3 receptor (such as antagonizing the D3 receptor), by administering a therapeutically effective amount of a compound of any of the embodiments of Formula I or a pharmaceutically acceptable salt thereof, and a pharmaceutically acceptable vehicle, diluent or carrier, to a patient in need thereof.

(2) Methods for treating conditions or diseases of the central nervous system and neurological disorders in which the D3 receptor may be involved, such as Parkinson's disease; cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI")); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and impulse control disorders such as obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence/addiction (i.e., addiction, including relapse addiction), such as narcotic dependence (including addiction to opioids such as heroin, oxycodone, morphine, hydrocodone, hydromorphone and the like), alcoholism, amphetamine dependence, methamphetamine dependence, cocaine dependence, nicotine dependence, cannabinoid dependence (such as marijuana (THC) dependence), and drug withdrawal syndrome); eating disorders (including anorexia, bulimia, binge eating disorder, hyperphagia, obesity, compulsive eating disorders and pagophagia); sexual dysfunction disorders, such as premature ejaculation; and pediatric psychiatric disorders (including attention deficit disorder, attention deficit/hyperactivity disorder, conduct disorder, and autism spectrum disorders) in a mammal, preferably a human, comprising administering to said mammal a therapeutically effective amount of a compound of Formula I or pharmaceutically acceptable salt thereof. The compounds of Formula I may also be useful for improving cognitive deficits and memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as Parkinson's disease; cognitive disorder; or a sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of kidney-related disorders associated with diabetes, including Type 1 and Type 2 diabetes;

(5) Methods for the treatment of eating disorders or obesity; and (6) Methods for the treatment of substance addiction, such as a relapse addiction, wherein the substance addiction includes, but is not limited to, alcohol, cocaine, amphetamine, methamphetamine, opioid, cannabinoid (marijuana) or nicotine addiction.

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided.

All patents, patent applications and references referred to herein are hereby incorporated by reference in their entirety.

Other features and advantages of this invention will be apparent from this specification and the appendant claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In reference to the treatment of a D3-mediated disease or disorder (e.g., an addiction, impulse control disorder, or schizophrenia), a therapeutically effective amount refers to that amount which has the effect of relieving to some extent (or, for example, eliminating) one or more symptoms associated with a D3-mediated disease or disorder (e.g., an addiction, impulse control disorder, schizophrenia, cognitive and negative symptoms in schizophrenia, or cognitive impairment associated with schizophrenia).

The term "treating", as used herein, unless otherwise indicated, means reversing, alleviating, inhibiting the progress of, delaying the progression of, delaying the onset of, or preventing the disease, disorder or condition to which such term applies, or one or more symptoms of such disease, disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms (a $C_1$-$C_6$alkyl). Non-limiting examples of such substituents include methyl, ethyl, propyl (including n-propyl and isopropyl), butyl (including n-butyl, isobutyl, sec-butyl and tert-butyl), pentyl, isoamyl, hexyl and the like. Another embodiment is an alkyl containing from one to three carbons (a $C_1$-$C_3$alkyl), which includes methyl, ethyl, propyl and isopropyl.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms (a $C_1$-$C_6$alkoxy). Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like. Another embodiment is an alkoxy containing from one to three carbons (a $C_1$-$C_3$alkoxy) including methoxy, ethoxy, propoxy and isopropoxy.

The term "alkylene" refers to an alkanediyl group (i.e., a substituent obtained from a hydrocarbon by removal of two hydrogens); in one embodiment containing from one to three carbons (a $C_1$-$C_3$alkylene). The alkylene group may be either a straight-chain or branched alkanediyl group. Non-limiting examples of such groups include methylene (i.e., —$CH_2$—), ethylene (i.e., —$CH_2CH_2$— or —$CH(CH_3)$—) and propylene (i.e., —$CH_2CH_2CH_2$—, —$CH(CH_2CH_3)$— or —$CH(CH_3)CH_2$—).

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$alkyl" refers to an alkyl substituent containing from 1 to 6 carbon atoms. Illustrating further, $C_3$-$C_7$-cycloalkyl or $C_{3-7}$cycloalkyl refers to a saturated cycloalkyl group containing from 3 to 7 carbon ring atoms.

The term "cycloalkyl" refers to a carbocyclic substituent obtained by removing a hydrogen from a saturated carbocyclic molecule, for example one having three to six carbon atoms or having three to seven carbon atoms. The term "cycloalkyl" includes mono-, bi- and tricyclic saturated carbocycles, as well as bridged and fused ring carbocycles and also spiro-fused carbocyclic ring systems. The term "$C_{3-7}$cycloalkyl" means a radical of a three- to seven-membered ring system, which includes the groups cyclopropyl, cyclobutyl, cyclopentyl, cyclohexyl, cycloheptyl, bicyclopentyl, bicyclohexyl, bicycloheptyl, spiropentyl, spirohexyl and spiroheptyl. The term "$C_{3-6}$cycloalkyl" means a radical of a three- to six-membered ring system, which includes the groups cyclopropyl, cyclobutyl, cyclopentyl, cyclohexyl, bicyclopentyl, bicyclohexyl, spiropentyl and spirohexyl. The term "$C_{3-7}$cycloalkoxy" refers to a three- to seven-membered cycloalkyl group attached to an oxygen radical. Examples include cyclopropoxy, cyclobutoxy, cyclopentoxy, cyclohexoxy and cycloheptoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 10-membered heterocycloalkyl" refers to a heterocycloalkyl containing from 4 to 10 atoms, including one to three heteroatoms, in the cyclic moiety of the heterocycloalkyl and "5- to 7-membered heterocycloalkyl" refers to a heterocycloalkyl containing from 5 to 7 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 10 ring atoms or 5 to 7 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a ring nitrogen atom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be a ring nitrogen atom, or it may be a ring carbon atom. Similarly, if the heteroaryl substituent is in turn substituted with a group or substituent, the group or substituent may be bound to a ring nitrogen atom, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, and pyrazolo[1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including 1,2,3-oxadiazolyl, 1,2,4-oxadiazolyl, 1,2,5-oxadiazolyl, or 1,3,4-oxadiazolyl), pyranyl (including 2H-pyranyl or 4H-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), and morpholinyl.

The term "heteroaryl" can also include, when specified as such, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes (including co-crystals). Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975). Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention (including salts thereof) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Also included within the scope of the invention are metabolites of compounds of Formula I, that is, compounds formed in vivo upon administration of the drug.

The compounds of the invention may have have asymmetric carbon atoms. The carbon-carbon bonds of the compounds of the invention may be depicted herein using a solid line ( —— ), a solid wedge ( —■ ), or a dotted wedge ( ·······). The use of a solid line to depict bonds to asymmetric carbon atoms is meant to indicate that all possible stereoisomers (e.g., specific enantiomers, racemic mixtures, etc.) at that carbon atom are included, unless otherwise specified. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included, unless otherwise specified. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

Certain of the compounds of Formula I may exhibit the phenomenon of tautomerism; it is to be understood that such tautomers are also regarded as compounds of the invention.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, P1-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long-chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Substitution with positron-emitting isotopes, such as $^{11}C$, $^{18}F$, $^{15}O$ and $^{13}N$, can be useful in Positron Emission Tomography (PET) studies for examining substrate receptor occupancy.

Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

Compounds of Formula I (including salts thereof) may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

A second embodiment of a first aspect of the present invention is the compound of the first embodiment of the first aspect wherein $R^1$ is hydrogen or $C_1$-$C_3$alkyl optionally substituted with a $C_1$-$C_3$alkoxy or fluoro; $R^2$ is $C_1$-$C_3$alkyl; a is 0 or 1; $R^3$ is $C_1$-$C_3$alkoxy optionally substituted with one to three fluoro; and $R^4$ is hydrogen; or a pharmaceutically acceptable salt thereof.

A third embodiment of a first aspect of the present invention is the compound of the second embodiment of the first aspect wherein $R^1$ is hydrogen, methyl, ethyl, propyl, 3-fluoropropyl or 2-methoxyethyl; a is 0; and $R^3$ is methoxy, difluoromethoxy or isopropoxy; or a pharmaceutically acceptable salt thereof.

A fourth embodiment of a first aspect of the present invention is the compound of any one of the first through third embodiments of the first aspect wherein A is phenyl or 6-membered heteroaryl, wherein the phenyl or 6-membered heteroaryl is optionally substituted with an $R^6$; or a pharmaceutically acceptable salt thereof.

A fifth embodiment of a first aspect of the present invention is the compound of the fourth embodiment of the first aspect wherein
A is

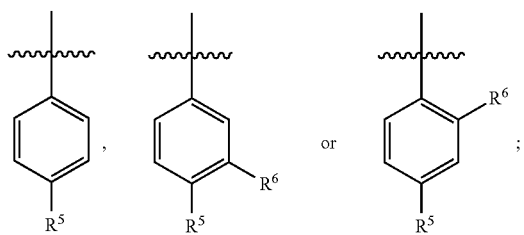

$R^5$ is selected from the group consisting of halo, $C_1$-$C_4$alkyl, $C_1$-$C_4$alkoxy, $C_1$-$C_4$alkoxy$C_1$-$C_4$alkyl, $C_3$-$C_6$cycloalkyl, $C_3$-$C_6$cycloalkoxy, 4- to 6-membered heterocycloalkyl and 4- to 6-membered heterocycloalkoxy; wherein the $C_1$-$C_4$alkyl, $C_1$-$C_4$alkoxy and $C_1$-$C_4$alkoxy$C_1$-$C_4$alkyl are optionally substituted with one to three independently selected halo or hydroxy; and wherein the $C_3$-$C_6$cycloalkyl, $C_3$-$C_6$cycloalkoxy, 4- to 6-membered heterocycloalkyl and 4- to 6-membered heterocycloalkoxy are optionally substituted with one to three $R^7$; $R^6$ is halo or $C_1$-$C_3$alkyl; or $R^5$ and $R^6$ when attached to adjacent carbons and taken together with the adjacent carbons to which they are attached form a fused 5- to 6-membered heterocycloalkyl ring, which is optionally substituted with one to three $R^8$; or a pharmaceutically acceptable salt thereof.

A sixth embodiment of a first aspect of the present invention is the compound of the fifth embodiment of the first aspect of the present invention wherein $R^5$ is selected from the group consisting of chloro, methyl, propyl, isopropyl, difluoromethoxy, ethoxy, 1-(methoxy)ethyl, cyclopropyl, cyclobutyl, cyclopentyl, cyclohexyl, oxetanyl, tetrahydrofuranyl, tetrahydropyranyl, cyclopentoxy, tetrahydrofuranoxy and tetrahydropyranoxy, wherein the cyclopropyl, cyclobutyl, cyclopentyl, cyclohexyl, oxetanyl, tetrahydrofuranyl, tetrahydropyranyl, cyclopentoxy, tetrahydrofuranoxy and tetrahydropyranoxy are each optionally substituted with one to two $R^7$; $R^6$ is fluoro or methyl; or $R^5$ and $R^6$ when attached to adjacent carbons and taken together with the adjacent carbons to which they are attached form a fused tetrahydrofuran or fused tetrahydropyran, each of which is optionally substituted with one to two $R^8$; $R^7$ at each occurrence is independently selected from the group consisting of fluoro, hydroxy, methyl, trifluoromethyl, methoxy, ethoxy and 2-fluoroethoxy; and $R^8$ at each occurrence is fluoro or methyl; or a pharmaceutically acceptable salt thereof.

A seventh embodiment of a first aspect of the present invention is the compound of the sixth embodiment of the first aspect wherein
A is

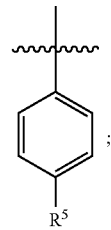

or a pharmaceutically acceptable salt thereof.

An eighth embodiment of a first aspect of the present invention is the compound of the sixth embodiment of the first aspect wherein
A is

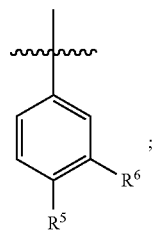

or a pharmaceutically acceptable salt thereof.

A ninth embodiment of a first aspect of the present invention is the compound of the sixth embodiment of the first aspect wherein A is

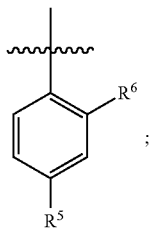

or a pharmaceutically acceptable salt thereof.

A tenth embodiment of a first aspect of the present invention is the compound of the seventh embodiment of the first aspect wherein $R^5$ is selected from the group consisting of methyl, cyclobutyl, cyclopentyl, tetrahydropyran-4-yl and tetrahydropyran-2-yl, wherein the cyclobutyl, cyclopentyl, tetrahydropyran-4-yl and tetrahydropyran-2-yl are each optionally substituted with one to two $R^7$; or a pharmaceutically acceptable salt thereof.

An eleventh embodiment of a first aspect of the present invention is the compound of the fourth embodiment of the first aspect wherein A is a 6-membered heteroaryl optionally substituted with an $R^6$; or a pharmaceutically acceptable salt thereof.

A twelfth embodiment of a first aspect of the present invention is the compound of the eleventh embodiment of the first aspect wherein A is pyridinyl or pyrimidinyl, each of which is optionally substituted with an $R^6$; or a pharmaceutically acceptable salt thereof.

A thirteenth embodiment of a first aspect of the present invention is the compound of the twelfth embodiment of the first aspect wherein
A is

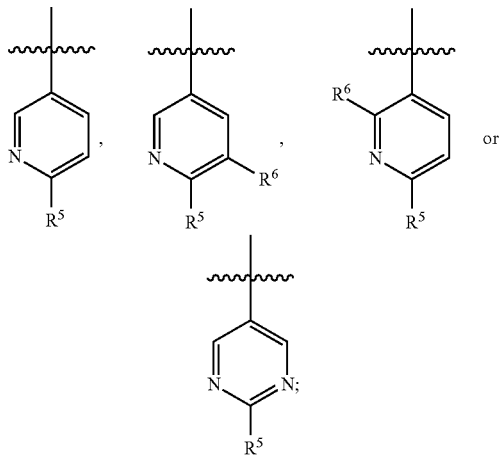

$R^5$ is selected from the group consisting of $C_1$-$C_4$alkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_1$-$C_3$alkyl, $C_3$-$C_6$cycloalkoxy, phenoxy, 4- to 6-membered heterocycloalkyl and 4- to 6-membered heterocycloalkoxy; wherein the $C_1$-$C_4$alkyl, $C_1$-$C_4$alkoxy and $C_1$-$C_4$alkoxy$C_1$-$C_4$alkyl are optionally substituted with one to three independently selected halo or hydroxy; and wherein the $C_3$-$C_6$cycloalkyl, $C_3$-$C_6$cycloalkyl$C_1$-$C_3$alkyl, $C_3$-$C_6$cycloalkoxy, phenoxy, 4- to 6-membered heterocycloalkyl and 4- to 6-membered heterocycloalkoxy are optionally substituted with one to three $R^7$; and $R^6$ is halo or $C_1$-$C_3$alkyl; or a pharmaceutically acceptable salt thereof.

A fourteenth embodiment of a first aspect of the present invention is the compound of the thirteenth embodiment of the first aspect wherein $R^5$ is selected from the group consisting of tert-butoxy, cyclobutyl, cyclopentyl, cyclohexyl, cyclobutoxy, cyclopentoxy, phenoxy, cyclopentylmethyl and tetrahydropyranyl, wherein the cyclobutyl, cyclopentyl, cyclohexyl, cyclobutoxy, cyclopentoxy, phenoxy, cyclopentylmethyl and tetrahydropyranyl are optionally substituted with one to two $R^7$; $R^6$ is fluoro or methyl; and $R^7$ at each occurrence is independently selected from the group consisting of fluoro, hydroxy, methyl, trifluoromethyl, methoxy, ethoxy and 2-fluoroethoxy; or a pharmaceutically acceptable salt thereof.

A fifteenth embodiment of a first aspect of the present invention is the compound of the fourteenth embodiment of the first aspect wherein
A is

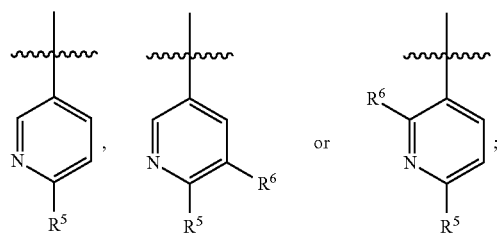

or a pharmaceutically acceptable salt thereof.

A sixteenth embodiment of a first aspect of the present invention is the compound of the fourteenth embodiment of the first aspect wherein
A is

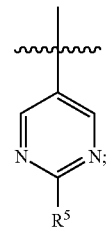

or a pharmaceutically acceptable salt thereof.

A seventeenth embodiment of a first aspect of the present invention is a compound of the first embodiment of the first aspect selected from the group consisting of:
6-cyclohexyl-N-(2-methoxy-7-methyl-6,7,8,9-tetrahydro-5H-pyrido[2,3-d]azepin-3-yl)pyridine-3-sulfonamide;
6-(cyclopentyloxy)-N-(7-ethyl-2-methoxy-6,7,8,9-tetrahydro-5H-pyrido[2,3-d]azepin-3-yl)pyridine-3-sulfonamide;
4-[trans-3-(2-fluoroethoxy)cyclobutyl]-N-(2-methoxy-7-methyl-6,7,8,9-tetrahydro-5H-pyrido[2,3-d]azepin-3-yl)benzenesulfonamide;
N-(2-methoxy-7-methyl-6,7,8,9-tetrahydro-5H-pyrido[2,3-d]azepin-3-yl)-4-tetrahydro-2H-pyran-4-yl)benzenesulfonamide;
N-(2-methoxy-7-methyl-6,7,8,9-tetrahydro-5H-pyrido[2,3-d]azepin-3-yl)-4-methylbenzenesulfonamide;
N-(2-methoxy-7-methyl-6,7,8,9-tetrahydro-5H-pyrido[2,3-d]azepin-3-yl)-4-tetrahydro-2H-pyran-2-yl)benzenesulfonamide;

N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide;
N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide;
N-(2-methoxy-6,7,8,9-tetrahydro-5H-pyrido[2,3-d]azepin-3-yl)-4-[(2R)-tetrahydro-2H-pyran-2-yl]benzenesulfonamide;
4-(trans-1-fluoro-3-methoxycyclobutyl)-N-(2-methoxy-7-methyl-6,7,8,9-tetrahydro-5H-pyrido[2,3-d]azepin-3-yl)benzenesulfonamide;
6-(1-fluorocyclopentyl)-N-(2-methoxy-7-methyl-6,7,8,9-tetrahydro-5H-pyrido[2,3-d]azepin-3-yl)pyridine-3-sulfonamide;
N-[2-(difluoromethoxy)-7-propyl-6,7,8,9-tetrahydro-5H-pyrido[2,3-d]azepin-3-yl]-4-(propan-2-yl)benzenesulfonamide;
N-(7-ethyl-2-methoxy-5-methyl-6,7,8,9-tetrahydro-5H-pyrido[2,3-d]azepin-3-yl)-4-methylbenzenesulfonamide;
4-ethoxy-N-[7-ethyl-2-(propan-2-yloxy)-6,7,8,9-tetrahydro-5H-pyrido[2,3-d]azepin-3-yl]benzenesulfonamide;
6-(cyclopentyloxy)-N-(2-methoxy-7-methyl-6,7,8,9-tetrahydro-5H-pyrido[2,3-d]azepin-3-yl)pyridine-3-sulfonamide;
6-cyclopentyl-N-(2-methoxy-7-methyl-6,7,8,9-tetrahydro-5H-pyrido[2,3-d]azepin-3-yl)pyridine-3-sulfonamide;
6-(cyclobutyloxy)-N-(2-methoxy-7-methyl-6,7,8,9-tetrahydro-5H-pyrido[2,3-d]azepin-3-yl)pyridine-3-sulfonamide;
2-(cyclopentyloxy)-N-(2-methoxy-7-methyl-6,7,8,9-tetrahydro-5H-pyrido[2,3-d]azepin-3-yl)pyrimidine-5-sulfonamide;
6-(1-fluorocyclohexyl)-N-(2-methoxy-7-methyl-6,7,8,9-tetrahydro-5H-pyrido[2,3-d]azepin-3-yl)pyridine-3-sulfonamide;
N-(7-ethyl-2-methoxy-6,7,8,9-tetrahydro-5H-pyrido[2,3-d]azepin-3-yl)-4-[trans-3-(2-fluoroethoxy)cyclobutyl]benzenesulfonamide;
4-(cis-3-ethoxycyclobutyl)-N-(2-methoxy-7-methyl-6,7,8,9-tetrahydro-5H-pyrido[2,3-d]azepin-3-yl)benzenesulfonamide;
4-(trans-3-ethoxycyclobutyl)-N-(2-methoxy-7-methyl-6,7,8,9-tetrahydro-5H-pyrido[2,3-d]azepin-3-yl)benzenesulfonamide;
N-(7-ethyl-2-methoxy-6,7,8,9-tetrahydro-5H-pyrido[2,3-d]azepin-3-yl)-6-(cis-1-hydroxy-3-methoxycyclobutyl)pyridine-3-sulfonamide;
6-cyclobutyl-5-fluoro-N-(2-methoxy-7-methyl-6,7,8,9-tetrahydro-5H-pyrido[2,3-d]azepin-3-yl)pyridine-3-sulfonamide;
6-(cis-1-fluoro-3-methylcyclobutyl)-N-(2-methoxy-7-methyl-6,7,8,9-tetrahydro-5H-pyrido[2,3-d]azepin-3-yl)pyridine-3-sulfonamide;
N-(2-methoxy-7-propyl-6,7,8,9-tetrahydro-5H-pyrido[2,3-d]azepin-3-yl)-4-methylbenzenesulfonamide;
4-chloro-N-(2-methoxy-7-methyl-6,7,8,9-tetrahydro-5H-pyrido[2,3-d]azepin-3-yl)benzenesulfonamide;
4-ethoxy-N-(2-methoxy-7-methyl-6,7,8,9-tetrahydro-5H-pyrido[2,3-d]azepin-3-yl)benzenesulfonamide;
4-ethoxy-N-[2-methoxy-7-(2-methoxyethyl)-6,7,8,9-tetrahydro-5H-pyrido[2,3-d]azepin-3-yl]benzenesulfonamide;
4-cyclopropyl-N-(7-ethyl-2-methoxy-6,7,8,9-tetrahydro-5H-pyrido[2,3-d]azepin-3-yl)benzenesulfonamide;
N-(2-methoxy-7-methyl-6,7,8,9-tetrahydro-5H-pyrido[2,3-d]azepin-3-yl)-3,4-dihydro-2H-chromene-6-sulfonamide;
4-(1-methoxyethyl)-N-(2-methoxy-7-methyl-6,7,8,9-tetrahydro-5H-pyrido[2,3-d]azepin-3-yl)benzenesulfonamide;
N-(2-methoxy-7-methyl-6,7,8,9-tetrahydro-5H-pyrido[2,3-d]azepin-3-yl)-4-(oxetan-3-yl)benzenesulfonamide;
N-(2-methoxy-7-methyl-6,7,8,9-tetrahydro-5H-pyrido[2,3-d]azepin-3-yl)-2,2-dimethyl-2,3-dihydro-1-benzofuran-5-sulfonamide;
N-(7-ethyl-2-methoxy-6,7,8,9-tetrahydro-5H-pyrido[2,3-d]azepin-3-yl)-3-fluoro-4-methylbenzenesulfonamide;
N-(2-methoxy-7-methyl-6,7,8,9-tetrahydro-5H-pyrido[2,3-d]azepin-3-yl)-4-(tetrahydrofuran-3-yl)benzenesulfonamide;
N-(2-methoxy-7-methyl-6,7,8,9-tetrahydro-5H-pyrido[2,3-d]azepin-3-yl)-4-[(3R)-tetrahydrofuran-3-yloxy]benzenesulfonamide;
4-(trans-4-methoxycyclohexyl)-N-(2-methoxy-7-methyl-6,7,8,9-tetrahydro-5H-pyrido[2,3-d]azepin-3-yl)benzenesulfonamide;
4-(cis-1-fluoro-4-methoxycyclohexyl)-N-(2-methoxy-7-methyl-6,7,8,9-tetrahydro-5H-pyrido[2,3-d]azepin-3-yl)benzenesulfonamide;
4-(4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide;
4-[(2R)-4,4-difluorotetrahydro-2H-pyran-2-yl]-N-(2-methoxy-7-methyl-6,7,8,9-tetrahydro-5H-pyrido[2,3-d]azepin-3-yl)benzenesulfonamide;
4-[(2S)-4,4-difluorotetrahydro-2H-pyran-2-yl]-N-(2-methoxy-7-methyl-6,7,8,9-tetrahydro-5H-pyrido[2,3-d]azepin-3-yl)benzenesulfonamide;
N-(7-ethyl-2-methoxy-6,7,8,9-tetrahydro-5H-pyrido[2,3-d]azepin-3-yl)-3-fluoro-4-[(2S)-tetrahydro-2H-pyran-2-yl]benzenesulfonamide;
N-[7-(3-fluoropropyl)-2-methoxy-6,7,8,9-tetrahydro-5H-pyrido[2,3-d]azepin-3-yl]-4-(propan-2-yl)benzenesulfonamide;
4-cyclohexyl-N-(2-methoxy-7-methyl-6,7,8,9-tetrahydro-5H-pyrido[2,3-d]azepin-3-yl)benzenesulfonamide;
4-(cyclopentyloxy)-N-(2-methoxy-7-methyl-6,7,8,9-tetrahydro-5H-pyrido[2,3-d]azepin-3-yl)benzenesulfonamide;
6-[cyclopentyl(difluoro)methyl]-N-(2-methoxy-7-methyl-6,7,8,9-tetrahydro-5H-pyrido[2,3-d]azepin-3-yl)pyridine-3-sulfonamide;
4-(trans-3-ethoxy-1-fluorocyclobutyl)-N-(7-ethyl-2-methoxy-6,7,8,9-tetrahydro-5H-pyrido[2,3-d]azepin-3-yl)benzenesulfonamide;
N-(2-methoxy-7-propyl-6,7,8,9-tetrahydro-5H-pyrido[2,3-d]azepin-3-yl)-4-(propan-2-yl)benzenesulfonamide;
4-ethoxy-N-(2-methoxy-7-propyl-6,7,8,9-tetrahydro-5H-pyrido[2,3-d]azepin-3-yl)benzenesulfonamide;
N-(7-ethyl-2-methoxy-6,7,8,9-tetrahydro-5H-pyrido[2,3-d]azepin-3-yl)-4-(propan-2-yl)benzenesulfonamide;
4-ethoxy-N-(7-ethyl-2-methoxy-6,7,8,9-tetrahydro-5H-pyrido[2,3-d]azepin-3-yl)benzenesulfonamide;
N-(7-ethyl-2-methoxy-6,7,8,9-tetrahydro-5H-pyrido[2,3-d]azepin-3-yl)-4-methylbenzenesulfonamide;
N-(2-methoxy-7-methyl-6,7,8,9-tetrahydro-5H-pyrido[2,3-d]azepin-3-yl)-4-(propan-2-yl)benzenesulfonamide;
N-(2-methoxy-7-methyl-6,7,8,9-tetrahydro-5H-pyrido[2,3-d]azepin-3-yl)-4-[1-(trifluoromethyl)cyclopropyl]benzenesulfonamide;
N-(7-ethyl-2-methoxy-5-methyl-6,7,8,9-tetrahydro-5H-pyrido[2,3-d]azepin-3-yl)-4-(propan-2-yl)benzenesulfonamide;
N-(7-ethyl-2-methoxy-6,7,8,9-tetrahydro-5H-pyrido[2,3-d]azepin-3-yl)-4-(tetrahydro-2H-pyran-4-yl)benzenesulfonamide;

N-(7-ethyl-2-methoxy-6,7,8,9-tetrahydro-5H-pyrido[2,3-d]
azepin-3-yl)-3,4-dihydro-2H-chromene-6-sulfonamide;
4-(difluoromethoxy)-N-(7-ethyl-2-methoxy-6,7,8,9-tetra-
hydro-5H-pyrido[2,3-d]azepin-3-yl)benzenesulfonamide;
N-(7-ethyl-2-methoxy-6,7,8,9-tetrahydro-5H-pyrido[2,3-d]
azepin-3-yl)-6-phenoxypyridine-3-sulfonamide;
N-(7-ethyl-2-methoxy-6,7,8,9-tetrahydro-5H-pyrido[2,3-d]
azepin-3-yl)-3,4-dimethylbenzenesulfonamide;
N-(7-ethyl-2-methoxy-6,7,8,9-tetrahydro-5H-pyrido[2,3-d]
azepin-3-yl)-4-propylbenzenesulfonamide;
4-(cyclopentyloxy)-N-(7-ethyl-2-methoxy-6,7,8,9-tetra-
hydro-5H-pyrido[2,3-d]azepin-3-yl)benzenesulfonamide;
N-(7-ethyl-2-methoxy-6,7,8,9-tetrahydro-5H-pyrido[2,3-d]
azepin-3-yl)-2,2-dimethyl-3,4-dihydro-2H-chromene-6-
sulfonamide;
N-(7-ethyl-2-methoxy-6,7,8,9-tetrahydro-5H-pyrido[2,3-d]
azepin-3-yl)-2,4-dimethylbenzenesulfonamide;
N-(7-ethyl-2-methoxy-6,7,8,9-tetrahydro-5H-pyrido[2,3-d]
azepin-3-yl)-2,4-dimethylbenzenesulfonamide;
N-[7-ethyl-2-(propan-2-yloxy)-6,7,8,9-tetrahydro-5H-
pyrido[2,3-d]azepin-3-yl]-3,4-dihydro-2H-chromene-6-
sulfonamide;
N-(7-ethyl-2-methoxy-6,7,8,9-tetrahydro-5H-pyrido[2,3-d]
azepin-3-yl)-2-methyl-2,3-dihydro-1-benzofuran-5-sul-
fonamide;
N-(7-ethyl-2-methoxy-6,7,8,9-tetrahydro-5H-pyrido[2,3-d]
azepin-3-yl)-4-(trans-3-methoxycyclobutyl)benzenesul-
fonamide;
N-(7-ethyl-2-methoxy-6,7,8,9-tetrahydro-5H-pyrido[2,3-d]
azepin-3-yl)-4-(4-methyltetrahydro-2H-pyran-4-yl)ben-
zenesulfonamide;
N-(7-ethyl-2-methoxy-6,7,8,9-tetrahydro-5H-pyrido[2,3-d]
azepin-3-yl)-4-(tetrahydro-2H-pyran-2-yl)benzenesulfo-
namide;
N-(7-ethyl-2-methoxy-6,7,8,9-tetrahydro-5H-pyrido[2,3-d]
azepin-3-yl)-4-(tetrahydrofuran-3-yl)benzenesulfona-
mide;
N-(7-ethyl-2-methoxy-6,7,8,9-tetrahydro-5H-pyrido[2,3-d]
azepin-3-yl)-4-(cis-3-methoxycyclobutyl)benzenesulfo-
namide;
N-(7-ethyl-2-methoxy-6,7,8,9-tetrahydro-5H-pyrido[2,3-d]
azepin-3-yl)-4-[(2R)-tetrahydro-2H-pyran-2-yl]benzene-
sulfonamide;
N-(7-ethyl-2-methoxy-6,7,8,9-tetrahydro-5H-pyrido[2,3-d]
azepin-3-yl)-4-[(2S)-tetrahydro-2H-pyran-2-yl]benzene-
sulfonamide;
N-(7-ethyl-2-methoxy-6,7,8,9-tetrahydro-5H-pyrido[2,3-d]
azepin-3-yl)-4-(4-fluorotetrahydro-2H-pyran-4-yl)benze-
nesulfonamide;
4-(trans-3-methoxycyclobutyl)-N-(2-methoxy-7-methyl-6,
7,8,9-tetrahydro-5H-pyrido[2,3-d]azepin-3-yl)benzene-
sulfonamide;
N-(2-methoxy-7-methyl-6,7,8,9-tetrahydro-5H-pyrido[2,3-
d]azepin-3-yl)-4-(tetrahydro-2H-pyran-3-yl)benzenesul-
fonamide;
N-(2-methoxy-7-methyl-6,7,8,9-tetrahydro-5H-pyrido[2,3-
d]azepin-3-yl)-4-(tetrahydro-2H-pyran-4-yloxy)benzene-
sulfonamide;
N-(2-methoxy-7-methyl-6,7,8,9-tetrahydro-5H-pyrido[2,3-
d]azepin-3-yl)-4-(4-methyltetrahydro-2H-pyran-4-yl)
benzenesulfonamide;
4-(4-fluorotetrahydro-2H-pyran-4-yl)-N-(2-methoxy-7-
methyl-6,7,8,9-tetrahydro-5H-pyrido[2,3-d]azepin-3-yl)
benzenesulfonamide;
4-(cis-3-methoxycyclobutyl)-N-(2-methoxy-7-methyl-6,7,
8,9-tetrahydro-5H-pyrido[2,3-d]azepin-3-yl)benzenesul-
fonamide;

N-(2-methoxy-7-methyl-6,7,8,9-tetrahydro-5H-pyrido[2,3-
d]azepin-3-yl)-4-(tetrahydrofuran-3-yloxy)benzenesulfo-
namide;
N-(2-methoxy-7-methyl-6,7,8,9-tetrahydro-5H-pyrido[2,3-
d]azepin-3-yl)-4-[(3R)-tetrahydro-2H-pyran-3-yl]benze-
nesulfonamide;
N-(2-methoxy-7-methyl-6,7,8,9-tetrahydro-5H-pyrido[2,3-
d]azepin-3-yl)-4-[(3S)-tetrahydro-2H-pyran-3-yl]benze-
nesulfonamide;
N-(2-methoxy-7-methyl-6,7,8,9-tetrahydro-5H-pyrido[2,3-
d]azepin-3-yl)-4-[(2S,4R)-2-methyltetrahydro-2H-pyran-
4-yl]benzenesulfonamide;
4-[(4R)-2,2-di methyltetrahydro-2H-pyran-4-yl]-N-(2-
methoxy-7-methyl-6,7,8,9-tetrahydro-5H-pyrido[2,3-d]
azepin-3-yl)benzenesulfonamide;
4-[(4S)-2,2-dimethyltetrahydro-2H-pyran-4-yl]-N-(2-
methoxy-7-methyl-6,7,8,9-tetrahydro-5H-pyrido[2,3-d]
azepin-3-yl)benzenesulfonamide;
N-(2-methoxy-7-methyl-6,7,8,9-tetrahydro-5H-pyrido[2,3-
d]azepin-3-yl)-4-[(2R,4S)-2-methyltetrahydro-2H-pyran-
4-yl]benzenesulfonamide;
4-[(1S)-1-methoxyethyl]-N-(2-methoxy-7-methyl-6,7,8,9-
tetrahydro-5H-pyrido[2,3-d]azepin-3-yl)benzenesulfona-
mide;
4-[(1R)-1-methoxyethyl]-N-(2-methoxy-7-methyl-6,7,8,9-
tetrahydro-5H-pyrido[2,3-d]azepin-3-yl)benzenesulfona-
mide;
N-(2-methoxy-7-methyl-6,7,8,9-tetrahydro-5H-pyrido[2,3-
d]azepin-3-yl)-4-[(3S)-tetrahydrofuran-3-yloxy]benzene-
sulfonamide;
4-(cis-4-methoxycyclohexyl)-N-(2-methoxy-7-methyl-6,7,
8,9-tetrahydro-5H-pyrido[2,3-d]azepin-3-yl)benzenesul-
fonamide;
4-(trans-1-fluoro-4-methoxycyclohexyl)-N-(2-methoxy-7-
methyl-6,7,8,9-tetrahydro-5H-pyrido[2,3-d]azepin-3-yl)
benzenesulfonamide;
N-(7-ethyl-2-methoxy-6,7,8,9-tetrahydro-5H-pyrido[2,3-d]
azepin-3-yl)-4-(1-fluoro-4-methoxycyclohexyl)benzene-
sulfonamide;
4-(1-methoxycyclopentyl)-N-(2-methoxy-7-methyl-6,7,8,9-
tetrahydro-5H-pyrido[2,3-d]azepin-3-yl)benzenesulfona-
mide;
N-(7-ethyl-2-methoxy-6,7,8,9-tetrahydro-5H-pyrido[2,3-d]
azepin-3-yl)-4-(trans-1-fluoro-3-methoxycyclobutyl)ben-
zenesulfonamide;
N-(2-methoxy-7-methyl-6,7,8,9-tetrahydro-5H-pyrido[2,3-
d]azepin-3-yl)-6-(tetrahydrofuran-3-yloxy)pyridine-3-
sulfonamide;
N-(2-methoxy-7-methyl-6,7,8,9-tetrahydro-5H-pyrido[2,3-
d]azepin-3-yl)-4-[(2S)-tetrahydrofuran-2-yl]benzenesul-
fonamide;
N-(2-methoxy-7-methyl-6,7,8,9-tetrahydro-5H-pyrido[2,3-
d]azepin-3-yl)-4-[(2R)-tetrahydrofuran-2-yl]benzenesul-
fonamide;
6-(1-methoxycyclopentyl)-N-(2-methoxy-7-methyl-6,7,8,9-
tetrahydro-5H-pyrido[2,3-d]azepin-3-yl)pyridine-3-sul-
fonamide;
N-(7-ethyl-2-methoxy-6,7,8,9-tetrahydro-5H-pyrido[2,3-d]
azepin-3-yl)-6-(1-fluorocyclopentyl)pyridine-3-sulfona-
mide;
6-cyclopentyl-N-(7-ethyl-2-methoxy-6,7,8,9-tetrahydro-
5H-pyrido[2,3-d]azepin-3-yl)pyridine-3-sulfonamide;
6-tert-butoxy-N-(2-methoxy-7-methyl-6,7,8,9-tetrahydro-
5H-pyrido[2,3-d]azepin-3-yl)pyridine-3-sulfonamide;
N-(2-methoxy-7-methyl-6,7,8,9-tetrahydro-5H-pyrido[2,3-
d]azepin-3-yl)-3-methyl-4-[(2R)-tetrahydro-2H-pyran-2-
yl]benzenesulfonamide;

N-(2-methoxy-7-methyl-6,7,8,9-tetrahydro-5H-pyrido[2,3-d]azepin-3-yl)-3-methyl-4-[(2S)-tetrahydro-2H-pyran-2-yl]benzenesulfonamide;
4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide;
N-(7-ethyl-2-methoxy-6,7,8,9-tetrahydro-5H-pyrido[2,3-d]azepin-3-yl)-3-methyl-4-[(2R)-tetrahydro-2H-pyran-2-yl]benzenesulfonamide;
4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-1;
4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-2;
3-fluoro-N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide;
3-fluoro-N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide;
N-(7-ethyl-2-methoxy-6,7,8,9-tetrahydro-5H-pyrido[2,3-d]azepin-3-yl)-6-(1-fluorocyclohexyl)pyridine-3-sulfonamide;
6-cyclobutyl-N-(2-methoxy-7-methyl-6,7,8,9-tetrahydro-5H-pyrido[2,3-d]azepin-3-yl)pyridine-3-sulfonamide;
6-cyclohexyl-N-(7-ethyl-2-methoxy-6,7,8,9-tetrahydro-5H-pyrido[2,3-d]azepin-3-yl)pyridine-3-sulfonamide;
N-[7-(3-fluoropropyl)-2-methoxy-6,7,8,9-tetrahydro-5H-pyrido[2,3-d]azepin-3-yl]-4-methylbenzenesulfonamide;
2-(cyclobutyloxy)-N-(2-methoxy-7-methyl-6,7,8,9-tetrahydro-5H-pyrido[2,3-d]azepin-3-yl)pyrimidine-5-sulfonamide;
2-tert-butoxy-N-(2-methoxy-7-methyl-6,7,8,9-tetrahydro-5H-pyrido[2,3-d]azepin-3-yl)pyrimidine-5-sulfonamide;
N-(2-methoxy-7-methyl-6,7,8,9-tetrahydro-5H-pyrido[2,3-d]azepin-3-yl)-4-propylbenzenesulfonamide;
N-(7-ethyl-2-methoxy-6,7,8,9-tetrahydro-5H-pyrido[2,3-d]azepin-3-yl)-4-[cis-3-(2-fluoroethoxy)cyclobutyl]benzenesulfonamide;
4-(cis-3-ethoxycyclobutyl)-N-(7-ethyl-2-methoxy-6,7,8,9-tetrahydro-5H-pyrido[2,3-d]azepin-3-yl)benzenesulfonamide;
4-(trans-3-ethoxycycyclobutyl)-N-(7-ethyl-2-methoxy-6,7,8,9-tetrahydro-5H-pyrido[2,3-d]azepin-3-yl)benzenesulfonamide;
6-(cyclopentyloxy)-N-[7-(3-fluoropropyl)-2-methoxy-6,7,8,9-tetrahydro-5H-pyrido[2,3-d]azepin-3-yl]pyridine-3-sulfonamide;
2-cyclopentyl-N-(2-methoxy-7-methyl-6,7,8,9-tetrahydro-5H-pyrido[2,3-d]azepin-3-yl)pyrimidine-5-sulfonamide;
6-(cyclopentyloxy)-N-(2-methoxy-7-methyl-6,7,8,9-tetrahydro-5H-pyrido[2,3-d]azepin-3-yl)-5-methylpyridine-3-sulfonamide;
6-(cyclopentyloxy)-N-(7-ethyl-2-methoxy-6,7,8,9-tetrahydro-5H-pyrido[2,3-d]azepin-3-yl)-5-methylpyridine-3-sulfonamide;
6-(cyclobutyloxy)-N-(2-methoxy-7-methyl-6,7,8,9-tetrahydro-5H-pyrido[2,3-d]azepin-3-yl)-5-methylpyridine-3-sulfonamide;
2-cyclohexyl-N-(2-methoxy-7-methyl-6,7,8,9-tetrahydro-5H-pyrido[2,3-d]azepin-3-yl)pyrimidine-5-sulfonamide;
6-(cyclopentyloxy)-N-(2-methoxy-7-methyl-6,7,8,9-tetrahydro-5H-pyrido[2,3-d]azepin-3-yl)-2-methylpyridine-3-sulfonamide;
N-(2-methoxy-7-methyl-6,7,8,9-tetrahydro-5H-pyrido[2,3-d]azepin-3-yl)-6-[(2R)-tetrahydro-2H-pyran-2-yl]pyridine-3-sulfonamide;
6-(cyclopentylmethyl)-N-(2-methoxy-7-methyl-6,7,8,9-tetrahydro-5H-pyrido[2,3-d]azepin-3-yl)pyridine-3-sulfonamide;
4-(trans-3-ethoxy-1-fluorocyclobutyl)-N-(2-methoxy-7-methyl-6,7,8,9-tetrahydro-5H-pyrido[2,3-d]azepin-3-yl)benzenesulfonamide;
4-[trans-1-fluoro-3-(2-fluoroethoxy)cyclobutyl]-N-(2-methoxy-7-methyl-6,7,8,9-tetrahydro-5H-pyrido[2,3-d]azepin-3-yl)benzenesulfonamide;
6-(trans-3-ethoxycyclobutyl)-N-(2-methoxy-7-methyl-6,7,8,9-tetrahydro-5H-pyrido[2,3-d]azepin-3-yl)pyridine-3-sulfonamide;
6-(cis-3-ethoxycyclobutyl)-N-(2-methoxy-7-methyl-6,7,8,9-tetrahydro-5H-pyrido[2,3-d]azepin-3-yl)pyridine-3-sulfonamide;
6-(trans-1-fluoro-3-methylcyclobutyl)-N-(2-methoxy-7-methyl-6,7,8,9-tetrahydro-5H-pyrido[2,3-d]azepin-3-yl)pyridine-3-sulfonamide;
6-(cyclopentyloxy)-5-fluoro-N-(2-methoxy-7-methyl-6,7,8,9-tetrahydro-5H-pyrido[2,3-d]azepin-3-yl)pyridine-3-sulfonamide;
4-Ethoxy-N-(7-ethyl-2-methyl-6,7,8,9-tetrahydro-5H-pyrido[2,3-d]azepin-3-yl)benzenesulfonamide;
4-chloro-N-(7-ethyl-2-methyl-6,7,8,9-tetrahydro-5H-pyrido[2,3-d]azepin-3-yl)benzenesulfonamide;
4-methyl-N-[7-methyl-2-(trifluoromethyl)-6,7,8,9-tetrahydro-5H-pyrido[2,3-d]azepin-3-yl]benzenesulfonamide; and
N-(2-ethyl-7-methyl-6,7,8,9-tetrahydro-5H-pyrido[2,3-d]azepin-3-yl)-4-[(2R)-tetrahydro-2H-pyran-2-yl]benzenesulfonamide;
or a pharmaceutically acceptable salt thereof.

An eighteenth embodiment of a first aspect of the present invention is the compound 6-(cyclopentyloxy)-N-(7-ethyl-2-methoxy-6,7,8,9-tetrahydro-5H-pyrido[2,3-d]azepin-3-yl)pyridine-3-sulfonamide or a pharmaceutically acceptable salt thereof.

A nineteenth embodiment of a first aspect of the present invention is the compound 4-[trans-3-(2-fluoroethoxy)cyclobutyl]-N-(2-methoxy-7-methyl-6,7,8,9-tetrahydro-5H-pyrido[2,3-d]azepin-3-yl)benzenesulfonamide or a pharmaceutically acceptable salt thereof.

A twentieth embodiment of a first aspect of the present invention is the compound N-(2-methoxy-7-methyl-6,7,8,9-tetrahydro-5H-pyrid[23-d]azepin-3tetrahydro-2H-pyran-4-yl)benzenesulfonamide or a pharmaceutically acceptable salt thereof.

A twenty-first embodiment of a first aspect of the present invention is the compound N-(2-methoxy-7-methyl-6,7,8,9-tetrahydro-5H-pyrido[2,3-d]azepin-3-yl)-4-methylbenzenesulfonamide or a pharmaceutically acceptable salt thereof.

A twenty-second embodiment of a first aspect of the present invention is the compound N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide or a pharmaceutically acceptable salt thereof.

A twenty-third embodiment of a first aspect of the present invention is the compound 4-(trans-1-fluoro-3-methoxycyclobutyl)-N-(2-methoxy-7-methyl-6,7,8,9-tetrahydro-5H-pyrido[2,3-d]azepin-3-yl)benzenesulfonamide or a pharmaceutically acceptable salt thereof.

A twenty-fourth embodiment of a first aspect of the present invention is the compound 6-(1-fluorocyclopentyl)-

N-(2-methoxy-7-methyl-6,7,8,9-tetrahydro-5H-pyrido [2,3-d]azepin-3-yl)pyridine-3-sulfonamide or a pharmaceutically acceptable salt thereof.

A first embodiment of a second aspect of the present invention is a pharmaceutical composition comprising a therapeutically effective amount of a compound of any one of the first through twenty-fourth embodiments of the first aspect or a pharmaceutically acceptable salt thereof and a pharmaceutically acceptable vehicle, diluent or carrier.

A first embodiment of a third aspect of the present invention is a method of treating a disease or disorder selected from the group consisting of Parkinson's disease, schizophrenia, dementia, psychosis, depression, mania, anxiety, dyskinesias, substance abuse, substance addiction, sexual disorders, restless leg syndrome, cardiovascular disease, metabolic disorder, hormonal disorder, renal insufficiency and diabetes, the method comprising administering a therapeutically effective amount of a compound of any one of the first through twenty-fourth embodiments of the first aspect or a pharmaceutically acceptable salt thereof to a patient in need of treatment thereof.

A second embodiment of a third aspect of the present invention is the method of the first embodiment of the third aspect wherein the disease or disorder is substance addiction.

A third embodiment of a third aspect of the present invention is the method of the second embodiment of the third aspect wherein the substance addiction is a relapse substance addiction.

A fourth embodiment of a third aspect of the present invention is the method of the second embodiment of the third aspect wherein the substance addiction is an alcohol, cocaine, amphetamine, methamphetamine, opioid, marijuana or nicotine addiction.

A first embodiment of a fourth aspect of the present invention is the use of a compound, wherein the compound is as defined in any one of the first through twenty-fourth embodiments of the first aspect, or a pharmaceutically acceptable salt of said compound, for the preparation of a medicament useful for treating a disease or disorder selected from the group consisting of Parkinson's disease, schizophrenia, dementia, psychosis, depression, mania, anxiety, dyskinesias, substance abuse, substance addiction, sexual disorders, restless leg syndrome, cardiovascular disease, metabolic disorder, hormonal disorder, renal insufficiency and diabetes.

A second embodiment of a fourth aspect of the present invention is the use of the first embodiment of the fourth aspect wherein the disease or disorder is substance addiction.

A third embodiment of a fourth aspect of the present invention is the use of the second embodiment of the fourth aspect wherein the substance addiction is a relapse substance addiction.

A fourth embodiment of a fourth aspect of the present invention is the use of the second embodiment of the fourth aspect wherein the substance addiction is an alcohol, cocaine, amphetamine, methamphetamine, opioid, marijuana or nicotine addiction.

A first embodiment of a fifth aspect of the present invention is the use of a compound, wherein the compound is as defined in any one of the first through twenty-fourth embodiments of the first aspect, or a pharmaceutically acceptable salt of said compound, for treating a disease or disorder selected from the group consisting of Parkinson's disease, schizophrenia, dementia, psychosis, depression, mania, anxiety, dyskinesias, substance abuse, substance addiction, sexual disorders, restless leg syndrome, cardiovascular disease, metabolic disorder, hormonal disorder, renal insufficiency and diabetes.

A second embodiment of a fifth aspect of the present invention is the use the first embodiment of the fifth aspect wherein the disease or disorder is substance addiction.

A third embodiment of a fifth aspect of the present invention is the use of the second embodiment of the fifth aspect wherein the substance addiction is a relapse substance addiction.

A fourth embodiment of a fifth aspect of the present invention is the use of the second embodiment of the fifth aspect wherein the substance addiction is an alcohol, cocaine, amphetamine, methamphetamine, opioid, marijuana or nicotine addiction.

The present invention also provides compositions (e.g., pharmaceutical compositions) comprising a novel compound of Formula I (including a pharmaceutically acceptable salt thereof) in the second aspect of the invention. Accordingly, in one embodiment, the invention provides a pharmaceutical composition comprising (a therapeutically effective amount of) a novel compound of Formula I (or a pharmaceutically acceptable salt thereof) and optionally comprising a pharmaceutically acceptable carrier. In one further embodiment, the invention provides a pharmaceutical composition comprising (a therapeutically effective amount of) a compound of Formula I (or a pharmaceutically acceptable salt thereof), optionally comprising a pharmaceutically acceptable carrier and, optionally, at least one additional medicinal or pharmaceutical agent (such as a medication used in the treatment of addiction, a medication used in the treatment of an impulse control disorder or an antipsychotic agent or anti-schizophrenia agent as described herein). In one embodiment, the additional medicinal or pharmaceutical agent is a medication used in the treatment of addiction. In another embodiment the additional medicinal or pharmaceutical agent is a medication used in the treatment of an impulse control disorder. In yet another embodiment the additional medicinal or pharmaceutical agent is an anti-schizophrenia agent as described herein.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream, or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or a pharmaceutically acceptable salt thereof) and a pharmaceutically acceptable carrier.

Compounds of Formula I (including pharmaceutically acceptable salts thereof) are D3R modulators. In some embodiments, a compound of Formula I is a D3R antagonist [i.e., binding (having affinity for) and deactivating D3R receptors]. As used herein, when referencing to a compound, the term "D3R modulator" or "D3R antagonist" refers to a compound that is a D3 receptor modulator or a D3 receptor antagonist, respectively (i.e., not necessarily entirely selective between/among subtypes of D2-like receptors; for example, the compound may be selective for the D3 receptor but may not be entirely so, particularly with respect to the closely related D2 receptor).

Administration of the compounds of Formula I may be affected by any method that enables delivery of the compounds to the site of action. These methods include, for example, enteral routes (e.g., oral routes, buccal routes, sublabial routes, sublingual routes), intranasal routes, inhaled routes, intraduodenal routes, parenteral injection (including intravenous, subcutaneous, intramuscular, intravascular or infusion), intrathecal routes, epidural routes, intracerebral routes, intracerebroventricular routes, topical routes, and rectal administration.

In one embodiment of the present invention, the compounds of Formula I may be administered by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors, such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual's need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose escalation as determined by the skilled artisan. Determining appropriate dosages and regimens for administration of the chemotherapeutic agent is well known in the relevant art and would be understood to be encompassed by the skilled artisan once provided the teachings disclosed herein.

The amount of the compound of Formula I or a pharmaceutically acceptable salt thereof administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with at least one additional pharmaceutical or medicinal agent (e.g., a medication used in the treatment of drug addiction or an anti-schizophrenia agent), either sequentially or simultaneously.

The present invention includes the use of a combination of a compound of Formula I (or a pharmaceutically acceptable salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula I (including pharmaceutically acceptable salts thereof), depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-ß (or fragments thereof), such as $Aß_{1-15}$ conjugated to pan HLA DR-binding epitope (PADRE) and ACC-001 (Elan/Wyeth);

(iii) antibodies to amyloid-ß (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);
(vi) beta-adrenergic receptor blocking agents (beta blockers) such as carteolol;
(vii) anticholinergics such as amitriptyline (ELAVIL, ENDEP);
(viii) anticonvulsants such as carbamazepine (TEGRETOL, CARBATROL);
(ix) antipsychotics, such as lurasidone (also known as SM-13496; Dainippon Sumitomo);
(x) calcium channel blockers such as nilvadipine (ESCOR, NIVADIL);
(xi) catechol O-methyltransferase (COMT) inhibitors such as tolcapone (TASMAR);
(xii) central nervous system stimulants such as caffeine;
(xiii) corticosteroids such as prednisone (STERAPRED, DELTASONE);
(xiv) dopamine receptor agonists such as apomorphine (APOKYN);
(xv) dopamine receptor antagonists such as tetrabenazine (NITOMAN, XENAZINE, dopamine D2 antagonists such as Quetiapine); dopamine D3 antagonists or partial agonists such as BP 897, PG 619, YQA14, RGH 188 (cariprazine), [$^3$H]LS-3-134, SB277011A, GSK598809, Buspirone (Buspar®), NGB 2904, CJB 090, PG01037, PG 622, R-PG 648, BAK 2-66, S33138, BP1.4979, SR 21502;
(xvi) dopamine reuptake inhibitors such as nomifensine maleate (MERITAL);
(xvii) gamma-aminobutyric acid (GABA) receptor agonists such as baclofen (LIORESAL, KEMSTRO);
(xviii) histamine 3 ($H_3$) antagonists such as ciproxifan;
(xix) immunomodulators such as glatiramer acetate (also known as copolymer-1; COPAXONE);
(xx) immunosuppressants such as methotrexate (TREXALL, RHEUMATREX);
(xxi) interferons, including interferon beta-la (AVONEX, REBIF) and interferon beta-lb (BETASERON, BETAFERON);
(xxii) levodopa (or its methyl or ethyl ester), alone or in combination with a DOPA decarboxylase inhibitor (e.g., carbidopa (SINEMET, CARBILEV, PARCOPA));
(xxiii) N-methyl-D-aspartate (NMDA) receptor antagonists such as memantine (NAMENDA, AXURA, EBIXA);
(xxiv) monoamine oxidase (MAO) inhibitors such as selegiline (EMSAM);
(xxv) muscarinic receptor (particularly M1 subtype) agonists such as bethanechol chloride (DUVOID, URECHOLINE);
(xxvi) neuroprotective drugs such as 2,3,4,9-tetrahydro-1H-carbazol-3-one oxime;
(xxvii) nicotinic receptor agonists such as epibatidine;
(xxviii) norepinephrine (noradrenaline) reuptake inhibitors such as atomoxetine (STRATTERA);
(xxix) phosphodiesterase (PDE) inhibitors, for example, PDE9 inhibitors such as BAY 73-6691 (Bayer AG) and PDE 10 (e.g., PDE10A) inhibitors such as papaverine;
(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));
(xxxi) quinolines such as quinine (including its hydrochloride, dihydrochloride, sulfate, bisulfate and gluconate salts);
(xxxii) β-secretase inhibitors such as WY-25105;
(xxxiii) γ-secretase inhibitors such as LY-411575 (Lilly);
(xxxiv) serotonin (5-hydroxytryptamine) 1A (5-$HT_{1A}$) receptor antagonists such as spiperone;
(xxxv) serotonin (5-hydroxytryptamine) 4 (5-$HT_4$) receptor agonists such as PRX-03140 (Epix);
(xxxvi) serotonin (5-hydroxytryptamine) 6 (5-$HT_6$) receptor antagonists such as mianserin (TORVOL, BOLVIDON, NORVAL);
(xxxvii) serotonin (5-HT) reuptake inhibitors such as alaproclate, citalopram (CELEXA, CIPRAMIL);
(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;
and the like.
(xxxix) medications used in the treatment of various drug addictions such as methadone, buprenorphine (Suboxone® and Subutex®), naloxone (Narcan®, Evzio®), naltrexone (ReVia®), Levo-alpha Acetyl Methadol (LAAM), bupropion (Wellbutrin®, Buproban®, Aplenzin®, Budeprion®, Zyban®), varenicline (Chantix®), nicotine patches or gums, acamprosate (Campral®), disulfiram (Antabuse®) and topiramate (Topamax®).

The compound of Formula I (including a pharmaceutically acceptable salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a D3-mediated disorder (e.g., a neurological and psychiatric disorder associated with D3), comprising administering to a mammal an effective amount of a compound of Formula I (including a pharmaceutically acceptable salt of the compound) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include medications used in the treatment of addiction, medications used to treat impulse control disorders, antidepressants, antipsychotics (such as anti-schizophrenia), anti-pain, anti-Parkinson's disease agents, anti-LID (levodopa-induced dyskinesia), anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical antidepressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT$_{1A}$) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT$_{1A}$ receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine A$_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine, milnacipran, guanfacine, bupropion, and atomoxetine.

As noted above, the compounds of Formula I (including pharmaceutically acceptable salts thereof) may be used in combination with one or more additional agents which are described herein. When a combination therapy is used, the one or more additional agents may be administered sequentially or simultaneously with the compound of the invention. In one embodiment, the additional agent is administered to a mammal (e.g., a human) prior to administration of the compound of the invention. In another embodiment, the additional agent is administered to the mammal after administration of the compound of the invention. In another embodiment, the additional agent is administered to the mammal (e.g., a human) simultaneously with the administration of the compound of the invention or a pharmaceutically acceptable salt thereof.

The invention also provides a pharmaceutical composition for the treatment of addiction in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) medications used in the treatment of addiction such as methadone, buprenorphine, naloxone, naltrexone, levo-alpha-acetylmethadol (LAAM), bupropion, varenicline, nicotine patches or gums, acamprosate, disulfiram and topiramate, wherein the amounts of the active agent and the combination when taken as a whole are therapeutically effective for treating the addiction. The selection of the additional agents used in the pharmaceutical composition may be targeted to the particular addiction(s) being treated.

The invention also provides a pharmaceutical composition for the treatment of impulse control disorders (including disorders such as intermittent explosive disorder, kleptomania, pathological gambling, pyromania, trichotillomania and dermatillomania) in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) agents used to treat impulse control disorders such as clomipramine, selective serotonin reuptake inhibitors (SSRIs), pimozide, anticonvulsants such as topiramate, anti-psychotics and anti-anxiolytics such as benzodiazepines, wherein the amounts of the active agent and the combination when taken as a whole are therapeutically effective for treating the particular impulse control disorder(s).

It will be understood that the compounds of Formula I depicted above are not limited to a particular stereoisomer (e.g., enantiomer or atropisomer) shown, but also include all stereoisomers and mixtures thereof.

The compounds of the invention, or their pharmaceutically acceptable salts, may be prepared by a variety of methods that are analogously known in the art. The reaction Schemes described below, together with synthetic methods known in the art of organic chemistry, or modifications and derivatizations that are familiar to those of ordinary skill in the art, illustrate methods for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XIII (published by Wiley-Interscience)). Preferred methods include, but are not limited to, those described below.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Via consideration of the particular reaction step, suitable solvents for a particular reaction step can be selected by the skilled artisan.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999; and T. W. Greene and P. G. M. Wuts, Protective Groups in Organic Chemistry, John Wiley & Sons, 2007, which are hereby incorporated by reference.

Compounds of the present invention or the pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Schemes 1 through 5 will be generated as a mixture of diastereomers and/or enantiomers; these may be separated at various stages of the synthetic Scheme using conventional techniques or a combination of such techniques, such as, but not limited to, crystallization, normal-phase chromatography, reversed-phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Schemes are representative of methods useful in synthesizing the compounds of the present invention. It is to be understood that they are not to constrain the scope of the invention in any way.

It is understood to those skilled in the art that some protecting groups (—Z) cannot withstand some of the reaction conditions described in the reaction schemes below. Therefore, some protecting group manipulations may be required in order to adequately complete the syntheses. Due to the multitude of protection-deprotection possibilities, these manipulations will not be expressly described.

Scheme 1 below illustrates two methods to access intermediate nitro-pyridylazepine F from commercially available starting materials A or B. Dibromopyridone A (wherein $R^3$ is OH) is commercially available. Treatment of A with the appropriate alkylating reagent, such as an alkyl halide in the presence of a base and potentially an additive such as silver carbonate (Synthesis 2009, 16, 2725-2728; Journal of Medicinal Chemistry 2003, 46(6), 921-924), can provide a desired dibromoalkyloxypyridine B. Alternatively, some dibromopyridines are commercially available and can be used directly as the starting point to make azepine F. Dibromopyridine B can then undergo a palladium-mediated coupling with the tetrahydropyran-protected trifluoroborate salt C as described in JOC 2012, 77(22), 10399-10408. Removal of the tetrahydropyran protecting group under acidic aqueous conditions provides intermediate D. Intermediate D is treated with a sulfonyl chloride such as methanesulfonyl chloride or p-toluenesulfonyl chloride and a base to activate the hydroxyl groups for eventual displacement with the appropriate nucleophiles. The disulfonate is treated with an amine source under mildly basic conditions to displace the sulfonates and provide the cyclized azepine ring, which provides compounds of general formula E. Examples of similar transformations from diols to azepines have been described in references such as WO 2008051547, CN 101712675, WO 2008038051, WO 2007028132, and WO 2005058328. The amine source (as shown, $NH_2Z$) can range from simple ammonia, an alkylamine with the desired $R^1$ moiety already in place (i.e., Z is the $R^1$ alkyl group), to variously protected amines depending on the types of chemistry that will subsequently be performed. Compounds of formula E can then be nitrated under standard nitration conditions ($HNO_3$, $H_2SO_4$, neat or with solvent, generally starting at <room temperature) to provide the nitro intermediate of formula F.

Alternately, compounds of formula F can be synthesized by starting with the azepinone of formula G, whose synthesis has previously been described in the literature (JACS 2012, 134(42), 17440-17443). The compound of formula G can be treated with nitroacetamide under basic conditions from room temperature to 150° C. to give the pyridinoneazepine of formula H. When a compound where $R^3$ is an appropriate alkoxy group (such as $C_1$-$C_6$alkoxy) is desired, the pyridinone H can be alkylated by treatment with an alkyl halide and base to provide compounds of formula F. Compound H can also be treated with phosphorus oxychloride, phosphorus oxybromide, or phosphorus pentoxide and tetrabutylammonium bromide, neat or in an appropriate solvent at temperatures from 20° C. to ~100° C., to provide compounds J, where X is Cl or Br. Intermediate J can be treated with the appropriate alcohols under general nucleophilic aromatic substitution reaction ($S_NAr$ examples: Australian Journal of Chemistry 2003, 56(9), 913-916; European Journal of Organic Chemistry 2004, 16, 3477-3483; Journal of Organic Chemistry 2003, 68(18), 7119-7122) conditions to give compound F, when $R^3$ is an appropriate alkoxy group. Intermediate J can also be used in a Suzuki-Miyaura type reaction (Chemical Society Reviews 2014, 43, 412-443; Accounts of Chemical Research 2013, 46, 2626-2634) where a palladium source, an appropriate phosphine ligand, base, and the appropriate boronate [$B(OR)_2R^3$] can be used to install an appropriate $R^3$ alkyl group.

Scheme 1

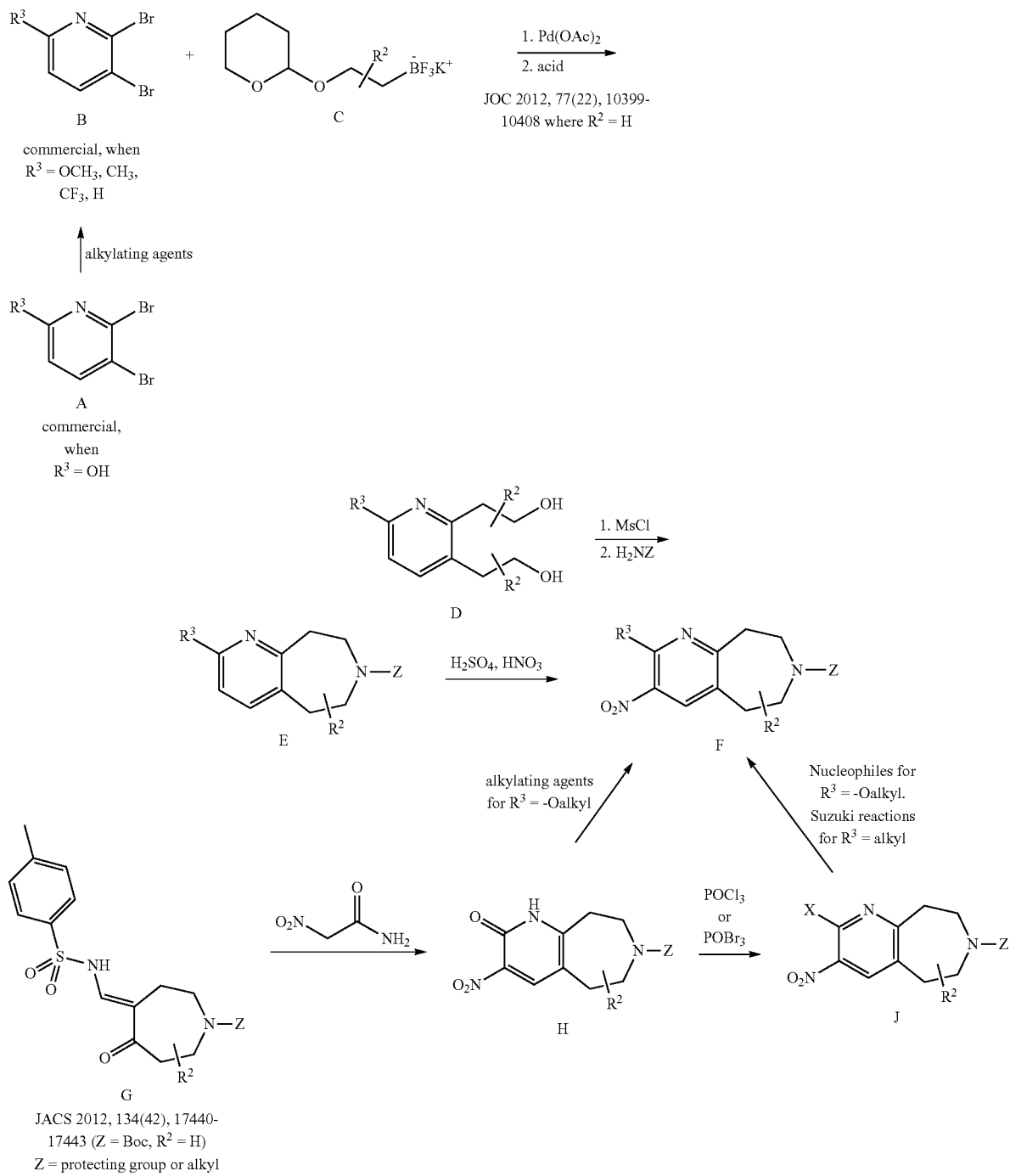

Scheme 2 describes synthetic manipulations to convert intermediate F into intermediate T. When substituent $R^3$ is a methoxy and not the desired final substituent, the methyl portion of the methoxy can be removed using many known methodologies, such as by treatment with hydrobromic acid and acetic acid at elevated temperatures (WO 2013025733) or by treatment with p-toluenesulfonic acid and lithium chloride at elevated temperatures (Synthetic Communications 2011, 41(12), 1852-1857) to give the nitropyridinoneazepine intermediate of formula H. The compound H can then be converted to the desired intermediate F by treatment of H with the appropriate alkylating reagent, such as an alkyl halide in the presence of a base and potentially an additive such as silver carbonate (Synthesis 2009, 16, 2725-2728; Journal of Medicinal Chemistry 2003, 46(6), 921-924). The nitro group of intermediate F can then be reduced to the desired amine of formula Y by treatment with palladium on carbon or Raney nickel in the presence of hydrogen gas (Tetrahedron 1997, 53(37), 12505-12524; Journal of Medicinal Chemistry 2005, 48(6), 1948-1964) or by treatment with a metal such as iron, tin or zinc usually in the presence of an acid source (Organic Letters 2009, 11(22) 5142-5145; ACS Medicinal Chemistry Letters 2010, 1(1), 39-43; WO 2008038051). If intermediate Y contains a Z wherein the group Z is a protecting group, the protecting group can be removed and the desired R¹ substituent can then be incorporated through the introduction of the desired alkyl halide (WO 2014188173, Journal of Medicinal Chemistry 2014, 57(24), 10424-10442; ACS Medicinal Chemistry Letters 2014, 5(4), 304-308) or by condensation with an appropriate aldehyde followed by treatment with an appropriate reducing agent (Journal of Medicinal Chemistry 2015, 58(20), 8236-8256; European Journal of Medicinal Chemistry 2014, 85, 16-26; Chemical Biology & Drug Design 2014, 83(2), 149-153) to provide intermediate T.

sion of a sulfonic acid to the corresponding sulfonyl chloride of formula J upon treatment with a chlorinating reagent such as phosphorus oxychloride, phosphorus pentachloride, or thionyl chloride (See e.g., WO 2015007668, WO 2014082379, WO 2014106800). The intermediate of formula P can be subjected to treatment with the appropriate sulfonamide of formula Q in the presence of a palladium catalyst, an appropriate ligand, and a base in a Hartwig-Buchwald-type coupling reaction to install the desired sulfonamide onto the pyridylazepine core (See e.g., Organic Letters 2011, 13(10), 2564-2567; WO 2010106436; Tetrahedron Letters 2008, 49(31), 4585-4587). A similar coupling between sulfonamides and aryl bromides has been described using copper, an appropriate ligand, and base usually at elevated temperatures (Tetrahedron 2005, 46(43), 7295-

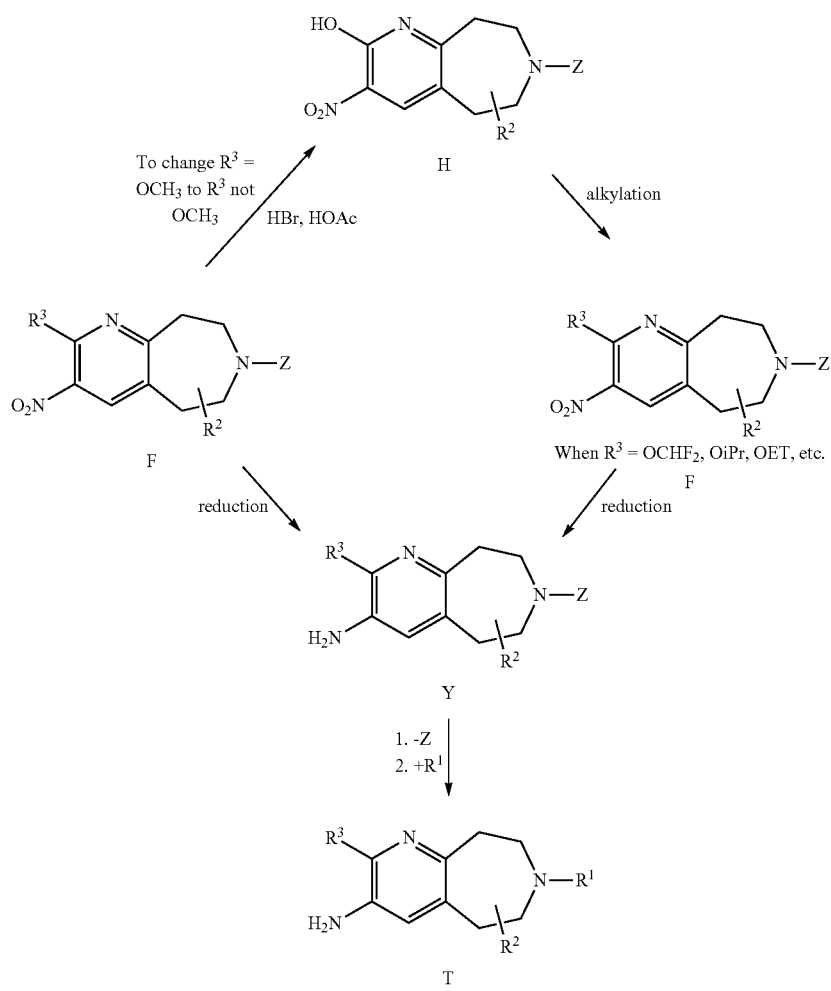

Scheme 2

7298; Journal of Chemical Sciences 2010, 122(2), 143-148; Tetrahedron Letters 2003, 44(16), 3385-3386). Protecting group removal, if necessary, provides compounds of general formula S. The compound of formula S can then be converted to a compound of Formula I' having the desired R¹ substituent by the treatment of amine S with the desired alkyl halide (WO 2014188173, Journal of Medicinal Chemistry 2014, 57(24), 10424-10442; ACS Medicinal Chemistry Letters 2014, 5(4), 304-308) or condensation with the appropriate aldehyde followed by treatment with a reducing agent Scheme 3 describes a synthetic route to compounds of Formula I' which is a compound of Formula I wherein $R^3$ is an appropriate $C_1$-$C_6$alkoxy group represented in this Scheme as $OR^{3'}$. The synthesis of compounds of formula P has previously been described (WO 2007/140213). Sulfonamides of formula Q are very common reactants and a large variety of these are available commercially. If the desired compound of formula Q is not commercially available, it can be synthesized from a sulfonyl chloride of formula J, which comes either from a commercial source or from the conver- (Journal of Medicinal Chemistry 2015, 58(20), 8236-8256; European Journal of Medicinal Chemistry 2014, 85, 16-26; Chemical Biology & Drug Design 2014, 83(2), 149-153).

Scheme 3

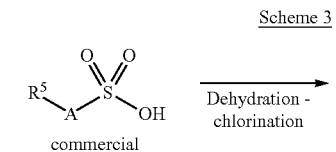

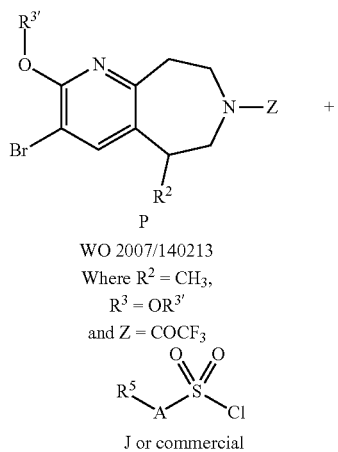

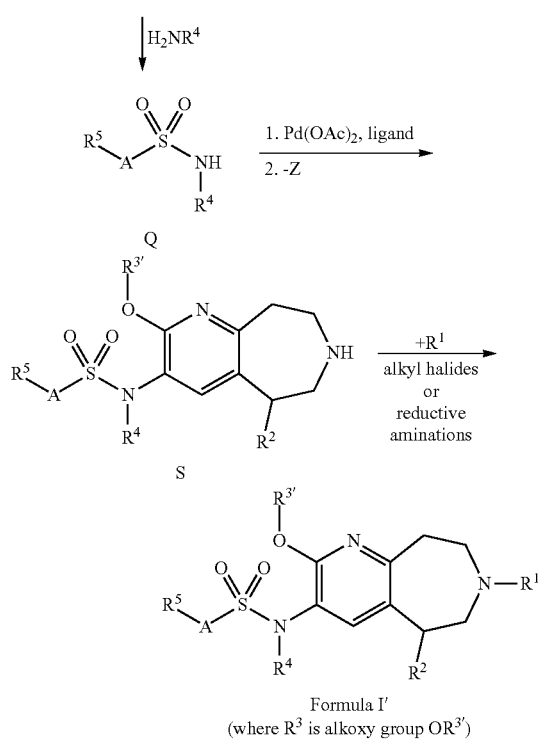

Scheme 4 describes an alternative synthetic path to sulfonyl chlorides that are not commercially available, which can be used to provide certain compounds of Formula I. An appropriately substituted aryl halide, such as a chloride, bromide, or iodide, can be coupled with a thiol (such as benzyl thiol, as shown, or p-methoxybenzyl thiol) using a catalyst (such as various palladium or copper catalysts), an appropriate ligand, a base, and a solvent, usually at elevated temperature, (Journal of Organic Chemistry 2011, 76(11), 4371-4378; Tetrahedron Letters 2007 48(40), 7199-7202; Tetrahedron 2005, 61(22), 5253-5259) to give intermediate U. Intermediate U can be treated with an oxidant and a chloride source to give the desired sulfonyl chloride J. Representative literature examples of this transformation include: Tetrahedron 2010 51(2), 418-421; Tetrahedron 1998 54(45), 13737-13750; Journal of Organic Chemistry 1996, 61(26), 9289-9292.

Scheme 4

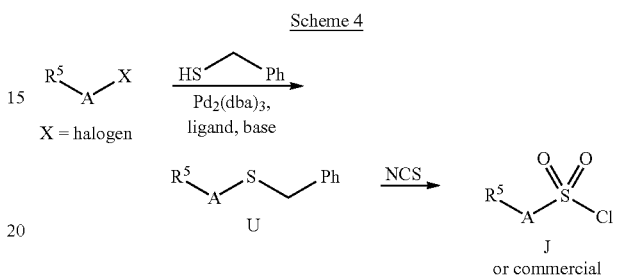

Scheme 5 depicts an additional method for synthesizing compounds of Formula I. Reaction of the protected intermediate Y with the desired sulfonyl chloride J by mixing the two in an appropriate solvent, with or without base, at temperatures from 0° C. to 100° C. provides intermediate W. Examples of similar condensations are known in the art and have been described in references such as Bioorganic & Medicinal Chemistry Letters 2009 19(22), 6452-6458; WO 2008038051; Bioorganic & Medicinal Chemistry Letters 2007, 17(2), 400-405. If a compound of Formula I wherein $R^4$ is hydrogen is desired, intermediate W can then be deprotected and the desired $R^1$ substituent can be introduced by treatment of the resultant amine with the desired alkyl halide (WO 2014188173; Journal of Medicinal Chemistry 2014, 57(24), 10424-10442; ACS Medicinal Chemistry Letters 2014, 5(4), 304-308) or condensation with the appropriate aldehyde followed by treatment with an appropriate reducing agent (similar reductive aminations are described in references such as: Journal of Medicinal Chemistry 2015, 58(20), 8236-8256; European Journal of Medicinal Chemistry 2014, 85, 16-26; Chemical Biology & Drug Design 2014, 83(2), 149-153) to provide a compound of Formula I where $R^4$ is hydrogen. If $R^4$ is desired to be an alkyl group, intermediate W can be treated with a base such as sodium hydride in the presence of the desired alkyl halide (See e.g., US 20050137186; WO2005118549), or under Mitsunobu conditions (See e.g., WO 2003068732; WO 2003068732) where the desired $R^4$ alkyl group comes from treatment of W with the appropriate alcohol to give intermediate AA. Deprotection of AA followed by the addition of the desired $R^1$ substituent by treatment of the resultant amine with the desired alkyl halide (WO 2014188173, Journal of Medicinal Chemistry 2014, 57(24), 10424-10442; ACS Medicinal Chemistry Letters 2014, 5(4), 304-308) or condensation with the appropriate aldehyde followed by treatment with a reducing agent such as sodium triacetoxyborohydride (similar reductive aminations have been described: Journal of Medicinal Chemistry 2015, 58(20), 8236-8256; European Journal of Medicinal Chemistry 2014, 85, 16-26; Chemical Biology & Drug Design 2014, 83(2), 149-153) provides a compound of Formula I wherein $R^4$ is alkyl.

When the desired $R^1$ group is already present on the azepine (i.e., intermediate T), treatment with the desired sulfonyl chloride J, with or without base, in an appropriate solvent at temperatures from 0° C. to 100° C. will give compounds of Formula I where $R^4$ is hydrogen (Bioorganic & Medicinal Chemistry Letters 2009 19(22), 6452-6458; WO2008038051; Bioorganic & Medicinal Chemistry Letters 2007, 17(2), 400-405). When a compound of Formula I where $R^4$ is an appropriate alkyl group is desired, the compound of Formula I where $R^4$ is hydrogen can be treated with a base such as sodium hydride in the presence of the desired alkyl halide (See e.g., US 20050137186; WO 2005118549) or under Mitsunobu conditions (See e.g., WO 2003068732; WO 2003068732) where the desired $R^4$ alkyl group comes from treatment of the compound of Formula I where R is hydrogen with the desired alcohol to provide the desired $R^4$ alkyl compound of Formula I.

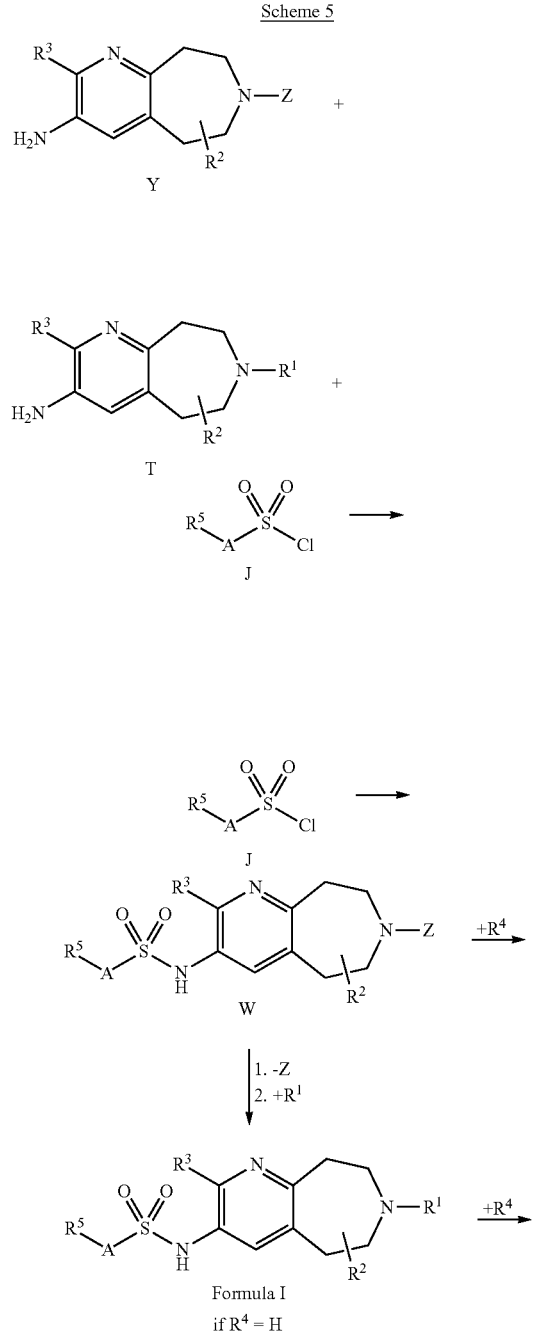

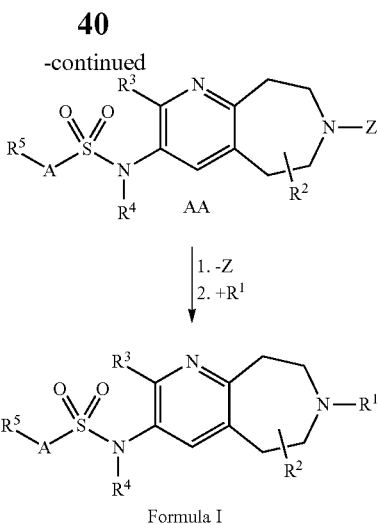

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC) or chiral supercritical fluid chromatography. Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I may be prepared by one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

The compounds of Formula I should be assessed for their biopharmaceutical properties, such as solubility and solution stability (across pH), permeability, etc., in order to select the most appropriate dosage form and route of administration for treatment of the proposed indication. Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form. Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention (including pharmaceutically acceptable salts thereof and N-oxides thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast-dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet. The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methylcellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin-film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high-energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methylcellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 μg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methylcellulose, hydroxyethyl cellulose, or methylcellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof, or a salt of such compound or prodrug, and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of the Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b)<180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. In some cases, racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

The following are abbreviations which may be used in the description of the experimental section:

br=broad; CDCl$_3$=deuterochloroform; CD$_3$OD=deuteromethanol; d=doublet, dd=doublet of doublets; EDC or EDCI=1-ethyl-3-(3-dimethylaminopropyl) carbodiimide hydrochloride; g=gram; GCMS=gas chromatography-mass spectrometry; h=hour; HATU=O-(7-azabenzotriazol-1-yl)-N,N,N',N'-tetramethyluronium hexafluorophosphate; HCl=hydrochloric acid; HPLC=high performance liquid chromatography; Hz=hertz; L=liter; LCMS=liquid chromatography-mass spectrometry; m=multiplet; M=molar; mg=milligram; MHz=megahertz; min=minute; μL=microliter; mL=milliliter, μmol=micromole; mmol=millimole; mol=mole; n-BuLi=n-butyllithium; NEt$_3$=triethylamine; NH$_4$Cl=ammonium chloride; NaHCO$_3$=sodium bicarbonate; NaOAc=sodium acetate; NaOCl=sodium hypochlorite; NaOH=sodium hydroxide; NaOMe=sodium methoxide; t-BuONa=sodium tert-butoxide; NH$_2$OH.HCl=hydroxylamine hydrochloride; NMR=nuclear magnetic resonance; NOE=Nuclear Overhauser effect; Pd$_2$(dba)$_3$=tris(dibenzylideneacetone)dipalladium(0); Pd(dppf)Cl$_2$=[1,1'-bis(diphenylphosphino) ferrocene]dichloropalladium(II); PPh$_3$=triphenylphosphine; psi=pounds per square inch; q=quartet; rt=room temperature; s=singlet; t=triplet; t-butylXPhos=di-tert-butyl[2',4',6'-tri(propan-2-yl)biphenyl-2-yl]phosphane; TFA or CF$_3$CO$_2$H=trifluoroacetic acid; Xantphos=4,5-bis(diphenylphosphino)-9,9-dimethylxanthene.

Preparation P1

2,2'-(6-Methoxypyridine-2,3-diyl)diethanol (P1)

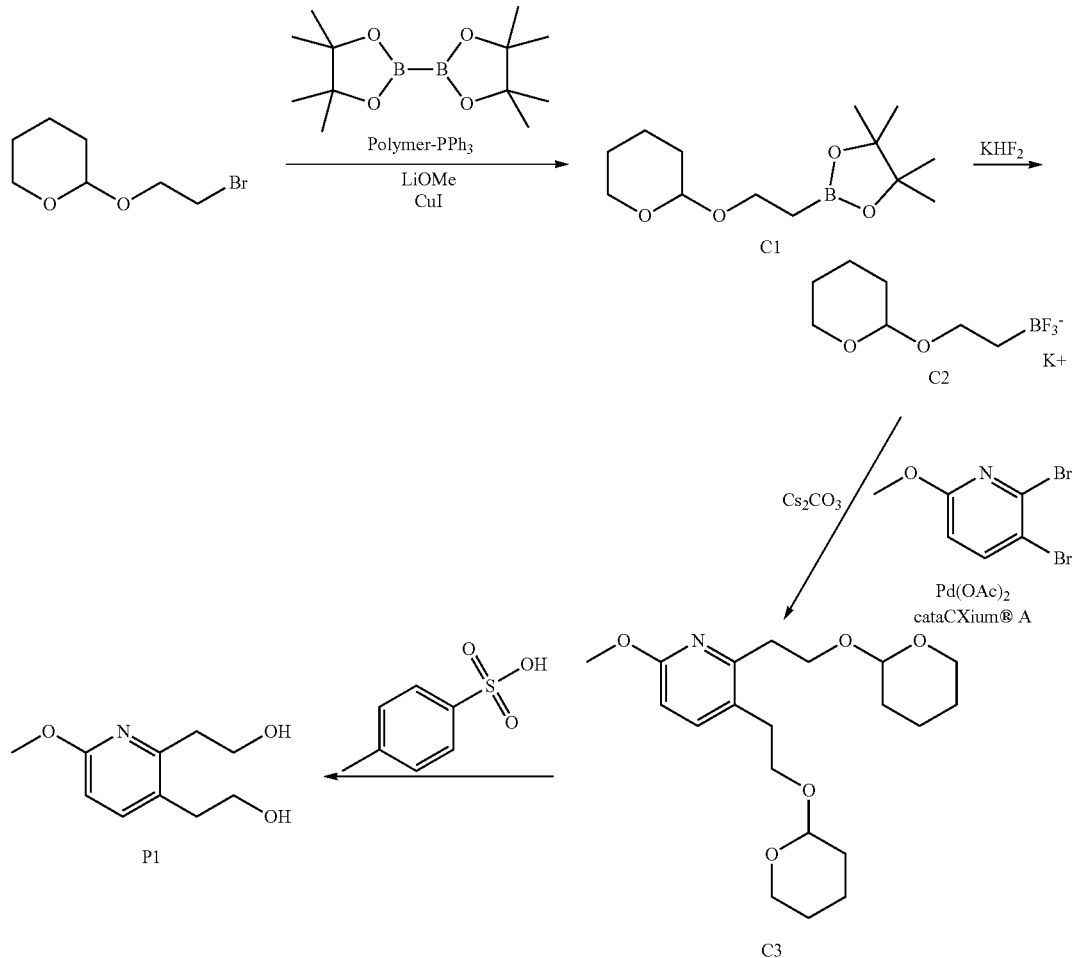

Step 1. Synthesis of 2-[2-(4,4,5,5-tetramethyl-1,3,2-dioxaborolan-2-yl)ethoxy]tetrahydro-2H-pyran (C1)

A mixture of 2-(2-bromoethoxy)tetrahydro-2H-pyran (84.0 g, 402 mmol), 4,4,4',4',5,5,5',5'-octamethyl-2,2'-bi-1,3,2-dioxaborolane (153 g, 602 mmol), lithium methoxide (30.5 g, 803 mmol), copper(I) iodide (7.65 g, 40.2 mmol), and polymer-bound triphenylphosphine (equivalent to 10.5 g, 40.0 mmol) in N,N-dimethylformamide (2.0 L) was stirred for 20 hours at room temperature. It was then diluted with dichloromethane (2 L) and filtered through a pad of diatomaceous earth; the filter pad was rinsed with dichloromethane (2×500 mL) and the combined filtrates were concentrated in vacuo. The residue was poured into saturated aqueous ammonium chloride solution (1.0 L) and the resulting mixture was extracted with diethyl ether (4×500 mL). After the combined organic layers had been washed with water (2×500 mL) and saturated aqueous sodium chloride solution (500 mL), they were dried over sodium sulfate, filtered, and concentrated under reduced pressure to afford the product as a colorless oil. Yield: 85 g, 330 mmol, 82%. ¹H NMR (400 MHz, CDCl₃) δ 4.60 (dd, J=4.1, 2.8 Hz, 1H), 3.92-3.84 (m, 2H), 3.56-3.44 (m, 2H), 1.87-1.76 (m, 1H), 1.73-1.64 (m, 1H), 1.62-1.44 (m, 4H), 1.23 (s, 12H), 1.17 (t, J=7.9 Hz, 2H).

Step 2. Synthesis of potassium trifluoro[2-(tetra-hydro-2H-pyran-2-yloxy)ethyl]borate (C2)

Saturated aqueous potassium hydrogenfluoride solution (56 g, 720 mmol) was added to a solution of C1 (60 g, 230 mmol) in tetrahydrofuran (900 mL). The reaction mixture was stirred at room temperature for 2 hours, whereupon it was concentrated in vacuo; the resulting viscous gum was washed with acetone (4×200 mL), and the acetone washes were filtered. The combined filtrates were concentrated under reduced pressure to a volume of approximately 150 mL. Diethyl ether was added until a small amount of precipitate formed, and the mixture was stirred at 0° C. for 30 minutes, whereupon it was filtered. The filter cake was washed with a small volume of diethyl ether to provide the product as a white solid. Yield: 40 g, 170 mmol, 74%. ¹H NMR (400 MHz, DMSO-d₆), characteristic peaks: δ 4.46-4.41 (m, 1H), 3.76-3.68 (m, 1H), 3.57 (ddd, J=13, 10, 5 Hz, 1H), 3.22 (ddd, J=13, 10, 5 Hz, 1H), 1.76-1.65 (m, 1H), 1.59-1.50 (m, 1H), 1.49-1.31 (m, 4H), 0.44-0.19 (m, 2H).

Step 3. Synthesis of 6-methoxy-2,3-bis[2-(tetra-hydro-2H-pyran-2-yloxy)ethyl]pyridine (C3)

1,4-Dioxane (450 mL) and water (150 mL) were added to a mixture of 2,3-dibromo-6-methoxypyridine (12 g, 45 mmol), C2 (31.8 g, 135 mmol), di(1-adamantyl)-n-butyl-phosphine (cataCXium® A; 3.22 g, 8.98 mmol), palladium (II) acetate (3.03 g, 13.5 mmol), and cesium carbonate (87.9 g, 270 mmol), and the reaction vessel was evacuated and charged with nitrogen. This evacuation cycle was repeated twice, and the reaction mixture was then stirred at reflux for 20 hours. After the reaction mixture had been partitioned between ethyl acetate (300 mL) and saturated aqueous sodium chloride solution (200 mL), the aqueous layer was extracted with ethyl acetate (2×200 mL); the combined organic layers were washed with saturated aqueous sodium chloride solution (200 mL), dried over sodium sulfate, filtered, and concentrated in vacuo. The residue was treated with triethylamine (3 mL), dissolved in dichloromethane and treated with silica gel; this mixture was concentrated to dryness and used for silica gel chromatography (Gradient: 0% to 6% ethyl acetate in petroleum ether) to afford the product as a brown oil. Yield: 10 g, 27 mmol, 60%. LCMS m/z 388.0 [M+Na⁺]. ¹H NMR (400 MHz, CDCl₃) δ 7.39 (d, J=8.3 Hz, 1H), 6.52 (d, J=8.3 Hz, 1H), 4.63 (dd, J=4.0, 2.8 Hz, 1H), 4.58 (dd, J=4.0, 2.8 Hz, 1H), 4.19-4.11 (m, 1H), 3.94-3.71 (m, 4H), 3.89 (s, 3H), 3.58-3.42 (m, 3H), 3.05 (t, J=7.2 Hz, 2H), 2.89 (t, J=7.2 Hz, 2H), 1.86-1.74 (m, 2H), 1.74-1.64 (m, 2H), 1.62-1.44 (m, 8H).

Step 4. Synthesis of 2,2'-(6-methoxypyridine-2,3-diyl)diethanol (P1)

A mixture of C3 (29.7 g, 81.3 mmol) and p-toluenesulfonic acid monohydrate (16.2 g, 85.2 mmol) in methanol (400 mL) was stirred at 15° C. overnight. After the reaction mixture had been concentrated in vacuo, the residue was partitioned between dichloromethane (300 mL) and saturated aqueous sodium bicarbonate solution (200 mL), and the aqueous layer was extracted with dichloromethane (5×200 mL). The combined organic layers were washed with saturated aqueous sodium chloride solution (50 mL), dried over sodium sulfate, filtered, and concentrated under reduced pressure to provide the product as a brown gum. Yield: 15.6 g, 79.1 mmol, 97%. LCMS m/z 198.2 [M+H]⁺. ¹H NMR (400 MHz, CDCl₃) δ 7.43 (d, J=8.3 Hz, 1H), 6.61 (d, J=8.4 Hz, 1H), 4.06 (t, J=5.3 Hz, 2H), 3.90 (s, 3H), 3.81 (t, J=6.7 Hz, 2H), 2.98 (t, J=5.3 Hz, 2H), 2.81 (t, J=6.6 Hz, 2H).

Preparation P2

1-(3-Amino-2-methoxy-5,6,8,9-tetrahydro-7H-pyrido[2,3-d]azepin-7-yl)-2,2,2-trifluoroethanone (P2)

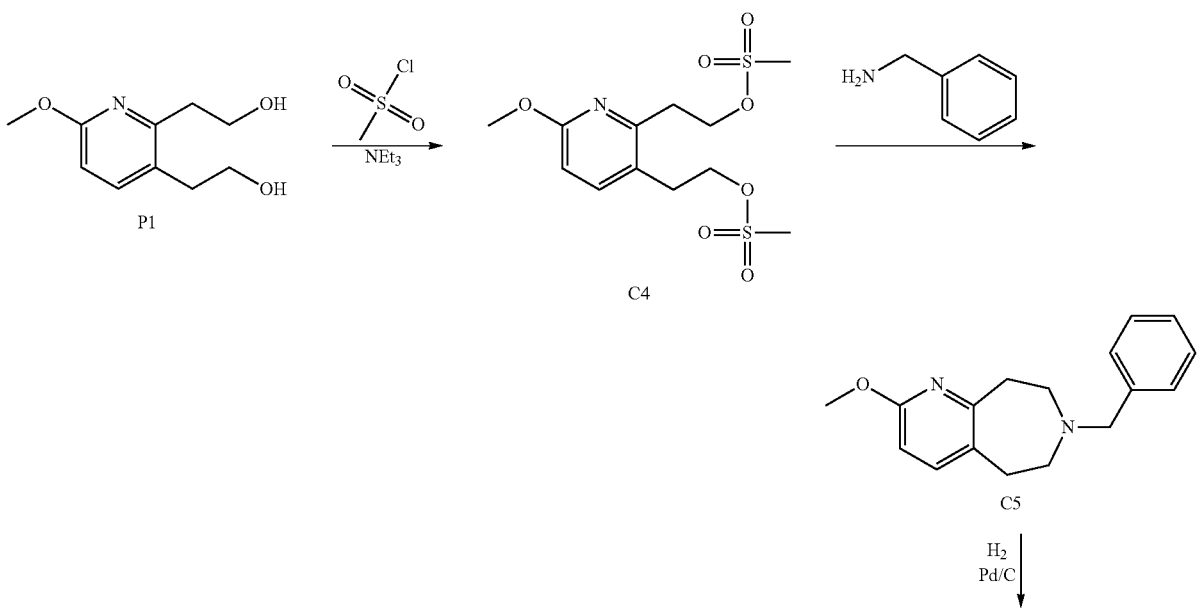

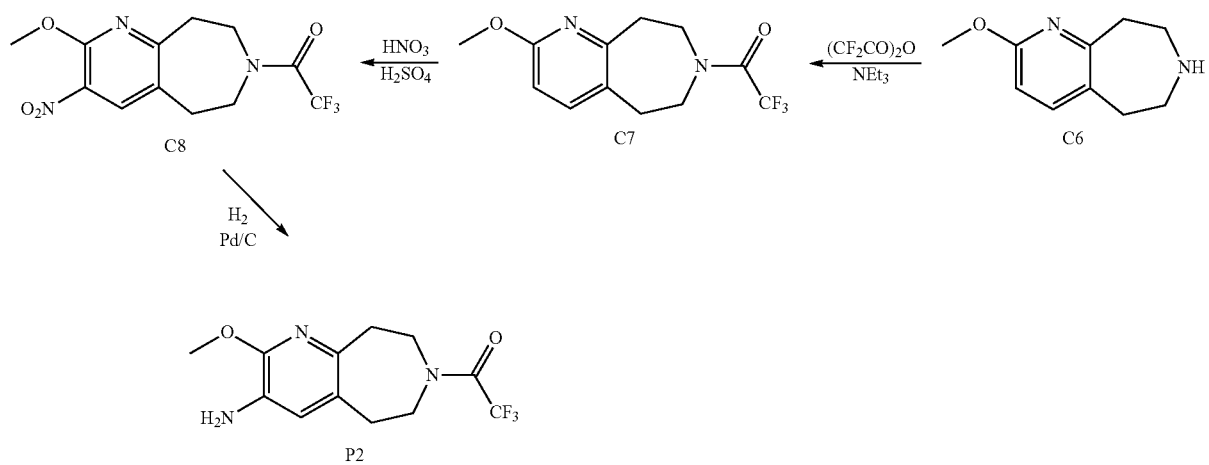

Step 1. Synthesis of (6-methoxypyridine-2,3-diyl)diethane-2,1-diyl dimethanesulfonate (C4)

Methanesulfonyl chloride (31.6 g, 276 mmol) was added to a 0° C. solution of P1 (15.6 g, 79.1 mmol) and triethylamine (40 g, 400 mmol) in dichloromethane (400 mL). The reaction mixture was stirred at room temperature for 20 minutes, whereupon it was quenched with saturated aqueous sodium bicarbonate solution (200 mL). The organic layer was washed with saturated aqueous sodium chloride solution (200 mL), dried over sodium sulfate, filtered, and concentrated in vacuo to afford the product as a brown gum, which solidified upon standing. Yield: 28 g, 79 mmol, 100%. $^1$H NMR (400 MHz, CDCl$_3$) δ 7.42 (d, J=8.4 Hz, 1H), 6.62 (d, J=8.4 Hz, 1H), 4.75 (t, J=6.5 Hz, 2H), 4.35 (t, J=7.0 Hz, 2H), 3.91 (s, 3H), 3.17 (t, J=6.4 Hz, 2H), 3.04 (t, J=6.9 Hz, 2H), 2.96 (s, 3H), 2.95 (s, 3H).

Step 2. Synthesis of 7-benzyl-2-methoxy-6,7,8,9-tetrahydro-5H-pyrido[2,3-d]azepine (C5)

A solution of C4 (12.5 g, 35.4 mmol) and benzylamine (40 mL, 370 mmol) in 1,2-dichloroethane (40 mL) was heated at 40° C. overnight. The reaction mixture was then diluted with dichloromethane (300 mL), washed sequentially with saturated aqueous sodium bicarbonate solution (300 mL) and saturated aqueous sodium chloride solution (100 mL), dried over sodium sulfate, filtered, and concentrated in vacuo. Silica gel chromatography (Gradient: 0% to 30% ethyl acetate in petroleum ether) provided the product as a yellow gum. Yield: 5.5 g, 20 mmol, 56%. LCMS m/z 269.0 [M+H]$^+$. $^1$H NMR (400 MHz, CDCl$_3$) δ 7.4-7.2 (m, 6H), 6.47 (d, J=8 Hz, 1H), 3.89 (s, 3H), 3.64 (s, 2H), 3.1-3.0 (m, 2H), 2.8-2.7 (m, 2H), 2.7-2.6 (m, 4H).

Step 3. Synthesis of 2-methoxy-6,7,8,9-tetrahydro-5H-pyrido[2,3-d]azepine (C6)

Wet palladium on carbon (10%, 3 g) was added to a solution of C5 (6.0 g, 22 mmol) in methanol (150 mL), and the reaction mixture was degassed under vacuum and subsequently purged with hydrogen; this evacuation cycle was repeated several times. The reaction mixture was then stirred under hydrogen (50 psi) at 50° C. for 72 hours, whereupon it was filtered through a pad of diatomaceous earth. The filter pad was washed with methanol (2×100 mL), and the combined filtrates were concentrated in vacuo, affording the product as a pale yellow gum. Yield: 3.85 g, 21.6 mmol, 98%. $^1$H NMR (400 MHz, CDCl$_3$) δ 7.28 (d, J=8 Hz, 1H), 6.47 (d, J=8.0 Hz, 1H), 3.90 (s, 3H), 3.08-3.03 (m, 2H), 3.02-2.96 (m, 2H), 2.96-2.91 (m, 2H), 2.83-2.77 (m, 2H).

Step 4. Synthesis of 2,2,2-trifluoro-1-(2-methoxy-5,6,8,9-tetrahydro-7H-pyrido[2,3-d]azepin-7-yl)ethanone (C7)

Trifluoroacetic anhydride (5.44 g, 25.9 mmol) was added to a 0° C. solution of C6 (3.85 g, 21.6 mmol) and triethylamine (6.56 g, 64.8 mmol) in dichloromethane (60 mL). The reaction mixture was stirred at 0° C. for 20 minutes, whereupon it was diluted with dichloromethane (50 mL), washed sequentially with saturated aqueous sodium bicarbonate solution (50 mL) and saturated aqueous sodium chloride solution (50 mL), dried over sodium sulfate, filtered, and concentrated in vacuo, providing the product as a yellow gum. Yield: 5.8 g, 21 mmol, 97%. This material was presumed, from analysis of the $^1$H NMR, to exist as a ~1:1 mixture of two rotamers at the trifluoroacetamide moiety. This was true of many subsequent intermediates bearing this functional group. LCMS m/z 274.9 [M+H]$^+$. $^1$H NMR (400 MHz, CDCl$_3$) δ [7.35 (d, J=8.3 Hz) and 7.33 (d, J=8.3 Hz), total 1H], [6.56 (d, J=8.2 Hz) and 6.55 (d, J=8.2 Hz), total 1H], [3.92 (s) and 3.91 (s), total 3H], 3.85-3.68 (m, 4H), 3.18-3.10 (m, 2H), 2.94-2.86 (m, 2H).

Step 5. Synthesis of 2,2,2-trifluoro-1-(2-methoxy-3-nitro-5,6,8,9-tetrahydro-7H-pyrido[2,3-d]azepin-7-yl)ethanone (C8)

Nitric acid (70%, 19 g, 211 mmol) was added to a solution of C7 (5.8 g, 21 mmol) in sulfuric acid (40 mL), and the reaction mixture was stirred at 45° C. for 16 hours. It was then poured into ice water (500 mL) and extracted with ethyl acetate (2×100 mL); the combined organic layers were washed with saturated aqueous sodium chloride solution (50 mL), dried over sodium sulfate, filtered, and concentrated in vacuo. Chromatography on silica gel (Gradient: 0% to 30% ethyl acetate in petroleum ether) afforded the product as a yellow gum. Yield: 4.2 g, 13 mmol, 62%. LCMS m/z 319.8

[M+H]⁺. ¹H NMR (400 MHz, CDCl₃) δ [8.13 (s) and 8.11 (s), total 1H], [4.11 (s) and 4.09 (s), total 3H], 3.89-3.73 (m, 4H), 3.27-3.18 (m, 2H), 3.04-2.96 (m, 2H).

Step 6. Synthesis of 1-(3-amino-2-methoxy-5,6,8,9-tetrahydro-7H-pyrido[2,3-d]azepin-7-yl)-2,2,2-trifluoroethanone (P2)

Wet palladium on carbon (10%, 1.00 g) was added to a solution of C8 (6.40 g, 20.0 mmol) in methanol (200 mL), and the reaction mixture was degassed under vacuum and subsequently purged with hydrogen; this evacuation cycle was repeated several times. The reaction mixture was stirred under hydrogen (30 psi) at 30° C. for 3 hours, whereupon it was filtered through a pad of diatomaceous earth. The filtrate was concentrated in vacuo, and the residue was dissolved in acetonitrile (100 mL). Removal of solvent under reduced pressure provided the product as a pale brown solid. Yield: 5.61 g, 19.4 mmol, 97%. LCMS m/z 289.8 [M+H]⁺. ¹H NMR (400 MHz, CDCl₃) δ 7.22-7.08 (m, 1H), 4.01 (s, 3H), 3.85-3.65 (m, 4H), 3.19-3.05 (m, 2H), 2.92-2.80 (m, 2H).

Preparations P3 and P4

2-Methoxy-7-methyl-6,7,8,9-tetrahydro-5H-pyrido[2,3-d]azepin-3-amine (P3) and 2-Meth oxy-7-methyl-6,7,8,9-tetrahydro-5H-pyrido[2,3-d]azepin-3-amine, hydrochloride salt (P4)

and formaldehyde (37% solution in water, 11.6 g, 143 mmol). After the reaction mixtures had been stirred at 70° C. for 2.5 hours, they were combined and basified to a pH of greater than 10 via addition of aqueous sodium hydroxide solution. The resulting suspension was extracted with ethyl acetate (3×90 mL), and the combined organic layers were washed with saturated aqueous sodium chloride solution, dried over sodium sulfate, filtered, and concentrated in vacuo. Silica gel chromatography (Gradient: 0% to 10% methanol in dichloromethane) provided the product as a yellow solid. Yield: 6.88 g, 29.0 mmol, 81%. ¹H NMR (400 MHz, CDCl₃) δ 8.04 (s, 1H), 4.09 (s, 3H), 3.18-3.10 (m, 2H), 2.94-2.87 (m, 2H), 2.66-2.55 (m, 4H), 2.40 (s, 3H).

Step 3. Synthesis of 2-methoxy-7-methyl-6,7,8,9-tetrahydro-5H-pyrido[2,3-d]azepin-3-amine (P3)

A suspension of C10 (6.80 g, 28.7 mmol) and palladium on carbon (10%, 800 mg) in methanol (250 mL) was stirred under hydrogen (30 psi) for 3 hours at 22° C. After the reaction mixture had been filtered, the filtrate was concentrated in vacuo. The residue was taken up in ethyl acetate and concentrated under reduced pressure to provide the product as a yellow gum. Yield: 5.7 g, 27 mmol, 94%. LCMS m/z 208.1 [M+H]⁺. ¹H NMR (400 MHz, CDCl₃) δ 6.67 (s, 1H), 3.95 (s, 3H), 3.7-3.5 (br s, 2H), 3.02-2.95 (m, 2H), 2.78-2.71 (m, 2H), 2.61-2.49 (m, 4H), 2.37 (s, 3H).

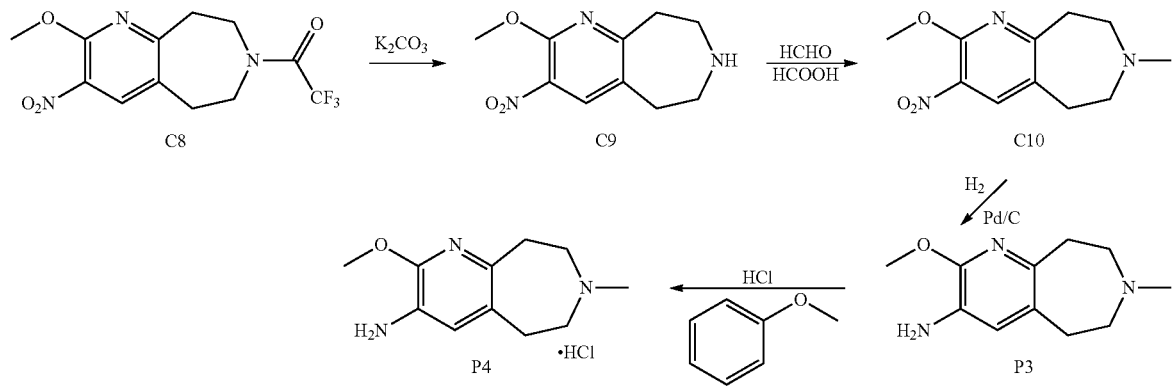

Step 1. Synthesis of 2-methoxy-3-nitro-6,7,8,9-tetrahydro-5H-pyrido[2,3-d]azepine (C9)

A mixture of C8 (12.0 g, 37.6 mmol) and potassium carbonate (7.79 g, 56.4 mmol) in methanol (100 mL) was stirred at 50° C. for 3 hours, whereupon the reaction mixture was partitioned between ethyl acetate (200 mL) and water (200 mL). The aqueous layer was concentrated in vacuo to remove methanol, and subsequently extracted with ethyl acetate (2×240 mL). The combined organic layers were washed with saturated aqueous sodium chloride solution (60 mL), dried over sodium sulfate, filtered, and concentrated under reduced pressure to afford the product as a brown solid. Yield: 8.03 g, 36.0 mmol, 96%. ¹H NMR (400 MHz, CDCl₃) δ 8.04 (s, 1H), 4.08 (s, 3H), 3.16-3.10 (m, 2H), 3.04-2.96 (m, 4H), 2.91-2.86 (m, 2H).

Step 2. Synthesis of 2-methoxy-7-methyl-3-nitro-6,7,8,9-tetrahydro-5H-pyrido[2,3-d]azepine (C10)

This experiment was carried out in two batches. To C9 (4.0 g, 18 mmol) were added formic acid (8.25 g, 179 mmol)

Step 4. Synthesis of 2-methoxy-7-methyl-6,7,8,9-tetrahydro-5H-pyrido[2,3-d]azepin-3-amine, hydrochloride salt (P4)

A mixture of P3 (by quantitative NMR, this batch had a purity of 85.7%; 6.19 g, 25.6 mmol) and methoxybenzene (40 mL) was stirred at room temp for 10 minutes, whereupon it was cooled in a bath of cold tap water and treated drop-wise with hydrogen chloride (1.25M solution in ethanol; 25 mL, 31.2 mmol). After the reaction mixture had stirred at room temperature overnight, the precipitate was collected via filtration, and the filter cake was washed with methoxybenzene (2×5 mL), affording the product as an off-white solid. Yield: 4.96 g, 20.3 mmol, 79%. ¹H NMR (400 MHz, DMSO-d₆) δ 11.11 (br s, 1H), 6.72 (s, 1H), 4.85 (br s, 2H), 3.82 (s, 3H), 3.59-3.43 (m, 2H), 3.40-3.26 (m, 1H, assumed; partially obscured by water peak), 3.23-3.09 (m, 1H), 3.06-2.89 (m, 2H), 2.89-2.68 (m, 2H), 2.76 (s, 3H).

Alternate Synthesis of C9

2-Methoxy-3-nitro-6,7,8,9-tetrahydro-5H-pyrido[2,3-d]azepine (C9)

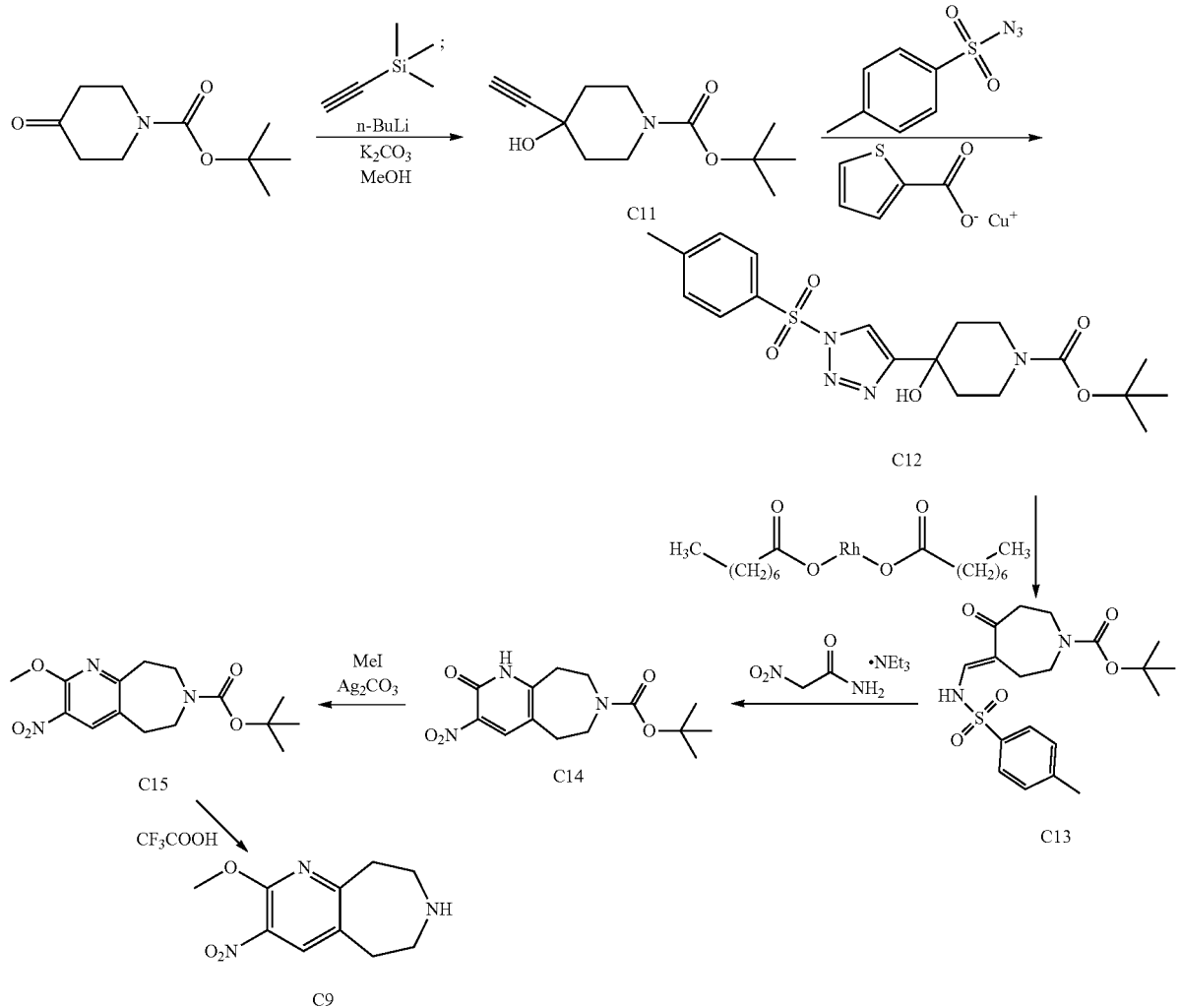

Step 1. Synthesis of tert-butyl 4-ethynyl-4-hydroxypiperidine-1-carboxylate (C11)

A solution of n-butyllithium in hexanes (2.5M, 50.5 mL, 126 mmol) was added in a drop-wise manner over 30 minutes to a −75° C. solution of ethynyl(trimethyl)silane (12.4 g, 126 mmol) in tetrahydrofuran (250 mL). After the reaction mixture had stirred at −75° C. for 30 minutes, a solution of tert-butyl 4-oxopiperidine-1-carboxylate (21.0 g, 105 mmol) in tetrahydrofuran (100 mL) was added drop-wise over 40 minutes; stirring was continued at this temperature for an additional 30 minutes, whereupon the reaction mixture was allowed to warm to room temperature and stir for 3 hours. To this solution was added methanol (120 mL), followed by potassium carbonate (16.0 g, 116 mmol), and the reaction mixture was stirred at room temperature for 5 hours. Solvent was then removed in vacuo and the residue was suspended in diethyl ether (200 mL), washed sequentially with water (50 mL) and with saturated aqueous sodium chloride solution (50 mL), dried over magnesium sulfate, filtered, and concentrated under reduced pressure. The residue was recrystallized from heptane to afford the product as a white solid. Yield: 22 g, 97 mmol, 92%. GCMS m/z 225.2 [M+]. $^1$H NMR (400 MHz, CDCl$_3$) δ 3.87-3.70 (m, 2H), 3.28 (ddd, J=13.4, 9.5, 3.1 Hz, 2H), 2.55 (s, 1H), 2.10 (s, 1H), 1.96-1.84 (m, 2H), 1.78-1.66 (m, 2H), 1.47 (s, 9H).

Step 2. Synthesis of tert-butyl 4-hydroxy-4-{1-[(4-methylphenyl)sulfonyl]-1H-1,2,3-triazol-4-yl}piperidine-1-carboxylate (C12)

4-Methylbenzenesulfonyl azide (3.24 g, 16.4 mmol, as a 15% solution in toluene) and copper(I) thiophene-2-carboxylate (94.5 mg, 0.496 mmol) were added to a 0° C. solution of C11 (3.7 g, 16 mmol) in toluene (30 mL). After 1 hour, the ice bath was removed, and the reaction mixture was allowed to stir for 10 hours. It was then cooled in an ice bath for 30 minutes and filtered; the collected solid was washed with cool toluene (5 mL) to provide the product as a pale white powder. Yield: 6.4 g, 15 mmol, 94%. $^1$H NMR (400 MHz, CDCl$_3$) δ 8.03-7.99 (m, 2H), 8.02 (s, 1H), 7.43-7.39 (m, 2H), 4.00-3.79 (m, 2H), 3.38-3.22 (m, 2H), 2.47 (s, 3H), 2.39-2.35 (m, 1H), 2.07-1.97 (m, 2H), 1.90-1.82 (m, 2H), 1.47 (s, 9H).

Step 3. Synthesis of tert-butyl (4E)-4-({[(4-methyl-phenyl)sulfonyl]amino}methylidene)-5-oxoazepane-1-carboxylate (C13)

A solution of C12 (6.1 g, 14 mmol) in toluene (50 mL) was degassed and purged with nitrogen. Rhodium(II) octanoate dimer (112 mg, 0.144 mmol) was added, and the reaction mixture was heated at 50° C. for 3 hours. After solvent had been removed in vacuo, the residue was purified by chromatography on silica gel (Gradient: 25% to 33% ethyl acetate in heptane) to afford the product as a pale white solid. Yield: 4.9 g, 12 mmol, 86%. $^1$H NMR (400 MHz, CDCl$_3$) δ 11.49 (br d, J=10 Hz, 1H), 7.75 (br d, J=8.4 Hz, 2H), 7.33 (br d, J=8.2 Hz, 2H), 6.92 (d, J=10.5 Hz, 1H), 3.57-3.47 (m, 4H), 2.69-2.61 (m, 2H), 2.47-2.39 (m, 2H), 2.44 (s, 3H), 1.46 (s, 9H).

Step 4. Synthesis of tert-butyl 3-nitro-2-oxo-1,2,5,6,8,9-hexahydro-7H-pyrido[2,3-d]azepine-7-carboxylate (C14)

To a solution of 2-nitroacetamide, triethylamine salt (838 mg, 4.08 mmol) in a mixture of water (0.9 mL) and 2-propanol (9 mL) was added C13 (1.24 g, 3.14 mmol). The reaction mixture was stirred at 50° C. for 15 hours, whereupon diethyl ether (10 mL) was added. The resulting mixture was stirred for 30 minutes and filtered; the collected solid (869 mg) was suspended in ethyl acetate (10 mL) and then heated at reflux for 10 minutes. Methanol (2 mL) was added until the mixture became a solution, which was allowed to cool overnight. The resulting solid was collected via filtration to afford the product as a bright yellow solid. Yield: 779 mg, 2.52 mmol, 80%. $^1$H NMR (400 MHz, CDCl$_3$) δ 13.71-13.54 (br s, 1H), 8.33 (s, 1H), 3.73-3.65 (m, 2H), 3.64-3.56 (m, 2H), 3.14-3.05 (m, 2H), 2.87-2.79 (m, 2H), 1.50 (s, 9H).

Step 5. Synthesis of tert-butyl 2-methoxy-3-nitro-5,6,8,9-tetrahydro-7H-pyrido[2,3-d]azepine-7-carboxylate (C15)

A mixture of C14 (73.7 mg, 0.238 mmol), iodomethane (69 mg, 0.49 mmol), and silver carbonate (133 mg, 0.482 mmol) in dichloromethane was stirred at room temperature for 48 hours. The reaction mixture was filtered, and the filtrate was concentrated in vacuo to provide the product. Yield: 69 mg, 0.21 mmol, 88%. LCMS m/z 268.3 [(M-2-methylprop-1-ene)+H]+. $^1$H NMR (400 MHz, CDCl$_3$) δ 8.08 (s, 1H), 4.09 (s, 3H), 3.68-3.55 (m, 4H), 3.17-3.09 (m, 2H), 2.93-2.85 (m, 2H), 1.50 (s, 9H).

Step 6. Synthesis of 2-methoxy-3-nitro-6,7,8,9-tetrahydro-5H-pyrido[2,3-d]azepine (C9)

Trifluoroacetic acid (3 mL) was added to a solution of C15 (620 mg, 1.92 mmol) in dichloromethane (3 mL), and the reaction mixture was stirred at room temperature for 3 hours, whereupon solvents were removed in vacuo and the residue was partitioned between ethyl acetate (50 mL) and saturated aqueous sodium bicarbonate solution (40 mL). The aqueous layer was extracted with ethyl acetate (2×40 mL), and the combined organic layers were dried over sodium sulfate, filtered, and concentrated under reduced pressure to afford the product as a yellow oil. Yield: 417 mg, 1.87 mmol, 97%. $^1$H NMR (400 MHz, CDCl$_3$) δ 8.16 (s, 1H), 4.12 (s, 3H), 3.49-3.40 (m, 6H), 3.26-3.20 (m, 2H).

Preparation P5

7-Ethyl-2-methoxy-6,7,8,9-tetrahydro-5H-pyrido[2,3-d]azepin-3-amine (P5)

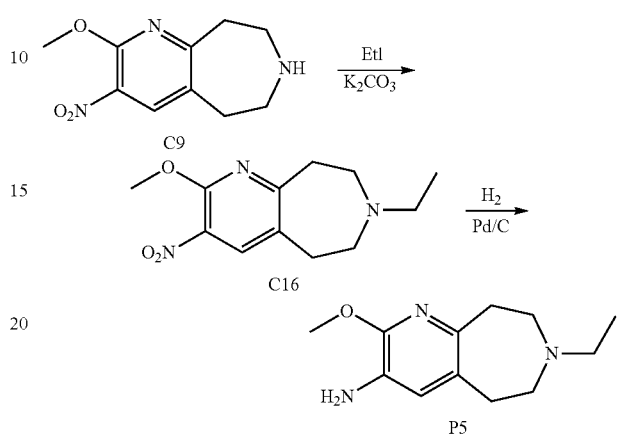

Step 1. Synthesis of 7-ethyl-2-methoxy-3-nitro-6,7,8,9-tetrahydro-5H-pyrido[2,3-d]azepine (C16)

Iodoethane (8.87 g, 56.9 mmol) was added to a 5° C. mixture of C9 (6.35 g, 28.4 mmol) and potassium carbonate (11.8 g, 85.4 mmol) in acetonitrile (100 mL). The reaction mixture was stirred at 25° C. for 5 hours, whereupon it was treated with water (350 mL) and extracted with dichloromethane (3×100 mL). The combined organic layers were dried over sodium sulfate, filtered, and concentrated in vacuo; chromatography on silica gel (Gradient: 0% to 6% methanol in dichloromethane) provided the product as an orange gum. Yield: 5.68 g, 22.6 mmol, 80%. $^1$H NMR (400 MHz, CDCl$_3$) δ 8.05 (s, 1H), 4.09 (s, 3H), 3.19-3.11 (m, 2H), 2.96-2.88 (m, 2H), 2.74-2.65 (m, 4H), 2.61 (q, J=7.2 Hz, 2H), 1.12 (t, J=7.2 Hz, 3H).

Step 2. Synthesis of 7-ethyl-2-methoxy-6,7,8,9-tetrahydro-5H-pyrido[2,3-d]azepin-3-amine (P5)

A suspension of C16 (5.28 g, 21.0 mmol) and wet palladium on carbon (10%, 1.35 g) in methanol (200 mL) was stirred at 27° C. under hydrogen (30 psi) for 4 hours, then was allowed to stand under hydrogen at 27° C. without stirring for 16 hours. The reaction mixture was filtered and the filtrate was concentrated in vacuo; the residue was combined with the product of a similar reaction carried out on C16 (1.39 g, 5.53 mmol), and dissolved in dichloromethane (150 mL). Removal of solvent under reduced pressure afforded the product (5.92 g, containing some dichloromethane by $^1$H NMR analysis) as an orange oil. Yield, corrected for dichloromethane: 5.74 g, 25.9 mmol, 98%. LCMS m/z 221.9 [M+H]+. $^1$H NMR (400 MHz, CDCl$_3$) δ 6.67 (s, 1H), 3.95 (s, 3H), 3.59 (br s, 2H), 3.03-2.95 (m, 2H), 2.78-2.71 (m, 2H), 2.67-2.58 (m, 4H), 2.58 (q, J=7.2 Hz, 2H), 1.10 (t, J=7.2 Hz, 3H).

Example 1
6-Cyclohexyl-N-(2-methoxy-7-methyl-6,7,8,9-tetrahydro-5H-pyrido[2,3-d]azepin-3-yl)pyridine-3-sulfonamide (1)
Step 1. Synthesis of 1-(5-bromopyridin-2-yl)cyclohexanol (C17)
To a −78° C. slurry of 2,5-dibromopyridine (10.0 g, 42.2 mmol) in toluene (150 mL) was added n-butyllithium (2.5M
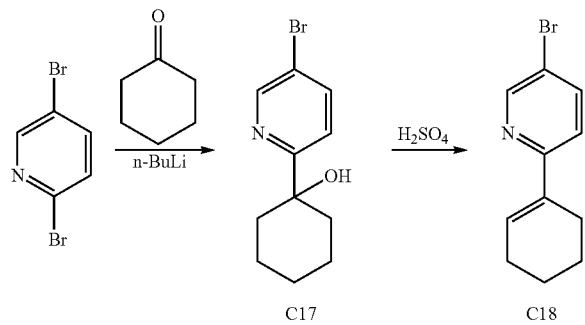
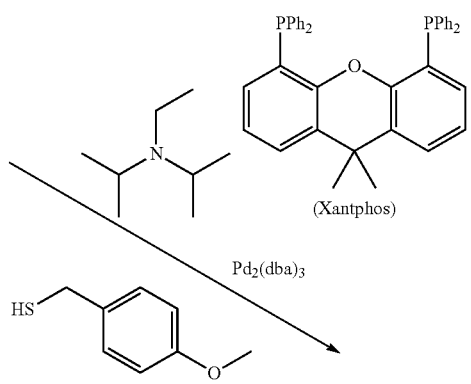
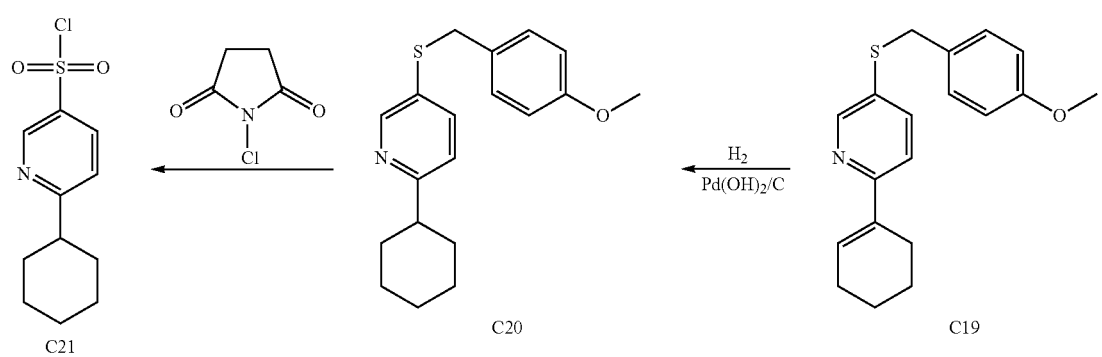
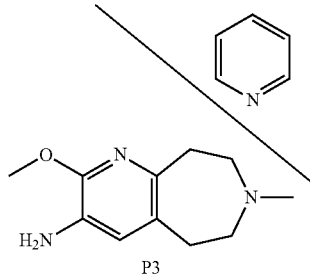
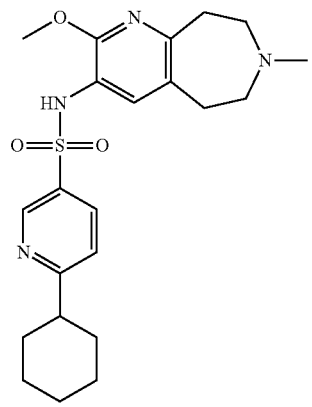

in hexanes, 18.6 mL, 46.4 mmol). A solution of cyclohexanone (6.21 g, 63.3 mmol) in toluene (10 mL) was then added drop-wise, and the reaction mixture was stirred for 2 hours at −78° C., whereupon it was quenched by addition of saturated aqueous ammonium chloride solution (20 mL). The mixture was extracted with ethyl acetate (150 mL) and the organic layer was washed sequentially with water (50 mL) and saturated aqueous sodium chloride solution (50 mL), dried over sodium sulfate, filtered, and concentrated in vacuo. Silica gel chromatography (Gradient: 0% to 20% ethyl acetate in petroleum ether) afforded the product as a yellow oil. Yield: 8.0 g, 31 mmol, 73%. $^1$H NMR (400 MHz, $CDCl_3$) δ 8.58 (dd, J=2.3, 0.7 Hz, 1H), 7.81 (dd, J=8.5, 2.3 Hz, 1H), 7.34 (dd, J=8.5, 0.7 Hz, 1H), 4.23 (br s, 1H), 1.92-1.27 (m, 10H, assumed; integrates to ~1.5 times 1 OH).

Step 2. Synthesis of 5-bromo-2-(cyclohex-1-en-1-yl)pyridine (C18)

To C17 (2.0 g, 7.8 mmol) was added concentrated sulfuric acid (2 mL) in a drop-wise manner at 15° C. After completion of the addition, the reaction mixture was stirred at 20° C. for 1 hour, whereupon it was poured into ice water (50 mL) and basified to a pH of >8 via addition of 20% aqueous sodium hydroxide solution. The resulting mixture was extracted with ethyl acetate (2×50 mL), and the combined organic layers were dried over sodium sulfate, filtered, and concentrated in vacuo to provide the product as a yellow oil. Yield: 1.7 g, 7.1 mmol, 91%. $^1$H NMR (400 MHz, $CDCl_3$) δ 8.58 (br d, J=2.3 Hz, 1H), 7.73 (dd, J=8.5, 2.4 Hz, 1H), 7.27 (br d, J=8.5 Hz, 1H), 6.73-6.68 (m, 1H), 2.51-2.44 (m, 2H), 2.29-2.22 (m, 2H), 1.83-1.75 (m, 2H), 1.72-1.64 (m, 2H).

Step 3. Synthesis of 2-(cyclohex-1-en-1-yl)-5-[(4-methoxybenzyl)sulfanyl]pyridine (C19)

A mixture of C18 (1.7 g, 7.1 mmol), (4-methoxyphenyl)methanethiol (1.43 g, 9.27 mmol), N,N-diisopropylethylamine (2.77 g, 21.4 mmol), tris(dibenzylideneacetone) dipalladium(0) (131 mg, 0.143 mmol), and 4,5-bis(diphenylphosphino)-9,9-dimethylxanthene (Xantphos; 207 mg, 0.358 mmol) in 1,4-dioxane (20 mL) was purged with nitrogen for 2 minutes at 22° C., and then stirred at 110° C. for 16 hours. The reaction mixture was combined with a similar reaction mixture employing C18 (400 mg, 1.7 mmol), concentrated in vacuo, and purified by chromatography on silica gel (Gradient: 0% to 20% ethyl acetate in petroleum ether) to afford the product as a yellow solid. Yield: 2.3 g, 7.4 mmol, 84%. $^1$H NMR (400 MHz, $CDCl_3$) δ 8.47 (d, J=2.1 Hz, 1H), 7.49 (dd, J=8.3, 2.3 Hz, 1H), 7.24 (d, J=8.4 Hz, 1H), 7.16 (br d, J=8.5 Hz, 2H), 6.81 (br d, J=8.5 Hz, 2H), 6.73-6.68 (m, 1H), 4.03 (s, 2H), 3.79 (s, 3H), 2.51-2.43 (m, 2H), 2.30-2.23 (m, 2H), 1.83-1.75 (m, 2H), 1.72-1.63 (m, 2H).

Step 4. Synthesis of 2-cyclohexyl-5-[(4-methoxybenzyl)sulfanyl]pyridine (C20)

Palladium hydroxide on carbon (10%, 1 g) was added to a solution of C19 (1.8 g, 5.78 mmol) in methanol (100 mL). The mixture was degassed under vacuum and then purged with hydrogen; this evacuation-purge cycle was carried out a total of three times. The reaction mixture was then stirred under hydrogen (50 psi) at 40° C. for 18 hours, whereupon it was filtered and concentrated in vacuo, providing the product as an off-white solid. By $^1$H NMR analysis, this material contained some impurities. Yield: 1.1 g, <3.5 mmol, <61%. LCMS m/z 313.9 $[M+H]^+$. $^1$H NMR (400 MHz, $CDCl_3$), characteristic product peaks: δ 8.45 (br d, J=2.3 Hz, 1H), 7.49 (dd, J=8.2, 2.4 Hz, 1H), 7.15 (br d, J=8.7 Hz, 2H), 7.03 (d, J=8.2 Hz, 1H), 6.81 (br d, J=8.7 Hz, 2H), 4.02 (s, 2H), 3.79 (s, 3H), 2.70-2.61 (m, 1H).

Step 5. Synthesis of 6-cyclohexylpyridine-3-sulfonyl chloride (C21)

N-Chlorosuccinimide (1.87 g, 14.0 mmol) was added to a suspension of C20 (1.1 g, 3.5 mmol) in acetic acid (20 mL) and water (5 mL), and the reaction mixture was stirred at 25° C. for 1 hour. It was then diluted with ethyl acetate (50 mL), washed sequentially with water (50 mL), saturated aqueous sodium bicarbonate solution (50 mL), and saturated aqueous sodium chloride solution (50 mL), and concentrated in vacuo. Chromatography on silica gel (Gradient: 0% to 5% ethyl acetate in petroleum ether) afforded the product as an off-white solid. Yield: 500 mg, 1.9 mmol, 54%. $^1$H NMR (400 MHz, $CDCl_3$) δ 9.14 (d, J=2.4 Hz, 1H), 8.20 (dd, J=8.4, 2.5 Hz, 1H), 7.41 (d, J=8.4 Hz, 1H), 2.86 (tt, J=11.8, 3.4 Hz, 1H), 2.02-1.86 (m, 4H), 1.84-1.75 (m, 1H), 1.64-1.51 (m, 2H), 1.51-1.37 (m, 2H), 1.37-1.24 (m, 1H).

Step 6. Synthesis of 6-cyclohexyl-N-(2-methoxy-7-methyl-6,7,8,9-tetrahydro-5H-pyrido[2,3-d]azepin-3-yl)pyridine-3-sulfonamide (1)

A solution of P3 (30 mg, 0.14 mmol) and C21 (45.1 mg, 0.174 mmol) in pyridine (2 mL) was stirred at 20° C. for 1 hour, and then allowed to stand at 20° C. for 18 hours. The reaction mixture was concentrated to dryness in vacuo; the residue was dissolved in dichloromethane (20 mL), washed sequentially with saturated aqueous sodium bicarbonate solution (10 mL) and saturated aqueous sodium chloride solution (10 mL), dried over sodium sulfate, filtered, and concentrated in vacuo. Silica gel chromatography (Gradient: 0% to 10% methanol in dichloromethane) provided the product as a white solid. Yield: 19.8 mg, 46.0 μmol, 33%. LCMS m/z 431.0 $[M+H]^+$. $^1$H NMR (400 MHz, $CD_3OD$) δ 8.68-8.63 (m, 1H), 7.96 (br d, J=8 Hz, 1H), 7.51 (s, 1H), 7.39 (d, J=8.0 Hz, 1H), 3.53 (s, 3H), 3.04-2.94 (m, 2H), 2.91-2.82 (m, 2H), 2.82-2.71 (m, 1H), 2.68-2.55 (m, 4H), 2.39 (s, 3H), 1.94-1.81 (m, 4H), 1.81-1.72 (m, 1H), 1.62-1.23 (m, 5H).

Example 2

6-(Cyclopentyloxy)-N-(7-ethyl-2-methoxy-6,7,8,9-tetrahydro-5H-pyrido[2,3-d]azepin-3-yl)pyridine-3-sulfonamide (2)

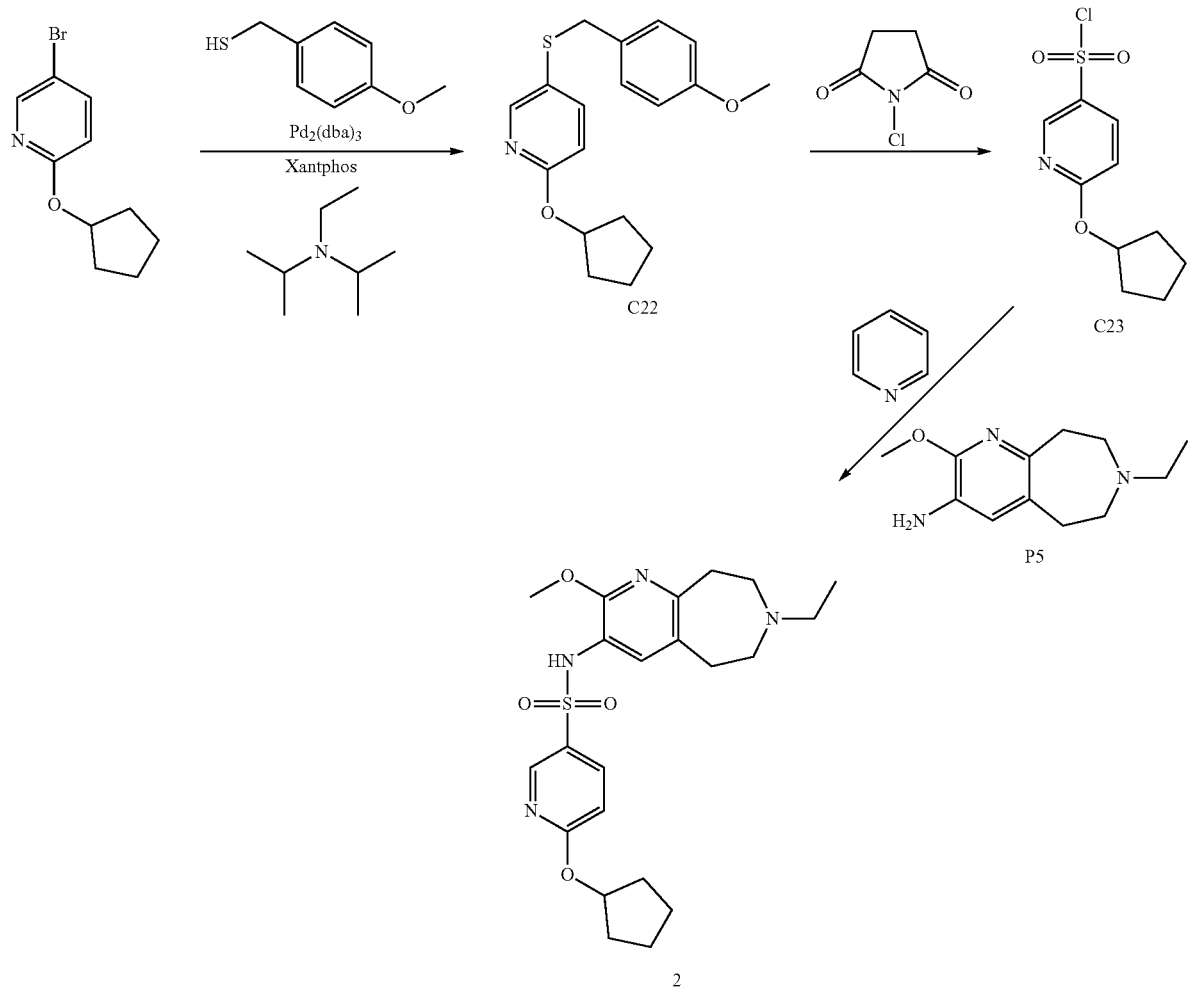

Step 1. Synthesis of 2-(cyclopentyloxy)-5-[(4-methoxybenzyl)sulfanyl]pyridine (C22)

A mixture of 5-bromo-2-(cyclopentyloxy)pyridine (2.90 g, 12.0 mmol), (4-methoxyphenyl)methanethiol (2.5 mL, 18 mmol), N,N-diisopropylethylamine (3.10 g, 24.0 mmol), tris(dibenzylideneacetone)dipalladium(0) (275 mg, 0.300 mmol), and 4,5-bis(diphenylphosphino)-9,9-dimethylxanthene (348 mg, 0.601 mmol) in 1,4-dioxane (20 mL) was purged with nitrogen for 1 minute. The reaction mixture was stirred at 105° C. for 16 hours, whereupon it was concentrated in vacuo; chromatography on silica gel (Gradient: 0% to 8% ethyl acetate in petroleum ether) afforded the product as a pale yellow oil. Yield: 3.41 g, 10.8 mmol, 90%. $^1$H NMR (400 MHz, CDCl$_3$) δ 8.08 (dd, J=2.4, 0.6 Hz, 1H), 7.43 (dd, J=8.5, 2.5 Hz, 1H), 7.08 (br d, J=8.8 Hz, 2H), 6.80 (br d, J=8.7 Hz, 2H), 6.56 (dd, J=8.6, 0.7 Hz, 1H), 5.38-5.31 (m, 1H), 3.90 (s, 2H), 3.79 (s, 3H), 2.01-1.89 (m, 2H), 1.84-1.73 (m, 4H), 1.68-1.57 (m, 2H, assumed; partially obscured by water peak).

Step 2. Synthesis of 6-(cyclopentyloxy)pyridine-3-sulfonyl chloride (C23)

N-Chlorosuccinimide (5.76 g, 43.1 mmol) was added to a 0° C. suspension of C22 (3.40 g, 10.8 mmol) in acetic acid (30 mL) and water (8 mL). After completion of the addition, the ice bath was removed, and the reaction mixture was stirred for 2 hours at 26° C. It was then poured into water (50 mL) and extracted with ethyl acetate (3×50 mL); the combined organic layers were dried over sodium sulfate, filtered, concentrated in vacuo, and combined with the crude product derived from a similar reaction employing C22 (1.51 g, 4.79 mmol). Chromatography on silica gel was carried out twice (Gradient: 0% to 10% ethyl acetate in petroleum ether) to provide the product as a colorless oil. Yield: 3.4 g, 13 mmol, 83%. $^1$H NMR (400 MHz, CDCl$_3$) δ 8.81 (dd, J=2.6, 0.5 Hz, 1H), 8.09 (dd, J=8.9, 2.8 Hz, 1H), 6.83 (dd, J=9.0, 0.6 Hz, 1H), 5.58-5.52 (m, 1H), 2.07-1.95 (m, 2H), 1.89-1.75 (m, 4H), 1.73-1.61 (m, 2H).

Step 3. Synthesis of 6-(cyclopentyloxy)-N-(7-ethyl-2-methoxy-6,7,8,9-tetrahydro-5H-pyrido[2,3-d]azepin-3-yl)pyridine-3-sulfonamide (2)

To a solution of P5 (25.4 mg, 0.115 mmol) in pyridine (2 mL) was added C23 (30.0 mg, 0.115 mmol) and the reaction mixture was stirred at 28° C. for 16 hours. After the reaction mixture had been concentrated in vacuo, the residue was partitioned between ethyl acetate (30 mL) and saturated aqueous sodium bicarbonate solution (30 mL). The aqueous layer was extracted with ethyl acetate (2×30 mL), and the combined organic layers were dried over sodium sulfate, filtered, and concentrated under reduced pressure. Purification via preparative thin-layer chromatography on silica gel (Eluent: 10:1 dichloromethane/methanol) afforded the product as a yellow gum. Yield: 36.4 mg, 81.5 μmol, 71%. LCMS m/z 447.1 [M+H]$^+$. $^1$H NMR (400 MHz, CD$_3$OD) δ 8.37 (d, J=2.5 Hz, 1H), 7.93 (dd, J=8.8, 2.6 Hz, 1H), 7.62 (s, 1H), 6.78 (d, J=8.8 Hz, 1H), 5.45-5.39 (m, 1H), 3.68 (s, 3H), 3.34-3.28 (m, 4H, assumed; obscured by solvent peak), 3.23-3.15 (m, 4H), 3.12-3.06 (m, 2H), 2.02-1.91 (m, 2H), 1.83-1.71 (m, 4H), 1.70-1.61 (m, 2H), 1.35 (t, J=7.3 Hz, 3H).

Example 3

4-[trans-3-(2-Fluoroethoxy)cyclobutyl]-N-(2-methoxy-7-methyl-6,7,8,9-tetrahydro-5H-pyrido[2,3-d]azepin-3-yl)benzenesulfonamide (3)

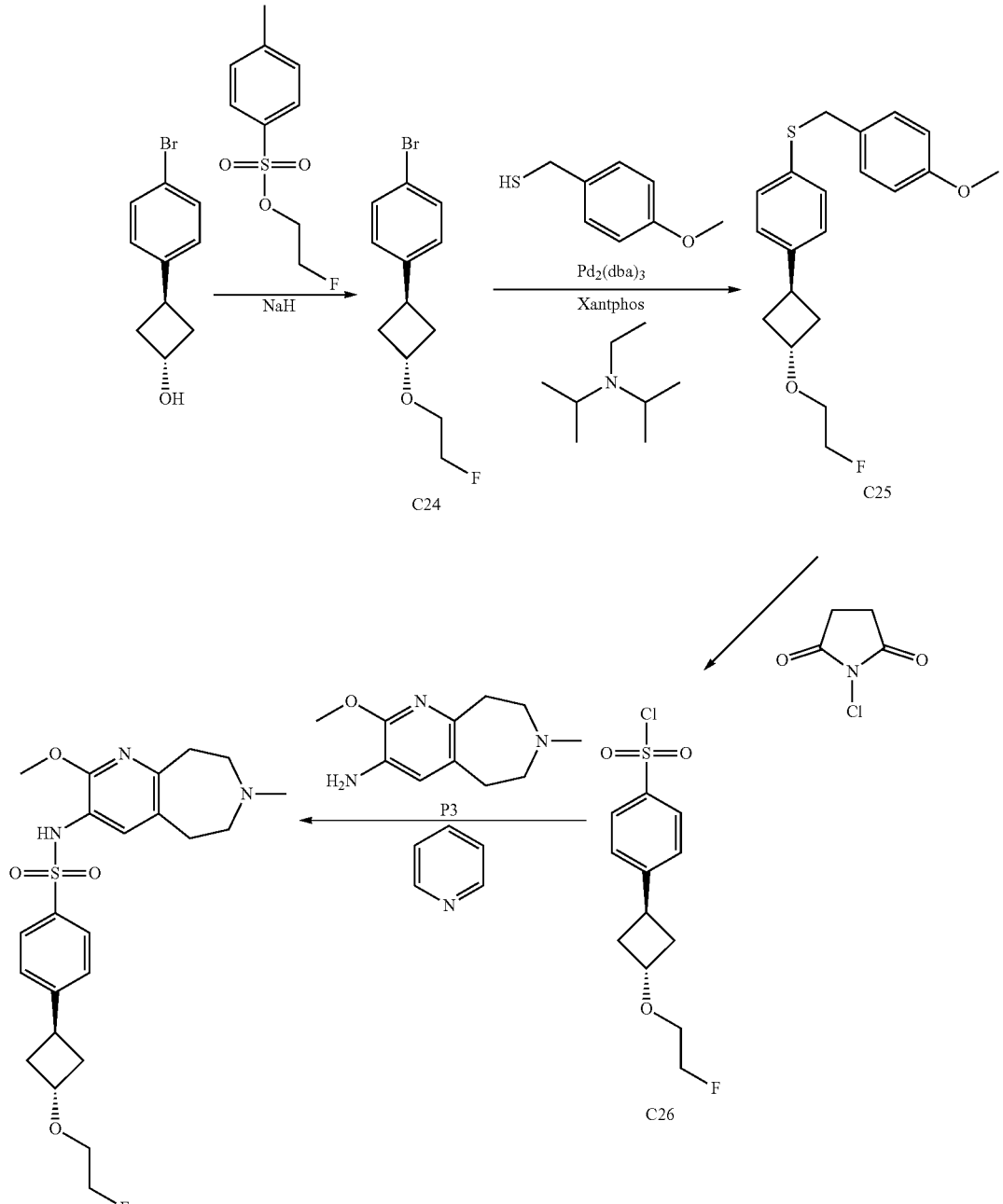

Step 1. Synthesis of 1-bromo-4-[trans-3-(2-fluoroethoxy)cyclobutyl]benzene (C24)

To a 0° C. solution of trans-3-(4-bromophenyl)cyclobutanol (300 mg, 1.32 mmol) in N,N-dimethylformamide (10 mL) was added sodium hydride (60% in oil, 79.3 mg, 1.98 mmol), and the reaction mixture was stirred at 15° C. for 30 minutes. 2-Fluoroethyl 4-methylbenzenesulfonate (346 mg, 1.59 mmol) was added, and stirring was continued at 15° C. for 1 hour, whereupon the reaction mixture was heated at 50° C. for 18 hours. Water (50 mL) was added, and the mixture was extracted with ethyl acetate (30 mL); the organic layer was washed with saturated aqueous sodium chloride solution (3×30 mL), dried over sodium sulfate, filtered, and concentrated in vacuo. Chromatography on silica gel (Gradient: 0% to 20% ethyl acetate in petroleum ether) provided the product as a pale yellow oil. Yield: 260 mg, 0.952 mmol, 72%. $^1$H NMR (400 MHz, CDCl$_3$) δ 7.43 (br d, J=8.3 Hz, 2H), 7.12 (br d, J=8.5 Hz, 2H), 4.59 (ddd, J=47.4, 4.1, 4.1 Hz, 2H), 4.26-4.18 (m, 1H), 3.64 (ddd, J=29.5, 4.1, 4.1 Hz, 2H), 3.6-3.54 (m, 1H), 2.57-2.47 (m, 2H), 2.43-2.34 (m, 2H).

Step 2. Synthesis of 1-[trans-3-(2-fluoroethoxy)cyclobutyl]-4-[(4-methoxybenzyl)sulfanyl]benzene (C25)

To a solution of C24 (260 mg, 0.952 mmol) in 1,4-dioxane (10 mL) were added (4-methoxyphenyl)methanethiol (161 mg, 1.04 mmol) and N,N-diisopropylethylamine (369 mg, 2.85 mmol). The mixture was degassed with nitrogen for 2 minutes, and then tris(dibenzylideneacetone)dipalladium(0) (21.8 mg, 23.8 µmol) and 4,5-bis(diphenylphosphino)-9,9-dimethylxanthene (27.5 mg, 47.5 µmol) were added. The reaction mixture was stirred at 100° C. for 18 hours, whereupon it was concentrated in vacuo; the residue was purified by silica gel chromatography (Gradient: 0% to 20% ethyl acetate in petroleum ether) to afford the product as a white solid. Yield: 265 mg, 0.765 mmol, 80%. $^1$H NMR (400 MHz, CDCl$_3$) δ 7.27 (br d, J=7.9 Hz, 2H, assumed; partially obscured by solvent peak), 7.21 (br d, J=8.4 Hz, 2H), 7.14 (br d, J=8.2 Hz, 2H), 6.83 (br d, J=8.4 Hz, 2H), 4.59 (ddd, J=47.6, 4.5, 3.8 Hz, 2H), 4.26-4.19 (m, 1H), 4.06 (s, 2H), 3.80 (s, 3H), 3.64 (ddd, J=29.5, 4.3, 3.9 Hz, 2H), 3.6-3.54 (m, 1H), 2.55-2.45 (m, 2H), 2.44-2.34 (m, 2H).

Step 3. Synthesis of 4-[trans-3-(2-fluoroethoxy)cyclobutyl]benzenesulfonyl chloride (C26)

N-Chlorosuccinimide (231 mg, 1.73 mmol) was added to a 10° C. solution of C25 (150 mg, 0.433 mmol) in acetic acid (5 mL) and water (1 mL), and the reaction mixture was stirred at 10° C. for 30 minutes. It was then diluted with ethyl acetate (30 mL), washed sequentially with saturated aqueous sodium bicarbonate solution (50 mL) and saturated aqueous sodium chloride solution (2×30 mL), dried over sodium sulfate, filtered, and concentrated in vacuo to afford the product as a pale yellow oil. Yield: 127 mg, assumed quantitative.

Step 4. Synthesis of 4-[trans-3-(2-fluoroethoxy)cyclobutyl]-N-(2-methoxy-7-methyl-6,7,8,9-tetrahydro-5H-pyrido[2,3-d]azepin-3-yl)benzenesulfonamide (3)

To a solution of P3 (40.0 mg, 0.193 mmol) in pyridine (3 mL) was added C26 (63.5 mg, 0.217 mmol), and the reaction mixture was stirred at 8 to 10° C. for 18 hours. After removal of solvent in vacuo, the residue was dissolved in dichloromethane (30 mL), washed sequentially with saturated aqueous sodium bicarbonate solution (20 mL) and saturated aqueous sodium chloride solution (20 mL), and concentrated under reduced pressure. Purification via preparative thin-layer chromatography on silica gel (Eluent: 10:1 dichloromethane/methanol) afforded a solid, which was dissolved in acetonitrile (3 mL), treated with water (~40 mL), and lyophilized, providing the product as a white solid. Yield: 29.7 mg, 64.1 µmol, 33%. LCMS m/z 464.0 [M+H]$^+$. $^1$H NMR (400 MHz, CDCl$_3$) δ 7.69 (br d, J=8.4 Hz, 2H), 7.53 (s, 1H), 7.29 (br d, J=8.2 Hz, 2H), 4.58 (ddd, J=47.7, 4.1, 4.1 Hz, 2H), 4.24-4.17 (m, 1H), 3.73 (s, 3H), 3.70-3.62 (m, 1H), 3.63 (ddd, J=29.7, 4.1, 4.1 Hz, 2H), 3.09-3.00 (m, 2H), 2.93-2.84 (m, 2H), 2.70-2.57 (m, 4H), 2.58-2.49 (m, 2H), 2.45-2.34 (m, 2H), 2.44 (s, 3H).

Example 4

N-(2-Methoxy-7-methyl-6,7,8,9-tetrahydro-5H-pyrido[2,3-d]azepin-3-yl)-4-(tetrahydro-2H-pyran-4-yl)benzenesulfonamide (4)

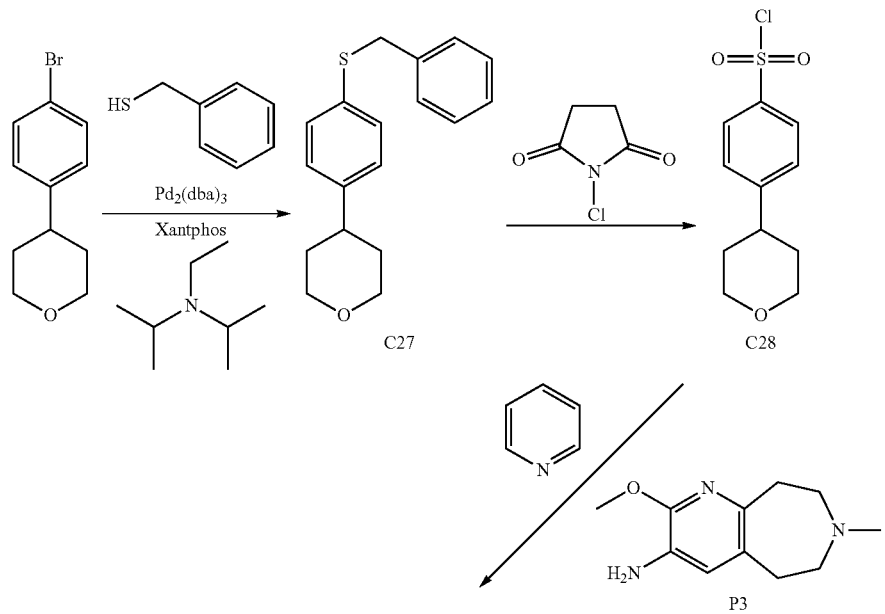

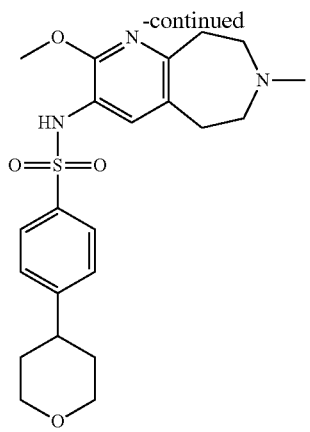

4

Step 1. Synthesis of 4-[4-(benzylsulfanyl)phenyl]tetrahydro-2H-pyran (C27)

Reaction of 4-(4-bromophenyl)tetrahydro-2H-pyran with phenylmethanethiol was carried out using the method described for synthesis of C19 from C18 in Example 1. The product was obtained as a yellow solid. Yield: 6.9 g, 24 mmol, 86%. $^1$H NMR (400 MHz, CDCl$_3$) δ 7.33-7.22 (m, 7H), 7.13 (br d, J=8.2 Hz, 2H), 4.14-4.05 (m, 2H), 4.11 (s, 2H), 3.57-3.48 (m, 2H), 2.77-2.67 (m, 1H), 1.85-1.70 (m, 4H).

Step 2. Synthesis of 4-(tetrahydro-2H-pyran-4-yl)benzenesulfonyl chloride (C28)

N-Chlorosuccinimide (14.8 g, 111 mmol) was added to a 0° C. slurry of C27 (10.0 g, 35.2 mmol) in acetic acid (60 mL) and water (20 mL). The reaction mixture was allowed to warm to 25° C. and stir for 2 hours, whereupon it was diluted with ethyl acetate (200 mL), washed sequentially with water (100 mL) and saturated aqueous sodium chloride solution (2×100 mL), dried over sodium sulfate, filtered, and concentrated in vacuo. Silica gel chromatography (Gradient: 0% to 60% ethyl acetate in petroleum ether) provided partially purified product as a solid; this material was washed with tert-butyl methyl ether (30 mL) and petroleum ether (20 mL). Isolation via filtration afforded the product as a white solid. Yield: 6.70 g, 25.7 mmol, 73%. $^1$H NMR (400 MHz, CDCl$_3$) δ 8.00 (br d, J=8.5 Hz, 2H), 7.48 (br d, J=8.3 Hz, 2H), 4.16-4.08 (m, 2H), 3.60-3.51 (m, 2H), 2.96-2.86 (m, 1H), 1.92-1.76 (m, 4H).

Step 3. Synthesis of N-(2-methoxy-7-methyl-6,7,8,9-tetrahydro-5H-pyrido[2,3-d]azepin-3-yl)-4-(tetrahydro-2H-pyran-4-yl)benzenesulfonamide (4)

A solution of P3 (1.50 g, 7.24 mmol) in pyridine (20 mL) was cooled in an ice bath and treated with C28 (1.98 g, 7.59 mmol) in five portions. The reaction mixture was then allowed to stir at 26° C. for 16 hours, whereupon it was concentrated in vacuo. The residue was dissolved in dichloromethane (200 mL), washed sequentially with saturated aqueous sodium bicarbonate solution (200 mL) and saturated aqueous sodium chloride solution (150 mL), dried over sodium sulfate, filtered, and concentrated under reduced pressure. The resulting material was dissolved in dichloromethane (10 mL) and slowly added over 10 minutes to petroleum ether (40 mL) that was stirring at 24 to 26° C. The mixture was then cooled to 5 to 10° C., and stirred for 10 minutes; the resulting precipitate was collected via filtration to afford the product as a yellow solid. Yield: 2.75 g, 6.37 mmol, 88%. LCMS m/z 432.1 [M+H]$^+$. $^1$H NMR (400 MHz, DMSO-d$_6$) δ 7.61 (br d, J=8.3 Hz, 2H), 7.41 (br d, J=8.3 Hz, 2H), 7.32 (s, 1H), 3.98-3.90 (m, 2H), 3.47 (s, 3H), 3.47-3.38 (m, 2H), 2.90-2.80 (m, 3H), 2.76-2.69 (m, 2H), 2.47-2.39 (m, 4H), 2.25 (s, 3H), 1.72-1.61 (m, 4H).

Example 5

N-(2-Methoxy-7-methyl-6,7,8,9-tetrahydro-5H-pyrido[2,3-d]azepin-3-yl)-4-methylbenzenesulfonamide (5)

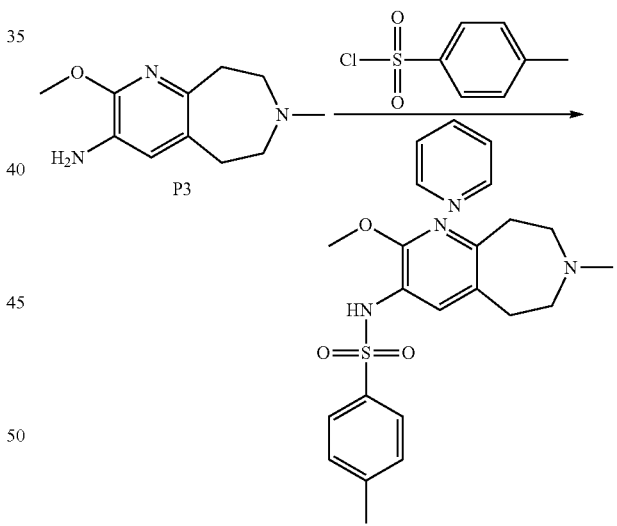

5

4-Methylbenzenesulfonyl chloride (404 mg, 2.12 mmol) was added to a solution of P3 (418 mg, 2.02 mmol) in pyridine (10 mL). After the reaction mixture had stirred for 30 minutes at room temperature, it was concentrated in vacuo. The residue was azeotroped with heptane and then partitioned between saturated aqueous sodium bicarbonate solution (25 mL) and dichloromethane (50 mL). The aqueous layer was extracted with dichloromethane (50 mL) and the combined organic layers were dried over magnesium sulfate, filtered, and concentrated under reduced pressure. Chromatography on silica gel (Eluent: 0.15% ammonium hydroxide in a 4:1 mixture of ethyl acetate and methanol) afforded the product as a very pale yellow solid. Yield: 500 mg, 1.38 mmol, 68%. LCMS m/z 362.2 [M+H]+. 1H NMR (400 MHz, CDCl3) δ 7.63 (br d, J=8.3 Hz, 2H), 7.50 (s, 1H), 7.24-7.19 (m, 2H), 3.72 (s, 3H), 3.00-2.95 (m, 2H), 2.84-2.79 (m, 2H), 2.58-2.50 (m, 4H), 2.37 (s, 6H).

Example 6

N-(2-Methoxy-7-methyl-6,7,8,9-tetrahydro-5H-pyrido[2,3-d]azepin-3-yl)-4-(tetrahydro-2H-pyran-2-yl)benzenesulfonamide (6)

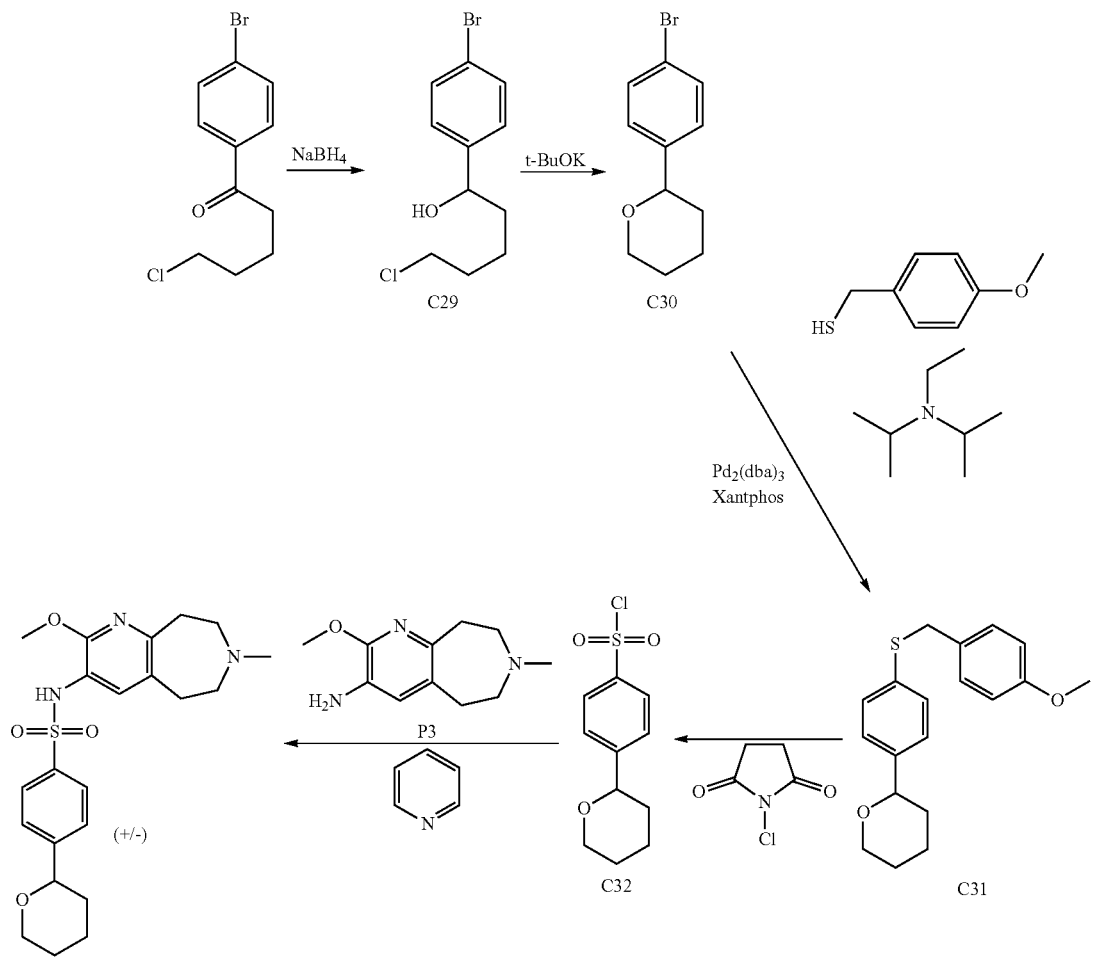

Step 1. Synthesis of 1-(4-bromophenyl)-5-chloropentan-1-ol (C29)

Sodium borohydride (412 mg, 10.9 mmol) was added to a solution of 1-(4-bromophenyl)-5-chloropentan-1-one (2.00 g, 7.26 mmol) in tetrahydrofuran (50 mL) and water (5 mL), and the reaction mixture was stirred at room temperature overnight. After addition of methanol (10 mL), the mixture was concentrated to dryness under reduced pressure; the residue was dissolved in ethyl acetate (50 mL) and filtered through a pad of diatomaceous earth. Concentration of the filtrate in vacuo afforded the product as a colorless gum. Yield: 1.95 g, 7.02 mmol, 97%. 1H NMR (400 MHz, CDCl3) δ 7.48 (br d, J=8.4 Hz, 2H), 7.23 (br d, J=8.3 Hz, 2H), 4.70-4.63 (m, 1H), 3.53 (t, J=6.6 Hz, 2H), 1.88 (d, J=3.4 Hz, 1H), 1.85-1.65 (m, 4H), 1.64-1.51 (m, 1H, assumed; partially obscured by water peak), 1.50-1.38 (m, 1H).

Step 2. Synthesis of 2-(4-bromophenyl)tetrahydro-2H-pyran (C30)

Potassium tert-butoxide (1.18 g, 10.5 mmol) was added to a 0° C. solution of C29 (1.95 g, 7.02 mmol) in tetrahydrofuran (50 mL). The reaction mixture was allowed to warm to ambient temperature (around 15° C.) and stirred overnight, whereupon it was partitioned between water (50 mL) and ethyl acetate (100 mL). The organic layer was washed with saturated aqueous sodium chloride solution (30 mL), dried over sodium sulfate, filtered, and concentrated in vacuo, providing the product as a yellow liquid that solidified on standing overnight. Yield: 1.62 g, 6.72 mmol, 96%. 1H NMR (400 MHz, CDCl3) δ 7.46 (br d, J=8.4 Hz, 2H), 7.23 (br d, J=8.3 Hz, 2H), 4.29 (dd, J=11, 2 Hz, 1H), 4.17-4.11 (m, 1H), 3.65-3.57 (m, 1H), 2.00-1.90 (m, 1H), 1.85-1.77 (m, 1H), 1.74-1.48 (m, 4H).

Step 3. Synthesis of 2-{4-[(4-methoxybenzyl)sulfanyl]phenyl}tetrahydro-2H-pyran (C31)

Reaction of C30 (1.62 g, 6.72 mmol) with (4-methoxyphenyl)methanethiol was effected using the method described for synthesis of C25 from C24 in Example 3. In this case, silica gel chromatography was carried out using a gradient of 0% to 30% dichloromethane in petroleum ether. The product was obtained as a white solid. Yield: 2.0 g, 6.4 mmol, 95%. $^1$H NMR (400 MHz, CDCl$_3$) δ 7.26 (br AB quartet, J$_{AB}$=8.5 Hz, Δν$_{AB}$=12 Hz, 4H), 7.20 (br d, J=8.7 Hz, 2H), 6.81 (br d, J=8.7 Hz, 2H), 4.32-4.26 (m, 1H), 4.17-4.10 (m, 1H), 4.06 (s, 2H), 3.79 (s, 3H), 3.65-3.57 (m, 1H), 1.98-1.91 (m, 1H), 1.84-1.77 (m, 1H), 1.73-1.62 (m, 2H), 1.62-1.53 (m, 2H, assumed; partially obscured by water peak).

Step 4. Synthesis of 4-(tetrahydro-2H-pyran-2-yl)benzenesulfonyl chloride (C32)

Conversion of C31 to C32 was carried out using the method described for synthesis of C21 from C20 in Example 1. The product was obtained as a white solid, which by $^1$H NMR analysis contained some impurities. Yield: 1.55 g, <5.94 mmol, <93%. $^1$H NMR (400 MHz, CDCl$_3$), product peaks only: δ 8.01 (br d, J=8.5 Hz, 2H), 7.60 (br d, J=8.7 Hz, 2H), 4.44 (br dd, J=11.2, 1.9 Hz, 1H), 4.21-4.15 (m, 1H), 3.68-3.59 (m, 1H), 2.02-1.96 (m, 1H), 1.93-1.86 (m, 1H), 1.76-1.60 (m, 3H), 1.57-1.45 (m, 1H).

Step 5. Synthesis of N-(2-methoxy-7-methyl-6,7,8,9-tetrahydro-5H-pyrido[2,3-d]azepin-3-yl)-4-(tetrahydro-2H-pyran-2-yl)benzenesulfonamide (6)

Reaction of C32 with P3 was effected according to the method described for synthesis of 1 from C21 and P3 in Example 1. Chromatographic purification in this case was carried out using preparative thin-layer chromatography on silica gel (Eluent: 10:1 dichloromethane/methanol), providing the product as a white solid. Yield: 54.1 mg, 0.125 mmol, 66%. LCMS m/z 431.9 [M+H]$^+$. $^1$H NMR (400 MHz, CD$_3$OD) δ 7.69 (br d, J=8.5 Hz, 2H), 7.60 (s, 1H), 7.44 (br d, J=8.3 Hz, 2H), 4.40 (br dd, J=11.2, 1.9 Hz, 1H), 4.12-4.06 (m, 1H), 3.66-3.58 (m, 1H), 3.64 (s, 3H), 3.31-3.20 (m, 4H), 3.20-3.12 (m, 2H), 3.09-3.01 (m, 2H), 2.86 (s, 3H), 1.97-1.89 (m, 1H), 1.88-1.80 (m, 1H), 1.79-1.55 (m, 3H), 1.50-1.39 (m, 1H).

Example 7

N-(2-Methoxy-7-methyl-6,7,8,9-tetrahydro-5H-pyrido[2,3-d]azepin-3-yl)-4-[(2R)-tetrahydro-2H-pyran-2-yl]benzenesulfonamide (7)

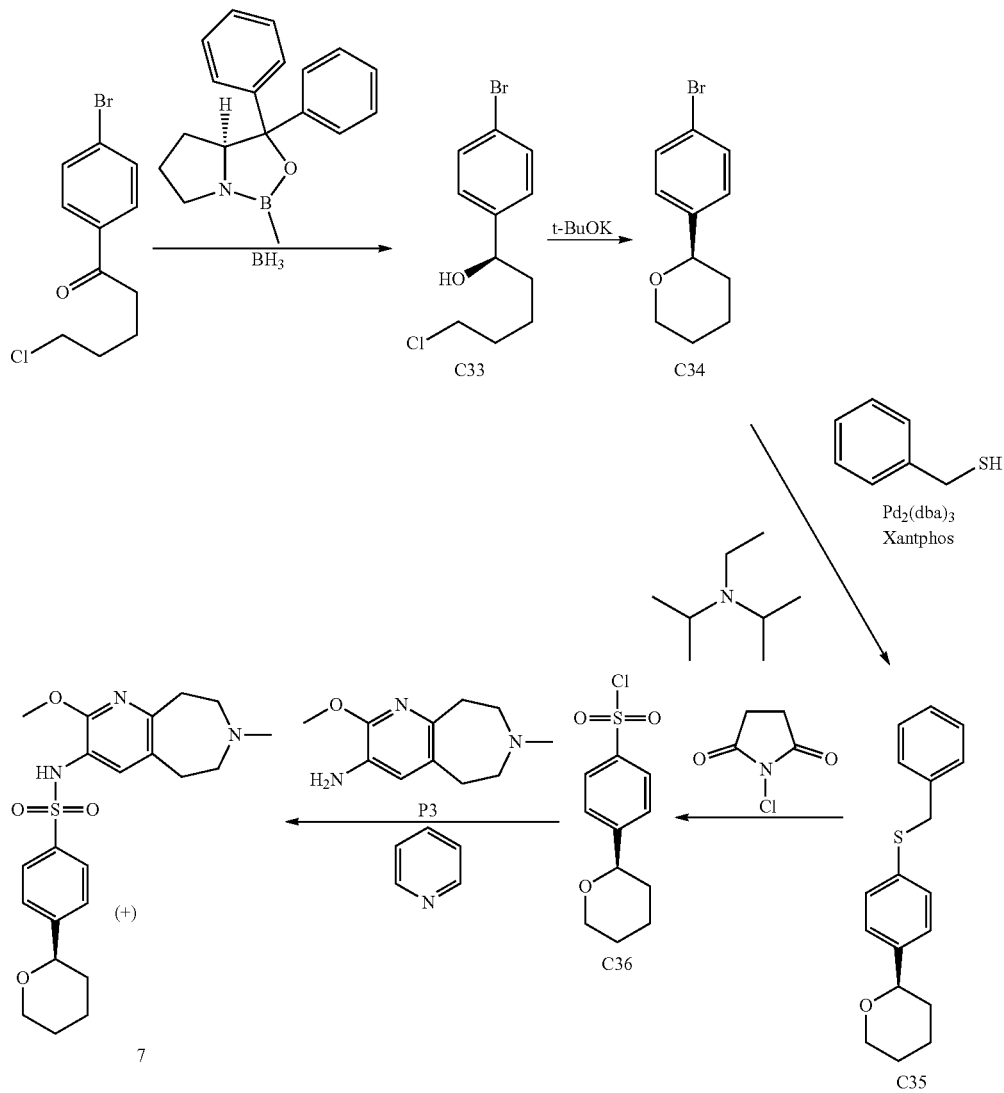

Step 1. Synthesis of (1R)-1-(4-bromophenyl)-5-chloropentan-1-ol (C33)

This experiment was carried out in three parallel batches. (3aS)-1-Methyl-3,3-diphenyltetrahydro-3H-pyrrolo[1,2-c][1,3,2]oxazaborole [(S)-2-methyl-CBS-oxazaborolidine; 1M solution in toluene, 16 mL, 16 mmol] was added to a 0° C. solution of borane (1M solution in tetrahydrofuran; 188 mL, 188 mmol) and tetrahydrofuran (500 mL). The reaction mixture was stirred at 0° C. for 45 minutes, whereupon it was cooled to −5° C. and a solution of 1-(4-bromophenyl)-5-chloropentan-1-one (43.0 g, 156 mmol) in tetrahydrofuran (600 mL) was added drop-wise over 4 hours while the reaction temperature was kept below −4° C. After the addition was complete, the reaction mixture was stirred at −5 to 0° C. for 10 minutes, at which time the reaction was quenched via addition of methanol (300 mL) at 0 to 5° C. The resulting mixture was stirred at −5 to 5° C. for 30 minutes, whereupon aqueous hydrochloric acid (1M, 450 mL) was added at 0° C. The mixture was allowed to warm to room temperature and stirred at 25° C. for 18 hours; it was then diluted with water (700 mL) and extracted with ethyl acetate (2×1 L). The combined organic layers were washed with saturated aqueous sodium chloride solution, dried over sodium sulfate, filtered, and concentrated in vacuo. The three batches were combined and subjected to silica gel chromatography (Gradient: 5% to 17% ethyl acetate in petroleum ether) to afford the product as a colorless oil. The indicated absolute stereochemistry was confirmed via X-ray crystal structure analysis carried out on 7 (see below). Yield: 130 g, 468 mmol, 100%. $^1$H NMR (400 MHz, CDCl$_3$) δ 7.48 (br d, J=8.4 Hz, 2H), 7.23 (br d, J=8.4 Hz, 2H), 4.66 (dd, J=7.3, 5.7 Hz, 1H), 3.53 (t, J=6.6 Hz, 2H), 1.86-1.36 (m, 6H).

Step 2. Synthesis of (2R)-2-(4-bromophenyl)tetrahydro-2H-pyran (C34)

This experiment was carried out in two parallel batches. Potassium tert-butoxide (1M solution in tetrahydrofuran; 330 mL, 330 mmol) was slowly added to a 0° C. solution of C33 (65.0 g, 234 mmol) in tetrahydrofuran (700 mL); after completion of the addition, the ice bath was removed and the reaction was stirred at 25° C. for 2 hours. The reaction mixture was then cooled to 0° C. and quenched via addition of aqueous hydrochloric acid (1M, 700 mL). The mixture was extracted with ethyl acetate (2×1 L), and the combined organic layers were washed with saturated aqueous sodium chloride solution, dried over sodium sulfate, filtered, and concentrated in vacuo. The batches were combined and purified by chromatography on silica gel (Gradient: 5% to 9% ethyl acetate in petroleum ether) to provide the product as a colorless oil. Yield: 109 g, 452 mmol, 97%. LCMS m/z 241.1, 243.1 [M+H]$^+$. $^1$H NMR (400 MHz, CDCl$_3$) δ 7.46 (br d, J=8.5 Hz, 2H), 7.23 (br d, J=8.3 Hz, 2H), 4.29 (br dd, J=11, 2 Hz, 1H), 4.17-4.11 (m, 1H), 3.65-3.57 (m, 1H), 2.00-1.90 (m, 1H), 1.85-1.78 (m, 1H), 1.73-1.48 (m, 4H, assumed; partially obscured by water peak).

Step 3. Synthesis of (2R)-2-[4-(benzylsulfanyl)phenyl]tetrahydro-2H-pyran (C35)

This experiment was carried out in two parallel batches. To a stirred solution of C34 (53.0 g, 220 mmol) in 1,4-dioxane (700 mL) were added phenylmethanethiol (35.5 g, 286 mmol), N,N-diisopropylethylamine (85.2 g, 660 mmol), 4,5-bis(diphenylphosphino)-9,9-dimethylxanthene (5.09 g, 8.80 mmol), and tris(dibenzylideneacetone)dipalladium(0) (4.03 g, 4.40 mmol). The vessel containing the reaction mixture was evacuated and charged with nitrogen; this cycle was repeated twice, and the reaction mixture was then stirred at 115° C. for 16 hours. After cooling to room temperature, the two crude mixtures were combined and concentrated in vacuo. Silica gel chromatography (Gradient: 2% to 5% ethyl acetate in petroleum ether) was followed by two recrystallizations from a mixture of dichloromethane and petroleum ether (1:12, 3.9 L), to afford the product as a yellow solid. Yield: 100 g, 352 mmol, 80%. $^1$H NMR (400 MHz, CDCl$_3$) δ 7.32-7.21 (m, 9H), 4.29 (br dd, J=11, 2 Hz, 1H), 4.17-4.11 (m, 1H), 4.10 (s, 2H), 3.65-3.57 (m, 1H), 1.99-1.90 (m, 1H), 1.85-1.77 (m, 1H), 1.73-1.51 (m, 4H, assumed; partially obscured by water peak).

Step 4. Synthesis of 4-[(2R)-tetrahydro-2H-pyran-2-yl]benzenesulfonyl chloride (C36)

This experiment was carried out in two parallel batches. N-Chlorosuccinimide (84.5 g, 633 mmol) was slowly added to a 0° C. stirred suspension of C35 (45.0 g, 158 mmol) in acetic acid (500 mL) and water (140 mL). The reaction mixture was then allowed to warm to room temperature, stirred at 22° C. for 1 hour, and poured into tert-butyl methyl ether (1.5 L); the resulting mixture was washed with water (3×1.5 L) and adjusted to a pH of 7 via addition of saturated aqueous sodium bicarbonate solution. The organic layer was washed with saturated aqueous sodium chloride solution, dried over sodium sulfate, filtered, and concentrated in vacuo. The two batches were combined and purified via silica gel chromatography (Gradient: 3% to 5% ethyl acetate in petroleum ether) followed by crystallization from tert-butyl methyl ether and petroleum ether (1:10, 1.1 L) at −65° C. under nitrogen, affording the product as a white solid. Yield: 63.0 g, 242 mmol, 77%. LCMS, after dissolution in dichloromethane and treatment with pyridine and benzylamine, m/z 332.1 [M+H]$^+$ for N-benzyl-4-[(2R)-tetrahydro-2H-pyran-2-yl]benzenesulfonamide. $^1$H NMR (400 MHz, CDCl$_3$) δ 8.01 (br d, J=8.7 Hz, 2H), 7.60 (br d, J=8.7 Hz, 2H), 4.44 (br dd, J=11.3, 2.0 Hz, 1H), 4.22-4.14 (m, 1H), 3.68-3.59 (m, 1H), 2.04-1.93 (m, 1H), 1.90 (br d, J=13 Hz, 1H), 1.78-1.6 (m, 3H), 1.57-1.45 (m, 1H).

Step 5. Synthesis of N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide (7)

A solution of C36 (2.38 g, 9.13 mmol) and P3 (1.80 g, 8.68 mmol) in pyridine (20 mL) was stirred at 28° C. for 4 hours. The reaction mixture was then concentrated in vacuo and the residue was partitioned between saturated aqueous sodium bicarbonate solution (40 mL) and ethyl acetate (40 mL). The aqueous layer was extracted with ethyl acetate (2×30 mL), and the combined organic layers were dried over sodium sulfate, filtered, and concentrated under reduced pressure. Chromatography on silica gel (Gradient: 0% to 10% methanol in dichloromethane) afforded the product as a white solid, which exhibited a positive (+) rotation. Yield:

2.66 g, 6.16 mmol, 71%. LCMS m/z 432.1 [M+H]$^+$. $^1$H NMR (400 MHz, CDCl$_3$) δ 7.72 (br d, J=8.5 Hz, 2H), 7.51 (s, 1H), 7.41 (brd, J=8.2 Hz, 2H), 4.34 (br dd, J=11.2 Hz, 1H), 4.17-4.10 (m, 1H), 3.73 (s, 3H), 3.63-3.55 (m, 1H), 3.00-2.94 (m, 2H), 2.84-2.78 (m, 2H), 2.58-2.49 (m, 4H), 2.37 (s, 3H), 1.98-1.91 (m, 1H), 1.85-1.78 (m, 1H), 1.74-1.56 (m, 3H, assumed; partially obscured by water peak), 1.53-1.41 (m, 1H).

A sample of 7 was crystallized from ethyl acetate and methanol; single-crystal X-ray structural analysis (see below) confirmed the absolute stereochemistry shown for 7.

Single-Crystal X-Ray Structure Determination on 7

Data collection was performed on a Bruker APEX diffractometer at room temperature. Data collection consisted of omega and phi scans.

The structure was solved by direct methods using SHELX software suite in the space group P2$_1$. The structure was subsequently refined by the full-matrix least squares method. All non-hydrogen atoms were found and refined using anisotropic displacement parameters.

The hydrogen atom located on nitrogen was found from the Fourier difference map and refined freely. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2010). The results indicate that the absolute structure has been correctly assigned. The method calculates that the probability that the structure is correct is 100.0. The Hooft parameter is reported as 0.12 with an esd of 0.06. Flack parameter refinement offers similar values of 0.08 (0.06).

The final R-index was 5.5%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-5.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE 1

Crystal data and structure refinement for 7.

| | |
|---|---|
| Empirical formula | C$_{22}$H$_{29}$N$_3$O$_4$S |
| Formula weight | 431.55 |
| Temperature | 296(2) K |
| Wavelength | 1.54178 Å |
| Crystal system | Monoclinic |
| Space group | P2$_1$ |
| Unit cell dimensions | a = 12.125(3) Å    α = 900 |
| | b = 5.0845(13) Å    β = 95.678(14)° |
| | c = 17.802(5) Å    γ = 90° |
| Volume | 1092.1(5) Å$^3$ |
| Z | 2 |
| Density (calculated) | 1.312 Mg/m$^3$ |
| Absorption coefficient | 1.594 mm$^{-1}$ |
| F(000) | 460 |
| Crystal size | 0.16 × 0.06 × 0.04 mm$^3$ |
| Theta range for data collection | 2.49 to 53.15° |
| Index ranges | −12 <= h <= 12, −3 <= k <= 3, −18 <= l <= 17 |
| Reflections collected | 3330 |
| Independent reflections | 1361 [R(int) = 0.0836] |
| Completeness to theta = 70.31° | 64.3% |
| Absorption correction | None |
| Max. and min. transmission | 0.9390 and 0.7846 |
| Refinement method | Full-matrix least-squares on F$^2$ |
| Data/restraints/parameters | 1361/1/278 |
| Goodness-of-fit on F$^2$ | 1.012 |
| Final R indices [I > 2sigma(I)] | R1 = 0.0552, wR2 = 0.1041 |
| R indices (all data) | R1 = 0.0926, wR2 = 0.1148 |
| Absolute structure parameter | 0.08(6) |
| Extinction coefficient | 0.0042(6) |
| Largest diff. peak and hole | 0.153 and −0.181 e.Å$^{-3}$ |

TABLE 2

Atomic coordinates (×10$^4$) and equivalent isotropic displacement parameters (Å$^2$ × 10$^3$) for 7.

| | x | y | z | U(eq) |
|---|---|---|---|---|
| S(1) | 4594(3) | 3038(8) | 7738(2) | 75(1) |
| N(1) | 5111(8) | 1220(30) | 7077(6) | 65(3) |
| N(2) | 8014(8) | 2350(30) | 6638(7) | 70(4) |
| N(3) | 8257(10) | 6270(30) | 4430(7) | 87(4) |

TABLE 2-continued

Atomic coordinates (×10⁴) and equivalent isotropic displacement parameters (Å² × 10³) for 7.

| | x | y | z | U(eq) |
|---|---|---|---|---|
| O(1) | 8612(9) | −570(20) | 10301(5) | 85(3) |
| O(2) | 3583(6) | 1670(17) | 7883(4) | 80(3) |
| O(3) | 4567(6) | 5710(20) | 7483(4) | 76(3) |
| O(4) | 7245(6) | −500(20) | 7464(5) | 80(3) |
| C(1) | 9529(11) | −930(30) | 10848(9) | 105(6) |
| C(2) | 9161(11) | −940(30) | 11638(7) | 92(5) |
| C(3) | 8549(12) | 1490(30) | 11798(7) | 88(5) |
| C(4) | 7619(11) | 1880(30) | 11168(8) | 92(5) |
| C(5) | 8076(12) | 1850(30) | 10415(8) | 73(5) |
| C(6) | 7178(13) | 2130(40) | 9768(9) | 61(5) |
| C(7) | 7217(11) | 4140(40) | 9245(11) | 84(5) |
| C(8) | 6414(15) | 4540(30) | 8635(9) | 71(5) |
| C(9) | 5558(12) | 2790(40) | 8562(8) | 61(4) |
| C(10) | 5472(11) | 820(30) | 9057(10) | 64(5) |
| C(11) | 6285(16) | 430(30) | 9663(9) | 71(5) |
| C(12) | 6032(11) | 2380(30) | 6717(9) | 66(5) |
| C(13) | 5876(12) | 4270(40) | 6175(8) | 88(5) |
| C(14) | 6803(14) | 5210(30) | 5859(8) | 66(5) |
| C(15) | 7843(13) | 4180(40) | 6098(8) | 74(5) |
| C(16) | 7115(15) | 1460(30) | 6926(7) | 68(4) |
| C(17) | 8375(9) | −1300(30) | 7730(6) | 98(6) |
| C(18) | 8888(8) | 5120(30) | 5763(7) | 83(5) |
| C(19) | 8875(10) | 4430(30) | 4936(9) | 93(5) |
| C(20) | 7059(11) | 6200(30) | 4469(6) | 95(5) |
| C(21) | 6689(9) | 7170(30) | 5232(8) | 86(5) |
| C(22) | 8426(10) | 5600(40) | 3635(6) | 134(7) |

U(eq) is defined as one-third of the trace of the orthogonalized $U^{ij}$ tensor.

TABLE 3

Bond lengths [Å] and angles [°] for 7.

| | |
|---|---|
| S(1)—O(3) | 1.431(9) |
| S(1)—O(2) | 1.455(7) |
| S(1)—N(1) | 1.665(11) |
| S(1)—C(9) | 1.788(13) |
| N(1)—C(12) | 1.464(16) |
| N(2)—C(16) | 1.330(14) |
| N(2)—C(15) | 1.338(15) |
| N(3)—C(19) | 1.455(13) |
| N(3)—C(20) | 1.462(12) |
| N(3)—C(22) | 1.489(12) |
| O(1)—C(5) | 1.416(15) |
| O(1)—C(1) | 1.416(12) |
| O(4)—C(16) | 1.378(13) |
| O(4)—C(17) | 1.462(10) |
| C(1)—C(2) | 1.517(13) |
| C(2)—C(3) | 1.483(15) |
| C(3)—C(4) | 1.523(13) |
| C(4)—C(5) | 1.500(14) |
| C(5)—C(6) | 1.512(15) |
| C(6)—C(11) | 1.384(14) |
| C(6)—C(7) | 1.387(16) |
| C(7)—C(8) | 1.399(14) |
| C(8)—C(9) | 1.364(15) |
| C(9)—C(10) | 1.346(14) |
| C(10)—C(11) | 1.401(14) |
| C(12)—C(13) | 1.361(16) |
| C(12)—C(16) | 1.409(15) |
| C(13)—C(14) | 1.391(15) |
| C(14)—C(15) | 1.391(16) |
| C(14)—C(21) | 1.493(15) |
| C(15)—C(18) | 1.529(15) |
| C(18)—C(19) | 1.513(14) |
| C(20)—C(21) | 1.552(13) |
| O(3)—S(1)—O(2) | 121.2(6) |
| O(3)—S(1)—N(1) | 107.5(7) |
| O(2)—S(1)—N(1) | 104.1(6) |
| O(3)—S(1)—C(9) | 108.6(8) |
| O(2)—S(1)—C(9) | 108.3(8) |
| N(1)—S(1)—C(9) | 106.2(6) |
| C(12)—N(1)—S(1) | 116.4(10) |

TABLE 3-continued

Bond lengths [Å] and angles [°] for 7.

| | |
|---|---|
| C(16)—N(2)—C(15) | 116.1(12) |
| C(19)—N(3)—C(20) | 114.0(11) |
| C(19)—N(3)—C(22) | 109.4(13) |
| C(20)—N(3)—C(22) | 105.7(10) |
| C(5)—O(1)—C(1) | 110.7(12) |
| C(16)—O(4)—C(17) | 117.6(11) |
| O(1)—C(1)—C(2) | 110.8(10) |
| C(3)—C(2)—C(1) | 112.0(13) |
| C(2)—C(3)—C(4) | 108.4(12) |
| C(5)—C(4)—C(3) | 110.1(11) |
| O(1)—C(5)—C(4) | 110.7(12) |
| O(1)—C(5)—C(6) | 106.2(13) |
| C(4)—C(5)—C(6) | 112.2(13) |
| C(11)—C(6)—C(7) | 116.6(14) |
| C(11)—C(6)—C(5) | 122.7(17) |
| C(7)—C(6)—C(5) | 120.8(17) |
| C(6)—C(7)—C(8) | 124.2(14) |
| C(9)—C(8)—C(7) | 116.2(13) |
| C(10)—C(9)—C(8) | 122.1(14) |
| C(10)—C(9)—S(1) | 120.2(16) |
| C(8)—C(9)—S(1) | 117.5(17) |
| C(9)—C(10)—C(11) | 121.0(13) |
| C(6)—C(11)—C(10) | 119.8(13) |
| O(13)—C(12)—C(16) | 118.8(14) |
| C(13)—C(12)—N(1) | 122.3(14) |
| C(16)—C(12)—N(1) | 118.9(17) |
| C(12)—C(13)—C(14) | 117.9(14) |
| O(13)—C(14)—C(15) | 119.4(15) |
| C(13)—C(14)—C(21) | 120.9(15) |
| C(15)—C(14)—C(21) | 119.5(14) |
| N(2)—C(15)—C(14) | 123.5(13) |
| N(2)—C(15)—C(18) | 114.8(15) |
| C(14)—C(15)—C(18) | 121.7(16) |
| N(2)—C(16)—O(4) | 118.3(15) |
| N(2)—C(16)—C(12) | 124.2(13) |
| O(4)—C(16)—C(12) | 117.5(17) |
| C(19)—C(18)—C(15) | 112.2(10) |
| N(3)—C(19)—C(18) | 114.2(13) |
| N(3)—C(20)—C(21) | 114.1(10) |
| C(14)—C(21)—C(20) | 115.3(11) |

Symmetry transformations used to generate equivalent atoms.

TABLE 4

Anisotropic displacement parameters (Å² × 10³) for 7.
The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 61(3) | 66(4) | 103(3) | 6(3) | 26(3) | 1(3) |
| N(1) | 47(8) | 35(10) | 115(10) | −2(9) | 10(7) | −12(7) |
| N(2) | 41(7) | 84(13) | 88(10) | 11(8) | 20(7) | −9(7) |
| N(3) | 63(9) | 120(13) | 80(11) | 12(9) | 22(8) | −10(8) |
| O(1) | 70(6) | 75(9) | 113(9) | −16(7) | 20(6) | 21(7) |
| O(2) | 48(5) | 92(8) | 105(7) | 4(5) | 29(5) | −12(5) |
| O(3) | 76(7) | 50(8) | 103(7) | 6(7) | 14(5) | 12(6) |
| O(4) | 59(6) | 67(8) | 116(8) | 17(7) | 16(6) | 10(6) |
| C(1) | 77(12) | 122(16) | 119(14) | 5(12) | 23(11) | 40(11) |
| C(2) | 84(11) | 79(16) | 112(15) | −4(11) | 1(9) | −2(11) |
| C(3) | 93(12) | 90(15) | 85(12) | −9(11) | 22(10) | 18(11) |
| C(4) | 86(12) | 98(13) | 98(12) | 8(10) | 41(11) | 14(10) |
| C(5) | 60(10) | 94(19) | 65(12) | 6(10) | 2(9) | 4(10) |
| C(6) | 81(13) | 31(15) | 76(13) | 13(10) | 37(11) | −7(11) |
| C(7) | 56(11) | 73(16) | 128(15) | 12(14) | 28(11) | −3(11) |
| C(8) | 57(10) | 38(12) | 123(16) | 38(12) | 35(10) | 9(11) |
| C(9) | 69(12) | 47(13) | 71(12) | 15(11) | 23(9) | 8(11) |

TABLE 4-continued

Anisotropic displacement parameters (Å² × 10³) for 7.
The anisotropic displacement factor exponent takes the form:
$-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(10) | 81(12) | 29(14) | 81(12) | 2(11) | −4(11) | −3(10) |
| C(11) | 88(11) | 33(14) | 94(15) | 30(10) | 16(11) | −22(11) |
| C(12) | 21(9) | 66(16) | 111(14) | −26(11) | 0(9) | −4(11) |
| C(13) | 60(11) | 95(16) | 111(14) | 29(12) | 19(10) | −2(11) |
| C(14) | 56(11) | 41(13) | 102(13) | 10(10) | 9(11) | 6(10) |
| C(15) | 76(13) | 84(16) | 65(12) | 19(10) | 18(10) | 0(12) |
| C(16) | 93(14) | 30(12) | 79(12) | 34(9) | −3(11) | 7(11) |
| C(17) | 65(9) | 102(16) | 125(12) | 72(11) | −4(8) | 2(9) |
| C(18) | 48(9) | 97(13) | 105(12) | −2(10) | 17(9) | −20(8) |
| C(19) | 73(10) | 121(16) | 90(14) | 2(12) | 30(10) | 8(11) |
| C(20) | 97(12) | 139(15) | 48(10) | 3(10) | 8(9) | 5(10) |
| C(21) | 78(10) | 61(14) | 119(14) | 40(12) | 8(9) | 10(9) |
| C(22) | 125(12) | 210(20) | 78(11) | 2(12) | 50(10) | −7(12) |

TABLE 5

Hydrogen coordinates (×10⁴) and isotropic displacement parameters (Å² × 10³) for 7.

| | x | y | z | U(eq) |
|---|---|---|---|---|
| H(1X) | 5160(70) | −800(200) | 7210(50) | 50(50) |
| H(1A) | 10061 | 473 | 10805 | 126 |
| H(1B) | 9891 | −2586 | 10757 | 126 |
| H(2A) | 8689 | −2450 | 11695 | 111 |
| H(2B) | 9807 | −1101 | 12003 | 111 |
| H(3A) | 9047 | 2992 | 11822 | 106 |
| H(3B) | 8244 | 1336 | 12280 | 106 |
| H(4A) | 7075 | 492 | 11187 | 110 |
| H(4B) | 7253 | 3550 | 11236 | 110 |
| H(5) | 8610 | 3286 | 10394 | 88 |
| H(7) | 7815 | 5288 | 9302 | 101 |
| H(8) | 6461 | 5932 | 8300 | 85 |
| H(10) | 4864 | −304 | 8995 | 77 |
| H(11) | 6224 | −969 | 9993 | 85 |
| H(13) | 5172 | 4911 | 6022 | 105 |
| H(17A) | 8784 | −1618 | 7305 | 147 |
| H(17B) | 8353 | −2874 | 8025 | 147 |
| H(17C) | 8729 | 77 | 8035 | 147 |
| H(18A) | 8954 | 7009 | 5823 | 99 |
| H(18B) | 9532 | 4318 | 6040 | 99 |
| H(19A) | 9633 | 4357 | 4807 | 112 |
| H(19B) | 8556 | 2693 | 4855 | 112 |
| H(20A) | 6803 | 4404 | 4383 | 114 |
| H(20B) | 6703 | 7275 | 4066 | 114 |
| H(21A) | 7122 | 8712 | 5390 | 103 |
| H(21B) | 5919 | 7707 | 5150 | 103 |
| H(22A) | 9195 | 5234 | 3599 | 201 |
| H(22B) | 8200 | 7063 | 3313 | 201 |
| H(22C) | 7991 | 4087 | 3479 | 201 |

Alternate Synthesis of Example 7

N-(2-Methoxy-7-methyl-6,7,8,9-tetrahydro-5H-pyrido[2,3-d]azepin-3-yl)-4-[(2R)-tetrahydro-2H-pyran-2-yl]benzenesulfonamide (7)

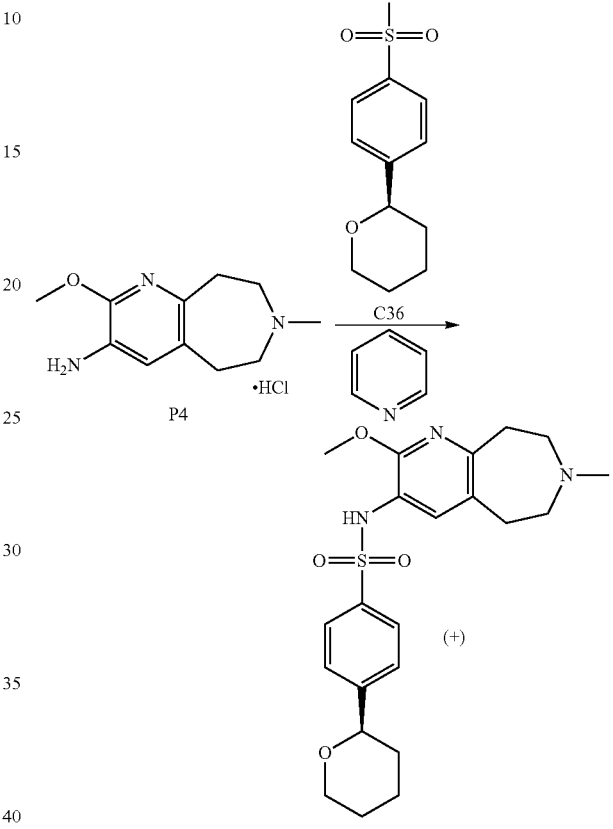

Compound C36 (3.98 g, 15.3 mmol) was added to a suspension of P4 (93%, 4.01 g, 15.2 mmol) and pyridine (1.4 mL, 17 mmol) in dichloromethane (40 mL), and the reaction mixture was stirred overnight at room temperature. Saturated aqueous sodium bicarbonate solution (20 mL) was added, and the mixture was stirred for 5 minutes at room temperature. The organic layer was washed sequentially with water (20 mL), aqueous hydrochloric acid (1M, 20 mL, 20 mmol), saturated aqueous sodium bicarbonate solution (20 mL), and saturated aqueous sodium chloride solution (20 mL), then dried over sodium sulfate, filtered, and concentrated in vacuo. The residue was dissolved in ethyl acetate (130 mL) via spinning the flask on a rotary evaporator using a warming bath at 80 to 85° C. The bath was cooled to 40° C., and the solution was concentrated to a total volume of approximately 65 mL, during which time it became cloudy. The solid was allowed to granulate overnight, whereupon the flask was cooled in an ice bath for 30 minutes. The precipitate was collected via filtration, using the mother liquor to wash the filter cake; it was then washed with chilled heptane (20 mL), affording the product as a white solid. Yield: 5.18 g, 12.0 mmol, 79%. ¹H NMR (400 MHz, DMSO-d₆) δ 9.7-9.45 (v br s, 1H), 7.63 (br d, J=8.4 Hz, 2H), 7.46 (br d, J=8.3 Hz, 2H), 7.32 (s, 1H), 4.38 (br d, J=11 Hz, 1H), 4.06-3.99 (m, 1H), 3.57-3.47 (m, 1H), 3.47 (s, 3H), 2.90-2.85 (m, 2H), 2.76-2.70 (m, 2H), 2.49-2.42 (m, 4H), 2.27 (s, 3H), 1.89-1.77 (m, 2H), 1.70-1.58 (m, 1H), 1.58-1.50 (m, 2H), 1.40-1.27 (m, 1H).

Example 8

N-(2-Methoxy-7-methyl-6,7,8,9-tetrahydro-5H-pyrido[2,3-d]azepin-3-yl)-4-[(2S)-tetrahydro-2H-pyran-2-yl]benzenesulfonamide (8)

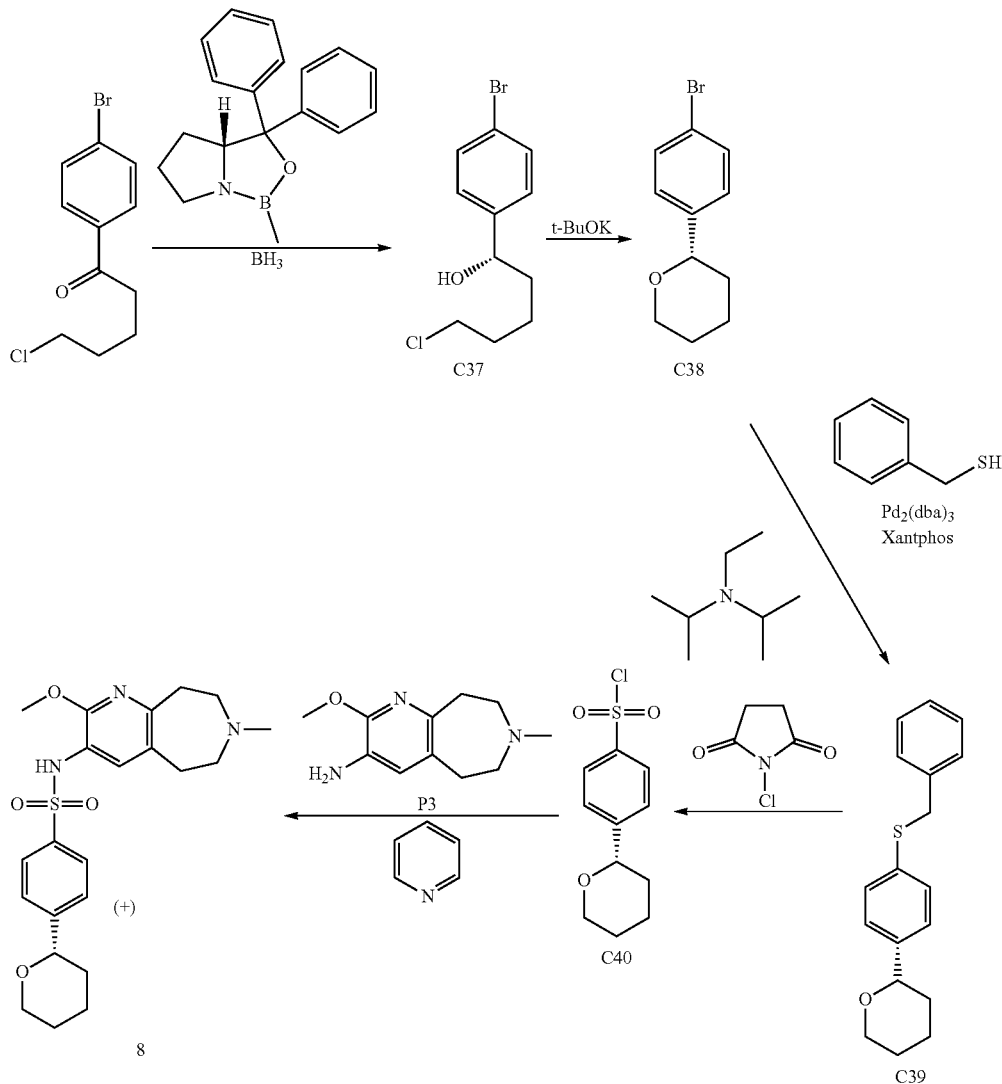

Step 1. Synthesis of (1S)-1-(4-bromophenyl)-5-chloropentan-1-ol (C37)

A mixture of (3aR)-1-methyl-3,3-diphenyltetrahydro-3H-pyrrolo[1,2-c][1,3,2]oxazaborole [(R)-2-methyl-CBS-oxazaborolidine; 1M solution in toluene, 3.63 mL, 3.63 mmol], borane (1M solution in tetrahydrofuran; 38.1 mL, 38.1 mmol), and tetrahydrofuran (100 mL) was cooled to 0° C. A solution of 1-(4-bromophenyl)-5-chloropentan-1-one (10.0 g, 36.3 mmol) in tetrahydrofuran (50 mL) was added in a drop-wise manner, while the internal reaction temperature was maintained below 5° C. After 30 minutes, the cooling bath was removed, and the reaction mixture was allowed to stir at 26° C. for 3 hours, whereupon the reaction mixture was cooled to 0° C. and treated with methanol (50 mL). The resulting mixture was stirred at 0° C. for 30 minutes, at which time aqueous hydrochloric acid (1M, 80 mL) was added and stirring was continued at 26° C. for 1 hour. After standing for 18 hours, the mixture was partitioned between ethyl acetate (150 mL) and saturated aqueous ammonium chloride solution (100 mL). The organic layer was washed with saturated aqueous sodium chloride solution (100 mL), dried over sodium sulfate, filtered, and concentrated in vacuo. The residue was dissolved in dichloromethane (200 mL) and filtered; concentration of the filtrate under reduced pressure afforded the product as a pale yellow oil. Yield: 10 g, 36 mmol, 99%. $^1$H NMR (400 MHz, CDCl$_3$), characteristic peaks: δ 7.49 (br d, J=8.4 Hz, 2H), 7.23 (br d, J=8.3 Hz, 2H), 4.67 (dd, J=7.0, 5.9 Hz, 1H), 3.53 (t, J=6.6 Hz, 2H).

Step 2. Synthesis of (2S)-2-(4-bromophenyl)tetrahydro-2H-pyran (C38)

Potassium tert-butoxide (1M solution in tetrahydrofuran; 54 mL, 54 mmol) was slowly added to a 0° C. solution of C37 (10 g, 36 mmol) in tetrahydrofuran (100 mL); after completion of the addition, the ice bath was removed and the reaction was stirred at 25° C. for 16 hours. The reaction mixture was then cooled to 0° C., treated with aqueous hydrochloric acid (1M, 80 mL) while keeping the internal reaction temperature below 10° C., and extracted with ethyl acetate (3×100 mL). The combined organic layers were washed with saturated aqueous sodium chloride solution (80 mL), dried over sodium sulfate, filtered, and concentrated in vacuo. Silica gel chromatography (Gradient: 0% to 20% ethyl acetate in petroleum ether) provided the product as a yellow oil. Yield: 7.5 g, 31 mmol, 86%. $^1$H NMR (400 MHz, CDCl$_3$) δ 7.46 (br d, J=8.4 Hz, 2H), 7.23 (br d, J=8.3 Hz, 2H), 4.29 (br d, J=11 Hz, 1H), 4.17-4.10 (m, 1H), 3.65-3.57 (m, 1H), 1.99-1.91 (m, 1H), 1.82 (br d, J=13 Hz, 1H), 1.73-1.48 (m, 4H, assumed; partially obscured by water peak).

Step 3. Synthesis of (2S)-2-[4-(benzylsulfanyl)phenyl]tetrahydro-2H-pyran (C39)

A mixture of C38 (7.5 g, 31 mmol), phenylmethanethiol (5.02 g, 40.4 mmol), N,N-diisopropylethylamine (12.1 g, 93.6 mmol), tris(dibenzylideneacetone)dipalladium(0) (570 mg, 0.622 mmol), and 4,5-bis(diphenylphosphino)-9,9-dimethylxanthene (720 mg, 0.1.24 mmol) in 1,4-dioxane (100 mL) was evacuated and charged with nitrogen; this cycle was repeated twice, and the reaction was then stirred at 110° C. for 16 hours. After solvent had been removed in vacuo, the residue was purified via silica gel chromatography (Gradient: 0% to 10% ethyl acetate in petroleum ether), and then subjected to supercritical fluid chromatography [Column: Chiral Technologies Chiralpak AD, 10 µm; Mobile phase: 35% (ethanol containing 0.1% ammonium hydroxide) in carbon dioxide]; the product was obtained as an off-white solid. Yield: 7.5 g, 26 mmol, 84%. $^1$H NMR (400 MHz, CDCl$_3$) δ 7.32-7.19 (m, 9H), 4.31-4.25 (m, 1H), 4.16-4.10 (m, 1H), 4.09 (s, 2H), 3.64-3.56 (m, 1H), 1.97-1.89 (m, 1H), 1.83-1.76 (m, 1H), 1.72-1.49 (m, 4H, assumed; partially obscured by water peak).

Step 4. Synthesis of 4-[(2S)-tetrahydro-2H-pyran-2-yl]benzenesulfonyl chloride (C40)

N-Chlorosuccinimide (14.1 g, 106 mmol) was added to a 0° C. suspension of C39 (7.5 g, 26 mmol) in acetic acid (70 mL) and water (20 mL). The ice bath was removed and the reaction mixture was allowed to stir for 2 hours at 25° C., whereupon it was diluted with ethyl acetate (80 mL), washed sequentially with water (50 mL) and saturated aqueous sodium chloride solution (2×50 mL), dried over sodium sulfate, filtered, and concentrated in vacuo. Silica gel chromatography was carried out twice (Gradient: 0% to 10% ethyl acetate in petroleum ether), to afford the product as a white solid. Yield: 5.52 g, 21.2 mmol, 82%. $^1$H NMR (400 MHz, CDCl$_3$) δ 8.03-7.99 (m, 2H), 7.62-7.58 (m, 2H), 4.44 (br dd, J=11.2, 2.1 Hz, 1H), 4.21-4.15 (m, 1H), 3.68-3.59 (m, 1H), 2.03-1.95 (m, 1H), 1.93-1.86 (m, 1H), 1.76-1.60 (m, 3H), 1.57-1.45 (m, 1H).

Step 5. Synthesis of N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide (8)

A solution of P3 (800 mg, 3.86 mmol) and C40 (1.00 g, 3.84 mmol) in pyridine (20 mL) was stirred at 25° C. for 16 hours. Another charge of C40 (200 mg, 0.77 mmol) was added, and stirring was continued for 5 hours. The reaction mixture was concentrated in vacuo, and the residue was dissolved in dichloromethane (50 mL), washed sequentially with saturated aqueous sodium bicarbonate solution (30 mL) and saturated aqueous sodium chloride solution (30 mL), dried over sodium sulfate, filtered, and concentrated under reduced pressure. Silica gel chromatography (Gradient: 0% to 7% methanol in dichloromethane) afforded the product as a white solid. This material exhibited a negative (−) optical rotation. Yield: 1.12 g, 2.60 mmol, 68%. LCMS m/z 432.0 [M+H]$^+$. $^1$H NMR (400 MHz, CDCl$_3$) δ 7.72 (br d, J=8.4 Hz, 2H), 7.51 (s, 1H), 7.41 (br d, J=8.3 Hz, 2H), 4.35 (brd, J=11 Hz, 1H), 4.17-4.10 (m, 1H), 3.73 (s, 3H), 3.63-3.55 (m, 1H), 3.01-2.94 (m, 2H), 2.84-2.78 (m, 2H), 2.58-2.50 (m, 4H), 2.37 (s, 3H), 1.98-1.91 (m, 1H), 1.86-1.78 (m, 1H), 1.76-1.55 (m, 3H, assumed; partially obscured by water peak), 1.53-1.41 (m, 1H).

Example 9

N-(2-Methoxy-6,7,8,9-tetrahydro-5H-pyrido[2,3-d]azepin-3-yl)-4-[(2R)-tetrahydro-2H-pyran-2-yl]benzenesulfonamide (9)

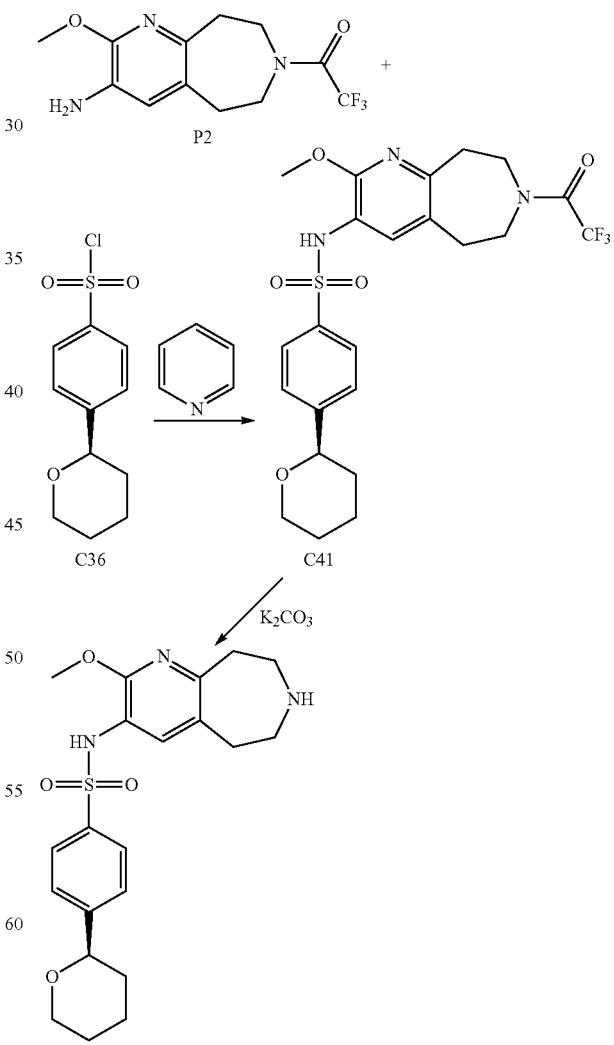

9

Step 1. Synthesis of N-[2-methoxy-7-(trifluoroacetyl)-6,7,8,9-tetrahydro-5H-pyrido[2,3-d]azepin-3-yl]-4-[(2R)-tetrahydro-2H-pyran-2-yl]benzenesulfonamide (C41)

To a solution of P2 (200 mg, 0.691 mmol) in pyridine (3 mL) was added C36 (198 mg, 0.759 mmol) in one portion, and the reaction mixture was stirred at 25° C. for 16 hours. After removal of solvent in vacuo, the residue was subjected to silica gel chromatography (Gradient: 0% to 30% ethyl acetate in petroleum ether, followed by 30% ethyl acetate in dichloromethane) to provide the product as a red solid. This material was judged to be a mixture of rotamers from the $^1$H NMR spectrum. Yield: 274 mg, 0.534 mmol, 77%. $^1$H NMR (400 MHz, CDCl$_3$) δ 7.78-7.71 (m, 2H), [7.55 (s) and 7.54 (s), total 1H], 7.46-7.40 (m, 2H), [6.82 (br s) and 6.81 (br s), total 1H], 4.35 (br d, J=11 Hz, 1H), 4.17-4.10 (m, 1H), 3.78-3.73 (m, 2H), 3.77 (s, 3H), 3.72-3.66 (m, 2H), 3.64-3.55 (m, 1H), 3.07-3.00 (m, 2H), 2.91-2.83 (m, 2H), 1.99-1.92 (m, 1H), 1.86-1.79 (m, 1H), 1.72-1.6 (m, 3H, assumed; partially obscured by water peak), 1.53-1.42 (m, 1H).

Step 2. Synthesis of N-(2-methoxy-6,7,8,9-tetrahydro-5H-pyrido[2,3-d]azepin-3-yl)-4-[(2R)-tetrahydro-2H-pyran-2-yl]benzenesulfonamide (9)

Potassium carbonate (258 mg, 1.87 mmol) was added to a solution of C41 (274 mg, 0.534 mmol) in methanol (25 mL), and the resulting suspension was stirred at 24° C. for 3 hours. The reaction mixture was then concentrated in vacuo and purified via reversed-phase HPLC (Column: Agela Durashell C18, 5 μm; Mobile phase A: ammonia in water, pH 10; Mobile phase B: acetonitrile; Gradient: 9% to 29% B) to afford the product as a pale yellow solid. Yield: 202 mg, 0.484 mmol, 91%. LCMS m/z 418.0 [M+H]$^+$. $^1$H NMR (400 MHz, CD$_3$OD) δ 7.71 (br d, J=8.4 Hz, 2H), 7.40 (br d, J=8.3 Hz, 2H), 7.31 (s, 1H), 4.38 (br dd, J=11.2, 2.2 Hz, 1H), 4.11-4.05 (m, 1H), 3.66 (s, 3H), 3.65-3.58 (m, 1H), 2.95-2.90 (m, 2H), 2.87-2.81 (m, 4H), 2.76-2.71 (m, 2H), 1.97-1.89 (m, 1H), 1.86-1.79 (m, 1H), 1.75-1.55 (m, 3H), 1.53-1.42 (m, 1H).

Example 10

4-(trans-1-Fluoro-3-methoxycyclobutyl)-N-(2-methoxy-7-methyl-6,7,8,9-tetrahydro-5H-pyrido[2,3-d]azepin-3-yl)benzenesulfonamide (10)

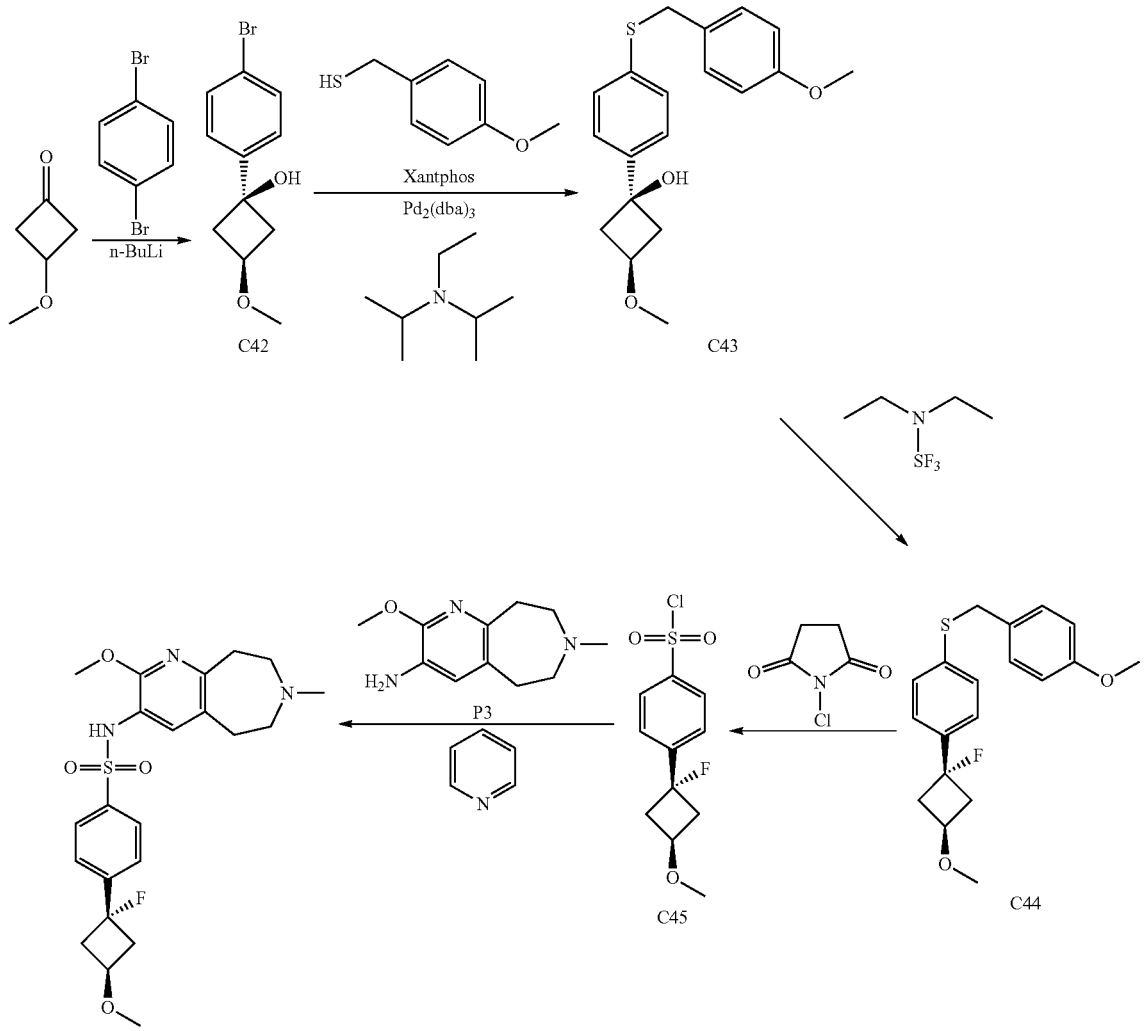

10

Step 1. Synthesis of cis-1-(4-bromophenyl)-3-methoxycyclobutanol (C42)

n-Butyllithium (2.5M solution in hexanes; 4.80 mL, 12.0 mmol) was added drop-wise, over a period of 10 minutes, to a −70° C. solution of 1,4-dibromobenzene (2.52 g, 10.7 mmol) in tetrahydrofuran (30 mL), while the internal temperature was maintained below −65° C. After completion of the addition, the suspension was stirred at −70° C. for 20 minutes, whereupon 3-methoxycyclobutanone (890 mg, 8.89 mmol) was added drop-wise over a period of 2 minutes. The reaction mixture was allowed to warm to 25° C. over 3 hours; it was then treated with aqueous citric acid solution (2M; ~30 mL) and extracted with ethyl acetate (3×50 mL). The combined organic layers were concentrated in vacuo, and the residue was purified by silica gel chromatography (Gradient: 0% to 30% ethyl acetate in petroleum ether) to afford the product as a yellow oil. 2-Dimensional NMR (NOE) supported the indicated relative stereochemistry. Yield: 1.39 g, 5.41 mmol, 61%. $^1$H NMR (400 MHz, CDCl$_3$) δ 7.53-7.48 (m, 2H), 7.38-7.34 (m, 2H), 3.75-3.67 (m, 1H), 3.30 (s, 3H), 2.93-2.85 (m, 2H), 2.42-2.34 (m, 3H).

Step 2. Synthesis of cis-3-methoxy-1-{4-[(4-methoxybenzyl)sulfanyl]phenyl}cyclobutanol (C43)

This experiment was carried out in two identical batches. (4-Methoxyphenyl)methanethiol (500 mg, 3.24 mmol) and N,N-diisopropylethylamine (750 mg, 5.80 mmol) were added to a solution of C42 (550 mg, 2.14 mmol) in 1,4-dioxane (20 mL), and the mixture was degassed with nitrogen for 2 minutes. Tris(dibenzylideneacetone)dipalladium (0) (50 mg, 55 µmol) and 4,5-bis(diphenylphosphino)-9,9-dimethylxanthene (60 mg, 0.10 mmol) were added, and the reaction mixture was stirred at 100° C. for 20 hours. It was then concentrated in vacuo, and the residue was dissolved in dichloromethane (100 mL), washed sequentially with saturated aqueous sodium bicarbonate solution (50 mL) and saturated aqueous sodium chloride solution (50 mL), and concentrated under reduced pressure. Chromatography on silica gel (Gradient: 20% to 50% ethyl acetate in petroleum ether) and combination of the two batches afforded the product as a yellow solid. Yield: 1.26 g, 3.81 mmol, 89%. $^1$H NMR (400 MHz, CDCl$_3$) δ 7.39-7.35 (m, 2H), 7.33-7.29 (m, 2H), 7.26-7.21 (m, 2H), 6.86-6.81 (m, 2H), 4.09 (s, 2H), 3.80 (s, 3H), 3.72-3.64 (m, 1H), 3.29 (s, 3H), 2.94-2.86 (m, 2H), 2.41-2.33 (m, 2H), 2.33-2.27 (br s, 1H).

Step 3. Synthesis of 1-(trans-1-fluoro-3-methoxycyclobutyl)-4-[(4-methoxybenzyl) sulfanyl]benzene (C44)

To a −50° C. solution of C43 (1 g, 3.03 mmol) in dichloromethane (40 mL) was added (diethylamino)sulfur trifluoride (732 mg, 4.54 mmol), and the reaction mixture was allowed to warm to −30° C. over a period of 30 minutes. The reaction was quenched via addition of saturated aqueous sodium bicarbonate solution (30 mL) at −30° C.; the organic layer was then washed with saturated aqueous sodium chloride solution (20 mL), dried over sodium sulfate, filtered, and concentrated in vacuo to afford the product as a yellow solid. 2-Dimensional NMR (NOE) studies supported the indicated relative stereochemistry. Yield: 1.00 g, 3.01 mmol, 99%. $^1$H NMR (400 MHz, CDCl$_3$) δ 7.31 (s, 4H), 7.26-7.21 (m, 2H), 6.86-6.81 (m, 2H), 4.33-4.25 (m, 1H), 4.10 (s, 2H), 3.80 (s, 3H), 3.31 (s, 3H), 2.98-2.84 (m, 2H), 2.51-2.36 (m, 2H).

Step 4. Synthesis of 4-(trans-1-fluoro-3-methoxycyclobutyl)benzenesulfonyl chloride (C45)

Conversion of C44 to C45 was carried out according to the method described for synthesis of C21 from C20 in Example 1. The product was obtained as a yellow solid, which contained some impurities via $^1$H NMR analysis. 2-Dimensional NMR (NOE) studies supported the indicated relative stereochemistry. Yield: 620 mg, <2.22 mmol, <74%. $^1$H NMR (400 MHz, CDCl$_3$), product peaks only: δ 8.09-8.04 (m, 2H), 7.75-7.69 (m, 2H), 4.37-4.28 (m, 1H), 3.34 (s, 3H), 3.06-2.92 (m, 2H), 2.58-2.43 (m, 2H).

Step 5. Synthesis of 4-(trans-1-fluoro-3-methoxycyclobutyl)-N-(2-methoxy-7-methyl-6,7,8,9-tetrahydro-5H-pyrido[2,3-d]azepin-3-yl)benzenesulfonamide (10)

Reaction of C45 with P3 was effected using the method described for synthesis of 2 from C23 and P5 in Example 2. The product was obtained as a yellow solid. Yield: 26.7 mg, 59.4 µmol, 49%. LCMS m/z 450.1 [M+H]$^+$. $^1$H NMR (400 MHz, CD$_3$OD) δ 7.75 (br d, J=8.0 Hz, 2H), 7.57 (s, 1H), 7.55 (br d, J=8 Hz, 2H), 4.32-4.23 (m, 1H), 3.60 (s, 3H), 3.30 (s, 3H), 3.13-3.06 (m, 2H), 3.05-2.95 (m, 6H), 2.95-2.83 (m, 2H), 2.68 (s, 3H), 2.53-2.37 (m, 2H).

Example 11

6-(1-Fluorocyclopentyl)-N-(2-methoxy-7-methyl-6,7,8,9-tetrahydro-5H-pyrido[2,3-d]azepin-3-yl)pyridine-3-sulfonamide (11)

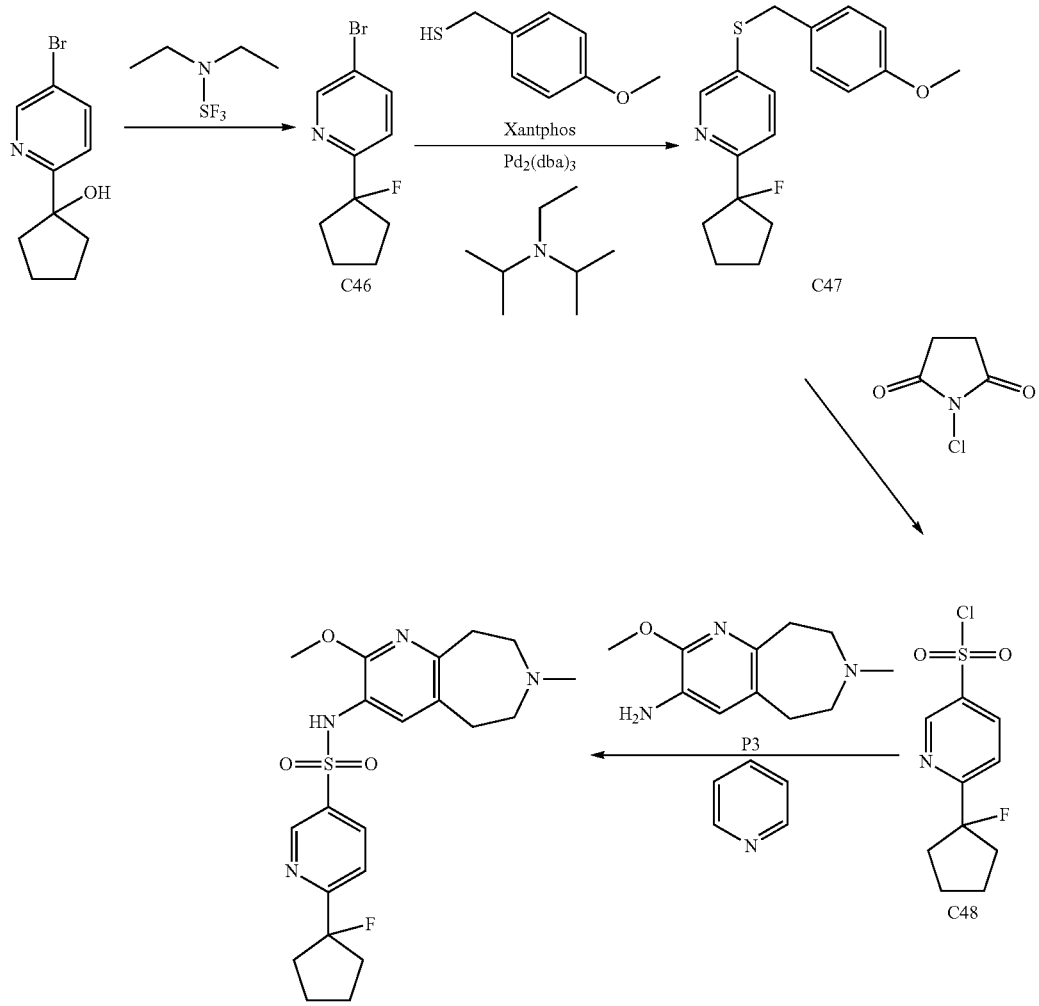

Step 1. Synthesis of 5-bromo-2-(1-fluorocyclopentyl)pyridine (C46)

(Diethylamino)sulfur trifluoride (899 mg, 5.58 mmol) was added drop-wise to a 0° C. mixture of 1-(5-bromopyridin-2-yl)cyclopentanol [which may be synthesized using the general method described by B. Guo et al., *J. Med. Chem.* 2013, 56, 2642-2650](900 mg, 3.72 mmol) in dichloromethane (30 mL). The reaction mixture was stirred at 0° C. for 30 minutes, whereupon it was quenched with water (10 mL) and extracted with dichloromethane (2×20 mL). The combined organic layers were washed with saturated aqueous sodium chloride solution (10 mL), dried over sodium sulfate, filtered, and concentrated in vacuo; silica gel chromatography (Gradient: 0% to 10% ethyl acetate in petroleum ether) afforded the product as a yellow oil. Yield: 650 mg, 2.66 mmol, 72%. $^1$H NMR (400 MHz, CDCl$_3$) δ 8.62-8.59 (m, 1H), 7.82 (dd, J=8.4, 2.4 Hz, 1H), 7.50 (ddd, J=8.4, 1.5, 0.7 Hz, 1H), 2.35-2.04 (m, 4H), 2.04-1.86 (m, 4H).

Step 2. Synthesis of 2-(1-fluorocyclopentyl)-5-[(4-methoxybenzyl)sulfanyl]pyridine (C47)

Conversion of C46 to C47 was carried out using the method described for synthesis of C22 in Example 2. The product was obtained as a white solid. Yield: 640 mg, 2.02 mmol, 76%. $^1$H NMR (400 MHz, CDCl$_3$) δ 8.47-8.44 (m, 1H), 7.58 (dd, half of ABX pattern, J=8.3, 2.3 Hz, 1H), 7.47 (ddd, half of ABXY pattern, J=8.3, 1.4, 0.8 Hz, 1H), 7.19 (br d, J=8.8 Hz, 2H), 6.83 (br d, J=8.8 Hz, 2H), 4.06 (s, 2H), 3.80 (s, 3H), 2.35-2.04 (m, 4H), 2.03-1.85 (m, 4H).

Step 3. Synthesis of 6-(1-fluorocyclopentyl)pyridine-3-sulfonyl chloride (C48)

Conversion of C47 to C48 was effected according to the method described for synthesis of C28 from C27 in Example 4. In this case, the crude product was subjected to silica gel chromatography twice (Gradient: 0% to 10% ethyl acetate in petroleum ether), affording the product as a white solid. Yield: 300 mg, 1.14 mmol, 56%. $^1$H NMR (400 MHz, CDCl$_3$) δ 9.18-9.15 (m, 1H), 8.31 (dd, J=8.5, 2.4 Hz, 1H), 7.90-7.85 (m, 1H), 2.42-2.10 (m, 4H), 2.09-1.92 (m, 4H).

Step 4. Synthesis of 6-(1-fluorocyclopentyl)-N-(2-methoxy-7-methyl-6,7,8,9-tetrahydro-5H-pyrido[2,3-d]azepin-3-yl)pyridine-3-sulfonamide (11)

A mixture of P3 (20 mg, 96 μmol) and C48 (25.4 mg, 96.3 μmol) in pyridine (2 mL) was stirred at 25° C. for 16 hours, whereupon it was concentrated in vacuo. The residue was dissolved in dichloromethane (30 mL), washed sequentially with saturated aqueous sodium bicarbonate solution (20 mL) and saturated aqueous sodium chloride solution (20 mL), and concentrated under reduced pressure. Preparative thin-layer chromatography on silica gel (Eluent: 10:1 dichloromethane/methanol) provided the product as a white solid. Yield: 21.2 mg, 48.8 μmol, 51%. LCMS m/z 435.1 [M+H]+. 1H NMR (400 MHz, CD3OD) δ 8.77-8.74 (m, 1H), 8.08 (dd, J=8.3, 2.3 Hz, 1H), 7.72-7.68 (m, 1H), 7.62 (s, 1H), 3.57 (s, 3H), 3.18-3.09 (m, 6H), 3.07-3.00 (m, 2H), 2.76 (s, 3H), 2.34-2.02 (m, 4H), 2.02-1.87 (m, 4H).

Example 12

N-[2-(Difluoromethoxy)-7-propyl-6,7,8,9-tetrahydro-5H-pyrido[2,3-d]azepin-3-yl]-4-(propan-2-yl)benzenesulfonamide (12)

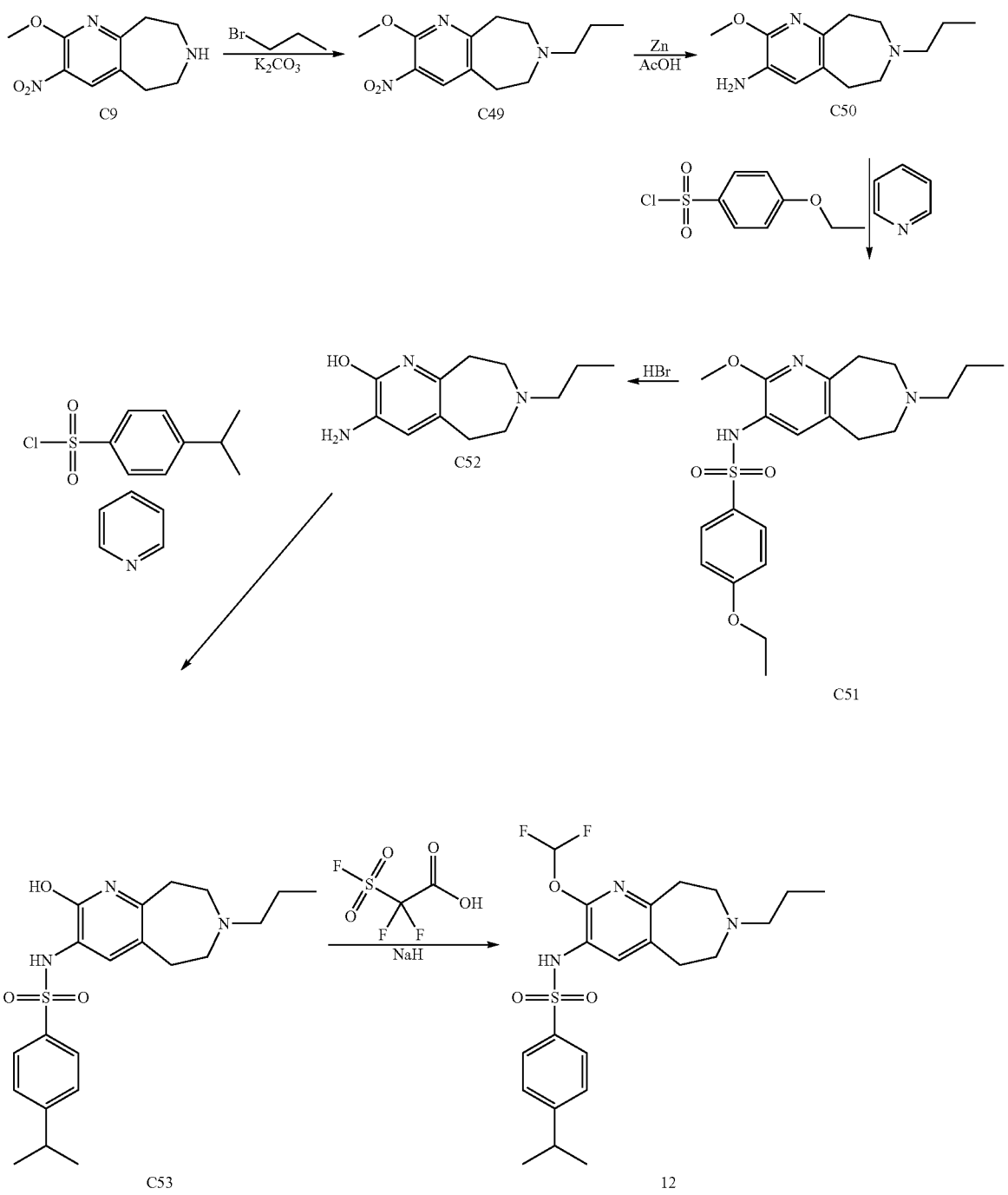

Step 1. Synthesis of 2-methoxy-3-nitro-7-propyl-6,7,8,9-tetrahydro-5H-pyrido[2,3-d]azepine (C49)

A mixture of C9 (830 mg, 3.72 mmol), potassium carbonate (1.54 g, 11.1 mmol), and 1-bromopropane (1.35 mL, 14.9 mmol) in acetonitrile (37 mL) was heated to 50° C. for 1.75 hours, at which time more 1-bromopropane (1.35 mL, 14.9 mmol) was added. After an additional 3 hours at 50° C., the reaction mixture was cooled and partitioned between ethyl acetate and saturated aqueous sodium bicarbonate solution. The aqueous layer was extracted with ethyl acetate and the combined organic layers were dried over magnesium sulfate, filtered, and concentrated in vacuo to afford the product as an oil, which solidified upon standing at room temperature. Yield: 930 mg, 3.50 mmol, 94%. LCMS m/z 266.3 [M+H]$^+$. $^1$H NMR (400 MHz, CDCl$_3$) δ 8.04 (s, 1H), 4.09 (s, 3H), 3.19-3.12 (m, 2H), 2.95-2.88 (m, 2H), 2.77-2.65 (m, 4H), 2.54-2.46 (m, 2H), 1.61-1.50 (m, 2H), 0.93 (t, J=7.3 Hz, 3H).

Step 2. Synthesis of 2-methoxy-7-propyl-6,7,8,9-tetrahydro-5H-pyrido[2,3-d]azepin-3-amine (C50)

Zinc powder (2.29 g, 35.0 mmol) was added to a mixture of C49 (930 mg, 3.50 mmol) and acetic acid (35 mL). The reaction mixture was heated to 30° C. for 2.5 hours, whereupon it was cooled to room temperature and filtered through a pad of diatomaceous earth. The filter pad was rinsed with dichloromethane, and the combined filtrates were concentrated in vacuo; the residue was carefully basified via addition of saturated aqueous sodium bicarbonate solution and solid sodium bicarbonate, and then extracted with dichloromethane (2×110 mL). The combined organic layers were dried over magnesium sulfate, filtered, and concentrated under reduced pressure, providing the product as a viscous orange gum. Yield: 830 mg, 3.5 mmol, 100%. LCMS m/z 236.3 [M+H]$^+$. $^1$H NMR (400 MHz, CD$_3$OD) δ 6.80 (s, 1H), 3.92 (s, 3H), 3.18-3.07 (m, 6H), 2.96-2.89 (m, 4H), 1.79-1.67 (m, 2H), 0.99 (t, J=7.4 Hz, 3H).

Step 3. Synthesis of 4-ethoxy-N-(2-methoxy-7-propyl-6,7,8,9-tetrahydro-5H-pyrido[2,3-d]azepin-3-yl)benzenesulfonamide (C51)

4-Ethoxybenzenesulfonyl chloride (778 mg, 3.53 mmol) was added to a room temperature solution of C50 (830 mg, 3.5 mmol) in pyridine (15 mL). After 5 minutes, the reaction mixture was concentrated in vacuo, and subsequently azeotroped three times with heptane; the residue was subjected to two chromatographic purifications on silica gel (Eluent #1: 15% methanol in ethyl acetate; Eluent #2: 8% methanol in ethyl acetate). The product was isolated as a light yellow solid. Yield: 441 mg, 1.05 mmol, 30%. LCMS m/z 420.4 [M+H]$^+$. $^1$H NMR (400 MHz, CDCl$_3$) δ 7.66 (br d, J=8.8 Hz, 2H), 7.49 (s, 1H), 6.86 (br d, J=9.0 Hz, 2H), 4.04 (q, J=7.0 Hz, 2H), 3.73 (s, 3H), 2.99-2.92 (m, 2H), 2.83-2.76 (m, 2H), 2.64-2.56 (m, 4H), 2.47-2.40 (m, 2H), 1.58-1.46 (m, 2H), 1.41 (t, J=6.9 Hz, 3H), 0.90 (t, J=7.4 Hz, 3H).

Step 4. Synthesis of 3-amino-7-propyl-6,7,8,9-tetrahydro-5H-pyrido[2,3-d]azepin-2-ol (C52)

A mixture of C51 (165 mg, 0.393 mmol) and aqueous hydrogen bromide solution (48%, 4 mL) was heated to 100° C. for 15 minutes, whereupon it was cooled to room temperature. The reaction mixture was slowly basified via addition of solid sodium bicarbonate, and then extracted with a mixture of chloroform and methanol (2×40 mL). The combined organic layers were dried over magnesium sulfate, filtered, and concentrated in vacuo, affording the product (165 mg) as a gum. By $^1$H NMR analysis, this material contained a significant impurity bearing the 4-ethoxybenzenesulfonyl group; it was taken to the following step without additional purification. LCMS exhibited a major peak with m/z 222.2 [M+H]$^+$. $^1$H NMR (400 MHz, CD$_3$OD), product peaks only: δ 6.69 (s, 1H), 3.29-3.15 (m, 4H), 3.10-2.96 (m, 4H), 2.93-2.86 (m, 2H), 1.82-1.69 (m, 2H), 0.98 (t, J=7.4 Hz, 3H).

Step 5. Synthesis of N-(2-hydroxy-7-propyl-6,7,8,9-tetrahydro-5H-pyrido[2,3-d]azepin-3-yl)-4-(propan-2-yl)benzenesulfonamide (C53)

4-(Propan-2-yl)benzenesulfonyl chloride (130 μL, 0.72 mmol) was added to a room temperature solution of C52 (from the previous step; 165 mg, ≤0.39 mmol) in pyridine (1.4 mL). After 15 minutes, the reaction mixture was concentrated in vacuo and azeotroped with heptane. The residue was partitioned between saturated aqueous sodium bicarbonate solution (10 mL) and dichloromethane (25 mL), and the aqueous layer was extracted with dichloromethane (25 mL); the combined organic layers were dried over magnesium sulfate, filtered, and concentrated under reduced pressure. Chromatography on silica gel (Eluent: 80:20:0.2 ethyl acetate/methanol/0.2% ammonium hydroxide) provided the product (100 mg) as a solid, which proved to be impure by LCMS and $^1$H NMR analysis. This material was taken to the following step without additional purification. LCMS exhibited a major peak with m/z 404.2 [M+H]$^+$.

Step 6. Synthesis of N-[2-(difluoromethoxy)-7-propyl-6,7,8,9-tetrahydro-5H-pyrido[2,3-d]azepin-3-yl]-4-(propan-2-yl)benzenesulfonamide (12)

Sodium hydride (60% suspension in mineral oil, 13.4 mg, 0.335 mmol; this was washed twice with heptane and subsequently dried under high vacuum before use) was added to a slurry of C53 (from the previous step; 75 mg, ≤0.19 mmol) in acetonitrile (1.9 mL). The reaction mixture was allowed to stir at room temperature for 15 minutes, whereupon difluoro(fluorosulfonyl)acetic acid (19.2 μL, 0.186 mmol) was added. After 10 minutes, the reaction was quenched via addition of a few drops of water; the mixture was then partitioned between saturated aqueous sodium bicarbonate solution and dichloromethane. The organic layer was combined with the organic layer from a similar reaction carried out using C53 (from the previous step; 25 mg, ≤62 μmol), and purified via silica gel chromatography (Eluent: 20% methanol in ethyl acetate), affording the product as a solid. Yield: 27 mg, 60 μmol, 15% over 3 steps. LCMS m/z 454.2 [M+H]$^+$. $^1$H NMR (400 MHz, benzene-d$_6$) δ 7.73 (s, 1H), 7.65 (br d, J=8.4 Hz, 2H), 7.02 (t, J$_{HF}$=72.9 Hz, 1H), 6.76 (br d, J=8.4 Hz, 2H), 2.78-2.71 (m, 2H), 2.47-2.33 (m, 3H), 2.31-2.18 (m, 4H), 2.17-2.10 (m, 2H), 1.37-1.26 (m, 2H), 0.85 (d, J=6.8 Hz, 6H), 0.80 (t, J=7.3 Hz, 3H).

Example 13

N-(7-Ethyl-2-methoxy-5-methyl-6,7,8,9-tetrahydro-5H-pyrido[2,3-d]azepin-3-yl)-4-methylbenzenesulfonamide (13)

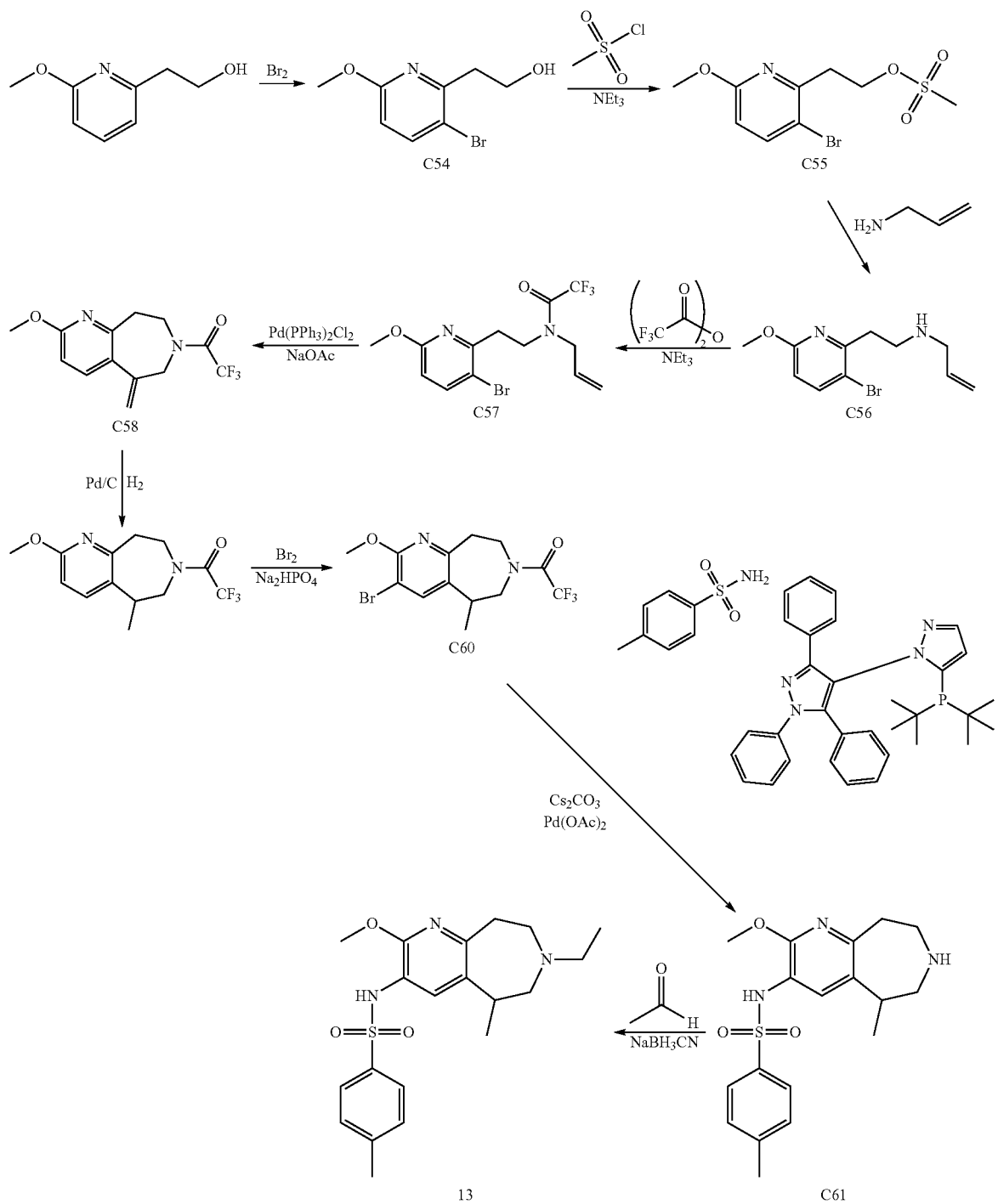

Step 1. Synthesis of 2-(3-bromo-6-methoxypyridin-2-yl)ethanol (C54)

To a 0° C. solution of 2-(6-methoxypyridin-2-yl)ethanol (2.10 g, 13.7 mmol) in ethanol (20 mL) was added bromine (3.29 g, 20.6 mmol); the reaction mixture was stirred at 0° C. for 1.5 hours, and then allowed to stir at room temperature overnight. After basification with 1M aqueous sodium hydroxide solution, the mixture was concentrated in vacuo to remove ethanol, and the aqueous residue was extracted with ethyl acetate (2×50 mL). The combined organic layers were washed with saturated aqueous sodium chloride solution, dried over sodium sulfate, filtered, and concentrated under reduced pressure to provide the product as a yellow liquid. Yield: 2.8 g, 12 mmol, 88%. $^1$H NMR (400 MHz, CDCl$_3$) δ 7.69 (d, J=8.7 Hz, 1H), 6.56 (d, J=8.7 Hz, 1H), 4.06 (t, J=5.5 Hz, 2H), 3.91 (s, 3H), 3.08 (t, J=5.5 Hz, 2H).

Step 2. Synthesis of 2-(3-bromo-6-methoxypyridin-2-yl)ethyl methanesulfonate (C55)

Methanesulfonyl chloride (3.33 g, 29.1 mmol) was added to a 0° C. solution of C54 (2.8 g, 12 mmol) and triethylamine (3.66 g, 36.2 mmol) in dichloromethane (50 mL). After 1 hour, saturated aqueous sodium bicarbonate solution was added, and the mixture was extracted with dichloromethane (2×50 mL). The combined organic layers were washed with saturated aqueous sodium chloride solution, dried over sodium sulfate, filtered, and concentrated in vacuo to afford the product as a yellow oil. Yield: 3.70 g, 11.9 mmol, 99%. $^1$H NMR (400 MHz, CDCl$_3$) δ 7.66 (d, J=8.7 Hz, 1H), 6.55 (d, J=8.7 Hz, 1H), 4.72 (t, J=6.8 Hz, 2H), 3.91 (s, 3H), 3.31 (t, J=6.7 Hz, 2H), 2.99 (s, 3H).

Step 3. Synthesis of N-[2-(3-bromo-6-methoxypyridin-2-yl)ethyl]prop-2-en-1-amine (C56)

To a solution of C55 (3.70 g, 11.9 mmol) in acetonitrile (40 mL) was added prop-2-en-1-amine (9.74 g, 171 mmol), and the reaction mixture was stirred at room temperature overnight. After solvent had been removed in vacuo, the residue was dissolved in ethyl acetate, washed sequentially with saturated aqueous sodium bicarbonate solution and saturated aqueous sodium chloride solution, dried over sodium sulfate, filtered, and concentrated under reduced pressure. The resulting material (3.3 g) was directly used in the next step, without further purification. LCMS m/z 270.9 (bromine isotope pattern observed) [M+H]$^+$.

Step 4. Synthesis of N-[2-(3-bromo-6-methoxypyridin-2-yl)ethyl]-2,2,2-trifluoro-N-(prop-2-en-1-yl)acetamide (C57)

Trifluoroacetic anhydride (3.07 g, 14.6 mmol) was added to a 5° C. to 10° C. solution of triethylamine (3.69 g, 36.5 mmol) and C56 (from the previous step; 3.3 g, ≤11.9 mmol) in dichloromethane (50 mL). The reaction mixture was stirred at this temperature for 10 minutes, whereupon it was partitioned between saturated aqueous sodium bicarbonate solution and dichloromethane. The organic layer was washed with saturated aqueous sodium chloride solution, dried over sodium sulfate, filtered, and concentrated in vacuo; silica gel chromatography (Gradient: 0% to 5% ethyl acetate in petroleum ether) provided the product as a pale yellow oil. From examination of the $^1$H NMR spectrum, this material was deemed to be a mixture of rotamers. Yield: 2.4 g, 6.5 mmol, 55% over 2 steps. $^1$H NMR (400 MHz, CDCl$_3$) δ [7.65 (d, J=8.8 Hz) and 7.64 (d, J=8.8 Hz), total 1H], [6.54 (d, J=8.5 Hz) and 6.52 (d, J=8.5 Hz), total 1H], 5.88-5.67 (m, 1H), 5.30-5.17 (m, 2H), [4.12 (d, J=5.8 Hz) and 3.92 (d, J=5.8 Hz), total 2H], 3.89 (s, 3H), 3.86-3.78 (m, 2H), 3.16 (dd, J=7.5, 7.3 Hz, 2H).

Step 5. Synthesis of 2,2,2-trifluoro-1-(2-methoxy-5-methylidene-5,6,8,9-tetrahydro-7H-pyrido[2,3-d]azepin-7-yl)ethanone (C58)

A mixture of C57 (2.4 g, 6.5 mmol), dichlorobis(triphenylphosphine)palladium(II) (2.29 g, 3.26 mmol), and sodium acetate (1.61 g, 19.6 mmol) in N,N-dimethylacetamide (20 mL) was degassed with nitrogen for several minutes. The resulting mixture was then stirred at 140° C. for 24 hours, whereupon it was concentrated in vacuo. The residue was purified by silica gel chromatography (Gradient: 0% to 10% ethyl acetate in petroleum ether) to afford the product as a yellow oil. From examination of the $^1$H NMR spectrum, this material was presumed to be a mixture of rotamers. Yield: 900 mg, 3.14 mmol, 48%. LCMS m/z 286.8 [M+H]$^+$. $^1$H NMR (400 MHz, CDCl$_3$) δ [7.52 (d, J=8.5 Hz) and 7.52 (d, J=8.4 Hz), total 1H], 6.62 (d, J=8.4 Hz, 1H), [5.44-5.41 (m), 5.37 (br s), 5.33 (br s), and 5.29 (br s), total 2H], [4.45 (br s) and 4.42 (br s), total 2H], 3.95-3.88 (m, 5H), 3.24-3.17 (m, 2H).

Step 6. Synthesis of 2,2,2-trifluoro-1-(2-methoxy-5-methyl-5,6,8,9-tetrahydro-7H-pyrido[2,3-d]azepin-7-yl)ethanone (C59)

Wet palladium on carbon (10%, 35 mg) was added to a solution of C58 (350 mg, 1.22 mmol) in methanol (20 mL); the mixture was subjected to several cycles of evacuation followed by purging with hydrogen. The reaction mixture was then stirred under hydrogen (15 psi) at room temperature for 1 hour, whereupon it was filtered, and the filtrate was concentrated in vacuo, providing the product as a colorless oil. From examination of the $^1$H NMR spectrum, this material was presumed to be a mixture of rotamers. Yield: 330 mg, 1.14 mmol, 93%. LCMS m/z 288.9 [M+H]$^+$. $^1$H NMR (400 MHz, CDCl$_3$) δ [7.39 (d, J=8.3 Hz) and 7.38 (d, J=8.4 Hz), total 1H], [6.60 (d, J=8.5 Hz) and 6.58 (d, J=8.3 Hz), total 1H], 4.14-3.79 (m, 2H), [3.92 (s) and 3.91 (s), total 3H], 3.66-3.38 (m, 2H), 3.33-3.21 (m, 1H), 3.18-3.05 (m, 2H), [1.33 (d, J=7.3 Hz) and 1.30 (d, J=7.3 Hz), total 3H].

Step 7. Synthesis of 1-(3-bromo-2-methoxy-5-methyl-5,6,8,9-tetrahydro-7H-pyrido[2,3-d]azepin-7-yl)-2,2,2-trifluoroethanone (C60)

To a solution of C59 (330 mg, 1.14 mmol) in a mixture of methanol (20 mL) and disodium hydrogen phosphate buffer solution (100 mL) was added bromine (274 mg, 1.71 mmol); the reaction mixture was stirred at room temperature for 2 hours, whereupon it was concentrated in vacuo to remove methanol. The aqueous residue was extracted with ethyl acetate (2×30 mL), and the combined organic layers were washed with saturated aqueous sodium chloride solution, dried over sodium sulfate, filtered, and concentrated under reduced pressure to afford the product as a yellow solid. From examination of the $^1$H NMR spectrum, this material was presumed to be a mixture of rotamers. Yield: 370 mg, 1.01 mmol, 89%. $^1$H NMR (400 MHz, CDCl$_3$) δ 7.60 (s, 1H), 4.19-3.79 (m, 2H), [3.99 (s) and 3.98 (s), total 3H], 3.67-3.35 (m, 2H), 3.29-3.18 (m, 1H), 3.17-3.03 (m, 2H), [1.34 (d, J=7.0 Hz) and 1.30 (d, J=7.3 Hz), total 3H].

Step 8. Synthesis of N-(2-methoxy-5-methyl-6,7,8,9-tetrahydro-5H-pyrido[2,3-d]azepin-3-yl)-4-methylbenzenesulfonamide (C61)

A mixture of C60 (50 mg, 0.14 mmol), 4-methylbenzenesulfonamide (32.6 mg, 0.190 mmol), and cesium carbonate (222 mg, 0.681 mmol) in 2-methylbutan-2-ol (5 mL) was degassed with nitrogen for several minutes. Palladium(II) acetate (1.63 mg, 7.26 µmol) and 5-(di-tert-butylphosphanyl)-1',3',5'-triphenyl-1'H-1,4'-bipyrazole (BippyPhos; 8.28 mg, 16.3 µmol) were added, and the reaction mixture was stirred at 120° C. overnight. It was then filtered and concentrated in vacuo; preparative thin-layer chromatography on silica gel (Eluent: 10:1 dichloromethane/methanol) provided the product as a yellow solid. Yield: 32 mg, 89 μmol, 64%. $^1$H NMR (400 MHz, CD$_3$OD), characteristic peaks: δ 7.66-7.6 (m, 3H), 7.29 (br d, J=8 Hz, 2H), 3.69 (s, 3H), 2.38 (s, 3H), 1.42 (d, J=7.3 Hz, 3H).

Step 9. Synthesis of N-(7-ethyl-2-methoxy-5-methyl-6,7,8,9-tetrahydro-5H-pyrido[2,3-d]azepin-3-yl)-4-methylbenzenesulfonamide (13)

Sodium cyanoborohydride (55.6 mg, 0.885 mmol) was added to a solution of C61 (32 mg, 89 μmol) and acetaldehyde (60% solution in ethanol; 65 mg, 0.89 mmol) in ethanol (3 mL), and the reaction mixture was stirred at room temperature overnight. After solvents had been removed in vacuo, the residue was partitioned between water and ethyl acetate; the organic layer was dried over sodium sulfate, filtered, and concentrated under reduced pressure. Purification was effected via preparative thin-layer chromatography on silica gel (Eluent: 10:1 dichloromethane/methanol) followed by reversed-phase HPLC (Column: Phenomenex Gemini C18, 8 μm; Mobile phase A: aqueous ammonia, pH 10; Mobile phase B: acetonitrile; Gradient: 26% to 46% B). The product was isolated as a gray solid. Yield: 9.9 mg, 25 μmol, 28%. LCMS m/z 390.0 [M+H]$^+$. $^1$H NMR (400 MHz, CD$_3$OD) δ 7.59 (br d, J=8.3 Hz, 2H), 7.53 (s, 1H), 7.28 (br d, J=8.0 Hz, 2H), 3.64 (s, 3H), 3.17-2.83 (m, 5H), 2.68-2.57 (m, 2H), 2.38 (s, 3H), 2.37-2.19 (m, 2H), 1.32 (d, J=7.3 Hz, 3H), 1.13 (t, J=7.1 Hz, 3H).

Example 14

4-Ethoxy-N-[7-ethyl-2-(propan-2-yloxy)-6,7,8,9-tetrahydro-5H-pyrido[2,3-d]azepin-3-yl]benzenesulfonamide (14)

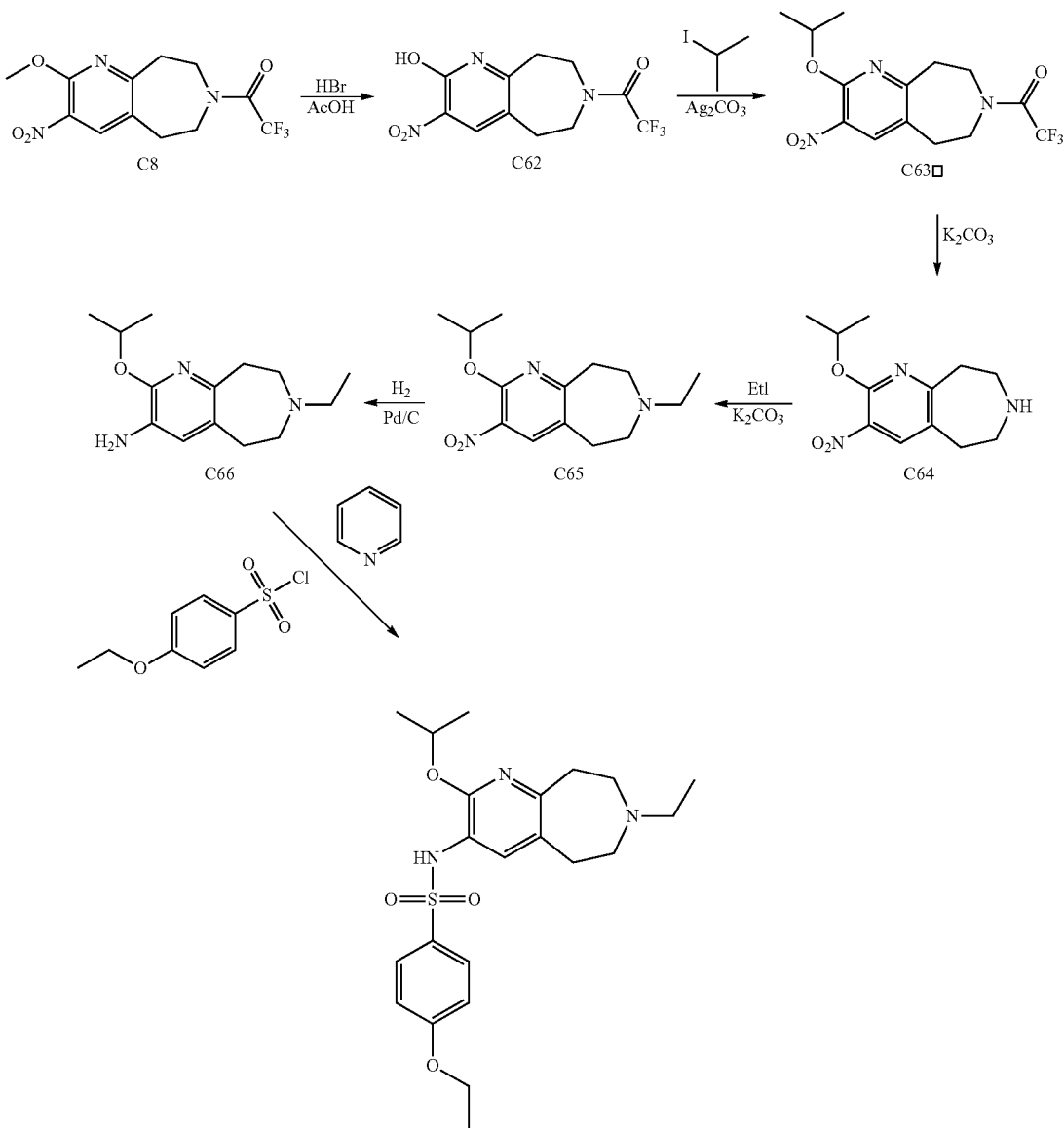

Step 1. Synthesis of 2,2,2-trifluoro-1-(2-hydroxy-3-nitro-5,6,8,9-tetrahydro-7H-pyrido[2,3-d]azepin-7-yl)ethanone (C62)

Hydrogen bromide in acetic acid (33 weight percent; 12 mL) and water (3 mL) were added to C8 (1.20 g, 3.76 mmol), and the resulting solution was stirred at room temperature for 10 minutes. The reaction mixture was neutralized by addition of saturated aqueous sodium bicarbonate solution and solid sodium bicarbonate, and then extracted with ethyl acetate (2×200 mL). The combined organic layers were dried over magnesium sulfate, filtered, and concentrated under reduced pressure; chromatography on silica gel (Gradient: 0% to 5% methanol in ethyl acetate) afforded the product as a yellow solid. From examination of the $^1$H NMR spectrum, this material was presumed to be a mixture of rotamers. Yield: 485 mg, 1.59 mmol, 42%. LCMS m/z 306.0 [M+H]$^+$. $^1$H NMR (400 MHz, CDCl$_3$) δ 13.75-12.70 (v br s, 1H), [8.36 (s) and 8.34 (s), total 1H], 3.96-3.72 (m, 4H), 3.25-3.15 (m, 2H), 3.00-2.90 (m, 2H).

Step 2. Synthesis of 2,2,2-trifluoro-1-[3-nitro-2-(propan-2-yloxy)-5,6,8,9-tetrahydro-7H-pyrido[2,3-d]azepin-7-yl]ethanone (C63)

A mixture of C62 (100 mg, 0.328 mmol), silver carbonate (109 mg, 0.395 mmol), and 2-iodopropane (279 mg, 1.64 mmol) in acetone (2.6 mL) was stirred at room temperature overnight, whereupon it was diluted with ethyl acetate (80 mL) and filtered through a pad of diatomaceous earth. The filtrate was washed with saturated aqueous sodium bicarbonate solution (15 mL), dried over magnesium sulfate, filtered, and concentrated in vacuo, providing the product as a gum. From examination of the $^1$H NMR spectrum, this material was presumed to be a mixture of rotamers. Yield: 110 mg, 0.317 mmol, 97%. $^1$H NMR (400 MHz, CDCl$_3$) δ [8.04 (s) and 8.02 (s), total 1H], 5.56-5.42 (m, 1H), 3.86-3.70 (m, 4H), 3.23-3.12 (m, 2H), 3.01-2.91 (m, 2H), [1.38 (d J=6.2 Hz) and 1.37 (d, J=6.2 Hz), total 6H].

Step 3. Synthesis of 3-nitro-2-(propan-2-yloxy)-6,7,8,9-tetrahydro-5H-pyrido[2,3-d]azepine (C64)

A mixture of C63 (110 mg, 0.317 mmol) and potassium carbonate (101 mg, 0.731 mmol) in methanol (3 mL) and water (0.6 mL) was heated to 60° C. for 15 minutes. The reaction mixture was then partitioned between saturated aqueous ammonium chloride solution (10 mL) and dichloromethane; the aqueous layer was extracted with dichloromethane and the combined organic layers were dried over magnesium sulfate, filtered, and concentrated in vacuo, affording the product as a brown gum. Yield: 61 mg, 0.24 mmol, 76%. LCMS m/z 252.1 [M+H]$^+$. $^1$H NMR (400 MHz, CD$_3$OD) δ 8.05 (s, 1H), 5.51 (septet, J=6.2 Hz, 1H), 3.18-3.11 (m, 2H), 3.04-2.91 (m, 6H), 1.36 (d, J=6.2 Hz, 6H).

Step 4. Synthesis of 7-ethyl-3-nitro-2-(propan-2-yloxy)-6,7,8,9-tetrahydro-5H-pyrido[2,3-d]azepine (C65)

To a solution of C64 (61 mg, 0.24 mmol) in acetonitrile (2.4 mL) was added potassium carbonate (101 mg, 0.731 mmol), followed by iodoethane (97.9 µL, 1.22 mmol), and the reaction mixture was allowed to stir at room temperature overnight. It was then partitioned between saturated aqueous sodium bicarbonate solution (20 mL) and ethyl acetate (50 mL), and the aqueous layer was extracted with ethyl acetate (50 mL). The combined organic layers were dried, filtered, and concentrated in vacuo; silica gel chromatography (Eluent: 25% methanol in ethyl acetate) provided the product as a colorless gum. Yield: 50 mg, 0.18 mmol, 75%. LCMS m/z 280.1 [M+H]$^+$. $^1$H NMR (400 MHz, CDCl$_3$) δ 7.98 (s, 1H), 5.51 (septet, J=6 Hz, 1H), 3.20-3.11 (m, 2H), 2.97-2.89 (m, 2H), 2.76-2.68 (m, 4H), 2.65 (q, J=7.1 Hz, 2H), 1.39 (d, J=6.2 Hz, 6H), 1.14 (t, J=7.1 Hz, 3H).

Step 5. Synthesis of 7-ethyl-2-(propan-2-yloxy)-6,7,8,9-tetrahydro-5H-pyrido[2,3-d]azepin-3-amine (C66)

A hydrogenation bomb was charged with palladium on carbon (10%, 50 mg); the catalyst was wetted via drop-wise addition of methanol, and a solution of C65 (50 mg, 0.18 mmol) in methanol (10 mL) was slowly added to the catalyst. The reaction vessel was then sealed, evacuated, filled with nitrogen, evacuated again, and charged with hydrogen. The hydrogenation reaction was carried out at room temperature under 50 psi of hydrogen for 2 hours. After the reaction mixture had been filtered through a pad of diatomaceous earth, the pad was rinsed with methanol and the combined filtrates were concentrated in vacuo, affording the product as a gum. Yield: 36 mg, 0.14 mmol, 78%. LCMS m/z 250.2 [M+H]$^+$. $^1$H NMR (400 MHz, CD$_3$OD) δ 6.78 (s, 1H), 5.27 (septet, J=6 Hz, 1H), 2.99-2.90 (m, 2H), 2.81-2.73 (m, 2H), 2.72-2.63 (m, 4H), 2.62 (q, J=7.1 Hz, 2H), 1.31 (d, J=6.1 Hz, 6H), 1.14 (t, J=7.2 Hz, 3H).

Step 6. Synthesis of 4-ethoxy-N-[7-ethyl-2-(propan-2-yloxy)-6,7,8,9-tetrahydro-5H-pyrido[2,3-d]azepin-3-yl]benzenesulfonamide (14)

A solution of C66 (11 mg, 44 µmol) in pyridine (0.5 mL) was treated with 4-ethoxybenzenesulfonyl chloride (10.2 mg, 46.2 µmol). After being stirred for 1 hour, the reaction mixture was partitioned between saturated aqueous sodium bicarbonate solution (3 mL) and ethyl acetate (15 mL); the organic layer was dried over magnesium sulfate, filtered, and concentrated in vacuo. Purification was carried out via reversed-phase HPLC (Column: Waters XBridge C18, 5 µm; Mobile phase A: 0.03% ammonium hydroxide in water; Mobile phase B: 0.03% ammonium hydroxide in acetonitrile; Gradient: 5% to 100% B). Yield: 10.9 mg, 25.1 µmol, 57%. LCMS m/z 434.3 [M+H]$^+$. $^1$H NMR (600 MHz, DMSO-d$_6$) δ 9.25-9.13 (br s, 1H), 7.62 (br d, J=8.9 Hz, 2H), 7.34 (s, 1H), 7.01 (br d, J=8.9 Hz, 2H), 5.00 (septet, J=6.1 Hz, 1H), 4.08 (q, J=7.0 Hz, 2H), 2.90-2.81 (br s, 2H), 2.77-2.69 (br s, 2H), 2.6-2.4 (m, 6H, assumed; obscured by solvent peak), 1.32 (t, J=7.0 Hz, 3H), 1.04 (d, J=6.1 Hz, 6H), 1.04-0.98 (br m, 3H).

Example 137

4-Ethoxy-N-(7-ethyl-2-methyl-6,7,8,9-tetrahydro-5H-pyrido[2,3-d]azepin-3-yl)benzenesulfonamide, trifluoroacetate salt (137)

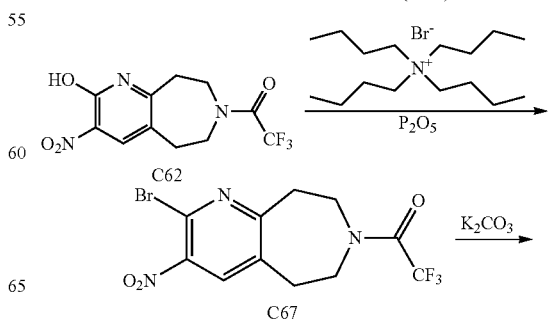

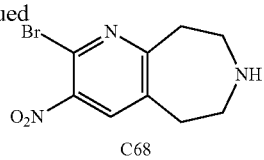

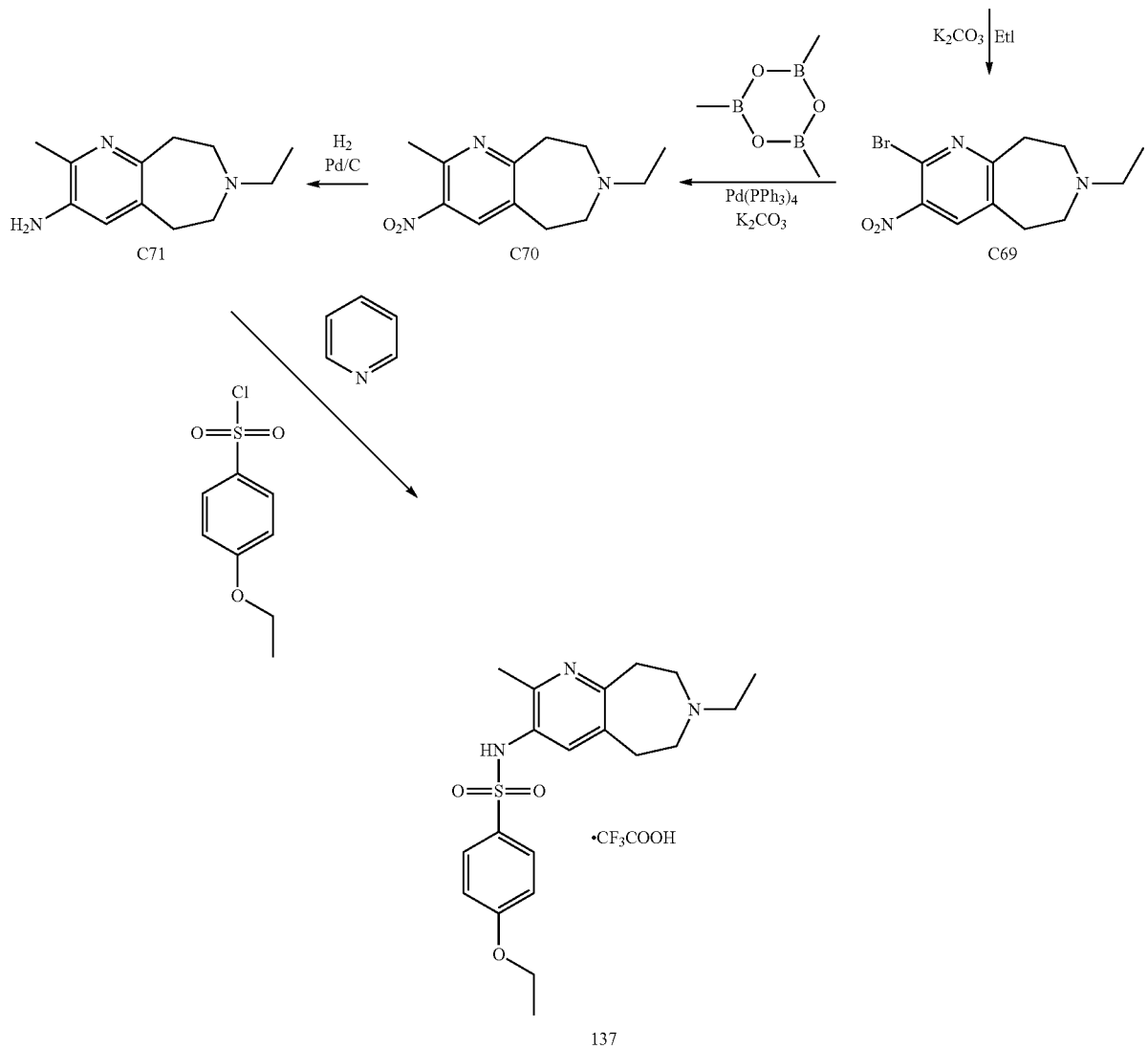

acetate in heptane) to provide the product as a colorless gum. By $^1$H NMR analysis, this was composed of a mixture of rotamers. Yield: 300 mg, 0.815 mmol, 47%. LCMS m/z 368.0 (bromine isotope pattern observed) [M+H]$^+$. $^1$H NMR (400 MHz, CDCl$_3$) δ [7.99 (s) and 7.96 (s), total 1H], 3.89-3.82 (m, 2H), 3.82-3.76 (m, 2H), 3.36-3.28 (m, 2H), 3.11-3.01 (m, 2H).

Step 1. Synthesis of 1-(2-bromo-3-nitro-5,6,8,9-tetrahydro-7H-pyrido[2,3-d]azepin-7-yl)-2,2,2-trifluoroethanone (C67)

A mixture of C62 (527 mg, 1.73 mmol), phosphorus pentoxide (613 mg, 4.32 mmol), and tetrabutylammonium bromide (741 mg, 2.30 mmol) in toluene (30 mL) was heated to 110° C. After 30 minutes, the reaction mixture was cooled to room temperature; the yellow supernatant was decanted (a dark brown material remained in the reaction flask) and concentrated in vacuo. The resulting material was purified via chromatography on silica gel (Eluent: 25% ethyl Step 2. Synthesis of 2-bromo-3-nitro-6,7,8,9-tetrahydro-5H-pyrido[2,3-d]azepine (C68)

A mixture of potassium carbonate (260 mg, 1.88 mmol) and C67 (300 mg, 0.815 mmol) in methanol (9 mL) and water (1.8 mL) was heated to 60° C. for 15 minutes, whereupon the reaction mixture was allowed to cool to room temperature. Saturated aqueous ammonium chloride solution (15 mL) was added, and the resulting mixture was extracted twice with ethyl acetate; the combined organic layers (100 mL) were dried over magnesium sulfate, filtered, and concentrated in vacuo, affording the product as a brown gum (230 mg). This material was used directly in the following step. LCMS m/z 272.0 (bromine isotope pattern observed) [M+H]$^+$.

Step 3. Synthesis of 2-bromo-7-ethyl-3-nitro-6,7,8,9-tetrahydro-5H-pyrido[2,3-d]azepine (C69)

A solution of C68 (from the previous step; 230 mg, ≤0.815 mmol) in acetonitrile (8.4 mL) was treated with potassium carbonate (350 mg, 2.53 mmol), followed by iodoethane (204 μL, 2.55 mmol). The reaction mixture was allowed to stir at room temperature overnight, whereupon it was diluted with saturated aqueous sodium bicarbonate solution (20 mL) and extracted with ethyl acetate (2×75 mL). The combined organic layers were dried, filtered, concentrated in vacuo, and subjected to silica gel chromatography (Eluent: 25% methanol in ethyl acetate), affording the product as a viscous orange oil. Yield: 128 mg, 0.426 mmol, 52% over 2 steps. LCMS m/z 300.0 (bromine isotope pattern observed) [M+H]$^+$. $^1$H NMR (400 MHz, CDCl$_3$) δ 7.88 (s, 1H), 3.27-3.20 (m, 2H), 3.00-2.93 (m, 2H), 2.73-2.66 (m, 4H), 2.59 (q, J=7.2 Hz, 2H), 1.09 (t, J=7.0 Hz, 3H).

Step 4. Synthesis of 7-ethyl-2-methyl-3-nitro-6,7,8,9-tetrahydro-5H-pyrido[2,3-d]azepine (C70)

A mixture of C69 (128 mg, 0.426 mmol), potassium carbonate (177 mg, 1.28 mmol), tetrakis(triphenylphosphine)palladium(0), (30.3 mg, 26.2 μmol) and trimethylboroxin (64 mg, 0.51 mmol) in 1,4-dioxane (2 mL) and water (2 mL) was degassed via bubbling nitrogen through it for 5 minutes. The reaction mixture was heated at reflux for 5 hours, cooled to room temperature, and diluted with ethyl acetate and water; the resulting slurry was filtered through a pad of diatomaceous earth. The filter pad was rinsed with additional water and ethyl acetate, and the organic layer of the combined filtrates was dried over magnesium sulfate, filtered, and concentrated in vacuo. Purification via silica gel chromatography (Eluent: 25% methanol in ethyl acetate) provided the product as a yellow gum. Yield: 40 mg, 0.17 mmol, 40%. LCMS m/z 236.1 [M+H]$^+$. $^1$H NMR (400 MHz, CDCl$_3$) δ 8.00 (s, 1H), 3.25-3.19 (m, 2H), 3.00-2.94 (m, 2H), 2.79 (s, 3H), 2.73-2.66 (m, 4H), 2.60 (q, J=7.1 Hz, 2H), 1.10 (t, J=7.1 Hz, 3H).

Step 5. Synthesis of 7-ethyl-2-methyl-6,7,8,9-tetrahydro-5H-pyrido[2,3-d]azepin-3-amine (C71)

Palladium on carbon (10%, 40 mg) was wetted via drop-wise addition of methanol, and a solution of C70 (40 mg, 0.17 mmol) in methanol (10 mL) was slowly added to the catalyst. The reaction vessel was then evacuated and filled with nitrogen. Hydrogenation was carried out at room temperature for 2 hours at 50 psi, whereupon the reaction mixture was filtered through a pad of diatomaceous earth. The filter pad was rinsed with methanol and the combined filtrates were concentrated in vacuo, providing the product as a gum. Yield: 35 mg, 0.17 mmol, 100%.

LCMS m/z 206.1 [M+H]$^+$. $^1$H NMR (400 MHz, CD$_3$OD) δ 6.89 (s, 1H), 3.11-3.04 (m, 2H), 2.94-2.86 (m, 6H), 2.82 (q, J=7.2 Hz, 2H), 2.31 (s, 3H), 1.21 (t, J=7.2 Hz, 3H).

Step 6. Synthesis of 4-ethoxy-N-(7-ethyl-2-methyl-6,7,8,9-tetrahydro-5H-pyrido[2,3-d]azepin-3-yl)benzenesulfonamide, trifluoroacetate salt (137)

4-Ethoxybenzenesulfonyl chloride (12.6 mg, 57.1 μmol) was added to a solution of C71 (11 mg, 54 μmol) in pyridine (0.5 mL). After the reaction mixture had stirred for 1 hour at room temperature, it was partitioned between saturated aqueous sodium bicarbonate solution (3 mL) and ethyl acetate (15 mL). The organic layer was dried over magnesium sulfate, filtered, and concentrated in vacuo; purification via reversed-phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5% to 40% B) afforded the product. Yield: 15.8 mg, 40.6 μmol, 75%. LCMS m/z 390.2 [M+H]$^+$. $^1$H NMR (600 MHz, DMSO-d$_6$), characteristic peaks: δ 9.62 (br s, 1H), 9.6-9.5 (v br s, 1H), 7.58 (br d, J=8.8 Hz, 2H), 7.29 (s, 1H), 7.05 (br d, J=8.9 Hz, 2H), 4.10 (q, J=7.0 Hz, 2H), 3.67-3.56 (m, 2H), 2.07 (s, 3H), 1.34 (t, J=7.0 Hz, 3H), 1.24 (t, J=7.2 Hz, 3H).

TABLE 6

Method of preparation, structure, and physicochemical properties for Examples 15-25.

| Example Number | Method of Preparation; Non-commercial starting materials | Structure | $^1$H NMR (400 MHz, CD$_3$OD) δ; Mass spectrum, observed ion m/z [M + H]$^+$ (unless otherwise indicated) |
|---|---|---|---|
| 15 | Example 2; P3, C23 | 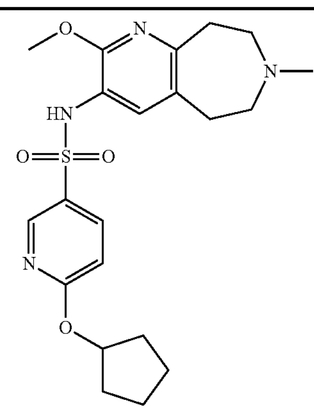 | 8.35 (dd, J = 2.5, 0.5 Hz, 1H), 7.88 (dd, J = 8.8, 2.6 Hz, 1H), 7.50 (s, 1H), 6.76 (dd, J = 8.8, 0.4 Hz, 1H), 5.46-5.38 (m, 1H), 3.63 (s, 3H), 3.03-2.96 (m, 2H), 2.90-2.83 (m, 2H), 2.67-2.57 (m, 4H), 2.39 (s, 3H), 2.04-1.90 (m, 2H), 1.84-1.71 (m, 4H), 1.70-1.59 (m, 2H); 433.0 |

TABLE 6-continued

Method of preparation, structure, and physicochemical properties for Examples 15-25.

| Example Number | Method of Preparation; Non-commercial starting materials | Structure | $^1$H NMR (400 MHz, CD$_3$OD) δ; Mass spectrum, observed ion m/z [M + H]$^+$ (unless otherwise indicated) |
|---|---|---|---|
| 16 | Example 1[1]; P3 | 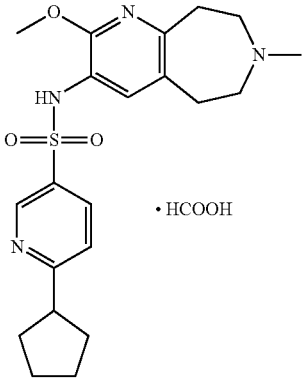 [SMILES: COc1nc2c(cc1NS(=O)(=O)c1ccc(C3CCCC3)nc1)CCN(C)CC2 ; "· HCOOH"] · HCOOH | 8.66 (dd, J = 2.3, 0.5 Hz, 1H), 7.97 (dd, J = 8.3, 2.4 Hz, 1H), 7.59 (s, 1H), 7.42 (br d, J = 8.3 Hz, 1H), 3.58 (s, 3H), 3.30-3.20 (m, 1H), 3.15-2.98 (m, 8H), 2.71 (s, 3H), 2.14-2.01 (m, 2H), 1.91-1.80 (m, 2H), 1.80-1.67 (m, 4H); 417.1 |
| 17 | Example 2[2]; P3 | 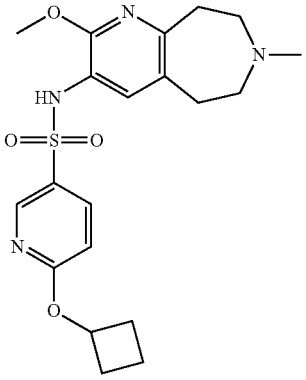 [SMILES: COc1nc2c(cc1NS(=O)(=O)c1ccc(OC3CCC3)nc1)CCN(C)CC2] | 8.34 (br d, J = 2 Hz, 1H), 7.89 (dd, J = 8.8, 2.4 Hz, 1H), 7.50 (s, 1H), 6.78 (d, J = 8.9 Hz, 1H), 5.23-5.13 (m, 1H), 3.62 (s, 3H), 3.01-2.95 (m, 2H), 2.88-2.82 (m, 2H), 2.64-2.55 (m, 4H), 2.49-2.40 (m, 2H), 2.38 (s, 3H), 2.17-2.04 (m, 2H), 1.90-1.78 (m, 1H), 1.77-1.63 (m, 1H); 419.1 |
| 18 | Example 2; P3 | 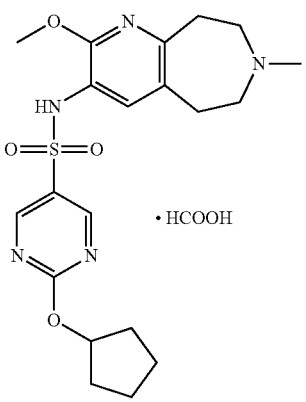 [SMILES: COc1nc2c(cc1NS(=O)(=O)c1cnc(OC3CCCC3)nc1)CCN(C)CC2 ; "· HCOOH"] · HCOOH | 8.71 (s, 2H), 7.55 (s, 1H), 5.53-5.46 (m, 1H), 3.64 (s, 3H), 3.10-3.03 (m, 2H), 2.97-2.91 (m, 2H), 2.87-2.77 (m, 4H), 2.54 (s, 3H), 2.07-1.92 (m, 2H), 1.88-1.75 (m, 4H), 1.74-1.62 (m, 2H); 434.1 |

TABLE 6-continued

Method of preparation, structure, and physicochemical properties for Examples 15-25.

| Example Number | Method of Preparation; Non-commercial starting materials | Structure | ¹H NMR (400 MHz, CD₃OD) δ; Mass spectrum, observed ion m/z [M + H]⁺ (unless otherwise indicated) |
|---|---|---|---|
| 19 | Example 11; P3, C17 | 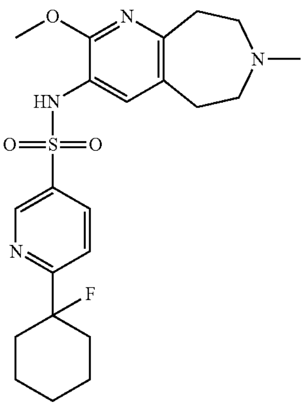 [SMILES: COc1nc2c(cc1NS(=O)(=O)c1ccc(C3(F)CCCCC3)nc1)CCN(C)CC2] | 8.74-8.71 (m, 1H), 8.05 (dd, J = 8.4, 2.3 Hz, 1H), 7.66 (br d, J = 8.4 Hz, 1H), 7.52 (s, 1H), 3.52 (s, 3H), 3.04-2.97 (m, 2H), 2.92-2.86 (m, 2H), 2.72-2.62 (m, 4H), 2.43 (s, 3H), 2.14-1.93 (m, 2H), 1.90-1.67 (m, 7H), 1.47-1.32 (m, 1H); 449.0 |
| 20 | Example 3; P5, C26 | 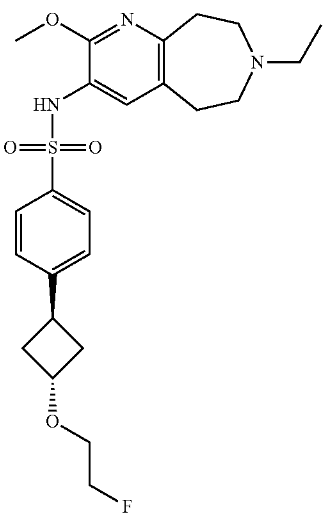 [SMILES: CCN1CCc2cc(NS(=O)(=O)c3ccc([C@H]4C[C@H](OCCF)C4)cc3)c(OC)nc2CC1] | ¹H NMR (400 MHz, CDCl₃) δ 7.70 (br d, J = 8.4 Hz, 2H), 7.54 (s, 1H), 7.30 (br d, J = 8.2 Hz, 2H), 4.66-4.62 (m, 1H), 4.55-4.49 (m, 1H), 4.25-4.17 (m, 1H), 3.75 (s, 3H), 3.70-3.62 (m, 2H), 3.62-3.58 (m, 1H), 3.27-2.67 (br m, 10H), 2.60-2.48 (m, 2H), 2.44-2.34 (m, 2H), 1.33-1.16 (br m, 3H); 478.0 |
| 21 | Example 3³; P3 | 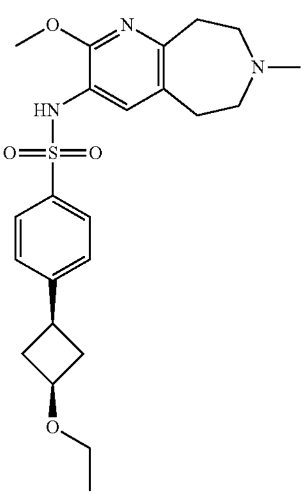 [SMILES: CCO[C@H]1C[C@@H](c2ccc(S(=O)(=O)Nc3cc4c(nc3OC)CCN(C)CC4)cc2)C1] | 7.64 (br d, J = 8.0 Hz, 2H), 7.52 (s, 1H), 7.33 (br d, J = 8.0 Hz, 2H), 4.04-3.95 (m, 1H), 3.60 (s, 3H), 3.47 (q, J = 7.0 Hz, 2H), 3.15-3.04 (m, 1H), 3.05-2.98 (m, 2H), 2.92-2.86 (m, 2H), 2.82-2.66 (m, 6H), 2.51 (s, 3H), 2.01-1.90 (m, 2H), 1.18 (t, J = 7.0 Hz, 3H); 446.0 |

TABLE 6-continued

Method of preparation, structure, and physicochemical properties for Examples 15-25.

| Example Number | Method of Preparation; Non-commercial starting materials | Structure | $^1$H NMR (400 MHz, CD$_3$OD) δ; Mass spectrum, observed ion m/z [M + H]$^+$ (unless otherwise indicated) |
|---|---|---|---|
| 22 | Example 19; P3 | 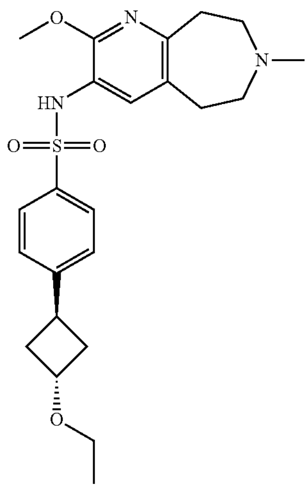 [SMILES: CCO[C@H]1C[C@H](c2ccc(S(=O)(=O)Nc3cc4c(nc3OC)CCN(C)CC4)cc2)C1] | 7.65 (br d, J = 8.4 Hz, 2H), 7.51 (s, 1H), 7.37 (br d, J = 8.5 Hz, 2H), 4.21-4.14 (m, 1H), 3.67-3.6 (m, 1H), 3.61 (s, 3H), 3.45 (q, J = 7 Hz, 2H), 3.02-2.97 (m, 2H), 2.89-2.84 (m, 2H), 2.73-2.64 (m, 4H), 2.51-2.34 (m, 7H), 1.20 (t, J = 7.0 Hz, 3H); 446.0 |
| 23 | Example 10$^4$; P5 | 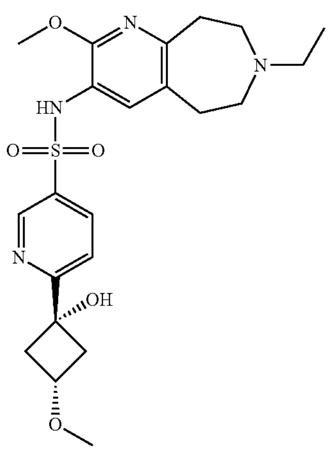 [SMILES: CCN1CCc2cc(NS(=O)(=O)c3ccc([C@]4(O)C[C@@H](OC)C4)nc3)c(OC)nc2CC1] | 8.78-8.75 (m, 1H), 8.02-7.98 (m, 1H), 7.71 (d, J = 8.4 Hz, 1H), 7.51 (s, 1H), 4.08-4.00 (m, 1H), 3.57 (s, 3H), 3.28 (s, 3H), 3.02-2.97 (m, 2H), 2.90-2.79 (m, 4H), 2.72-2.65 (m, 4H), 2.62 (q, J = 7 Hz, 2H), 2.35-2.27 (m, 2H), 1.14 (t, J = 7.1 Hz, 3H); 463.0 |
| 24 | Example 1$^5$; P3 | 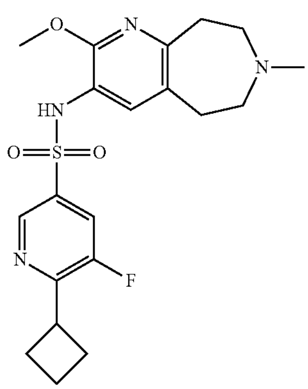 [SMILES: COc1nc2c(cc1NS(=O)(=O)c1cnc(C3CCC3)c(F)c1)CCN(C)CC2] | 8.57-8.55 (m, 1H), 7.73 (dd, J = 9.1, 1.8 Hz, 1H), 7.51 (s, 1H), 4.02-3.91 (m, 1H), 3.59 (s, 3H), 3.04-2.98 (m, 2H) 2.90-2.85 (m, 2H), 2.68-2.59 (m, 4H), 2.48-2.29 (m, 4H), 2.40 (s, 3H), 2.20-2.06 (m, 1H), 1.98-1.89 (m, 1H); 420.9 |

TABLE 6-continued

Method of preparation, structure, and physicochemical properties for Examples 15-25.

| Example Number | Method of Preparation; Non-commercial starting materials | Structure | $^1$H NMR (400 MHz, CD$_3$OD) δ; Mass spectrum, observed ion m/z [M + H]$^+$ (unless otherwise indicated) |
|---|---|---|---|
| 25 | Example 10[6]; P3 | [structure] | 8.81-8.79 (m, 1H), 8.06 (dd, J = 8.3, 2.3 Hz, 1H), 7.60 (ddd, J = 8.3, 1.3, 0.8 Hz, 1H), 7.56 (s, 1H), 3.56 (s, 3H), 3.09-3.03 (m, 2H), 2.97-2.92 (m, 2H), 2.89-2.73 (m, 6H), 2.55 (s, 3H), 2.42-2.30 (m, 1H), 2.26-2.11 (m, 2H), 1.24 (d, J = 6.6 Hz, 3H); 435.0 |

[1]The requisite 1-(5-bromopyridin-2-yl)cyclopentanol may be synthesized using the general method described by B. Guo et al., *J. Med. Chem.* 2013, 56, 2642-2650.

[2]Starting material 5-bromo-2-(cyclobutyloxy)pyridine was synthesized via sodium hydride-mediated reaction of 5-bromo-2-fluoropyridine with cyclobutanol.

[3]cis-3-(4-Bromophenyl)cyclobutanol was deprotonated with sodium hydride and alkylated with iodoethane to generate the requisite 1-bromo-4-(cis-3-ethoxycyclobutyl)benzene.

[4]2,5-Dibromopyridine was reacted with n-butyllithium, followed by 3-methoxycyclobutanone, to afford the requisite cis-1-(5-bromopyridin-2-yl)-3-methoxycyclobutanol.

[5]In this case, the dehydration reaction was carried out via treatment with sodium hydride and methanesulfonyl chloride, rather than acid.

[6]The fluorination product 2-(1-fluoro-3-methylcyclobutyl)-5-[(4-methoxybenzyl)sulfanyl]pyridine was obtained as a mixture of isomers; supercritical fluid chromatography [Column: Chiral Technologies Chiralcel OJ, 10 μm; Mobile phase: 4:1 carbon dioxide/(0.1% ammonium hydroxide in ethanol)]afforded the two isomers. The second-eluting isomer was assigned as 2-(cis-1-fluoro-3-methylcyclobutyl)-5-[(4-methoxybenzyl)sulfanyl]pyridine on the basis of NOE studies, and this material was used to synthesize Example 25.

TABLE 7

Method of preparation, structure, and mass spectrometry data for Examples 26-136 and 138-140

| Example Number | Method of Preparation; Non-commercial starting materials | Structure | Mass spectrum m/z [M + H]$^+$ (unless otherwise indicated) |
|---|---|---|---|
| 26 | Example 5[1]; C9 | [structure] · HCOOH | 390.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 27 | Example 5; P3 | 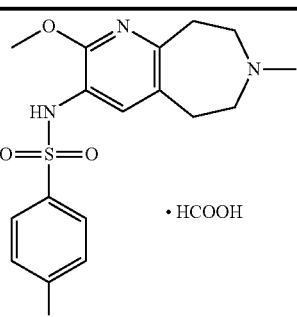 | 381.9, chlorine isotope pattern observed |
| 28 | Example 5; P3 | 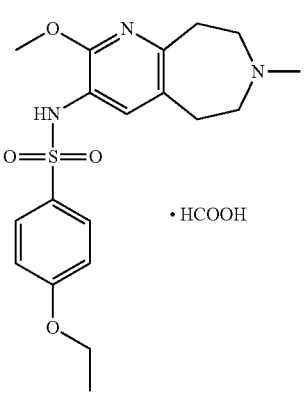 [SMILES: CCOc1ccc(S(=O)(=O)Nc2cc3c(nc2OC)CCN(C)CC3)cc1 ; "· HCOOH"] | 392.0 |
| 29 | Example 5[1]; C9 | 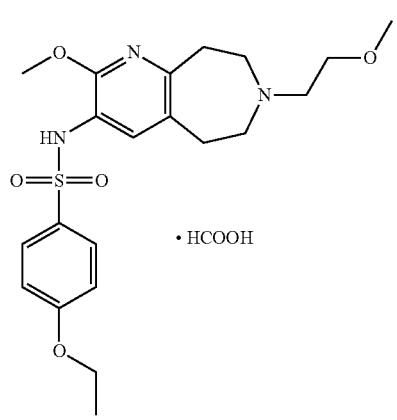 [SMILES: CCOc1ccc(S(=O)(=O)Nc2cc3c(nc2OC)CCN(CCOC)CC3)cc1 ; "· HCOOH"] | 436.1 |
| 30 | Example 5; P5 | 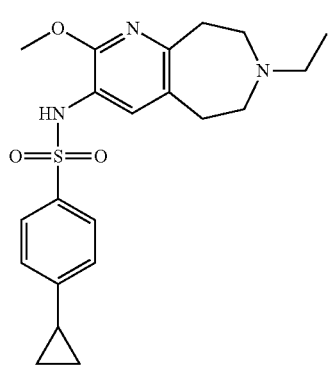 | 402.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 31 | Example 5; P3 | 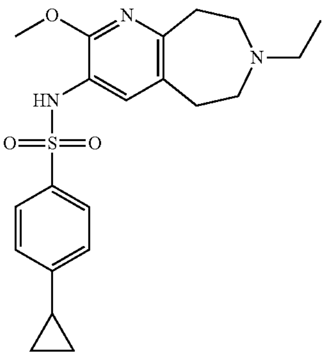 [SMILES: CCN1CCc2cc(NS(=O)(=O)c3ccc(C4CC4)cc3)c(OC)nc2CC1] | 403.9 |
| 32 | Example 2[2]; P3 | 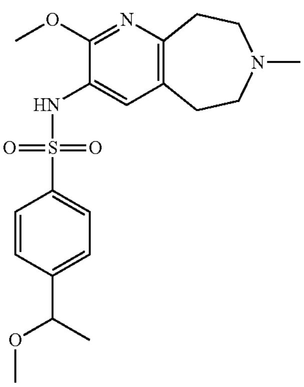 [SMILES: COc1nc2c(cc1NS(=O)(=O)c1ccc(C(C)OC)cc1)CCN(C)CC2] | 405.9 |
| 33 | Example 2[3]; P3 | 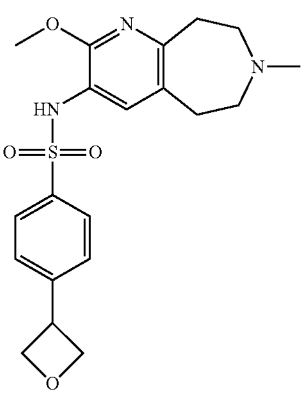 [SMILES: COc1nc2c(cc1NS(=O)(=O)c1ccc(C3COC3)cc1)CCN(C)CC2] | 403.9 |
| 34 | Example 5[4]; P3 | 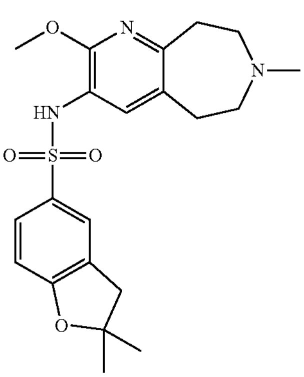 [SMILES: COc1nc2c(cc1NS(=O)(=O)c1ccc3c(c1)CC(C)(C)O3)CCN(C)CC2] | 417.9 |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 35 | Example 5; P5 | 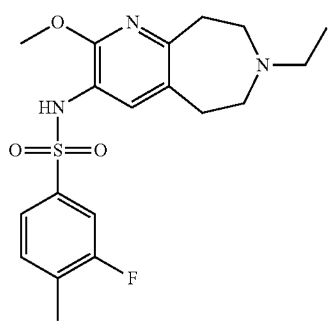 [SMILES: CCN1CCc2cc(NS(=O)(=O)c3ccc(C)c(F)c3)c(OC)nc2CC1] | 394.1 |
| 36 | Example 33; P3 | 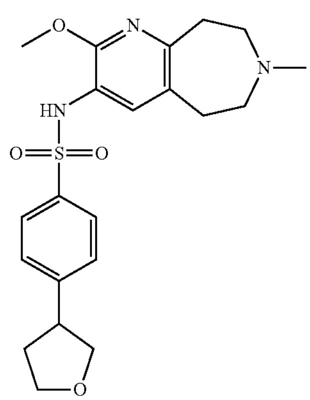 [SMILES: COc1nc2c(cc1NS(=O)(=O)c1ccc(C3CCOC3)cc1)CCN(C)CC2] | 418.0 |
| 37 | Example 2[5]; P3 | 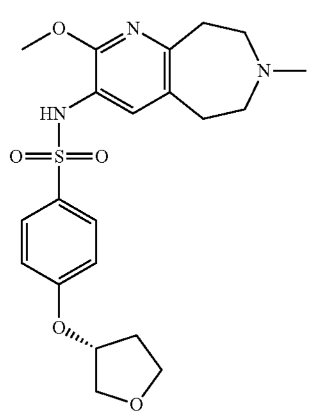 [SMILES: COc1nc2c(cc1NS(=O)(=O)c1ccc(O[C@@H]3CCOC3)cc1)CCN(C)CC2] | 434.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 38 | Example 1[6]; P3 | 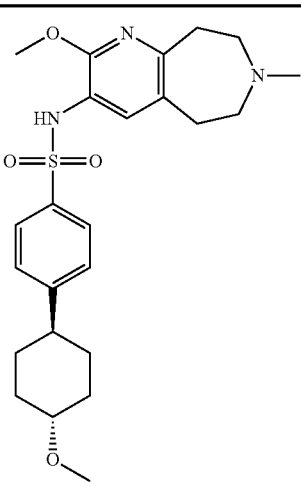 | 460.1 |
| 39 | Example 10[7]; P3 | 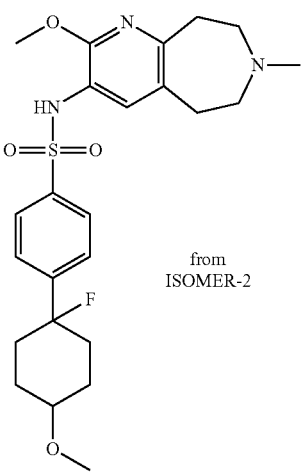 [SMILES: COc1nc2c(cc1NS(=O)(=O)c1ccc(C3(F)CCC(OC)CC3)cc1)CCN(C)CC2] from ISOMER-2 | 478.1 |
| 40 | Example 2[8]; P3 | 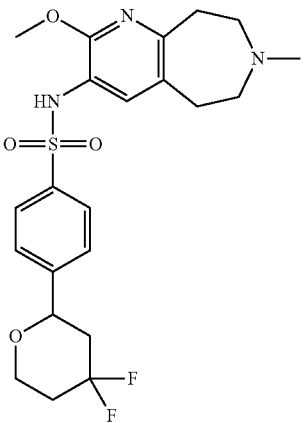 [SMILES: COc1nc2c(cc1NS(=O)(=O)c1ccc(C3CC(F)(F)CCO3)cc1)CCN(C)CC2] | 468.2 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 41 | Example 40[9] | 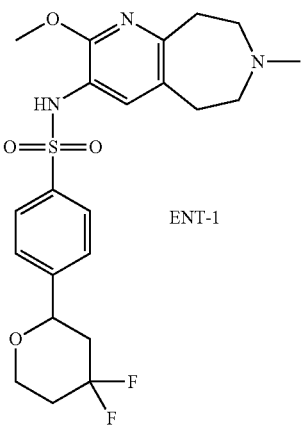 [SMILES: COc1nc2c(cc1NS(=O)(=O)c1ccc(C3CC(F)(F)CCO3)cc1)CCN(C)CC2] ENT-1 | 468.2 |
| 42 | Example 40[9] | 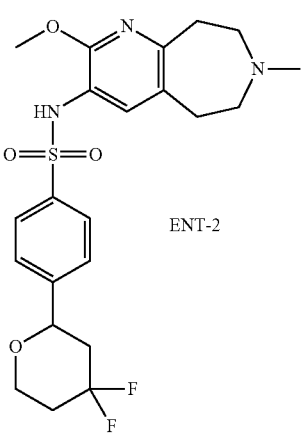 [SMILES: COc1nc2c(cc1NS(=O)(=O)c1ccc(C3CC(F)(F)CCO3)cc1)CCN(C)CC2] ENT-2 | 468.2 |
| 43 | Example 7[10,11]; P5 | 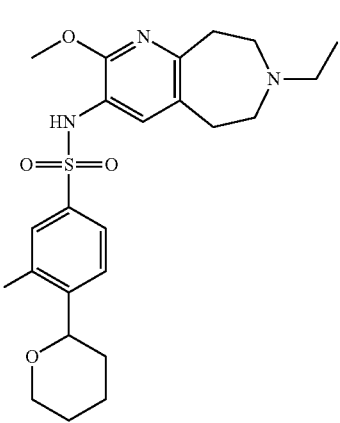 | 464.1 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 44 | Example 5[1,12]; C9 | 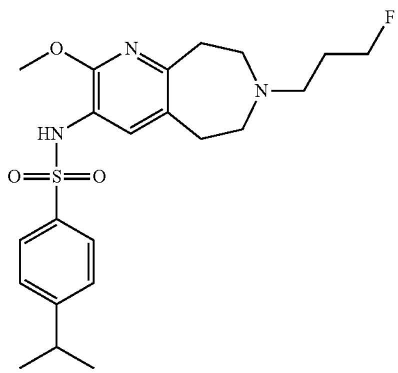 [SMILES: COc1nc2c(cc1NS(=O)(=O)c1ccc(C(C)C)cc1)CCN(CCCF)CC2] | 436.0 |
| 45 | Example 5; P3 | 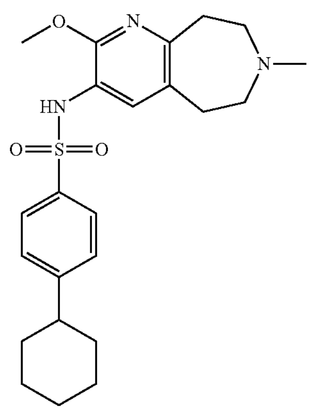 | 430.0 |
| 46 | Example 5; P3 | 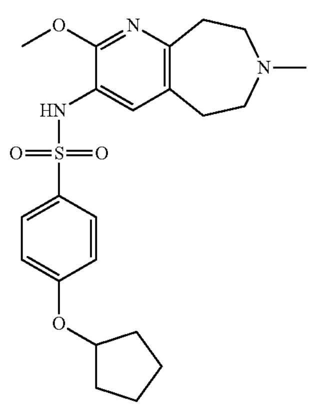 [SMILES: COc1nc2c(cc1NS(=O)(=O)c1ccc(OC3CCCC3)cc1)CCN(C)CC2] | 432.0 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 47 | Example 2[13]; P3 | 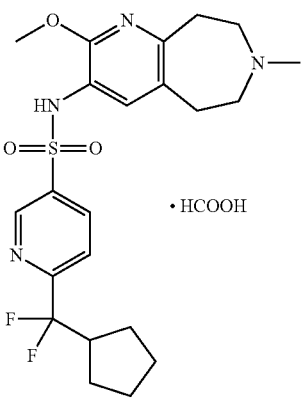 [SMILES: COc1nc2c(cc1NS(=O)(=O)c1ccc(C(F)(F)C3CCCC3)nc1)CCN(C)CC2 ; "· HCOOH"] · HCOOH | 467.0 |
| 48 | Example 10; P5 | 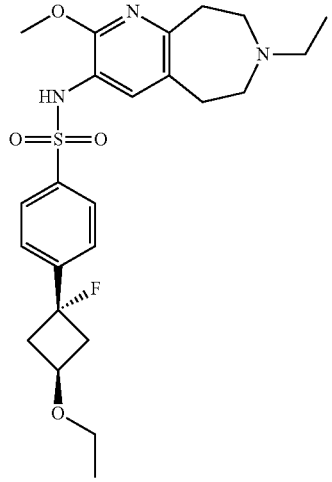 [SMILES: CCO[C@H]1C[C@@](F)(c2ccc(S(=O)(=O)Nc3cc4c(nc3OC)CCN(CC)CC4)cc2)C1] | 478.0 |
| 49 | Example 5[1]; C9 | 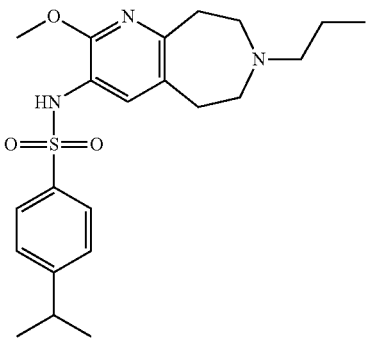 [SMILES: CCCN1CCc2cc(NS(=O)(=O)c3ccc(C(C)C)cc3)c(OC)nc2CC1] | 418.3 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 50 | Example 5[1]; C9 | 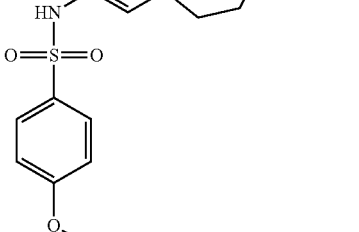 | 420.4 |
| 51 | Example 5; P5 | 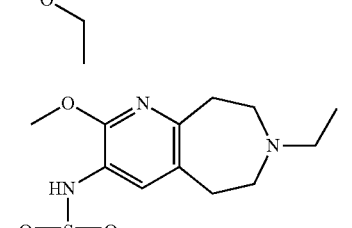 · HCOOH | 404.1 |
| 52 | Example 5; P5 | 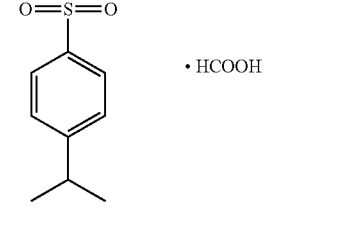 | 406.2 |
| 53 | Example 5; P5 | 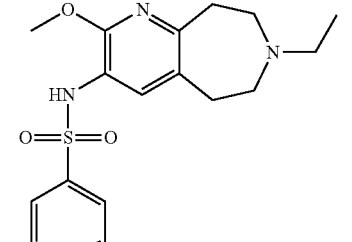 · HCOOH | 376.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 54 | Example 5; P3 | 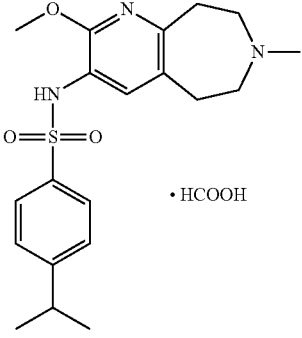 [SMILES: COc1nc2c(cc1NS(=O)(=O)c1ccc(C(C)C)cc1)CCN(C)CC2 ; "· HCOOH"] • HCOOH | 390.0 |
| 55 | Example 5[14]; P3 | 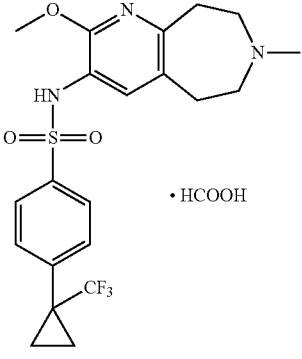 [SMILES: COc1nc2c(cc1NS(=O)(=O)c1ccc(C3(C(F)(F)F)CC3)cc1)CCN(C)CC2 ; "· HCOOH"] • HCOOH | 456.0 |
| 56 | Example 13; C60 | 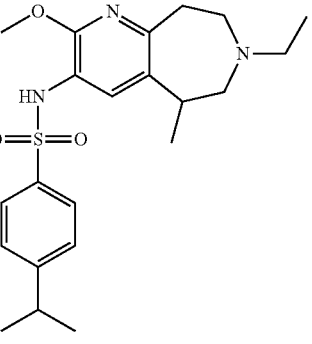 | 418.0 |
| 57 | Example 2; P5 | 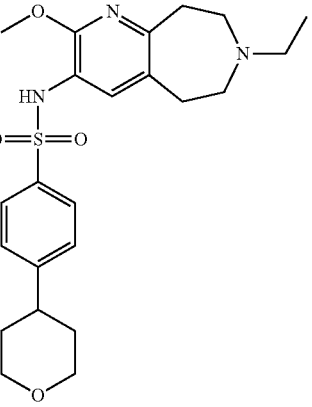 | 446.2 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 58 | Example 5; P5 | 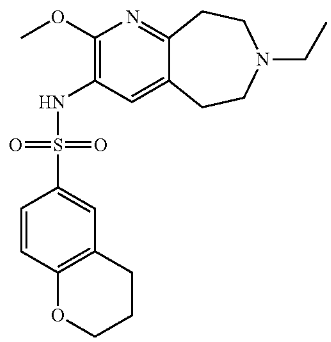 [SMILES: CCN1CCc2cc(NS(=O)(=O)c3ccc4c(c3)CCCO4)c(OC)nc2CC1] | 418.1 |
| 59 | Example 5; P5 | 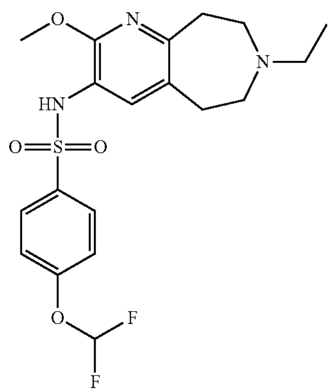 [SMILES: CCN1CCc2cc(NS(=O)(=O)c3ccc(OC(F)F)cc3)c(OC)nc2CC1] | 428.0 |
| 60 | Example 5; P5 | 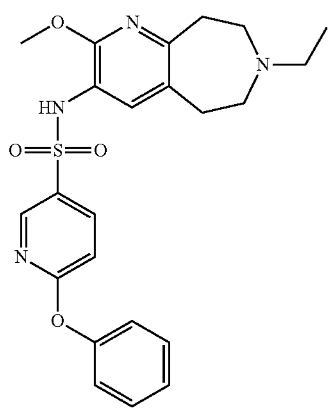 [SMILES: CCN1CCc2cc(NS(=O)(=O)c3ccc(Oc4ccccc4)nc3)c(OC)nc2CC1] | 455.1 |
| 61 | Example 5; P5 | 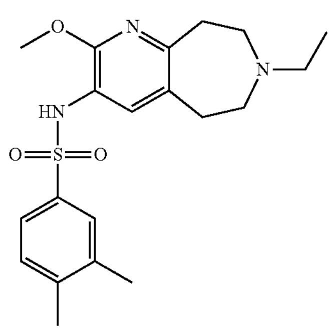 [SMILES: CCN1CCc2cc(NS(=O)(=O)c3ccc(C)c(C)c3)c(OC)nc2CC1] | 390.1 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 62 | Example 5; P5 | *(structure)* | 404.1 |
| 63 | Example 5; P5 | *(structure)* | 446.1 |
| 64 | Example 5; P5 | *(structure)* | 446.1 |
| 65 | Example 5; P5 | *(structure)* | 390.1 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 66 | Example 5; C66 | 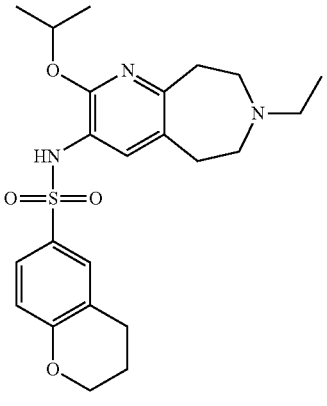 [SMILES: CCN1CCc2cc(NS(=O)(=O)c3ccc4c(c3)CCCO4)c(OC(C)C)nc2CC1] | 446.3 |
| 67 | Example 5; P5 | 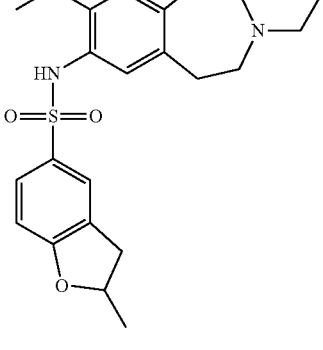 | 418.3 |
| 68 | Example 2[2]; P5 | 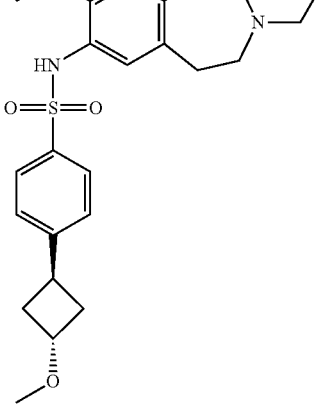 | 446.0 |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 69 | Example 2[15]; P5 | 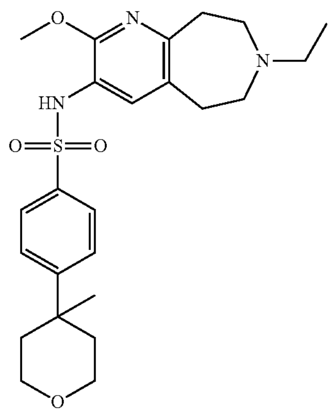 [SMILES: CCN1CCc2cc(NS(=O)(=O)c3ccc(C4(C)CCOCC4)cc3)c(OC)nc2CC1] | 460.0 |
| 70 | Example 5; P5, C32 | 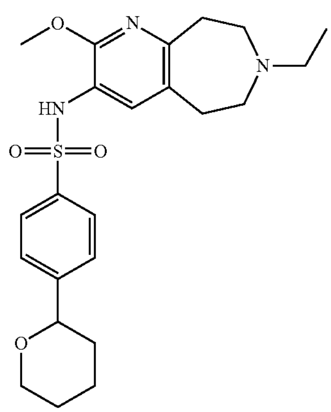 [SMILES: CCN1CCc2cc(NS(=O)(=O)c3ccc(C4CCCCO4)cc3)c(OC)nc2CC1] | 446.0 |
| 71 | Example 33; P5 | 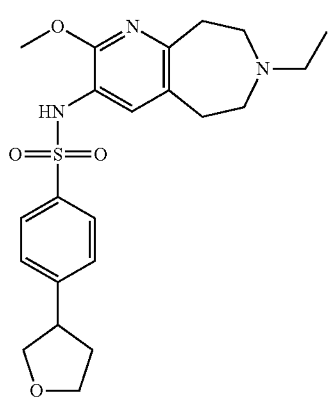 [SMILES: CCN1CCc2cc(NS(=O)(=O)c3ccc(C4CCOC4)cc3)c(OC)nc2CC1] | 432.0 |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 72 | Example 2[2]; P5 | 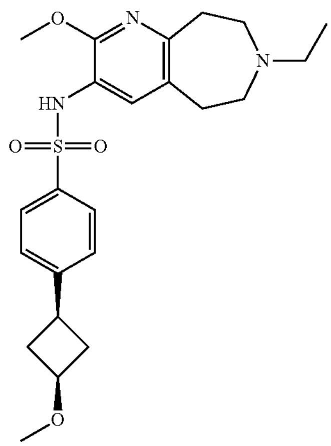 [SMILES: CCN1CCc2cc(NS(=O)(=O)c3ccc([C@H]4C[C@@H](OC)C4)cc3)c(OC)nc2CC1] | 446.0 |
| 73 | Example 70[16] | ENT-1 | 446.0 |
| 74 | Example 70[16] | ENT-2 | 446.0 |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 75 | Example 11; P5 | 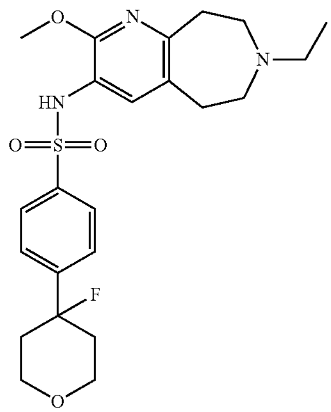 [SMILES: CCN1CCc2cc(NS(=O)(=O)c3ccc(C4(F)CCOCC4)cc3)c(OC)nc2CC1] | 464.0 |
| 76 | Example 2[2]; P3 | 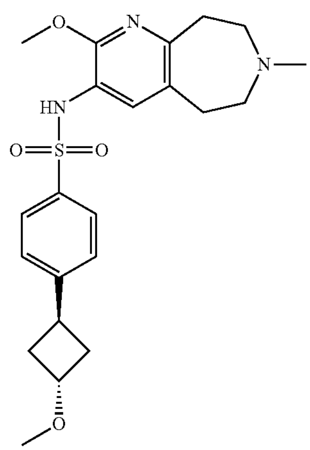 [SMILES: COc1nc2c(cc1NS(=O)(=O)c1ccc([C@H]3C[C@H](OC)C3)cc1)CCN(C)CC2] | 432.0 |
| 77 | Example 33; P3 | 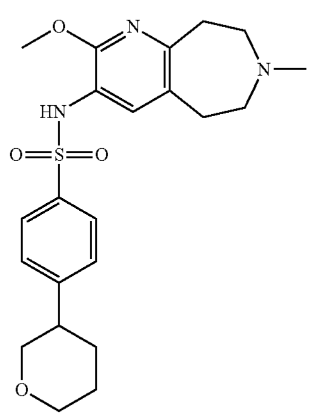 [SMILES: COc1nc2c(cc1NS(=O)(=O)c1ccc(C3CCCOC3)cc1)CCN(C)CC2] | 432.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 78 | Example 5[17]; P3 | 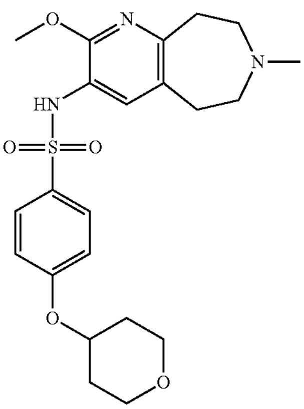 [SMILES: COc1nc2c(cc1NS(=O)(=O)c1ccc(OC3CCOCC3)cc1)CCN(C)CC2] | 448.0 |
| 79 | Example 2[15]; P3 | 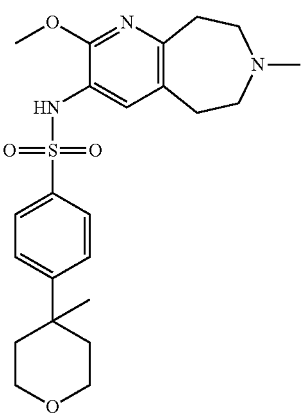 [SMILES: COc1nc2c(cc1NS(=O)(=O)c1ccc(C3(C)CCOCC3)cc1)CCN(C)CC2] | 446.0 |
| 80 | Example 11; P3 | 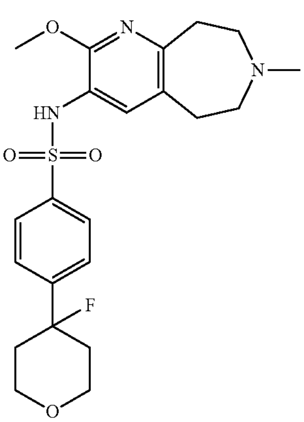 [SMILES: COc1nc2c(cc1NS(=O)(=O)c1ccc(C3(F)CCOCC3)cc1)CCN(C)CC2] | 450.1 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 81 | Example 2[2]; P3 | 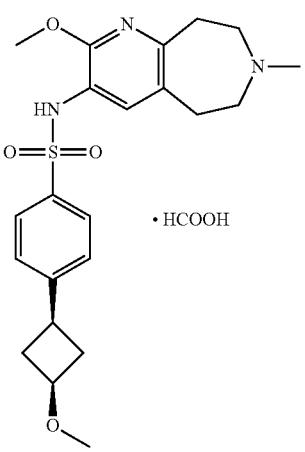 [SMILES: COc1nc2c(cc1NS(=O)(=O)c1ccc([C@H]3C[C@@H](OC)C3)cc1)CCN(C)CC2 ; "· HCOOH"] · HCOOH | 432.0 |
| 82 | Example 37; P3 | 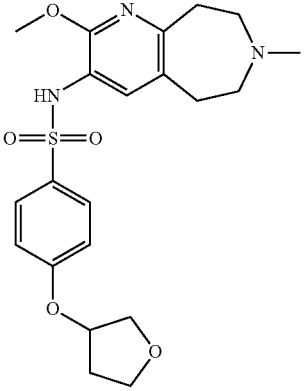 | 434.0 |
| 83 | Example 77[18] | 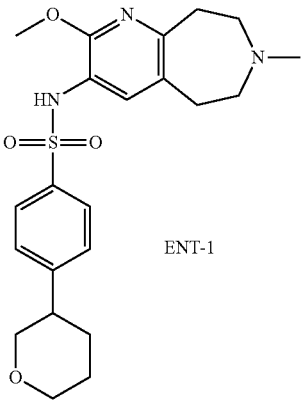 [SMILES: COc1nc2c(cc1NS(=O)(=O)c1ccc(C3CCCOC3)cc1)CCN(C)CC2] ENT-1 | 432.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 84 | Example 77[18] | 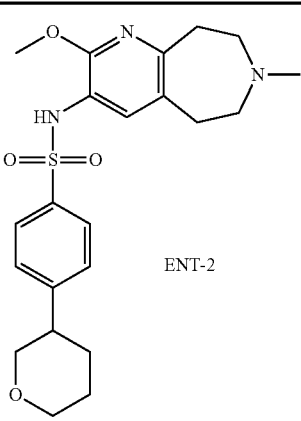 ENT-2 | 432.0 |
| 85 | Example 1[6,19]; P3 | 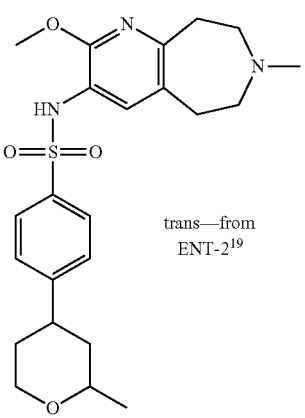 [SMILES: COc1nc2c(cc1NS(=O)(=O)c1ccc(C3CCOC(C)C3)cc1)CCN(C)CC2] trans—from ENT-2[19] | 446.0 |
| 86 | Example 1[6,20]; P3 | 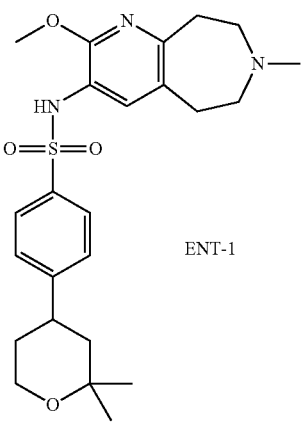 [SMILES: COc1nc2c(cc1NS(=O)(=O)c1ccc(C3CCOC(C)(C)C3)cc1)CCN(C)CC2] ENT-1 | 460.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 87 | Example 1[6,20]; P3 | 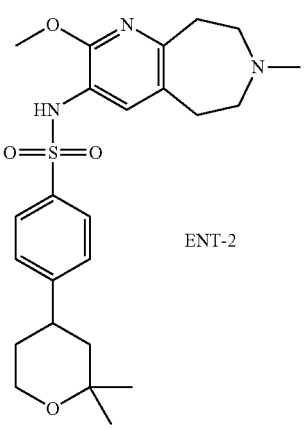 [SMILES: COc1nc2c(cc1NS(=O)(=O)c1ccc(C3CCOC(C)(C)C3)cc1)CCN(C)CC2] ENT-2 | 460.0 |
| 88 | Example 1[6,19]; P3 | 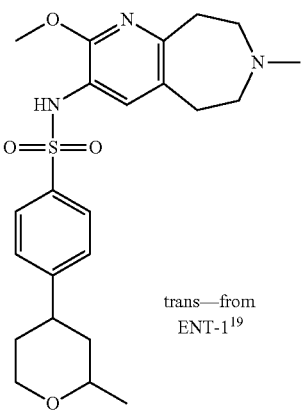 [SMILES: COc1nc2c(cc1NS(=O)(=O)c1ccc(C3CCOC(C)C3)cc1)CCN(C)CC2] trans—from ENT-1[19] | 446.0 |
| 89 | Example 2[2]; P3 | 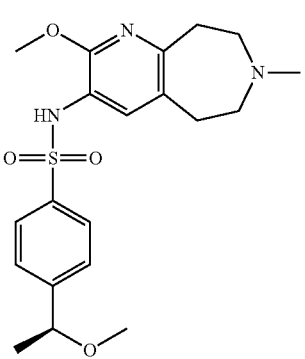 [SMILES: COc1nc2c(cc1NS(=O)(=O)c1ccc([C@H](C)OC)cc1)CCN(C)CC2] | 406.1 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 90 | Example 2[2]; P3 | 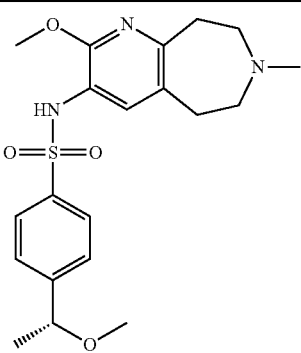 | 406.1 |
| 91 | Example 37; P3 | 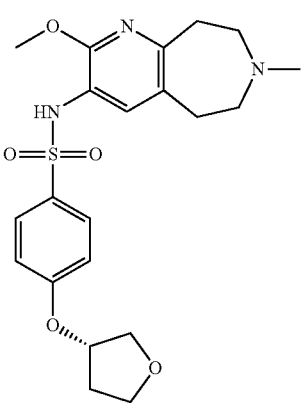 | 434.0 |
| 92 | Example 1[6]; P3 | 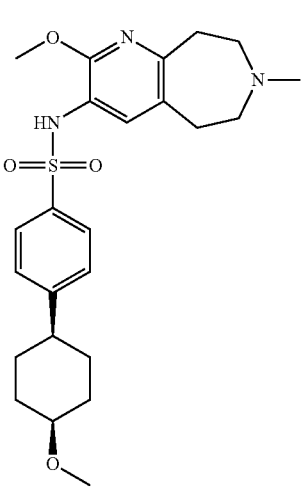 [SMILES: COc1nc2c(cc1NS(=O)(=O)c1ccc([C@H]3CC[C@@H](OC)CC3)cc1)CCN(C)CC2] | 460.1 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 93 | Example 10[7]; P3 | 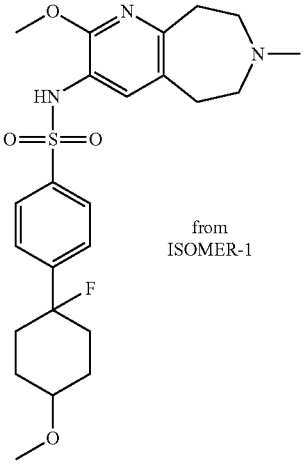 [SMILES: COc1nc2c(cc1NS(=O)(=O)c1ccc(C3(F)CCC(OC)CC3)cc1)CCN(C)CC2] from ISOMER-1 | 478.1 |
| 94 | Example 10[7]; P5 | 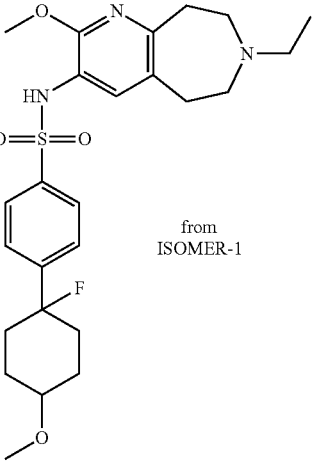 from ISOMER-1 | 492.2 |
| 95 | Example 5[2,21]; P3 | 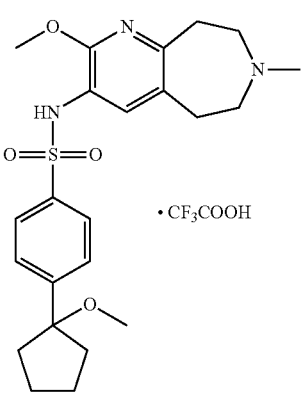 [SMILES: COc1nc2c(cc1NS(=O)(=O)c1ccc(C3(OC)CCCC3)cc1)CCN(C)CC2 ; "· CF3COOH"] · CF₃COOH | 446.4 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 96 | Example 5; P5, C45 | 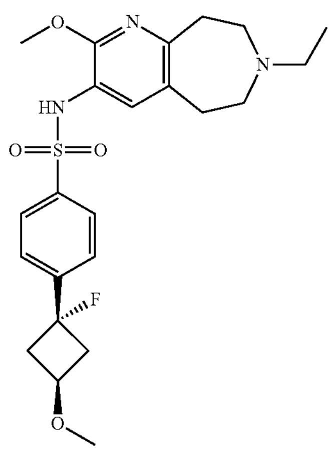 [SMILES: CCN1CCc2cc(NS(=O)(=O)c3ccc([C@]4(F)C[C@H](OC)C4)cc3)c(OC)nc2CC1] | 464.1 |
| 97 | Example 2; P3 | 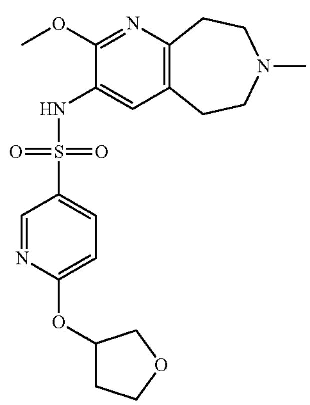 [SMILES: COc1nc2c(cc1NS(=O)(=O)c1ccc(OC3CCOC3)nc1)CCN(C)CC2] | 435.1 |
| 98 | Example 7[11]; P3 | 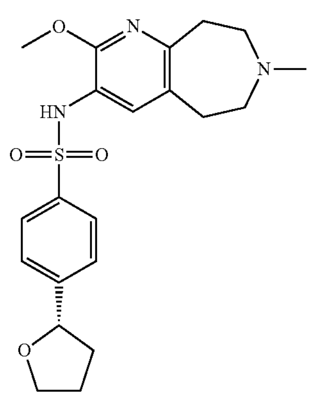 [SMILES: COc1nc2c(cc1NS(=O)(=O)c1ccc([C@@H]3CCCO3)cc1)CCN(C)CC2] | 418.1 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]⁺ (unless otherwise indicated) |
|---|---|---|---|
| 99 | Example 7; P3 | 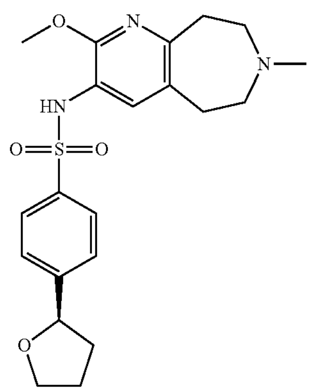 [SMILES: COc1nc2c(cc1NS(=O)(=O)c1ccc([C@H]3CCCO3)cc1)CCN(C)CC2] | 418.1 |
| 100 | Example 11[22,23]; P3 | 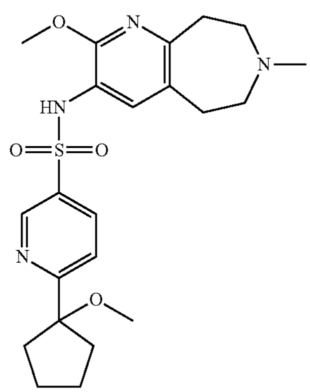 [SMILES: COc1nc2c(cc1NS(=O)(=O)c1ccc(C3(OC)CCCC3)nc1)CCN(C)CC2] | 447.2 |
| 101 | Example 5; P5, C48 | 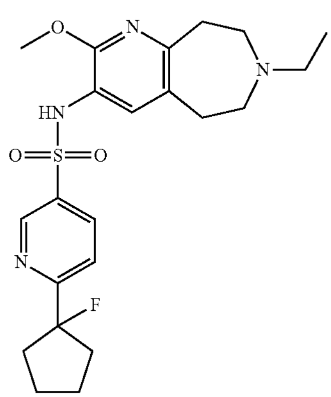 [SMILES: CCN1CCc2cc(NS(=O)(=O)c3ccc(C4(F)CCCC4)nc3)c(OC)nc2CC1] | 449.1 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 102 | Example 1[22]; P5 | 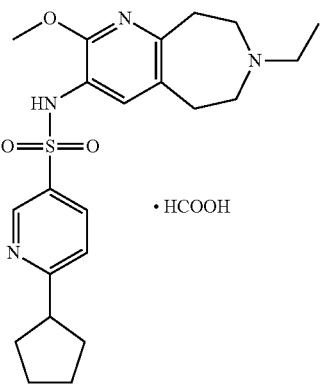 [SMILES: CCN1CCc2cc(NS(=O)(=O)c3ccc(C4CCCC4)nc3)c(OC)nc2CC1 ; "· HCOOH"] · HCOOH | 431.2 |
| 103 | Example 2[24]; P3 | 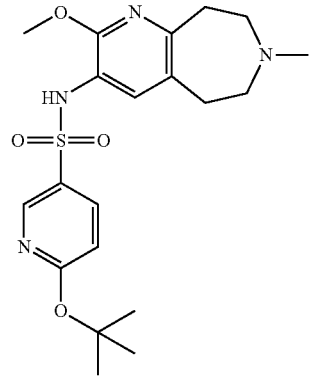 [SMILES: COc1nc2c(cc1NS(=O)(=O)c1ccc(OC(C)(C)C)nc1)CCN(C)CC2] | 421.1 |
| 104 | Example 7[10]; P3 | 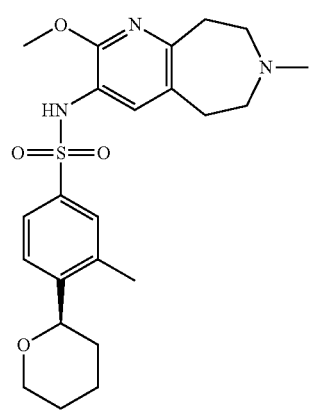 [SMILES: COc1nc2c(cc1NS(=O)(=O)c1ccc([C@H]3CCCCO3)c(C)c1)CCN(C)CC2] | 446.1 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 105 | Example 7[10,11]; P3 | 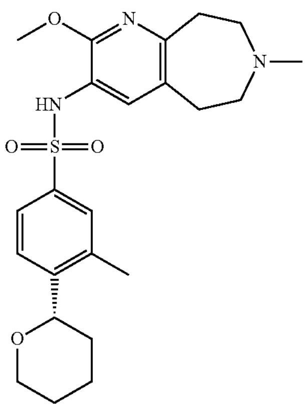 [SMILES: COc1nc2c(cc1NS(=O)(=O)c1ccc([C@@H]3CCCCO3)c(C)c1)CCN(C)CC2] | 446.2 |
| 106 | Example 2[25,26]; P3 | • HCOOH from second-eluting isomer[26] | 450.1 |
| 107 | Example 7[10]; P5 | 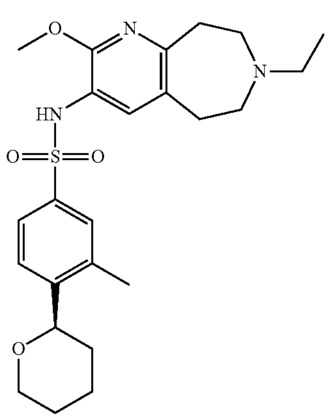 [SMILES: CCN1CCc2cc(NS(=O)(=O)c3ccc([C@H]4CCCCO4)c(C)c3)c(OC)nc2CC1] | 460.1 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 108 | Example 2[25,26,27]; P3 | 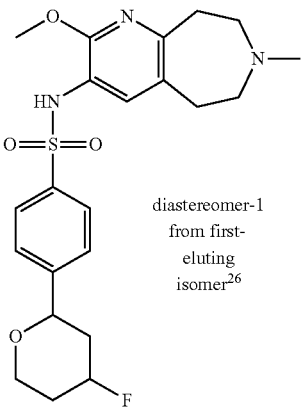 [SMILES: COc1nc2c(cc1NS(=O)(=O)c1ccc(C3CC(F)CCO3)cc1)CCN(C)CC2] diastereomer-1 from first-eluting isomer[26] | 450.0 |
| 109 | Example 2[25,26,27]; P3 | 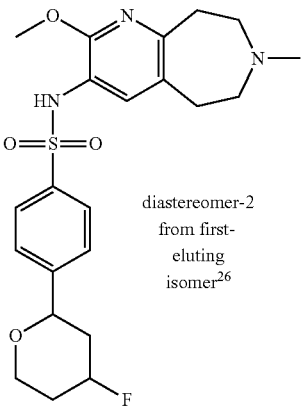 [SMILES: COc1nc2c(cc1NS(=O)(=O)c1ccc(C3CC(F)CCO3)cc1)CCN(C)CC2] diastereomer-2 from first-eluting isomer[26] | 450.0 |
| 110 | Example 7[10]; P3 | 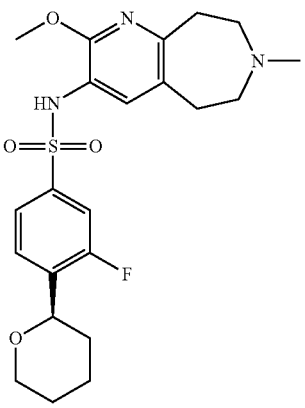 [SMILES: COc1nc2c(cc1NS(=O)(=O)c1ccc([C@H]3CCCCO3)c(F)c1)CCN(C)CC2] | 450.1 |

US 10,590,128 B2
TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 111 | Example 7[10,11]; P3 | 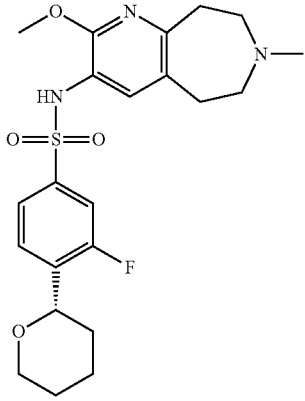 [SMILES: COc1nc2c(cc1NS(=O)(=O)c1ccc([C@@H]3CCCCO3)c(F)c1)CCN(C)CC2] | 450.1 |
| 112 | Example 11; P5 | 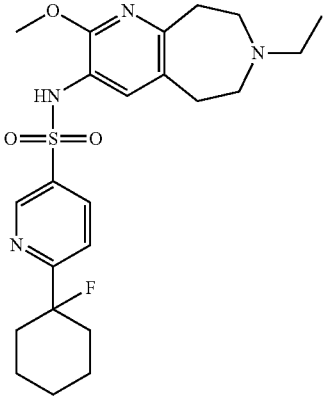 [SMILES: CCN1CCc2cc(NS(=O)(=O)c3ccc(C4(F)CCCCC4)nc3)c(OC)nc2CC1] | 463.1 |
| 113 | Example 2; P3 | 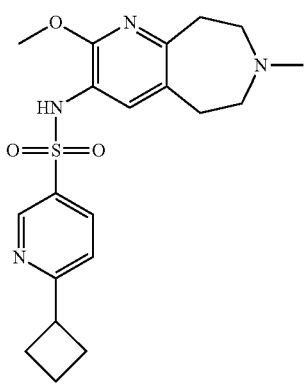 [SMILES: COc1nc2c(cc1NS(=O)(=O)c1ccc(C3CCC3)nc1)CCN(C)CC2] | 403.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 114 | Example 5; P5, C21 | 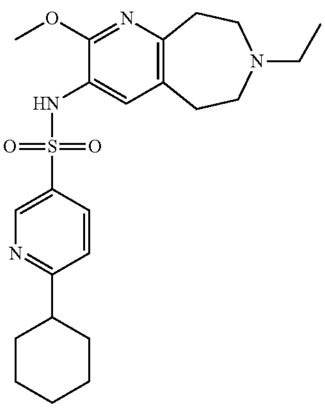 [SMILES: CCN1CCc2cc(NS(=O)(=O)c3ccc(C4CCCCC4)nc3)c(OC)nc2CC1] | 445.0 |
| 115 | Example 5[1,12]; C9 | 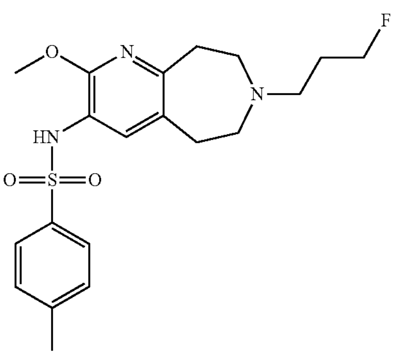 [SMILES: COc1nc2c(cc1NS(=O)(=O)c1ccc(C)cc1)CCN(CCCF)CC2] | 407.9 |
| 116 | Example 2[28]; P3 | 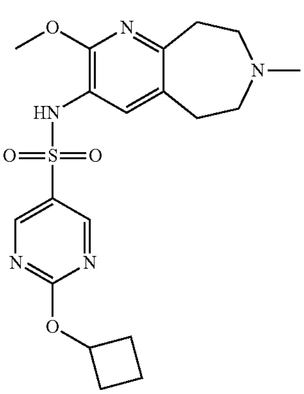 [SMILES: COc1nc2c(cc1NS(=O)(=O)c1cnc(OC3CCC3)nc1)CCN(C)CC2] | 420.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 117 | Example 2[29]; P3 | 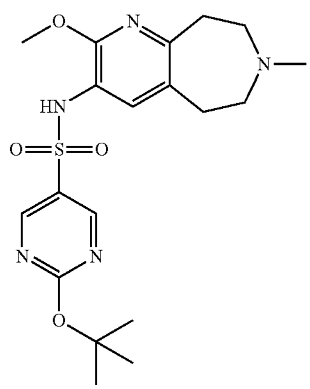 [SMILES: COc1nc2c(cc1NS(=O)(=O)c1cnc(OC(C)(C)C)nc1)CCN(C)CC2] | 422.0 |
| 118 | Example 5; P3 | 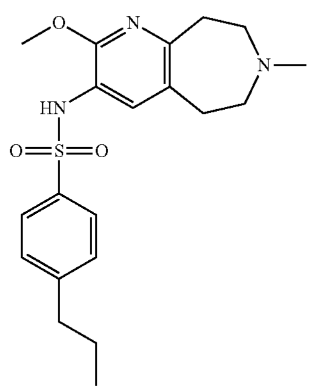 [SMILES: CCCc1ccc(S(=O)(=O)Nc2cc3c(nc2OC)CCN(C)CC3)cc1] | 390.0 |
| 119 | Example 3; P5 | 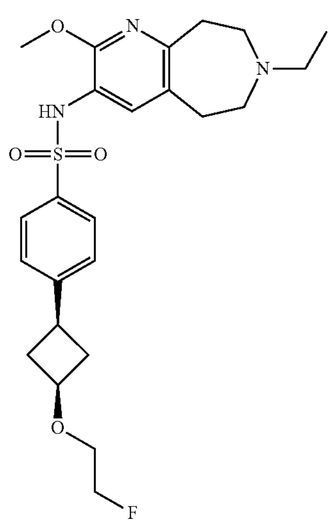 [SMILES: CCN1CCc2cc(NS(=O)(=O)c3ccc([C@H]4C[C@@H](OCCF)C4)cc3)c(OC)nc2CC1] | 478.1 |

TABLE 7-continued
Method of preparation, structure, and mass spectrometry data for Examples 26-136 and 138-140
| Example Number | Method of Preparation; Non-commercial starting materials | Structure | Mass spectrum m/z [M + H]+ (unless otherwise indicated) |
|---|---|---|---|
| 120 | Example 2[30]; P5 | 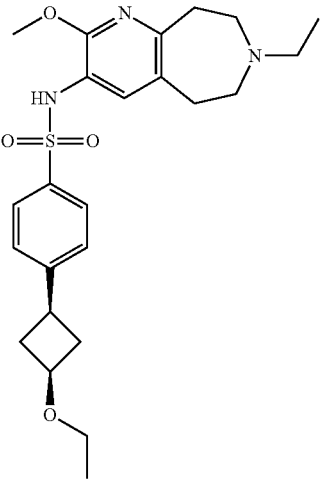 [SMILES: CCO[C@H]1C[C@@H](c2ccc(S(=O)(=O)Nc3cc4c(nc3OC)CCN(CC)CC4)cc2)C1] | 460.0 |
| 121 | Example 120; P5 | 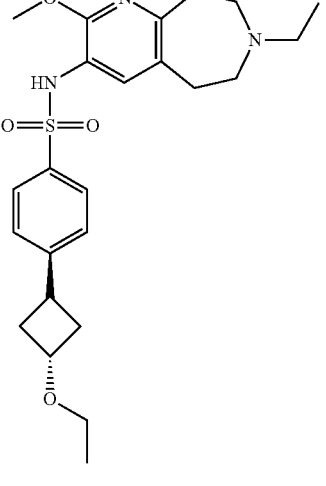 | 460.1 |
| 122 | Example 5[1,12]; C9, C23 | 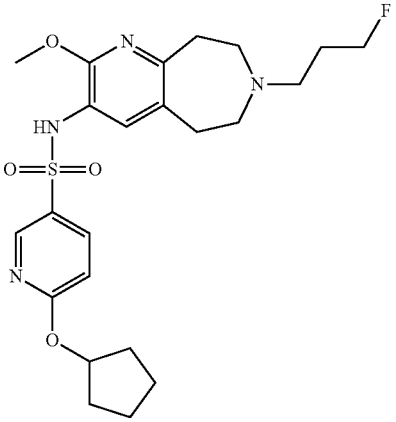 [SMILES: COc1nc2c(cc1NS(=O)(=O)c1ccc(OC3CCCC3)nc1)CCN(CCCF)CC2] | 479.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 123 | Example 1; P3 | 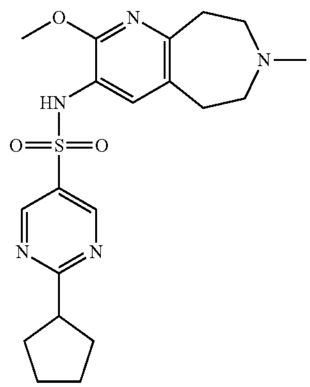 [SMILES: COc1nc2c(cc1NS(=O)(=O)c1cnc(C3CCCC3)nc1)CCN(C)CC2] | 418.0 |
| 124 | Example 2[31]; P3 | 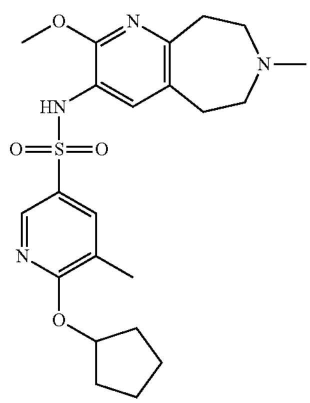 | 447.0 |
| 125 | Example 2[31]; P5 | 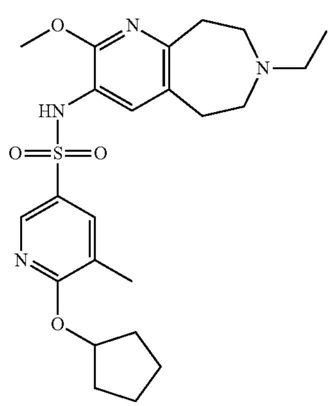 [SMILES: CCN1CCc2cc(NS(=O)(=O)c3cnc(OC4CCCC4)c(C)c3)c(OC)nc2CC1] | 461.0 |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 126 | Example 2[32]; P3 | 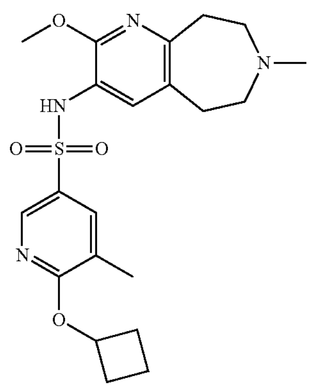 [SMILES: COc1nc2c(cc1NS(=O)(=O)c1cnc(OC3CCC3)c(C)c1)CCN(C)CC2] | 432.9 |
| 127 | Example 1; P3 | 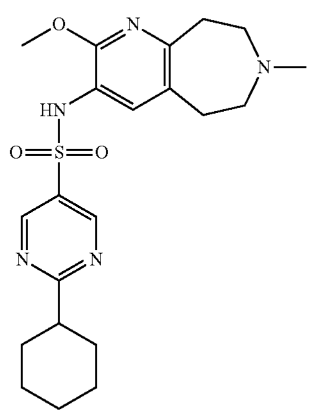 [SMILES: COc1nc2c(cc1NS(=O)(=O)c1cnc(C3CCCCC3)nc1)CCN(C)CC2] | 432.0 |
| 128 | Example 124; P3 | 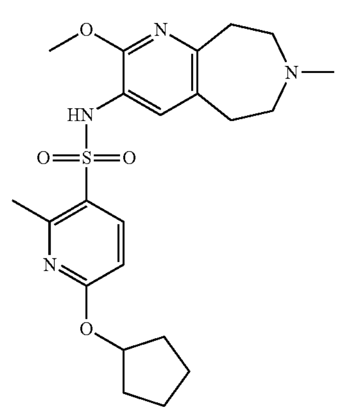 | 447.0 |

TABLE 7-continued
Method of preparation, structure, and mass spectrometry data for
Examples 26-136 and 138-140
| Example Number | Method of Preparation; Non-commercial starting materials | Structure | Mass spectrum m/z [M + H]+ (unless otherwise indicated) |
|---|---|---|---|
| 129 | Example 7[33]; P3 | 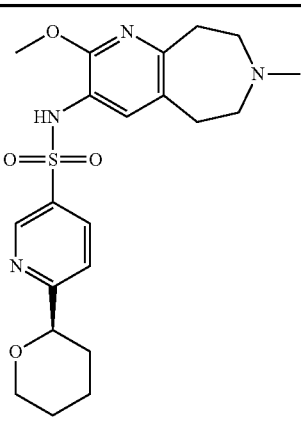 | 433.0 |
| 130 | Example 126; P3 | 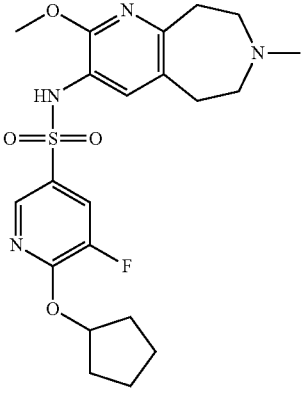 [SMILES: COc1nc2c(cc1NS(=O)(=O)c1cnc(OC3CCCC3)c(F)c1)CCN(C)CC2] | 451.0 |
| 131 | Example 10[34]; P3 | 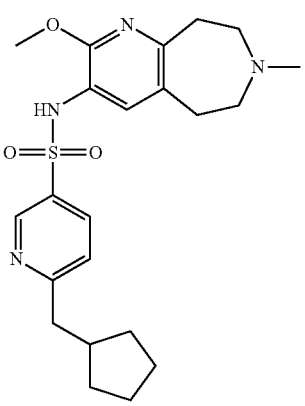 [SMILES: COc1nc2c(cc1NS(=O)(=O)c1ccc(CC3CCCC3)nc1)CCN(C)CC2] | 431.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 132 | Example 10[35]; P3 | 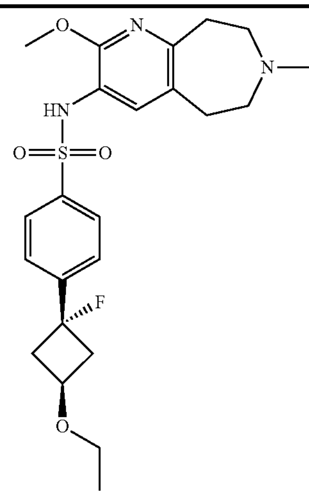 | 464.0 |
| 133 | Example 10[36]; P3 | 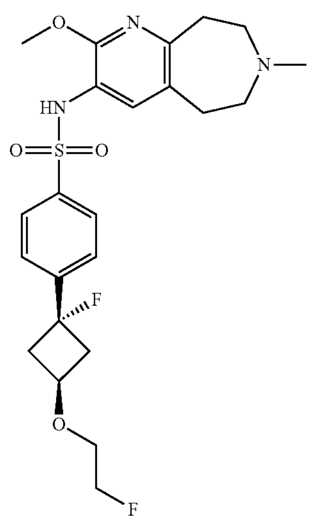 [SMILES: COc1nc2c(cc1NS(=O)(=O)c1ccc([C@]3(F)C[C@H](OCCF)C3)cc1)CCN(C)CC2] | 482.1 |
| 134 | Example 120; P3 | 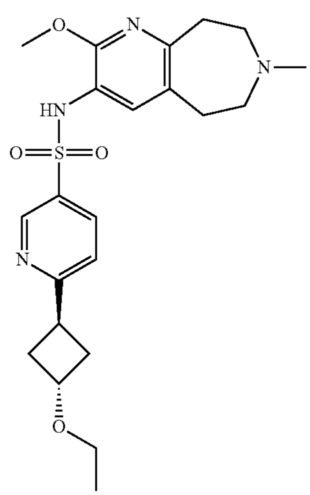 [SMILES: CCO[C@H]1C[C@H](c2ccc(S(=O)(=O)Nc3cc4c(nc3OC)CCN(C)CC4)cn2)C1] | 447.0 |

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
|---|---|---|---|
| 135 | Example 120; P3 | 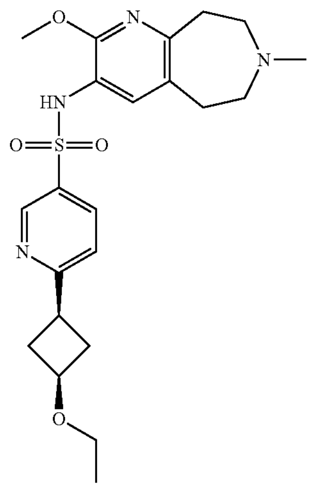 [SMILES: CCO[C@H]1C[C@@H](c2ccc(S(=O)(=O)Nc3cc4c(nc3OC)CCN(C)CC4)cn2)C1] | 447.0 |
| 136 | Example 10[37]; P3 | 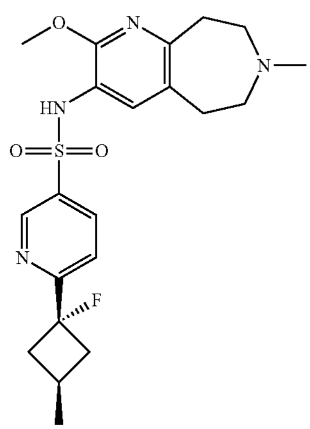 [SMILES: COc1nc2c(cc1NS(=O)(=O)c1ccc([C@]3(F)C[C@H](C)C3)nc1)CCN(C)CC2] | 435.0 |
| 138 | Example 137; C71 | 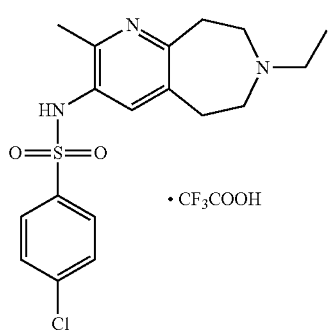 [SMILES: CCN1CCc2cc(NS(=O)(=O)c3ccc(Cl)cc3)c(C)nc2CC1 ; "· CF3COOH"] | 380.1 (chlorine isotope pattern observed) |

TABLE 7-continued

Method of preparation, structure, and mass spectrometry data for Examples 26-136 and 138-140

| Example Number | Method of Preparation; Non-commercial starting materials | Structure | Mass spectrum m/z [M + H]+ (unless otherwise indicated) |
|---|---|---|---|
| 139 | Preparations P3 and P4[38,39]; C67 | 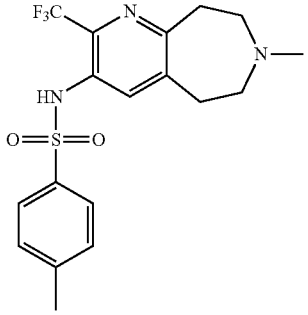 [SMILES: Cc1ccc(S(=O)(=O)Nc2cc3c(nc2C(F)(F)F)CCN(C)CC3)cc1] | 400.2 |
| 140 | Example 137[40]; C36, C67 | 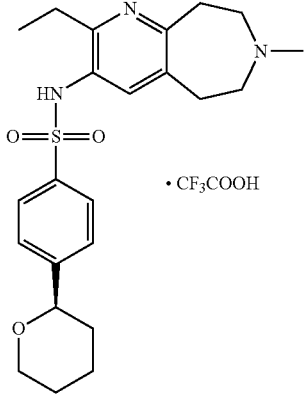 [SMILES: CCc1nc2c(cc1NS(=O)(=O)c1ccc([C@H]3CCCCO3)cc1)CCN(C)CC2 ; "· CF3COOH"] | 430.4 |

[1] The requisite 7-substituted 2-methoxy-6,7,8,9-tetrahydro-5H-pyrido[2,3-d]azepin-3-amine was synthesized from C9 using the procedure described in Preparation P5.
[2] The methyl ether moiety of the requisite bromoaromatic intermediate was installed via reaction of the commercially available alcohol with sodium hydride and iodomethane.
[3] 3-(4-Bromophenyl)oxetane was prepared via a nickel-catalyzed Suzuki-Miyaura coupling reaction of (4-bromophenyl)boronic acid with 3-iodooxetane.
[4] Reaction of 2-hydroxybenzaldehyde with (propan-2-yl)magnesium bromide afforded 2-(1-hydroxy-2-methylpropyl)phenol; treatment with Amberlyst 15 at elevated temperature then gave 2,2-dimethyl-2,3-dihydro-1-benzofuran. Subsequent reaction with chlorosulfonic acid provided the requisite 2,2-dimethyl-2,3-dihydro-1-benzofuran-5-sulfonyl chloride.
[5] Mitsunobu reaction of 4-bromophenol and (3S)-tetrahydrofuran-3-ol provided the requisite (3R)-3-(4-bromophenoxy)tetrahydrofuran.
[6] In this case, the alcohol derived from addition of the lithiated aromatic reagent to the ketone was deoxygenated via treatment with triethylsilane and trifluoroacetic acid.
[7] In this case, both isomers of 4-(1-fluoro-4-methoxycyclohexyl)benzenesulfonyl chloride were obtained; these were separated via chromatography on silica gel (Gradient: 0% to 10% ethyl acetate in petroleum ether). The first-eluting isomer (ISOMER-1) was taken on to Examples 93 and 94, and the second-eluting isomer (ISOMER-2) was used for Example 39.
[8] Treatment of 4-bromobenzaldehyde with but-3-en-1-ol and sulfuric acid at elevated temperature, followed by pyridinium chlorochromate oxidation of the resulting alcohol, provided 2-(4-bromophenyl)tetrahydro-4H-pyran-4-one. Reaction with (diethylamino)sulfur trifluoride afforded the requisite 2-(4-bromophenyl)-4,4-difluorotetrahydro-2H-pyran.
[9] Racemic Example 40 was separated into its component enantiomers via supercritical fluid chromatography [Column: Chiral Technologies Chiralpak AD, 5 μm; Mobile phase: 65:35 carbon dioxide/(0.1% ammonium hydroxide in ethanol)]. Example 41 was the first-eluting enantiomer, and Example 42 was the second-eluting enantiomer.
[10] The requisite bromoaryl ketone starting material was generated via a Friedel-Crafts reaction between the appropriate bromoaromatic and acid chloride reactants.
[11] In this case, (3aR)-1-methyl-3,3-diphenyltetrahydro-3H-pyrrolo[1,2-c][1,3,2]oxazaborole[(R)-2-methyl-CBS-oxazaborolidine] was employed for ketone reduction.
[12] In this case, alkylation of C9 was carried out with a 4-methylbenzenesulfonate reagent, rather than a bromo or chloro derivative.
[13] 2,5-Dibromopyridine was lithiated with n-butyllithium and treated with cyclopentanecarbaldehyde; the resulting (5-bromopyridin-2-yl)(cyclopentyl)methanol was oxidized to the ketone with iodine and potassium carbonate in tert-butanol. Subsequent reaction with (diethylamino)sulfur trifluoride provided the requisite 5-bromo-2-[cyclopentyl(difluoro)methyl]pyridine.
[14] The requisite 4-[1-(trifluoromethyl)cyclopropyl]benzenesulfonyl chloride was synthesized via treatment of [1-(trifluoromethyl)cyclopropyl]benzene with chlorosulfonic acid.
[15] Reaction of 1-bromo-4-iodobenzene with (propan-2-yl)magnesium chloride, followed by introduction of tetrahydro-4H-pyran-4-one, afforded 4-(4-bromophenyl)tetrahydro-2H-pyran-4-ol; this material was reacted with a mixture of titanium(IV) chloride and dimethylzinc to provide the requisite 4-(4-bromophenyl)-4-methyltetrahydro-2H-pyran.
[16] Racemic Example 70 was separated into its component enantiomers via supercritical fluid chromatography [Column: Chiral Technologies Chiralcel OJ, 5 μm; Mobile phase: 7:3 carbon dioxide/(0.1% ammonium hydroxide in ethanol)]. Example 73 was the first-eluting enantiomer, and Example 74 was the second-eluting enantiomer.
[17] Cesium carbonate-mediated alkylation of 4-(benzylsulfanyl)phenol with tetrahydro-2H-pyran-4-yl 4-methylbenzenesulfonate provided 4-[4-(benzylsulfanyl)phenoxy]tetrahydro-2H-pyran, which was reacted with N-chlorosuccinimide in acetic acid and water to afford the requisite 4-(tetrahydro-2H-pyran-4-yloxy)benzenesulfonyl chloride.
[18] Racemic Example 77 was separated into its component enantiomers via supercritical fluid chromatography [Column: Chiral Technologies Chiralpak AD, 5 μm; Mobile phase: 3:2 carbon dioxide/(0.1% ammonium hydroxide in methanol)]. Example 83 was the first-eluting enantiomer, and Example 84 was the second-eluting.
[19] Intermediate trans-4-{4-[(4-methoxybenzyl)sulfanyl]phenyl}-2-methyltetrahydro-2H-pyran was separated into its enantiomers via supercritical fluid chromatography [Column: Chiral Technologies Chiralpak AS, 10 μm; Mobile phase: 3:1 carbon dioxide/(0.1% ammonium hydroxide in ethanol)]. The second-eluting enantiomer (ENT-2) was taken on to Example 85, and the first-eluting enantiomer (ENT-1) to Example 88.

TABLE 7-continued

Method of preparation, structure, and mass spectrometry data for
Examples 26-136 and 138-140

| Example Number | Method of Preparation; Non-commercial starting materials | Structure | Mass spectrum m/z [M + H]+ (unless otherwise indicated) |
| --- | --- | --- | --- |

[20]The racemic product was separated into its component enantiomers via supercritical fluid chromatography [Column: Chiral Technologies Chiralpak AD, 5 µm; Mobile phase: 7:3 carbon dioxide/(0.1% ammonium hydroxide in methanol)]. Example 86 was the first-eluting enantiomer, and Example 87 was the second-eluting enantiomer.
[21]1-Bromo-4-(1-methoxycyclopentyl)benzene was treated with n-butyllithium, sulfur dioxide, and sulfuryl chloride to generate the requisite 4-(1-methoxycyclopentyl)benzenesulfonyl chloride.
[22]The requisite 1-(5-bromopyridin-2-yl)cyclopentanol may be synthesized using the general method described by B. Guo et al., *J. Med. Chem.* 2013, 56, 2642-2650.
[23]In this case, the alcohol of intermediate 1-(5-bromopyridin-2-yl)cyclopentanol was methylated with sodium hydride and iodomethane, rather than being converted to the fluoride.
[24]Reaction of 2,5-dibromopyridine with potassium tert-butoxide provided 5-bromo-2-tert-butoxypyridine.
[25]2-(4-Bromophenyl)-4-fluorotetrahydro-2H-pyran may be prepared via reaction of 4-bromobenzaldehyde with but-3-en-1-ol and boron trifluoride diethyl etherate, followed by treatment with trifluoromethanesulfonic anhydride and cesium fluoride.
[26]The isomers of 4-fluoro-2-{4-[(4-methoxybenzyl)sulfanyl]phenyl}tetrahydro-2H-pyran were separated via supercritical fluid chromatography [Column: Chiral Technologies Chiralpak AD, 10 µm; Mobile phase A: carbon dioxide; Mobile phase B: 0.1% ammonium hydroxide in ethanol; Gradient: 50% to 80% B). The first-eluting material proved to be a racemate, which was used to synthesize Examples 108 and 109. The second-eluting material was one enantiomer of the other geometric isomer, which was used to prepare Example 106. The third-eluting material, by $^{1}$H NMR analysis, was the enantiomer of the second-eluting material.
[27]Racemic 4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, derived from the first-eluting material described in footnote 26, was separated into its component enantiomers via supercritical fluid chromatography [Column: Chiral Technologies Chiralcel OJ, 5 µm; Mobile phase 4:1 carbon dioxide/(0.05% diethylamine in ethanol)]. Example 108 was the first-eluting enantiomer (ENT-1), and Example 109 was the second-eluting enantiomer (ENT-2).
[28]Reaction of cyclobutanol with sodium hydride and 5-bromo-2-chloropyrimidine provided the requisite 5-bromo-2-(cyclobutyloxy)pyrimidine.
[29]Reaction of 5-bromo-2-chloropyrimidine with potassium tert-butoxide afforded 5-bromo-2-tert-butoxypyrimidine.
[30]cis-3-(4-Bromophenyl)cyclobutanol was deprotonated with sodium hydride and alkylated with iodoethane to generate the requisite 1-bromo-4-(cis-3-ethoxycyclobutyl)benzene.
[31]The requisite 5-bromo-2-(cyclopentyloxy)-3-methylpyridine was prepared via reaction of 5-bromo-3-methylpyridin-2(1H)-one with bromocyclopentane and silver carbonate.
[32]Reaction of cyclobutanol with sodium hydride and 5-bromo-2-fluoro-3-methylpyridine afforded the requisite 5-bromo-2-(cyclobutyloxy)-3-methylpyridine.
[33]Reaction of 5-chloropentanoyl chloride with N,O-dimethylhydroxylamine provided 5-chloro-N-methoxy-N-methylpentanamide. 2,5-Dibromopyridine was treated with n-butyllithium and added to 5-chloro-N-methoxy-N-methylpentanamide to afford 1-(5-bromopyridin-2-yl)-5-chloropentan-1-one.
[34]In this case, cyclopentanecarbaldehyde was used; rather than being fluorinated, the intermediate cyclopentyl{5-[(4-methoxybenzyl)sulfanyl]pyridin-2-yl}methanol was deoxygenated via treatment with carbon tetrabromide and triphenylphosphine followed by zinc in acetic acid. The product was then carried on to the requisite 6-(cyclopentylmethyl)pyridine-3-sulfonyl chloride.
[35]Intermediate 1-(trans-3-ethoxy-1-fluorocyclobutyl)-4-[(4-methoxybenzyl)sulfanyl]benzene was analyzed using NOE studies to confirm the orientation of substituents on the cyclobutane.
[36]3-Oxocyclobutyl acetate was used in this case; the acetate group was maintained until trans-3-fluoro-3-{4-[(4-methoxybenzyl)sulfanyl]phenyl}cyclobutyl acetate was prepared, whereupon it was removed via treatment with lithium hydroxide. The resulting alcohol was alkylated with sodium hydride and 2-fluoroethyl 4-methylbenzenesulfonate to provide 1-[trans-1-fluoro-3-(2-fluoroethoxy)cyclobutyl]-4-[(4-methoxybenzyl)sulfanyl]benzene.
[37]Intermediate 2-(1-fluoro-3-methylcyclobutyl)-5-[(4-methoxybenzyl)sulfanyl]pyridine was subjected to supercritical fluid chromatography (Column: Chiral Technologies Chiralcel OJ, 10 µm; Mobile phase: 4:1 carbon dioxide/(0.1% ammonium hydroxide in ethanol)]. The first-eluting isomer was analyzed by NOE studies and assigned as 2-(trans-1-fluoro-3-methylcyclobutyl)-5-[(4-methoxybenzyl)sulfanyl]pyridine; this material was used to synthesize Example 136.
[38]Reaction of C67 with methyl difluoro(fluorosulfonyl)acetate and copper(I) iodide in the presence of N,N,N',N',N'',N''-hexamethylphosphoric triamide provided 2,2,2-trifluoro-1-[3-nitro-2-(trifluoromethyl)-5,6,8,9-tetrahydro-7H-pyrido[2,3-d]azepin-7-yl]ethanone; this material was converted to the requisite 7-methyl-2-(trifluoromethyl)-6,7,8,9-tetrahydro-5H-pyrido[2,3-d]azepin-3-amine using the chemistry described in Preparations P3 and P4.
[39]Reaction of 7-methyl-2-(trifluoromethyl)-6,7,8,9-tetrahydro-5H-pyrido[2,3-d]azepin-3-amine with 4-methylbenzenesulfonyl chloride and triethylamine in dichloromethane provided largely the disulfonylated product 4-methyl-N-[(4-methylphenyl)sulfonyl]-N-[7-methyl-2-(trifluoromethyl)-6,7,8,9-tetrahydro-5H-pyrido[2,3-d]azepin-3-yl]benzenesulfonamide; this material was treated with sodium hydroxide and methanol at 50° C. to afford Example 139.
[40]Reaction of C67 with tributyl(ethenyl)stannane, tetrakis(triphenylphosphine) palladium(0), and triphenylphosphine provided 1-(2-ethenyl-3-nitro-5,6,8,9-tetrahydro-7H-pyrido[2,3-d]azepin-7-yl)-2,2,2-trifluoroethanone. This material was converted to the requisite 2-ethyl-7-methyl-6,7,8,9-tetrahydro-5H-pyrido[2,3-d]azepin-3-amine using the chemistry described in Preparations P3 and P4.

Human D2 Receptor and Human D3 Receptor Binding Assays:

Saturation binding studies using Chinese hamster ovary cells expressing human dopamine D2 receptor (hD2R) with [$^{3}$H]-Spiperone, or human dopamine D3 receptor (hD3R) using [$^{3}$H]-7-OH-DPAT, were performed to determine $K_d$ values. The $K_d$ for hD2 is 1.61 nM and 1.37 nM for hD3. The optimal amount of cell homogenate was determined to be 4 mg/mL for hD2 and 7 mg/mL for hD3 per 96 well plate with 2 nM of [$^{3}$H]-Spiperone or 1.5 nM of [$^{3}$H]-7-OH-DPAT. These determined ligand and tissue concentrations were utilized in time course studies to determine linearity and equilibrium conditions for binding. Binding was at equilibrium with the specified amount of tissue in 20 minutes at 37° C. for both receptors. The hD2R assay buffer contains 50 mM Tris (pH 7.4 @ 37° C.), 100 mM NaCl and 1 mM MgCl$_2$. The hD3R assay buffer consists of 50 mM Tris (pH 7.4 at 37° C.), 120 mM NaCl, 5 mM MgCl$_2$, 5 mM KCl and 2 mM CaCl$_2$. Competitive binding experiments were initiated by the addition of 200 µL of the respective cell homogenate to 96-well plates containing 2.5 µL test drugs (10 concentrations using ½ log dilutions) and 50 µL of $^{3}$H-radioligand for a final volume of 250 µL. Non-specific binding was determined by radioligand binding in the presence of a saturating concentration of Haldol (10 µM). After the 20 minute incubation at 37° C., assay samples were rapidly filtered through Unifilter-96 GF/B PEI-coated filter plates and rinsed with ice-cold 50 mM Tris buffer (pH 7.4 at 4° C.). Membrane bound [$^{3}$H]-Spiperone or [$^{3}$H]-7-OH-DPAT levels were determined by liquid scintillation counting of the filterplates in 50 µL Ecolume. The IC$_{50}$ value (concentration at which 50% inhibition of specific binding occurs) was calculated by linear regression of the concentration-response data in ActivityBase. $K_i$ values were then calculated according to the Cheng-Prusoff equation:

$$K_i = \frac{IC_{50}}{1 + ([L]/K_d)}$$

where [L]=concentration of free radioligand and $K_d$=dissociation constant of radioligand for D3 receptor or D2 receptor.

TABLE 8

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 1 | 1.75 | 38.8 | 6-cyclohexyl-N-(2-methoxy-7-methyl-6,7,8,9-tetrahydro-5H-pyrido[2,3-d] azepin-3-yl)pyridine-3-sulfonamide |
| 2 | 0.859[b] | 76.0 | 6-(cyclopentyloxy)-N-(7-ethyl-2-methoxy-6,7,8,9-tetrahydro-5H-pyrido[2,3-d]azepin-3-yl)pyridine-3-sulfonamide |
| 3 | 1.56 | 85.9 | 4-[trans-3-(2-fluoroethoxy) cyclobutyl]-N-(2-methoxy-7-methyl-6,7,8,9-tetrahydro-5H-pyrido[2,3-d] azepin-3-yl)benzenesulfonamide |
| 4 | 1.53 | 104 | N-(2-methoxy-7-methyl-6,7,8,9-tetrahydro-5H-pyrido[2,3-d]azepin-3-yl)-4-(tetrahydro-2H-pyran-4-yl)benzenesulfonamide |
| 5 | 3.72[b] | 333[b] | N-(2-methoxy-7-methyl-6,7,8,9-tetrahydro-5H-pyrido[2,3-d]azepin-3-yl)-4-methylbenzenesulfonamide |
| 6 | 0.866[b] | 54.6[b] | N-(2-methoxy-7-methyl-6,7,8,9-tetrahydro-5H-pyrido[2,3-d]azepin-3-yl)-4-(tetrahydro-2H-pyran-2-yl)benzenesulfonamide |
| 7 | 1.39 | 65.5 | N-(2-methoxy-7-methyl-6,7,8,9-tetrahydro-5H-pyrido[2,3-d]azepin-3-yl)-4-[(2R)-tetrahydro-2H-pyran-2-yl] benzenesulfonamide |
| 8 | 2.09 | 180 | N-(2-methoxy-7-methyl-6,7,8,9-tetrahydro-5H-pyrido[2,3-d]azepin-3-yl)-4-[(2S)-tetrahydro-2H-pyran-2-yl] benzenesulfonamide |
| 9 | 7.68 | 1270 | N-(2-methoxy-6,7,8,9-tetrahydro-5H-pyrido[2,3-d]azepin-3-yl)-4-[(2R)-tetrahydro-2H-pyran-2-yl] benzene sulfonamide |
| 10 | 1.16 | 99.0 | 4-(trans-1-fluoro-3-methoxy cyclobutyl)-N-(2-methoxy-7-methyl-6,7,8,9-tetrahydro-5H-pyrido[2,3-d] azepin-3-yl)benzenesulfonamide |
| 11 | 3.31[b] | 106[b] | 6-(1-fluorocyclopentyl)-N-(2-methoxy-7-methyl-6,7,8,9-tetrahydro-5H-pyrido[2,3-d]azepin-3-yl)pyridine-3-sulfonamide |
| 12 | 281[b] | 260[b] | N-[2-(difluoromethoxy)-7-propyl-6,7,8,9-tetrahydro-5H-pyrido[2,3-d] azepin-3-yl]-4-(propan-2-yl) benzenesulfonamide |
| 13 | 10.8[b] | 923[b] | N-(7-ethyl-2-methoxy-5-methyl-6,7,8,9-tetrahydro-5H-pyrido[2,3-d]azepin-3-yl)-4-methyl benzenesulfonamide |
| 14 | 3.81[b] | 36.6[b] | 4-ethoxy-N-[7-ethyl-2-(propan-2-yloxy)-6,7,8,9-tetrahydro-5H-pyrido [2,3-d]azepin-3-yl] benzenesulfonamide |
| 137 | 152[b] | >4190[b] | 4-ethoxy-N-(7-ethyl-2-methyl-6,7,8,9-tetrahydro-5H-pyrido[2,3-d] azepin-3-yl)benzenesulfonamide, trifluoroacetate salt |
| 15 | 0.714 | 13.3 | 6-(cyclopentyloxy)-N-(2-methoxy-7-methyl-6,7,8,9-tetrahydro-5H-pyrido [2,3-d]azepin-3-yl)pyridine-3-sulfonamide |
| 16 | 2.41 | 122 | 6-cyclopentyl-N-(2-methoxy-7-methyl-6,7,8,9-tetrahydro-5H-pyrido[2,3-d]azepin-3-yl)pyridine-3-sulfonamide, formate salt |
| 17 | 1.95 | 90.2 | 6-(cyclobutyloxy)-N-(2-methoxy-7-methyl-6,7,8,9-tetrahydro-5H-pyrido[2,3-d]azepin-3-yl)pyridine-3-sulfonamide |
| 18 | 3.58 | 142 | 2-(cyclopentyloxy)-N-(2-methoxy-7-methyl-6,7,8,9-tetrahydro-5H-pyrido[2,3-d]azepin-3-yl)pyrimidine-5-sulfonamide, formate salt |
| 19 | 2.76 | 91.2 | 6-(1-fluorocyclohexyl)-N-(2-methoxy-7-methyl-6,7,8,9-tetrahydro-5H-pyrido[2,3-d]azepin-3-yl)pyridine-3-sulfonamide |
| 20 | 1.74 | 116[b] | N-(7-ethyl-2-methoxy-6,7,8,9-tetrahydro-5H-pyrido[2,3-d]azepin-3-yl)-4-[trans-3-(2-fluoroethoxy) cyclobutyl]benzenesulfonamide |
| 21 | 0.967 | 25.5 | 4-(cis-3-ethoxycyclobutyl)-N-(2-methoxy-7-methyl-6,7,8,9-tetrahydro-5H-pyrido[2,3-d]azepin-3-yl)benzenesulfonamide |
| 22 | 2.64[b] | 30.3[b] | 4-(trans-3-ethoxycyclobutyl)-N-(2-methoxy-7-methyl-6,7,8,9-tetrahydro-5H-pyrido[2,3-d]azepin-3-yl)benzenesulfonamide |
| 23 | >459[b] | >4600[b] | N-(7-ethyl-2-methoxy-6,7,8,9-tetrahydro-5H-pyrido[2,3-d]azepin-3-yl)-6-(cis-1-hydroxy-3-methoxy cyclobutyl)pyridine-3-sulfonamide |

TABLE 8-continued

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 24 | 4.20[b] | 232[b] | 6-cyclobutyl-5-fluoro-N-(2-methoxy-7-methyl-6,7,8,9-tetrahydro-5H-pyrido[2,3-d]azepin-3-yl)pyridine-3-sulfonamide |
| 25 | 5.07[b] | 542[b] | 6-(cis-1-fluoro-3-methylcyclobutyl)-N-(2-methoxy-7-methyl-6,7,8,9-tetrahydro-5H-pyrido[2,3-d]azepin-3-yl)pyridine-3-sulfonamide |
| 26 | 2.43[b] | 522[b] | N-(2-methoxy-7-propyl-6,7,8,9-tetrahydro-5H-pyrido[2,3-d]azepin-3-yl)-4-methylbenzenesulfonamide, formate salt |
| 27 | 3.26[b] | 400[b] | 4-chloro-N-(2-methoxy-7-methyl-6,7,8,9-tetrahydro-5H-pyrido[2,3-d]azepin-3-yl)benzenesulfonamide, formate salt |
| 28 | 2.33[b] | 124[b] | 4-ethoxy-N-(2-methoxy-7-methyl-6,7,8,9-tetrahydro-5H-pyrido[2,3-d] azepin-3-yl)benzenesulfonamide, formate salt |
| 29 | 11.1[b] | 1070[b] | 4-ethoxy-N-[2-methoxy-7-(2-methoxy ethyl)-6,7,8,9-tetrahydro-5H-pyrido [2,3-d]azepin-3-yl] benzene sulfonamide, formate salt |
| 30 | 0.89[b] | 55.0[b] | 4-cyclopropyl-N-(7-ethyl-2-methoxy-6,7,8,9-tetrahydro-5H-pyrido[2,3-d]azepin-3-yl)benzenesulfonamide |
| 31 | 1.24[b] | 564[b] | N-(2-methoxy-7-methyl-6,7,8,9-tetrahydro-5H-pyrido[2,3-d]azepin-3-yl)-3,4-dihydro-2H-chromene-6-sulfonamide |
| 32 | 1.05[b] | 204[b] | 4-(1-methoxyethyl)-N-(2-methoxy-7-methyl-6,7,8,9-tetrahydro-5H-pyrido [2,3-d]azepin-3-yl)benzene sulfonamide |
| 33 | 3.68[b] | N.D.[c] | N-(2-methoxy-7-methyl-6,7,8,9-tetrahydro-5H-pyrido[2,3-d]azepin-3-yl)-4-(oxetan-3-yl)benzene sulfonamide |
| 34 | 0.65[b] | 26.3[b] | N-(2-methoxy-7-methyl-6,7,8,9-tetrahydro-5H-pyrido[2,3-d]azepin-3-yl)-2,2-dimethyl-2,3-dihydro-1-benzofuran-5-sulfonamide |
| 35 | 3.70[b] | 995[b] | N-(7-ethyl-2-methoxy-6,7,8,9-tetrahydro-5H-pyrido[2,3-d]azepin-3-yl)-3-fluoro-4-methylbenzene sulfonamide |
| 36 | 3.29[b] | 260[b] | N-(2-methoxy-7-methyl-6,7,8,9-tetrahydro-5H-pyrido[2,3-d]azepin-3-yl)-4-(tetrahydrofuran-3-yl)benzenesulfonamide |
| 37 | 3.21[b] | 260[b] | N-(2-methoxy-7-methyl-6,7,8,9-tetrahydro-5H-pyrido[2,3-d]azepin-3-yl)-4-[(3R)-tetrahydrofuran-3-yloxy] benzenesulfonamide |
| 38 | 2.93[b] | 339[b] | 4-(trans-4-methoxycyclohexyl)-N-(2-methoxy-7-methyl-6,7,8,9-tetrahydro-5H-pyrido[2,3-d]azepin-3-yl)benzenesulfonamide |
| 39 | 1.95[b] | 561[b] | 4-(1-fluoro-4-methoxycyclohexyl)-N-(2-methoxy-7-methyl-6,7,8,9-tetrahydro-5H-pyrido[2,3-d]azepin-3-yl)benzenesulfonamide, from ISOMER-2 (see footnote 7 in Table 7) |
| 40 | 2.59[b] | 134[b] | 4-(4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide |
| 41 | 2.31 | 177 | 4-(4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide, ENT-1 |
| 42 | 5.91[b] | 402[b] | 4-(4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide, ENT-2 |
| 43 | 1.79[b] | 131[b] | N-(7-ethyl-2-methoxy-6,7,8,9-tetrahydro-5H-pyrido[2,3-d]azepin-3-yl)-3-fluoro-4-[(2S)-tetrahydro-2H-pyran-2-yl]benzenesulfonamide |
| 44 | 2.25 | 162 | N-[7-(3-fluoropropyl)-2-methoxy-6,7,8,9-tetrahydro-5H-pyrido[2,3-d]azepin-3-yl]-4-(propan-2-yl)benzenesulfonamide |
| 45 | 0.32 | 3.20 | 4-cyclohexyl-N-(2-methoxy-7-methyl-6,7,8,9-tetrahydro-5H-pyrido[2,3-d] azepin-3-yl)benzenesulfonamide |
| 46 | 0.48 | 3.21 | 4-(cyclopentyloxy)-N-(2-methoxy-7-methyl-6,7,8,9-tetrahydro-5H-pyrido [2,3-d]azepin-3-yl) benzene sulfonamide |
| 47 | 2.33[b] | 176[b] | 6-[cyclopentyl(difluoro)methyl]-N-(2-methoxy-7-methyl-6,7,8,9-tetrahydro-5H-pyrido[2,3-d]azepin-3-yl)pyridine-3-sulfonamide, formate salt |

TABLE 8-continued

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 48 | 7.25[b] | 933[b] | 4-(trans-3-ethoxy-1-fluorocyclobutyl)-N-(7-ethyl-2-methoxy-6,7,8,9-tetrahydro-5H-pyrido[2,3-d]azepin-3-yl)benzenesulfonamide |
| 49 | 0.88[b] | 102[b] | N-(2-methoxy-7-propyl-6,7,8,9-tetrahydro-5H-pyrido[2,3-d]azepin-3-yl)-4-(propan-2-yl)benzene sulfonamide |
| 50 | 3.20[b] | 337[b] | 4-ethoxy-N-(2-methoxy-7-propyl-6,7,8,9-tetrahydro-5H-pyrido[2,3-d]azepin-3-yl)benzenesulfonamide |
| 51 | 1.12[b] | 105[b] | N-(7-ethyl-2-methoxy-6,7,8,9-tetrahydro-5H-pyrido[2,3-d]azepin-3-yl)-4-(propan-2-yl)benzene sulfonamide, formate salt |
| 52 | 2.56[b] | 435[b] | 4-ethoxy-N-(7-ethyl-2-methoxy-6,7,8,9-tetrahydro-5H-pyrido[2,3-d] azepin-3-yl)benzenesulfonamide |
| 53 | 2.75[b] | 313[b] | N-(7-ethyl-2-methoxy-6,7,8,9-tetrahydro-5H-pyrido[2,3-d]azepin-3-yl)-4-methylbenzenesulfonamide, formate salt |
| 54 | 0.38[b] | 14.4[b] | N-(2-methoxy-7-methyl-6,7,8,9-tetrahydro-5H-pyrido[2,3-d]azepin-3-yl)-4-(propan-2-yl)benzene sulfonamide, formate salt |
| 55 | 0.52[b] | 29.1[b] | N-(2-methoxy-7-methyl-6,7,8,9-tetrahydro-5H-pyrido[2,3-d]azepin-3-yl)-4-[1-(trifluoromethyl)cyclopropyl] benzenesulfonamide, formate salt |
| 56 | 2.12[b] | 162[b] | N-(7-ethyl-2-methoxy-5-methyl-6,7,8,9-tetrahydro-5H-pyrido[2,3-d]azepin-3-yl)-4-(propan-2-yl) benzenesulfonamide |
| 57 | 3.14[b] | 229[b] | N-(7-ethyl-2-methoxy-6,7,8,9-tetrahydro-5H-pyrido[2,3-d]azepin-3-yl)-4-(tetrahydro-2H-pyran-4-yl) benzenesulfonamide |
| 58 | 4.40[b] | 760[b] | N-(7-ethyl-2-methoxy-6,7,8,9-tetrahydro-5H-pyrido[2,3-d]azepin-3-yl)-3,4-dihydro-2H-chromene-6-sulfonamide |
| 59 | 11.6[b] | 2310[b] | 4-(difluoromethoxy)-N-(7-ethyl-2-methoxy-6,7,8,9-tetrahydro-5H-pyrido[2,3-d]azepin-3-yl) benzenesulfonamide |
| 60 | 2.94[b] | 395[b] | N-(7-ethyl-2-methoxy-6,7,8,9-tetrahydro-5H-pyrido[2,3-d]azepin-3-yl)-6-phenoxypyridine-3-sulfonamide |
| 61 | 2.33[b] | 388[b] | N-(7-ethyl-2-methoxy-6,7,8,9-tetrahydro-5H-pyrido[2,3-d]azepin-3-yl)-3,4-dimethylbenzenesulfonamide |
| 62 | 0.40[b] | 52.8[b] | N-(7-ethyl-2-methoxy-6,7,8,9-tetrahydro-5H-pyrido[2,3-d]azepin-3-yl)-4-propylbenzenesulfonamide |
| 63 | 0.32[b] | 11.4[b] | 4-(cyclopentyloxy)-N-(7-ethyl-2-methoxy-6,7,8,9-tetrahydro-5H-pyrido[2,3-d]azepin-3-yl) benzenesulfonamide |
| 64 | 0.48[b] | 21.2[b] | N-(7-ethyl-2-methoxy-6,7,8,9-tetrahydro-5H-pyrido[2,3-d]azepin-3-yl)-2,2-dimethyl-3,4-dihydro-2H-chromene-6-sulfonamide |
| 65 | 1.54[b] | 276[b] | N-(7-ethyl-2-methoxy-6,7,8,9-tetrahydro-5H-pyrido[2,3-d]azepin-3-yl)-2,4-dimethylbenzenesulfonamide |
| 66 | 8.78[b] | 1460[b] | N-[7-ethyl-2-(propan-2-yloxy)-6,7,8,9-tetrahydro-5H-pyrido[2,3-d]azepin-3-yl]-3,4-dihydro-2H-chromene-6-sulfonamide |
| 67 | 4.02[b] | 660[b] | N-(7-ethyl-2-methoxy-6,7,8,9-tetrahydro-5H-pyrido[2,3-d]azepin-3-yl)-2-methyl-2,3-dihydro-1-benzofuran-5-sulfonamide |
| 68 | 1.26 | 338 | N-(7-ethyl-2-methoxy-6,7,8,9-tetrahydro-5H-pyrido[2,3-d]azepin-3-yl)-4-(trans-3-methoxycyclobutyl) benzenesulfonamide |
| 69 | 4.77[b] | 392[b] | N-(7-ethyl-2-methoxy-6,7,8,9-tetrahydro-5H-pyrido[2,3-d]azepin-3-yl)-4-(4-methyltetrahydro-2H-pyran-4-yl)benzenesulfonamide |
| 70 | 2.00[b] | 294[b] | N-(7-ethyl-2-methoxy-6,7,8,9-tetrahydro-5H-pyrido[2,3-d]azepin-3-yl)-4-(tetrahydro-2H-pyran-2-yl)benzenesulfonamide |
| 71 | 4.84[b] | 754[b] | N-(7-ethyl-2-methoxy-6,7,8,9-tetrahydro-5H-pyrido[2,3-d]azepin-3-yl)-4-(tetrahydrofuran-3-yl) benzenesulfonamide |
| 72 | 2.65 | 420 | N-(7-ethyl-2-methoxy-6,7,8,9-tetrahydro-5H-pyrido[2,3-d]azepin-3-yl)-4-(cis-3-methoxycyclobutyl) benzenesulfonamide |
| 73 | 4.41[b] | 1040[b] | N-(7-ethyl-2-methoxy-6,7,8,9-tetrahydro-5H-pyrido[2,3-d]azepin-3-yl)-4-(tetrahydro-2H-pyran-2-yl) benzenesulfonamide, ENT-1 |

TABLE 8-continued

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 74 | 2.58[b] | 202[b] | N-(7-ethyl-2-methoxy-6,7,8,9-tetrahydro-5H-pyrido[2,3-d]azepin-3-yl)-4-(tetrahydro-2H-pyran-2-yl)benzenesulfonamide, ENT-2 |
| 75 | 3.20[b] | 262[b] | N-(7-ethyl-2-methoxy-6,7,8,9-tetrahydro-5H-pyrido[2,3-d]azepin-3-yl)-4-(4-fluorotetrahydro-2H-pyran-4-yl)benzenesulfonamide |
| 76 | 1.28[b] | 203[b] | 4-(trans-3-methoxycyclobutyl)-N-(2-methoxy-7-methyl-6,7,8,9-tetrahydro-5H-pyrido[2,3-d]azepin-3-yl)benzenesulfonamide |
| 77 | 4.52[b] | 549[b] | N-(2-methoxy-7-methyl-6,7,8,9-tetrahydro-5H-pyrido[2,3-d]azepin-3-yl)-4-(tetrahydro-2H-pyran-3-yl)benzenesulfonamide |
| 78 | 7.56[b] | 718[b] | N-(2-methoxy-7-methyl-6,7,8,9-tetrahydro-5H-pyrido[2,3-d]azepin-3-yl)-4-(tetrahydro-2H-pyran-4-yloxy)benzenesulfonamide |
| 79 | 3.67[b] | 403[b] | N-(2-methoxy-7-methyl-6,7,8,9-tetrahydro-5H-pyrido[2,3-d]azepin-3-yl)-4-(4-methyltetrahydro-2H-pyran-4-yl)benzenesulfonamide |
| 80 | 1.77 | 238 | 4-(4-fluorotetrahydro-2H-pyran-4-yl)-N-(2-methoxy-7-methyl-6,7,8,9-tetrahydro-5H-pyrido[2,3-d]azepin-3-yl)benzenesulfonamide |
| 81 | 1.19[b] | 311[b] | 4-(cis-3-methoxycyclobutyl)-N-(2-methoxy-7-methyl-6,7,8,9-tetrahydro-5H-pyrido[2,3-d]azepin-3-yl)benzenesulfonamide, formate salt |
| 82 | 4.37[b] | 342[b] | N-(2-methoxy-7-methyl-6,7,8,9-tetrahydro-5H-pyrido[2,3-d]azepin-3-yl)-4-(tetrahydrofuran-3-yloxy)benzenesulfonamide |
| 83 | 4.69[b] | 436[b] | N-(2-methoxy-7-methyl-6,7,8,9-tetrahydro-5H-pyrido[2,3-d]azepin-3-yl)-4-(tetrahydro-2H-pyran-3-yl)benzenesulfonamide, ENT-1 |
| 84 | 4.58[b] | 503[b] | N-(2-methoxy-7-methyl-6,7,8,9-tetrahydro-5H-pyrido[2,3-d]azepin-3-yl)-4-(tetrahydro-2H-pyran-3-yl)benzenesulfonamide, ENT-2 |
| 85 | 3.24[b] | 303[b] | N-(2-methoxy-7-methyl-6,7,8,9-tetrahydro-5H-pyrido[2,3-d]azepin-3-yl)-4-(trans-2-methyltetrahydro-2H-pyran-4-yl)benzenesulfonamide, from ENT-2 (see footnote 19 in Table 7) |
| 86 | 35.2[b] | 1390[b] | 4-(2,2-dimethyltetrahydro-2H-pyran-4-yl)-N-(2-methoxy-7-methyl-6,7,8,9-tetrahydro-5H-pyrido[2,3-d]azepin-3-yl)benzenesulfonamide, ENT-1 |
| 87 | 3.61[b] | 276[b] | 4-(2,2-dimethyltetrahydro-2H-pyran-4-yl)-N-(2-methoxy-7-methyl-6,7,8,9-tetrahydro-5H-pyrido[2,3-d]azepin-3-yl)benzenesulfonamide, ENT-2 |
| 88 | 6.84[b] | 651[b] | N-(2-methoxy-7-methyl-6,7,8,9-tetrahydro-5H-pyrido[2,3-d]azepin-3-yl)-4-(trans-2-methyltetrahydro-2H-pyran-4-yl)benzenesulfonamide, from ENT-1 (see footnote 19 in Table 7) |
| 89 | 1.67[b] | 76.0[b] | 4-[(1S)-1-methoxyethyl]-N-(2-methoxy-7-methyl-6,7,8,9-tetrahydro-5H-pyrido[2,3-d]azepin-3-yl)benzenesulfonamide |
| 90 | 1.93[b] | 207[b] | 4-[(1R)-1-methoxyethyl]-N-(2-methoxy-7-methyl-6,7,8,9-tetrahydro-5H-pyrido[2,3-d]azepin-3-yl)benzenesulfonamide |
| 91 | 3.37[b] | 208[b] | N-(2-methoxy-7-methyl-6,7,8,9-tetrahydro-5H-pyrido[2,3-d]azepin-3-yl)-4-[(3S)-tetrahydrofuran-3-yloxy]benzenesulfonamide |
| 92 | 5.53[b] | 600[b] | 4-(cis-4-methoxycyclohexyl)-N-(2-methoxy-7-methyl-6,7,8,9-tetrahydro-5H-pyrido[2,3-d]azepin-3-yl)benzenesulfonamide |
| 93 | 2.03 | 366 | 4-(1-fluoro-4-methoxycyclohexyl)-N-(2-methoxy-7-methyl-6,7,8,9-tetrahydro-5H-pyrido[2,3-d]azepin-3-yl)benzenesulfonamide, from ISOMER-1 (see footnote 7 in Table 7) |
| 94 | 2.71[b] | 727[b] | N-(7-ethyl-2-methoxy-6,7,8,9-tetrahydro-5H-pyrido[2,3-d]azepin-3-yl)-4-(1-fluoro-4-methoxycyclohexyl)benzenesulfonamide, from ISOMER-1 (see footnote 7 in Table 7) |
| 95 | 0.60[b] | 45.3[b] | 4-(1-methoxycyclopentyl)-N-(2-methoxy-7-methyl-6,7,8,9-tetrahydro-5H-pyrido[2,3-d]azepin-3-yl)benzenesulfonamide, trifluoroacetate salt |
| 96 | 2.79 | 317 | N-(7-ethyl-2-methoxy-6,7,8,9-tetrahydro-5H-pyrido[2,3-d]azepin-3-yl)-4-(trans-1-fluoro-3-methoxy cyclobutyl)benzenesulfonamide |

TABLE 8-continued

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 97 | 5.89[b] | 983[b] | N-(2-methoxy-7-methyl-6,7,8,9-tetrahydro-5H-pyrido[2,3-d]azepin-3-yl)-6-(tetrahydrofuran-3-yloxy)pyridine-3-sulfonamide |
| 98 | 4.01[b] | 488[b] | N-(2-methoxy-7-methyl-6,7,8,9-tetrahydro-5H-pyrido[2,3-d]azepin-3-yl)-4-[(2S)-tetrahydrofuran-2-yl]benzenesulfonamide |
| 99 | 3.05[b] | 314[b] | N-(2-methoxy-7-methyl-6,7,8,9-tetrahydro-5H-pyrido[2,3-d]azepin-3-yl)-4-[(2R)-tetrahydrofuran-2-yl]benzenesulfonamide |
| 100 | 6.35[b] | 663[b] | 6-(1-methoxycyclopentyl)-N-(2-methoxy-7-methyl-6,7,8,9-tetrahydro-5H-pyrido[2,3-d]azepin-3-yl)pyridine-3-sulfonamide |
| 101 | 6.26[b] | 677[b] | N-(7-ethyl-2-methoxy-6,7,8,9-tetrahydro-5H-pyrido[2,3-d]azepin-3-yl)-6-(1-fluorocyclopentyl)pyridine-3-sulfonamide |
| 102 | 2.81 | 325 | 6-cyclopentyl-N-(7-ethyl-2-methoxy-6,7,8,9-tetrahydro-5H-pyrido[2,3-d]azepin-3-yl)pyridine-3-sulfonamide, formate salt |
| 103 | 1.85 | 45.2 | 6-tert-butoxy-N-(2-methoxy-7-methyl-6,7,8,9-tetrahydro-5H-pyrido[2,3-d]azepin-3-yl)pyridine-3-sulfonamide |
| 104 | 0.39[b] | 3.91[b] | N-(2-methoxy-7-methyl-6,7,8,9-tetrahydro-5H-pyrido[2,3-d]azepin-3-yl)-3-methyl-4-[(2R)-tetrahydro-2H-pyran-2-yl]benzenesulfonamide |
| 105 | 0.46[b] | 26.1[b] | N-(2-methoxy-7-methyl-6,7,8,9-tetrahydro-5H-pyrido[2,3-d]azepin-3-yl)-3-methyl-4-[(2S)-tetrahydro-2H-pyran-2-yl]benzenesulfonamide |
| 106 | 4.31 | 320 | 4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, formate salt, from second-eluting isome (see footnote 26 in Table 7) |
| 107 | 0.46[b] | 7.24[b] | N-(7-ethyl-2-methoxy-6,7,8,9-tetrahydro-5H-pyrido[2,3-d]azepin-3-yl)-3-methyl-4-[(2R)-tetrahydro-2H-pyran-2-yl]benzenesulfonamide |
| 108 | 15.1[b] | 1930[b] | 4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-1, from first-eluting isomer (see footnotes 26 and 27 in Table 7) |
| 109 | 3.16 | 208 | 4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-2, from first-eluting isomer (see footnotes 26 and 27 in Table 7) |
| 110 | 1.27 | 25.0 | 3-fluoro-N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide |
| 111 | 2.30 | 100 | 3-fluoro-N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide |
| 112 | 2.36[b] | 45.7[b] | N-(7-ethyl-2-methoxy-6,7,8,9-tetrahydro-5H-pyrido[2,3-d]azepin-3-yl)-6-(1-fluorocyclohexyl)pyridine-3-sulfonamide |
| 113 | 3.94 | 143 | 6-cyclobutyl-N-(2-methoxy-7-methyl-6,7,8,9-tetrahydro-5H-pyrido[2,3-d]azepin-3-yl)pyridine-3-sulfonamide |
| 114 | 3.15[b] | 146[b] | 6-cyclohexyl-N-(7-ethyl-2-methoxy-6,7,8,9-tetrahydro-5H-pyrido[2,3-d]azepin-3-yl)pyridine-3-sulfonamide |
| 115 | 14.8[b] | 213[b] | N-[7-(3-fluoropropyl)-2-methoxy-6,7,8,9-tetrahydro-5H-pyrido[2,3-d]azepin-3-yl]-4-methylbenzenesulfonamide |
| 116 | 7.17[b] | 379[b] | 2-(cyclobutyloxy)-N-(2-methoxy-7-methyl-6,7,8,9-tetrahydro-5H-pyrido[2,3-d]azepin-3-yl)pyrimidine-5-sulfonamide |
| 117 | 9.93 | 464 | 2-tert-butoxy-N-(2-methoxy-7-methyl-6,7,8,9-tetrahydro-5H-pyrido[2,3-d]azepin-3-yl)pyrimidine-5-sulfonamide |
| 118 | 0.57 | 5.41 | N-(2-methoxy-7-methyl-6,7,8,9-tetrahydro-5H-pyrido[2,3-d]azepin-3-yl)-4-propylbenzenesulfonamide |
| 119 | 2.42[b] | 89.9[b] | N-(7-ethyl-2-methoxy-6,7,8,9-tetrahydro-5H-pyrido[2,3-d]azepin-3-yl)-4-[cis-3-(2-fluoroethoxy)cyclobutyl]benzenesulfonamide |
| 120 | 1.28 | 54.0 | 4-(cis-3-ethoxycyclobutyl)-N-(7-ethyl-2-methoxy-6,7,8,9-tetrahydro-5H-pyrido[2,3-d]azepin-3-yl)benzenesulfonamide |

TABLE 8-continued

Biological activity and IUPAC name for Examples 1-140.

| Example Number | hD3 in CHO cells $K_i$ (nM)[a] | Human CHO D2 $K_i$ (nM)[a] | IUPAC Name |
|---|---|---|---|
| 121 | 2.53[b] | 39.8[b] | 4-(trans-3-ethoxycyclobutyl)-N-(7-ethyl-2-methoxy-6,7,8,9-tetrahydro-5H-pyrido[2,3-d]azepin-3-yl)benzenesulfonamide |
| 122 | 4.58[b] | 128[b] | 6-(cyclopentyloxy)-N-[7-(3-fluoropropyl)-2-methoxy-6,7,8,9-tetrahydro-5H-pyrido[2,3-d]azepin-3-yl]pyridine-3-sulfonamide |
| 123 | 12.9[b] | 164[b] | 2-cyclopentyl-N-(2-methoxy-7-methyl-6,7,8,9-tetrahydro-5H-pyrido[2,3-d]azepin-3-yl)pyrimidine-5-sulfonamide |
| 124 | 0.79[b] | 3.89[b] | 6-(cyclopentyloxy)-N-(2-methoxy-7-methyl-6,7,8,9-tetrahydro-5H-pyrido[2,3-d]azepin-3-yl)-5-methylpyridine-3-sulfonamide |
| 125 | 1.46[b] | 4.05[b] | 6-(cyclopentyloxy)-N-(7-ethyl-2-methoxy-6,7,8,9-tetrahydro-5H-pyrido[2,3-d]azepin-3-yl)-5-methylpyridine-3-sulfonamide |
| 126 | 1.85[b] | 10.9[b] | 6-(cyclobutyloxy)-N-(2-methoxy-7-methyl-6,7,8,9-tetrahydro-5H-pyrido[2,3-d]azepin-3-yl)-5-methylpyridine-3-sulfonamide |
| 127 | 32.2[b] | 457[b] | 2-cyclohexyl-N-(2-methoxy-7-methyl-6,7,8,9-tetrahydro-5H-pyrido[2,3-d]azepin-3-yl)pyrimidine-5-sulfonamide |
| 128 | 1.24[b] | 4.07[b] | 6-(cyclopentyloxy)-N-(2-methoxy-7-methyl-6,7,8,9-tetrahydro-5H-pyrido[2,3-d]azepin-3-yl)-2-methylpyridine-3-sulfonamide |
| 129 | 16.7[b] | 786[b] | N-(2-methoxy-7-methyl-6,7,8,9-tetrahydro-5H-pyrido[2,3-d]azepin-3-yl)-6-[(2R)-tetrahydro-2H-pyran-2-yl]pyridine-3-sulfonamide |
| 130 | 1.69[b] | 25.2[b] | 6-(cyclopentyloxy)-5-fluoro-N-(2-methoxy-7-methyl-6,7,8,9-tetrahydro-5H-pyrido[2,3-d]azepin-3-yl)pyridine-3-sulfonamide |
| 131 | 2.30[b] | 36.1[b] | 6-(cyclopentylmethyl)-N-(2-methoxy-7-methyl-6,7,8,9-tetrahydro-5H-pyrido[2,3-d]azepin-3-yl)pyridine-3-sulfonamide |
| 132 | 2.23[b] | 367[b] | 4-(trans-3-ethoxy-1-fluorocyclobutyl)-N-(2-methoxy-7-methyl-6,7,8,9-tetrahydro-5H-pyrido[2,3-d]azepin-3-yl)benzenesulfonamide |
| 133 | 2.47[b] | 428[b] | 4-[trans-1-fluoro-3-(2-fluoroethoxy) cyclobutyl]-N-(2-methoxy-7-methyl-6,7,8,9-tetrahydro-5H-pyrido[2,3-d]azepin-3-yl) benzenesulfonamide |
| 134 | 14.8[b] | 1810[b] | 6-(trans-3-ethoxycyclobutyl)-N-(2-methoxy-7-methyl-6,7,8,9-tetrahydro-5H-pyrido[2,3-d]azepin-3-yl)pyridine-3-sulfonamide |
| 135 | 23.6[b] | >3140[b] | 6-(cis-3-ethoxycyclobutyl)-N-(2-methoxy-7-methyl-6,7,8,9-tetrahydro-5H-pyrido[2,3-d]azepin-3-yl)pyridine-3-sulfonamide |
| 136 | 7.46[b] | 1220[b] | 6-(trans-1-fluoro-3-methylcyclobutyl)-N-(2-methoxy-7-methyl-6,7,8,9-tetrahydro-5H-pyrido[2,3-d]azepin-3-yl)pyridine-3-sulfonamide |
| 138 | 288[b] | >4190[b] | 4-chloro-N-(7-ethyl-2-methyl-6,7,8,9-tetrahydro-5H-pyrido[2,3-d]azepin-3-yl)benzenesulfonamide, trifluoroacetate salt |
| 139 | 713[b] | >4280[b] | 4-methyl-N-[7-methyl-2-(trifluoromethyl)-6,7,8,9-tetrahydro-5H-pyrido[2,3-d]azepin-3-yl]benzenesulfonamide |
| 140 | 27.5[b] | 3300[b] | N-(2-ethyl-7-methyl-6,7,8,9-tetrahydro-5H-pyrido[2,3-d]azepin-3-yl)-4-[(2R)-tetrahydro-2H-pyran-2-yl]benzenesulfonamide, trifluoroacetate salt |

[a]Reported $K_i$ values are the geometric mean of 2-5 determinations, unless otherwise indicated.
[b]The $K_i$ value is from a single determination.
[c]N.D—not determined.

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound of Formula I

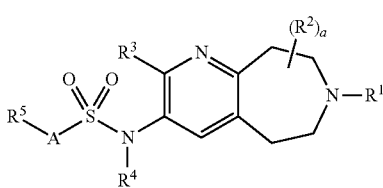

wherein
R$^1$ is selected from the group consisting of hydrogen, C$_1$-C$_6$alkyl, C$_3$-C$_7$cycloalkyl and C$_3$-C$_7$cycloalkylC$_1$-C$_3$alkyl; wherein the C$_1$-C$_6$alkyl, C$_3$-C$_7$cycloalkyl and C$_3$-C$_7$cycloalkylC$_1$-C$_3$alkyl are each optionally substituted with one to three independently selected halo, hydroxy or C$_1$-C$_3$alkoxy;
R$^2$ is independently selected at each occurrence from the group consisting of halo, hydroxy and C$_1$-C$_3$alkyl;
a is 0, 1, 2, 3 or 4;
R$^3$ is selected from the group consisting of hydrogen, hydroxy, C$_1$-C$_6$alkyl and C$_1$-C$_6$alkoxy, wherein the C$_1$-C$_6$alkyl and C$_1$-C$_6$alkoxy are each optionally substituted with 1 to 3 fluoro;
R$^4$ is hydrogen or C$_1$-C$_6$alkyl optionally substituted with one to three substituents independently selected from the group consisting of fluoro, C$_1$-C$_3$alkoxy and hydroxy;
A is selected from the group consisting of C$_6$-C$_{10}$aryl and 5- to 10-membered heteroaryl; wherein the C$_6$-C$_{10}$aryl and 5- to 10-membered heteroaryl are optionally substituted with 1 to 3 R$^6$;
R$^5$ is selected from the group consisting of halo, C$_1$-C$_6$alkyl, C$_1$-C$_6$alkoxy, C$_1$-C$_6$alkoxyC$_1$-C$_6$alkyl, C$_3$-C$_7$cycloalkyl, C$_3$-C$_7$cycloalkylC$_1$-C$_6$alkyl, C$_3$-C$_7$cycloalkoxy, phenoxy, 4- to 10-membered heterocycloalkyl and 4- to 10-membered heterocycloalkoxy; wherein the C$_1$-C$_6$alkyl, C$_1$-C$_6$alkoxy and C$_1$-C$_6$alkoxyC$_1$-C$_6$alkyl are optionally substituted with one to four independently selected halo or hydroxy; and wherein the C$_3$-C$_7$cycloalkyl, C$_3$-C$_7$cycloalkylC$_1$-C$_6$alkyl, C$_3$-C$_7$cycloalkoxy, phenoxy, 4- to 10-membered heterocycloalkyl and 4- to 10-membered heterocycloalkoxy are optionally substituted with one to four R$^7$;
or R$^4$ and R$^5$ taken together are a C$_1$-C$_3$alkylene;
R$^6$ is selected from the group consisting of halo, cyano, C$_1$-C$_6$alkyl optionally substituted with one to three fluoro, C$_1$-C$_6$alkoxy optionally substituted with one to three fluoro, and C$_1$-C$_6$alkoxyC$_1$-C$_6$alkyl;
or R$^4$ and R$^6$ taken together are a C$_1$-C$_3$alkylene;
or R$^5$ and R$^6$ when attached to adjacent carbons and taken together with the adjacent carbons to which they are attached form a fused 5- to 7-membered cycloalkyl ring or a 5- to 7-membered heterocycloalkyl ring, each of which is optionally substituted with one to four R$^8$;

R$^7$ at each occurrence is independently selected from the group consisting of halo, hydroxy, C$_1$-C$_3$alkyl optionally substituted with one to three fluoro or C$_1$-C$_3$alkoxy, and C$_1$-C$_3$alkoxy optionally substituted with one to three fluoro; and
R$^8$ at each occurrence is independently selected from halo, hydroxy, C$_1$-C$_3$alkyl optionally substituted with one to three fluoro, and C$_1$-C$_3$alkoxy optionally substituted with one to three fluoro;
or a pharmaceutically acceptable salt thereof.

2. The compound of claim 1 wherein
R$^1$ is hydrogen or C$_1$-C$_3$alkyl optionally substituted with a C$_1$-C$_3$alkoxy or fluoro;
R$^2$ is C$_1$-C$_3$alkyl;
a is 0 or 1;
R$^3$ is C$_1$-C$_3$alkoxy optionally substituted with one to three fluoro; and
R$^4$ is hydrogen;
or a pharmaceutically acceptable salt thereof.

3. The compound of claim 2 wherein
R$^1$ is hydrogen, methyl, ethyl, propyl, 3-fluoropropyl or 2-methoxyethyl;
a is 0; and
R$^3$ is methoxy, difluoromethoxy or isopropoxy;
or a pharmaceutically acceptable salt thereof.

4. The compound of claim 1 wherein
A is phenyl or 6-membered heteroaryl, wherein the phenyl or 6-membered heteroaryl is optionally substituted with one R$^6$;
or a pharmaceutically acceptable salt thereof.

5. The compound of claim 4 wherein
A is

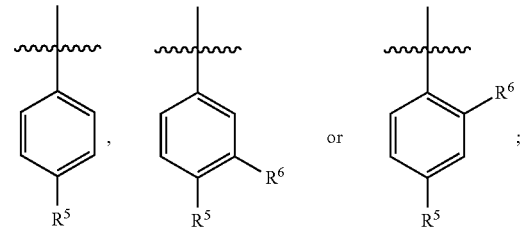

R$^5$ is selected from the group consisting of halo, C$_1$-C$_4$alkyl, C$_1$-C$_4$alkoxy, C$_1$-C$_4$alkoxyC$_1$-C$_4$alkyl, C$_3$-C$_6$cycloalkyl, C$_3$-C$_6$cycloalkoxy, 4- to 6-membered heterocycloalkyl and 4- to 6-membered heterocycloalkoxy; wherein the C$_1$-C$_4$alkyl, C$_1$-C$_4$alkoxy and C$_1$-C$_4$alkoxyC$_1$-C$_4$alkyl are optionally substituted with one to three independently selected halo or hydroxy; and wherein the C$_3$-C$_6$cycloalkyl, C$_3$-C$_6$cycloalkoxy, 4- to 6-membered heterocycloalkyl and 4- to 6-membered heterocycloalkoxy are optionally substituted with one to three R$^7$;
the optional R$^6$ substituent is halo or C$_1$-C$_3$alkyl;
or R$^5$ and R$^6$ when attached to adjacent carbons and taken together with the adjacent carbons to which they are attached form a fused 5- to 6-membered heterocycloalkyl ring which is optionally substituted with one to three R$^8$;
or a pharmaceutically acceptable salt thereof.

6. The compound of claim 5 wherein
R$^5$ is selected from the group consisting of chloro, methyl, propyl, isopropyl, difluoromethoxy, ethoxy, 1-(methoxy)ethyl, cyclopropyl, cyclobutyl, cyclopentyl, cyclohexyl, oxetanyl, tetrahydrofuranyl, tetrahydropyranyl, cyclopentoxy, tetrahydrofuranoxy and tetrahydropyranoxy, wherein the cyclopropyl, cyclobutyl, cyclopentyl, cyclohexyl, oxetanyl, tetrahydrofuranyl, tetrahydropyranyl, cyclopentoxy, tetrahydrofuranoxy and tetrahydropyranoxy are each optionally substituted with one to two $R^7$;

the optional $R^6$ substituent is fluoro or methyl;

or $R^5$ and $R^6$ when attached to adjacent carbons and taken together with the adjacent carbons to which they are attached form a fused tetrahydrofuran or fused tetrahydropyran, each of which is optionally substituted with one to two $R^8$;

$R^7$ at each occurrence is independently selected from the group consisting of fluoro, hydroxy, methyl, trifluoromethyl, methoxy, ethoxy and 2-fluoroethoxy; and $R^8$ at each occurrence is fluoro or methyl;

or a pharmaceutically acceptable salt thereof.

7. The compound of claim 6 wherein
A is

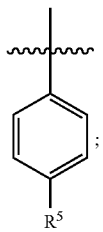

or a pharmaceutically acceptable salt thereof.

8. The compound of claim 6 wherein
A is

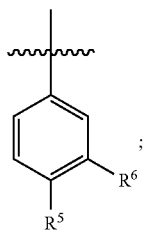

or a pharmaceutically acceptable salt thereof.

9. The compound of claim 6 wherein
A is

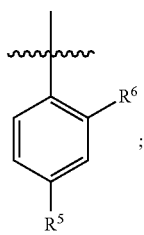

or a pharmaceutically acceptable salt thereof.

10. The compound of claim 7 wherein
$R^5$ is selected from the group consisting of methyl, cyclobutyl, cyclopentyl, tetrahydropyran-4-yl and tetrahydropyran-2-yl, wherein the cyclobutyl, cyclopentyl, tetrahydropyran-4-yl and tetrahydropyran-2-yl are each optionally substituted with one to two $R^7$;

or a pharmaceutically acceptable salt thereof.

11. The compound of claim 4 wherein
A is a 6-membered heteroaryl optionally substituted with one $R^6$;

or a pharmaceutically acceptable salt thereof.

12. The compound of claim 11 wherein
A is pyridinyl or pyrimidinyl, each of which is optionally substituted with one $R^6$;

or a pharmaceutically acceptable salt thereof.

13. The compound of claim 12 wherein
A is

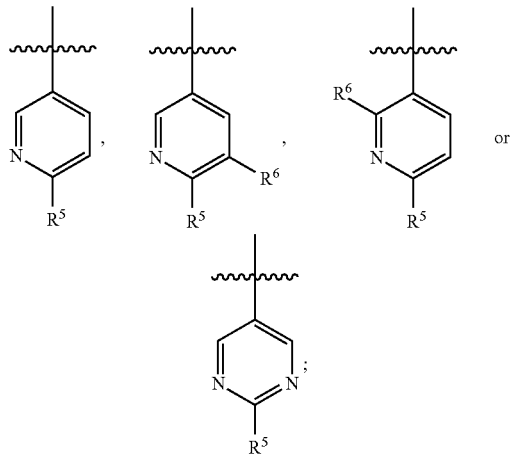

$R^5$ is selected from the group consisting of $C_1$-$C_4$alkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_1$-$C_3$alkyl, $C_3$-$C_6$cycloalkoxy, phenoxy, 4- to 6-membered heterocycloalkyl and 4- to 6-membered heterocycloalkoxy; wherein the $C_1$-$C_4$alkyl, $C_1$-$C_4$alkoxy and $C_1$-$C_4$alkoxy$C_1$-$C_4$alkyl are optionally substituted with one to three independently selected halo or hydroxy; and wherein the $C_3$-$C_6$cycloalkyl, $C_3$-$C_6$cycloalkyl$C_1$-$C_3$alkyl, $C_3$-$C_6$cycloalkoxy, phenoxy, 4- to 6-membered heterocycloalkyl and 4- to 6-membered heterocycloalkoxy are optionally substituted with one to three $R^7$; and the optional $R^6$ substituent is halo or $C_1$-$C_3$alkyl;

or a pharmaceutically acceptable salt thereof.

14. The compound of claim 13 wherein
$R^5$ is selected from the group consisting of tert-butoxy, cyclobutyl, cyclopentyl, cyclohexyl, cyclobutoxy, cyclopentoxy, phenoxy, cyclopentylmethyl and tetrahydropyranyl, wherein the cyclobutyl, cyclopentyl, cyclohexyl, cyclobutoxy, cyclopentoxy, phenoxy, cyclopentylmethyl and tetrahydropyranyl are optionally substituted with one to two $R^7$;

the optional $R^6$ substituent is fluoro or methyl; and $R^7$ at each occurrence is independently selected from the group consisting of fluoro, hydroxy, methyl, trifluoromethyl, methoxy, ethoxy and 2-fluoroethoxy;

or a pharmaceutically acceptable salt thereof.

15. The compound of claim 14 wherein
A is

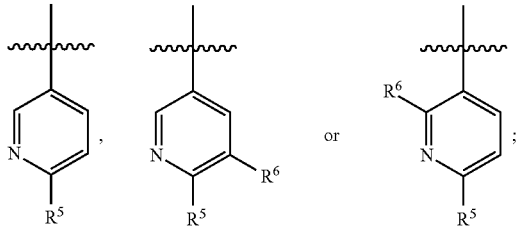

or a pharmaceutically acceptable salt thereof.

16. The compound of claim 14 wherein
A is

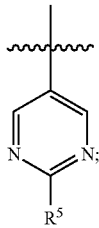

or a pharmaceutically acceptable salt thereof.

17. A compound of claim 1 selected from the group consisting of
  6-cyclohexyl-N-(2-methoxy-7-methyl-6,7,8,9-tetrahydro-5H-pyrido[2,3-d]azepin-3-yl)pyridine-3-sulfonamide;
  6-(cyclopentyloxy)-N-(7-ethyl-2-methoxy-6,7,8,9-tetrahydro-5H-pyrido[2,3-d]azepin-3-yl)pyridine-3-sulfonamide;
  4-[trans-3-(2-fluoroethoxy)cyclobutyl]-N-(2-methoxy-7-methyl-6,7,8,9-tetrahydro-5H-pyrido[2,3-d]azepin-3-yl)benzenesulfonamide;
  N-(2-methoxy-7-methyl-6,7,8,9-tetrahydro-5H-pyrido[2,3-d]azepin-3-yl)-4-(tetrahydro-2H-pyran-4-yl)benzenesulfonamide;
  N-(2-methoxy-7-methyl-6,7,8,9-tetrahydro-5H-pyrido[2,3-d]azepin-3-yl)-4-methylbenzenesulfonamide;
  N-(2-methoxy-7-methyl-6,7,8,9-tetrahydro-5H-pyrido[2,3-d]azepin-3-yl)-4-(tetrahydro-2H-pyran-2-yl)benzenesulfonamide;
  N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide;
  N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide;
  N-(2-methoxy-6,7,8,9-tetrahydro-5H-pyrido[2,3-d]azepin-3-yl)-4-[(2R)-tetrahydro-2H-pyran-2-yl]benzenesulfonamide;
  4-(trans-1-fluoro-3-methoxycyclobutyl)-N-(2-methoxy-7-methyl-6,7,8,9-tetrahydro-5H-pyrido[2,3-d]azepin-3-yl)benzenesulfonamide;
  6-(1-fluorocyclopentyl)-N-(2-methoxy-7-methyl-6,7,8,9-tetrahydro-5H-pyrido[2,3-d]azepin-3-yl)pyridine-3-sulfonamide;
  N-[2-(difluoromethoxy)-7-propyl-6,7,8,9-tetrahydro-5H-pyrido[2,3-d]azepin-3-yl]-4-(propan-2-yl)benzenesulfonamide;
  N-(7-ethyl-2-methoxy-5-methyl-6,7,8,9-tetrahydro-5H-pyrido[2,3-d]azepin-3-yl)-4-methylbenzenesulfonamide;
  4-ethoxy-N-[7-ethyl-2-(propan-2-yloxy)-6,7,8,9-tetrahydro-5H-pyrido[2,3-d]azepin-3-yl]benzenesulfonamide;
  6-(cyclopentyloxy)-N-(2-methoxy-7-methyl-6,7,8,9-tetrahydro-5H-pyrido[2,3-d]azepin-3-yl)pyridine-3-sulfonamide;
  6-cyclopentyl-N-(2-methoxy-7-methyl-6,7,8,9-tetrahydro-5H-pyrido[2,3-d]azepin-3-yl)pyridine-3-sulfonamide;
  6-(cyclobutyloxy)-N-(2-methoxy-7-methyl-6,7,8,9-tetrahydro-5H-pyrido[2,3-d]azepin-3-yl)pyridine-3-sulfonamide;
  2-(cyclopentyloxy)-N-(2-methoxy-7-methyl-6,7,8,9-tetrahydro-5H-pyrido[2,3-d]azepin-3-yl)pyrimidine-5-sulfonamide;
  6-(1-fluorocyclohexyl)-N-(2-methoxy-7-methyl-6,7,8,9-tetrahydro-5H-pyrido[2,3-d]azepin-3-yl)pyridine-3-sulfonamide;
  N-(7-ethyl-2-methoxy-6,7,8,9-tetrahydro-5H-pyrido[2,3-d]azepin-3-yl)-4-[trans-3-(2-fluoroethoxy)cyclobutyl]benzenesulfonamide;
  4-(cis-3-ethoxycyclobutyl)-N-(2-methoxy-7-methyl-6,7,8,9-tetrahydro-5H-pyrido[2,3-d]azepin-3-yl)benzenesulfonamide;
  4-(trans-3-ethoxycyclobutyl)-N-(2-methoxy-7-methyl-6,7,8,9-tetrahydro-5H-pyrido[2,3-d]azepin-3-yl)benzenesulfonamide;
  N-(7-ethyl-2-methoxy-6,7,8,9-tetrahydro-5H-pyrido[2,3-d]azepin-3-yl)-6-(cis-1-hydroxy-3-methoxycyclobutyl)pyridine-3-sulfonamide;
  6-cyclobutyl-5-fluoro-N-(2-methoxy-7-methyl-6,7,8,9-tetrahydro-5H-pyrido[2,3-d]azepin-3-yl)pyridine-3-sulfonamide;
  6-(cis-1-fluoro-3-methylcyclobutyl)-N-(2-methoxy-7-methyl-6,7,8,9-tetrahydro-5H-pyrido[2,3-d]azepin-3-yl)pyridine-3-sulfonamide;
  N-(2-methoxy-7-propyl-6,7,8,9-tetrahydro-5H-pyrido[2,3-d]azepin-3-yl)-4-methylbenzene sulfonamide;
  4-chloro-N-(2-methoxy-7-methyl-6,7,8,9-tetrahydro-5H-pyrido[2,3-d]azepin-3-yl) benzenesulfonamide;
  4-ethoxy-N-(2-methoxy-7-methyl-6,7,8,9-tetrahydro-5H-pyrido[2,3-d]azepin-3-yl) benzenesulfonamide;
  4-ethoxy-N-[2-methoxy-7-(2-methoxyethyl)-6,7,8,9-tetrahydro-5H-pyrido[2,3-d]azepin-3-yl]benzenesulfonamide;
  4-cyclopropyl-N-(7-ethyl-2-methoxy-6,7,8,9-tetrahydro-5H-pyrido[2,3-d]azepin-3-yl) benzenesulfonamide;
  N-(2-methoxy-7-methyl-6,7,8,9-tetrahydro-5H-pyrido[2,3-d]azepin-3-yl)-3,4-dihydro-2H-chromene-6-sulfonamide;
  4-(1-methoxyethyl)-N-(2-methoxy-7-methyl-6,7,8,9-tetrahydro-5H-pyrido[2,3-d]azepin-3-yl) benzenesulfonamide;
  N-(2-methoxy-7-methyl-6,7,8,9-tetrahydro-5H-pyrido[2,3-d]azepin-3-yl)-4-(oxetan-3-yl) benzenesulfonamide;
  N-(2-methoxy-7-methyl-6,7,8,9-tetrahydro-5H-pyrido[2,3-d]azepin-3-yl)-2,2-dimethyl-2,3-dihydro-1-benzofuran-5-sulfonamide;
  N-(7-ethyl-2-methoxy-6,7,8,9-tetrahydro-5H-pyrido[2,3-d]azepin-3-yl)-3-fluoro-4-methylbenzenesulfonamide;
  N-(2-methoxy-7-methyl-6,7,8,9-tetrahydro-5H-pyrido[2,3-d]azepin-3-yl)-4-(tetrahydrofuran-3-yl)benzenesulfonamide;

N-(2-methoxy-7-methyl-6,7,8,9-tetrahydro-5H-pyrido[2,3-d]azepin-3-yl)-4-[(3R)-tetrahydrofuran-3-yloxy]benzenesulfonamide;

4-(trans-4-methoxycyclohexyl)-N-(2-methoxy-7-methyl-6,7,8,9-tetrahydro-5H-pyrido[2,3-d]azepin-3-yl)benzenesulfonamide;

4-(cis-1-fluoro-4-methoxycyclohexyl)-N-(2-methoxy-7-methyl-6,7,8,9-tetrahydro-5H-pyrido[2,3-d]azepin-3-yl)benzenesulfonamide;

4-(4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide;

4-((2R)-4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide;

4-((2S)-4,4-difluorotetrahydro-2H-pyran-2-yl)-N-(2-methoxy-7-methyl-6,7,8,9-tetrahydro-5H-pyrido[2,3-d]azepin-3-yl)benzenesulfonamide;

N-(7-ethyl-2-methoxy-6,7,8,9-tetrahydro-5H-pyrido[2,3-d]azepin-3-yl)-3-fluoro-4-[(2S)-tetrahydro-2H-pyran-2-yl]benzenesulfonamide;

N-[7-(3-fluoropropyl)-2-methoxy-6,7,8,9-tetrahydro-5H-pyrido[2,3-d]azepin-3-yl]-4-(propan-2-yl)benzenesulfonamide;

4-cyclohexyl-N-(2-methoxy-7-methyl-6,7,8,9-tetrahydro-5H-pyrido[2,3-d]azepin-3-yl) benzenesulfonamide;

4-(cyclopentyloxy)-N-(2-methoxy-7-methyl-6,7,8,9-tetrahydro-5H-pyrido[2,3-d]azepin-3-yl) benzenesulfonamide;

6-[cyclopentyl(difluoro)methyl]-N-(2-methoxy-7-methyl-6,7,8,9-tetrahydro-5H-pyrido[2,3-d]azepin-3-yl)pyridine-3-sulfonamide;

4-(trans-3-ethoxy-1-fluorocyclobutyl)-N-(7-ethyl-2-methoxy-6,7,8,9-tetrahydro-5H-pyrido[2,3-d]azepin-3-yl)benzenesulfonamide;

N-(2-methoxy-7-propyl-6,7,8,9-tetrahydro-5H-pyrido[2,3-d]azepin-3-yl)-4-(propan-2-yl) benzenesulfonamide;

4-ethoxy-N-(2-methoxy-7-propyl-6,7,8,9-tetrahydro-5H-pyrido[2,3-d]azepin-3-yl) benzenesulfonamide;

N-(7-ethyl-2-methoxy-6,7,8,9-tetrahydro-5H-pyrido[2,3-d]azepin-3-yl)-4-(propan-2-yl) benzenesulfonamide;

4-ethoxy-N-(7-ethyl-2-methoxy-6,7,8,9-tetrahydro-5H-pyrido[2,3-d]azepin-3-yl) benzenesulfonamide;

N-(7-ethyl-2-methoxy-6,7,8,9-tetrahydro-5H-pyrido[2,3-d]azepin-3-yl)-4-methylbenzenesulfonamide;

N-(2-methoxy-7-methyl-6,7,8,9-tetrahydro-5H-pyrido[2,3-d]azepin-3-yl)-4-(propan-2-yl) benzenesulfonamide;

N-(2-methoxy-7-methyl-6,7,8,9-tetrahydro-5H-pyrido[2,3-d]azepin-3-yl)-4-[1-(trifluoromethyl)cyclopropyl] benzenesulfonamide;

N-(7-ethyl-2-methoxy-5-methyl-6,7,8,9-tetrahydro-5H-pyrido[2,3-d]azepin-3-yl)-4-(propan-2-yl) benzenesulfonamide;

N-(7-ethyl-2-methoxy-6,7,8,9-tetrahydro-5H-pyrido[2,3-d]azepin-3-yl)-4-(tetrahydro-2H-pyran-4-yl)benzenesulfonamide;

N-(7-ethyl-2-methoxy-6,7,8,9-tetrahydro-5H-pyrido[2,3-d]azepin-3-yl)-3,4-dihydro-2H-chromene-6-sulfonamide;

4-(difluoromethoxy)-N-(7-ethyl-2-methoxy-6,7,8,9-tetrahydro-5H-pyrido[2,3-d]azepin-3-yl) benzenesulfonamide;

N-(7-ethyl-2-methoxy-6,7,8,9-tetrahydro-5H-pyrido[2,3-d]azepin-3-yl)-6-phenoxypyridine-3-sulfonamide;

N-(7-ethyl-2-methoxy-6,7,8,9-tetrahydro-5H-pyrido[2,3-d]azepin-3-yl)-3,4-dimethyl benzenesulfonamide;

N-(7-ethyl-2-methoxy-6,7,8,9-tetrahydro-5H-pyrido[2,3-d]azepin-3-yl)-4-propylbenzenesulfonamide;

4-(cyclopentyloxy)-N-(7-ethyl-2-methoxy-6,7,8,9-tetrahydro-5H-pyrido[2,3-d]azepin-3-yl) benzenesulfonamide;

N-(7-ethyl-2-methoxy-6,7,8,9-tetrahydro-5H-pyrido[2,3-d]azepin-3-yl)-2,2-dimethyl-3,4-dihydro-2H-chromene-6-sulfonamide;

N-(7-ethyl-2-methoxy-6,7,8,9-tetrahydro-5H-pyrido[2,3-d]azepin-3-yl)-2,4-dimethylbenzenesulfonamide;

N-(7-ethyl-2-methoxy-6,7,8,9-tetrahydro-5H-pyrido[2,3-d]azepin-3-yl)-2,4-dimethylbenzenesulfonamide;

N-[7-ethyl-2-(propan-2-yloxy)-6,7,8,9-tetrahydro-5H-pyrido[2,3-d]azepin-3-yl]-3,4-dihydro-2H-chromene-6-sulfonamide;

N-(7-ethyl-2-methoxy-6,7,8,9-tetrahydro-5H-pyrido[2,3-d]azepin-3-yl)-2-methyl-2,3-dihydro-1-benzofuran-5-sulfonamide;

N-(7-ethyl-2-methoxy-6,7,8,9-tetrahydro-5H-pyrido[2,3-d]azepin-3-yl)-4-(trans-3-methoxycyclobutyl)benzenesulfonamide;

N-(7-ethyl-2-methoxy-6,7,8,9-tetrahydro-5H-pyrido[2,3-d]azepin-3-yl)-4-(4-methyltetrahydro-2H-pyran-4-yl) benzenesulfonamide;

N-(7-ethyl-2-methoxy-6,7,8,9-tetrahydro-5H-pyrido[2,3-d]azepin-3-yl)-4-(tetrahydro-2H-pyran-2-yl)benzenesulfonamide;

N-(7-ethyl-2-methoxy-6,7,8,9-tetrahydro-5H-pyrido[2,3-d]azepin-3-yl)-4-(tetrahydrofuran-3-yl) benzenesulfonamide;

N-(7-ethyl-2-methoxy-6,7,8,9-tetrahydro-5H-pyrido[2,3-d]azepin-3-yl)-4-(cis-3-methoxycyclobutyl)benzenesulfonamide;

N-(7-ethyl-2-methoxy-6,7,8,9-tetrahydro-5H-pyrido[2,3-d]azepin-3-yl)-4-((2R)-tetrahydro-2H-pyran-2-yl)benzenesulfonamide;

N-(7-ethyl-2-methoxy-6,7,8,9-tetrahydro-5H-pyrido[2,3-d]azepin-3-yl)-4-((2S)-tetrahydro-2H-pyran-2-yl)benzenesulfonamide;

N-(7-ethyl-2-methoxy-6,7,8,9-tetrahydro-5H-pyrido[2,3-d]azepin-3-yl)-4-(4-fluorotetrahydro-2H-pyran-4-yl) benzenesulfonamide;

4-(trans-3-methoxycyclobutyl)-N-(2-methoxy-7-methyl-6,7,8,9-tetrahydro-5H-pyrido[2,3-d]azepin-3-yl)benzenesulfonamide;

N-(2-methoxy-7-methyl-6,7,8,9-tetrahydro-5H-pyrido[2,3-d]azepin-3-yl)-4-(tetrahydro-2H-pyran-3-yl)benzenesulfonamide;

N-(2-methoxy-7-methyl-6,7,8,9-tetrahydro-5H-pyrido[2,3-d]azepin-3-yl)-4-(tetrahydro-2H-pyran-4-yloxy)benzenesulfonamide;

N-(2-methoxy-7-methyl-6,7,8,9-tetrahydro-5H-pyrido[2,3-d]azepin-3-yl)-4-(4-methyltetrahydro-2H-pyran-4-yl)benzenesulfonamide;

4-(4-fluorotetrahydro-2H-pyran-4-yl)-N-(2-methoxy-7-methyl-6,7,8,9-tetrahydro-5H-pyrido[2,3-d]azepin-3-yl)benzenesulfonamide;

4-(cis-3-methoxycyclobutyl)-N-(2-methoxy-7-methyl-6,7,8,9-tetrahydro-5H-pyrido[2,3-d]azepin-3-yl)benzenesulfonamide;

N-(2-methoxy-7-methyl-6,7,8,9-tetrahydro-5H-pyrido[2,3-d]azepin-3-yl)-4-(tetrahydrofuran-3-yloxy)benzenesulfonamide;

N-(2-methoxy-7-methyl-6,7,8,9-tetrahydro-5H-pyrido[2,3-d]azepin-3-yl)-4-((3R)-tetrahydro-2H-pyran-3-yl) benzenesulfonamide;

N-(2-methoxy-7-methyl-6,7,8,9-tetrahydro-5H-pyrido[2,3-d]azepin-3-yl)-4-((3S)-tetrahydro-2H-pyran-3-yl)benzenesulfonamide;

N-(2-methoxy-7-methyl-6,7,8,9-tetrahydro-5H-pyrido[2,3-d]azepin-3-yl)-4-(trans-2-methyltetrahydro-2H-pyran-4-yl)benzenesulfonamide;

4-((4R)-2,2-dimethyltetrahydro-2H-pyran-4-yl)-N-(2-methoxy-7-methyl-6,7,8,9-tetrahydro-5H-pyrido[2,3-d]azepin-3-yl)benzenesulfonamide;

4-((4S)-2,2-dimethyltetrahydro-2H-pyran-4-yl)-N-(2-methoxy-7-methyl-6,7,8,9-tetrahydro-5H-pyrido[2,3-d]azepin-3-yl)benzenesulfonamide;

N-(2-methoxy-7-methyl-6,7,8,9-tetrahydro-5H-pyrido[2,3-d]azepin-3-yl)-4-(trans-2-methyltetrahydro-2H-pyran-4-yl)benzenesulfonamide;

4-[(1S)-1-methoxyethyl]-N-(2-methoxy-7-methyl-6,7,8,9-tetrahydro-5H-pyrido[2,3-d]azepin-3-yl)benzenesulfonamide;

4-[(1R)-1-methoxyethyl]-N-(2-methoxy-7-methyl-6,7,8,9-tetrahydro-5H-pyrido[2,3-d]azepin-3-yl)benzenesulfonamide;

N-(2-methoxy-7-methyl-6,7,8,9-tetrahydro-5H-pyrido[2,3-d]azepin-3-yl)-4-[(3S)-tetrahydrofuran-3-yloxy]benzenesulfonamide;

4-(cis-4-methoxycyclohexyl)-N-(2-methoxy-7-methyl-6,7,8,9-tetrahydro-5H-pyrido[2,3-d]azepin-3-yl)benzenesulfonamide;

4-(trans-1-fluoro-4-methoxycyclohexyl)-N-(2-methoxy-7-methyl-6,7,8,9-tetrahydro-5H-pyrido[2,3-d]azepin-3-yl)benzenesulfonamide;

N-(7-ethyl-2-methoxy-6,7,8,9-tetrahydro-5H-pyrido[2,3-d]azepin-3-yl)-4-(1-fluoro-4-methoxycyclohexyl)benzenesulfonamide;

4-(1-methoxycyclopentyl)-N-(2-methoxy-7-methyl-6,7,8,9-tetrahydro-5H-pyrido[2,3-d]azepin-3-yl)benzenesulfonamide;

N-(7-ethyl-2-methoxy-6,7,8,9-tetrahydro-5H-pyrido[2,3-d]azepin-3-yl)-4-(trans-1-fluoro-3-methoxycyclobutyl)benzenesulfonamide;

N-(2-methoxy-7-methyl-6,7,8,9-tetrahydro-5H-pyrido[2,3-d]azepin-3-yl)-6-(tetrahydrofuran-3-yloxy)pyridine-3-sulfonamide;

N-(2-methoxy-7-methyl-6,7,8,9-tetrahydro-5H-pyrido[2,3-d]azepin-3-yl)-4-[(2S)-tetrahydrofuran-2-yl]benzenesulfonamide;

N-(2-methoxy-7-methyl-6,7,8,9-tetrahydro-5H-pyrido[2,3-d]azepin-3-yl)-4-[(2R)-tetrahydrofuran-2-yl]benzenesulfonamide;

6-(1-methoxycyclopentyl)-N-(2-methoxy-7-methyl-6,7,8,9-tetrahydro-5H-pyrido[2,3-d]azepin-3-yl)pyridine-3-sulfonamide;

N-(7-ethyl-2-methoxy-6,7,8,9-tetrahydro-5H-pyrido[2,3-d]azepin-3-yl)-6-(1-fluorocyclopentyl)pyridine-3-sulfonamide;

6-cyclopentyl-N-(7-ethyl-2-methoxy-6,7,8,9-tetrahydro-5H-pyrido[2,3-d]azepin-3-yl)pyridine-3-sulfonamide;

6-tert-butoxy-N-(2-methoxy-7-methyl-6,7,8,9-tetrahydro-5H-pyrido[2,3-d]azepin-3-yl)pyridine-3-sulfonamide;

N-(2-methoxy-7-methyl-6,7,8,9-tetrahydro-5H-pyrido[2,3-d]azepin-3-yl)-3-methyl-4-[(2R)-tetrahydro-2H-pyran-2-yl]benzenesulfonamide;

N-(2-methoxy-7-methyl-6,7,8,9-tetrahydro-5H-pyrido[2,3-d]azepin-3-yl)-3-methyl-4-[(2S)-tetrahydro-2H-pyran-2-yl]benzenesulfonamide;

4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide;

N-(7-ethyl-2-methoxy-6,7,8,9-tetrahydro-5H-pyrido[2,3-d]azepin-3-yl)-3-methyl-4-[(2R)-tetrahydro-2H-pyran-2-yl]benzenesulfonamide;

4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-1;

4-(4-fluorotetrahydro-2H-pyran-2-yl)-N-(2-methoxy-7-methyl-6,7,8,9-tetrahydro-5H-pyrido[2,3-d]azepin-3-yl)benzenesulfonamide, diastereomer-2;

3-fluoro-N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide;

3-fluoro-N-(2-methoxy-7-methyl-6,7,8,9-tetrahydro-5H-pyrido[2,3-d]azepin-3-yl)-4-[(2S)-tetrahydro-2H-pyran-2-yl]benzenesulfonamide;

N-(7-ethyl-2-methoxy-6,7,8,9-tetrahydro-5H-pyrido[2,3-d]azepin-3-yl)-6-(1-fluorocyclohexyl)pyridine-3-sulfonamide;

6-cyclobutyl-N-(2-methoxy-7-methyl-6,7,8,9-tetrahydro-5H-pyrido[2,3-d]azepin-3-yl)pyridine-3-sulfonamide;

6-cyclohexyl-N-(7-ethyl-2-methoxy-6,7,8,9-tetrahydro-5H-pyrido[2,3-d]azepin-3-yl)pyridine-3-sulfonamide;

N-[7-(3-fluoropropyl)-2-methoxy-6,7,8,9-tetrahydro-5H-pyrido[2,3-d]azepin-3-yl]-4-methylbenzenesulfonamide;

2-(cyclobutyloxy)-N-(2-methoxy-7-methyl-6,7,8,9-tetrahydro-5H-pyrido[2,3-d]azepin-3-yl)pyrimidine-5-sulfonamide;

2-tert-butoxy-N-(2-methoxy-7-methyl-6,7,8,9-tetrahydro-5H-pyrido[2,3-d]azepin-3-yl)pyrimidine-5-sulfonamide;

N-(2-methoxy-7-methyl-6,7,8,9-tetrahydro-5H-pyrido[2,3-d]azepin-3-yl)-4-propylbenzenesulfonamide;

N-(7-ethyl-2-methoxy-6,7,8,9-tetrahydro-5H-pyrido[2,3-d]azepin-3-yl)-4-[cis-3-(2-fluoroethoxy)cyclobutyl]benzenesulfonamide;

4-(cis-3-ethoxycyclobutyl)-N-(7-ethyl-2-methoxy-6,7,8,9-tetrahydro-5H-pyrido[2,3-d]azepin-3-yl)benzenesulfonamide;

4-(trans-3-ethoxycyclobutyl)-N-(7-ethyl-2-methoxy-6,7,8,9-tetrahydro-5H-pyrido[2,3-d]azepin-3-yl)benzenesulfonamide;

6-(cyclopentyloxy)-N-[7-(3-fluoropropyl)-2-methoxy-6,7,8,9-tetrahydro-5H-pyrido[2,3-d]azepin-3-yl]pyridine-3-sulfonamide;

2-cyclopentyl-N-(2-methoxy-7-methyl-6,7,8,9-tetrahydro-5H-pyrido[2,3-d]azepin-3-yl) pyrimidine-5-sulfonamide;

6-(cyclopentyloxy)-N-(2-methoxy-7-methyl-6,7,8,9-tetrahydro-5H-pyrido[2,3-d]azepin-3-yl)-5-methylpyridine-3-sulfonamide;

6-(cyclopentyloxy)-N-(7-ethyl-2-methoxy-6,7,8,9-tetrahydro-5H-pyrido[2,3-d]azepin-3-yl)-5-methylpyridine-3-sulfonamide;

6-(cyclobutyloxy)-N-(2-methoxy-7-methyl-6,7,8,9-tetrahydro-5H-pyrido[2,3-d]azepin-3-yl)-5-methylpyridine-3-sulfonamide;

2-cyclohexyl-N-(2-methoxy-7-methyl-6,7,8,9-tetrahydro-5H-pyrido[2,3-d]azepin-3-yl) pyrimidine-5-sulfonamide;

6-(cyclopentyloxy)-N-(2-methoxy-7-methyl-6,7,8,9-tetrahydro-5H-pyrido[2,3-d]azepin-3-yl)-2-methylpyridine-3-sulfonamide;

N-(2-methoxy-7-methyl-6,7,8,9-tetrahydro-5H-pyrido[2,3-d]azepin-3-yl)-6-[(2R)-tetrahydro-2H-pyran-2-yl]pyridine-3-sulfonamide;

6-(cyclopentylmethyl)-N-(2-methoxy-7-methyl-6,7,8,9-tetrahydro-5H-pyrido[2,3-d]azepin-3-yl) pyridine-3-sulfonamide;

4-(trans-3-ethoxy-1-fluorocyclobutyl)-N-(2-methoxy-7-methyl-6,7,8,9-tetrahydro-5H-pyrido[2,3-d]azepin-3-yl)benzenesulfonamide;

4-[trans-1-fluoro-3-(2-fluoroethoxy)cyclobutyl]-N-(2-methoxy-7-methyl-6,7,8,9-tetrahydro-5H-pyrido[2,3-d]azepin-3-yl)benzenesulfonamide;

6-(trans-3-ethoxycyclobutyl)-N-(2-methoxy-7-methyl-6,7,8,9-tetrahydro-5H-pyrido[2,3-d]azepin-3-yl)pyridine-3-sulfonamide;

6-(cis-3-ethoxycyclobutyl)-N-(2-methoxy-7-methyl-6,7,8,9-tetrahydro-5H-pyrido[2,3-d]azepin-3-yl)pyridine-3-sulfonamide;

6-(trans-1-fluoro-3-methylcyclobutyl)-N-(2-methoxy-7-methyl-6,7,8,9-tetrahydro-5H-pyrido[2,3-d]azepin-3-yl)pyridine-3-sulfonamide;

6-(cyclopentyloxy)-5-fluoro-N-(2-methoxy-7-methyl-6,7,8,9-tetrahydro-5H-pyrido[2,3-d]azepin-3-yl)pyridine-3-sulfonamide;

4-Ethoxy-N-(7-ethyl-2-methyl-6,7,8,9-tetrahydro-5H-pyrido[2,3-d]azepin-3-yl) benzenesulfonamide;

4-chloro-N-(7-ethyl-2-methyl-6,7,8,9-tetrahydro-5H-pyrido[2,3-d]azepin-3-yl) benzenesulfonamide;

4-methyl-N-[7-methyl-2-(trifluoromethyl)-6,7,8,9-tetrahydro-5H-pyrido[2,3-d]azepin-3-yl]benzenesulfonamide; and N-(2-ethyl-7-methyl-6,7,8,9-tetrahydro-5H-pyrido[2,3-d]azepin-3-yl)-4-[(2R)-tetrahydro-2H-pyran-2-yl]benzenesulfonamide;

or a pharmaceutically acceptable salt thereof.

18. A compound of claim 1 that is 6-(cyclopentyloxy)-N-(7-ethyl-2-methoxy-6,7,8,9-tetrahydro-5H-pyrido[2,3-d]azepin-3-yl)pyridine-3-sulfonamide or a pharmaceutically acceptable salt thereof.

19. A compound of claim 1 that is 4-[trans-3-(2-fluoroethoxy) cyclobutyl]-N-(2-methoxy-7-methyl-6,7,8,9-tetrahydro-5H-pyrido[2,3-d]azepin-3-yl) benzenesulfonamide or a pharmaceutically acceptable salt thereof.

20. A compound of claim 1 that is N-(2-methoxy-7-methyl-6,7,8,9-tetrahydro-5H-pyrido[2,3-d]azepin-3-yl)-4-(tetrahydro-2H-pyran-4-yl)benzenesulfonamide or a pharmaceutically acceptable salt thereof.

21. A compound of claim 1 that is N-(2-methoxy-7-methyl-6,7,8,9-tetrahydro-5H-pyrido[2,3-d]azepin-3-yl)-4-methylbenzenesulfonamide or a pharmaceutically acceptable salt thereof.

22. A compound of claim 1 that is N-(2-methoxy-7-methyl-6,7,8,9-tetrahydro-5H-pyrido[2,3-d]azepin-3-yl)-4-[(2R)-tetrahydro-2H-pyran-2-yl]benzenesulfonamide or a pharmaceutically acceptable salt thereof.

23. A compound of claim 1 that is 4-(trans-1-fluoro-3-methoxycyclobutyl)-N-(2-methoxy-7-methyl-6,7,8,9-tetrahydro-5H-pyrido[2,3-d]azepin-3-yl)benzenesulfonamide or a pharmaceutically acceptable salt thereof.

24. A compound of claim 1 that is 6-(1-fluorocyclopentyl)-N-(2-methoxy-7-methyl-6,7,8,9-tetrahydro-5H-pyrido[2,3-d]azepin-3-yl)pyridine-3-sulfonamide or a pharmaceutically acceptable salt thereof.

25. A pharmaceutical composition comprising a therapeutically effective amount of a compound of claim 1 or a pharmaceutically acceptable salt thereof and a pharmaceutically acceptable vehicle, diluent or carrier.

26. A method for treating a patient suffering from a disease or disorder associated with dysregulated activation of the D3 receptor, comprising administering to the patient a therapeutically effective amount of a compound of claim 1 or a pharmaceutically acceptable salt of said compound, wherein the disease or disorder is selected from the group consisting of Parkinson's disease, schizophrenia, dementia, psychosis, depression, mania, anxiety, dyskinesias, substance addiction, pathological gambling, hypersexuality, compulsive shopping, eating disorder, renal insufficiency and diabetes.

27. The method of claim 26 wherein the disease or disorder is substance addiction.

28. The method of claim 27 wherein the substance addiction is a relapse substance addiction.

29. The method of claim 26 wherein the substance addiction is an alcohol, cocaine, amphetamine, methamphetamine, opioid, marijuana or nicotine addiction.

* * * * *